US008183241B2

(12) United States Patent
Kenda et al.

(10) Patent No.: US 8,183,241 B2
(45) Date of Patent: *May 22, 2012

(54) 2-OXO-1-PYRROLIDINE DERIVATIVES

(75) Inventors: Benoît Kenda, Emines (BE); Yannick Quesnel, Wavre (BE); Ali Ates, Marbais (BE); Philippe Michel, Beersel (BE); Laurent Turet, Hamme-Mille (BE); Joël Mercier, Soye (BE)

(73) Assignee: UCB Pharma, S.A., Brussels (BE)

( * ) Notice: Subject to any disclaimer, the term of this patent is extended or adjusted under 35 U.S.C. 154(b) by 947 days.

This patent is subject to a terminal disclaimer.

(21) Appl. No.: 11/916,231

(22) PCT Filed: May 31, 2006

(86) PCT No.: PCT/EP2006/005199
§ 371 (c)(1),
(2), (4) Date: Jul. 17, 2008

(87) PCT Pub. No.: WO2006/128692
PCT Pub. Date: Dec. 7, 2006

(65) Prior Publication Data
US 2009/0156607 A1 Jun. 18, 2009

(30) Foreign Application Priority Data

Jun. 1, 2005 (EP) .................... 05011779
Jun. 1, 2005 (EP) .................... 05011780

(51) Int. Cl.
| | |
|---|---|
| *A61K 31/50* | (2006.01) |
| *A61K 31/501* | (2006.01) |
| *A61K 43/42* | (2006.01) |
| *A61K 31/44* | (2006.01) |
| *A61K 31/415* | (2006.01) |
| *A01N 43/56* | (2006.01) |
| *C07D 487/00* | (2006.01) |
| *C07D 513/02* | (2006.01) |
| *C07D 515/02* | (2006.01) |
| *C07D 209/02* | (2006.01) |
| *C07D 405/00* | (2006.01) |

(52) U.S. Cl. .................. 514/252.05; 514/299; 514/300; 514/403; 544/236; 546/118; 548/364.7; 548/465

(58) Field of Classification Search .................. None
See application file for complete search history.

(56) References Cited

U.S. PATENT DOCUMENTS 5,334,720 A  8/1994  Schmiesing et al.
6,303,638 B1  10/2001  Latli et al.

FOREIGN PATENT DOCUMENTS

| EP | 0 162 036 | 5/1985 |
| EP | 0 165 919 | 5/1985 |
| EP | 172 096 | 7/1985 |
| EP | 1 020 447 | 7/2000 |
| GB | 1003645 | * 9/1965 |
| GB | 1309692 | 3/1973 |
| GB | 2225322 A | 5/1990 |

OTHER PUBLICATIONS

Stezhko, et. al., Khimiko-Farmatsevticheskii Zhurnal (1984), 18(10), 1198-203.*
Scott, et. al., Journal of Medicinal Chemistry (1992), 35(3), 552-8.*
Database Registry XP002398821 abstract Nov. 16, 1984.
Cheng, Yung-Chi, et al., "Relationship Between the Inhibition Constant (Kr) and the Concentration of Inhibitor Which Causes 50 Per Cent Inhibition (I50) of an Enzymatic Reaction," Biochemical Pharmacology, 1973, vol. 22, pp. 3099-3108.
Noyer, Michel, et al., "The Novel Antiepileptic Drug Levetiracetam (ucb L059) Appears to Act Via a Specific Binding Site in CNS Membranes," European Journal of Pharmacology, 1995, vol. 286, pp. 137-146.
Fang, Xiang, et al., "Synthesis of Monofluorinated Indolizines and Their Derivatives by the 1,3-dipolar Reaction of N-Yields With Fluorinated Vinyl Tosylates," Tetrahedron, 2004, vol. 60, pp. 5487-5493.
Kondrat'Ev, P.N., et al., "Conformational Structure of Esters of Fluorinated," Bull.Acad.Sci.USSR Div. Chem.Sci, 39:6, 1990, Plenum Publishing Corporation, pp. 1273-1277.
Batt, Douglas, et al., "Polyfunctional Pyridines from Nitroacetamidine and B-Diketones. A Useful Synthesis of Substituted Imidazo [4,5-b] Pyridines and Related Compounds," J. Heterocyclic Chem., 1995, vol. 32, pp. 963-969.
Kenda, Benoit M., et al., "Discovery of 4-Substituted Pyrrolidone Butanamidess as New Agents with significant Antiepileptic Activity," J. Med. Chem., 2004, vol. 47, pp. 530-549.
Buchhalter, Jeffrey R., "Animal Models of Inherited Epilepsy," Epilepsia, vol. 34, Suppl. 3, 1993, pp. S31-S41.
Loscher, Wolfgang, et al., "Which Animal Models Should be Used in the Search for New Antiepileptic Drugs? A Proposal Based on Experimental and Clinical Considerations," Epilepsy Research, vol. 2, 1988, pp. 145-181.
Padwa, Albert, et al., "Cyclization-Cycloaddition Cascade of Rhodium Carbenoids Using Different Carbonyl Groups. Highlighting the Position of Interaction," J. Org. Chem., 2000, vol. 65, pp. 5223-5232.
Gower, Alma J., et al, "UCB L059, A Novel Anti-Convulsant Drug: Pharmacological Profile in Animals," European Journal of Pharmacology, vol. 222, 1992, pp. 193-203.
Mertens, Hubert, et al., "Zur Struktur des Nitroacetamidins," Arch. Pharm., 1986, vol. 319, No. 1, pp. 14-17.
Ried, Walter, et al., "Uber Nitroacetimidsaure-ester," Chem. Ber., 1963, vol. 96, pp. 3306-3311.
Yu, Belavin I., et al., Khimiko-Farmatsevticheskii Zhurnal, 1992, vol. 26, pp. 74-76.

* cited by examiner

*Primary Examiner* — Jeffrey Murray
(74) *Attorney, Agent, or Firm* — McDonnell Boehnen Hulbert & Berghoff LLP

(57) ABSTRACT

The present invention concerns 2-oxo-1-pyrrolidine derivatives, processes for preparing them, pharmaceutical compositions containing them and their use as pharmaceuticals.

14 Claims, No Drawings

2-OXO-1-PYRROLIDINE DERIVATIVES

This is a National Stage of International Application No. PCT/EP2006/005199, filed May 31, 2006.

INTRODUCTION

The present invention concerns 2-oxo-1-pyrrolidine derivatives, processes for preparing them, pharmaceutical compositions containing them and their use as pharmaceuticals.

European Patent No. 0 162 036 B1 discloses compound (S)-α-ethyl-2-oxo-1-pyrrolidine acetamide, which is known under the International Nonproprietary Name (INN) Levetiracetam.

Levetiracetam, a laevorotary compound, is disclosed as a protective agent for the treatment and prevention of hypoxic and ischemic type aggressions of the central nervous system. This compound is also effective in the treatment of epilepsy, a therapeutic indication for which it has been demonstrated that its dextrorotatory enantiomer (R)-α-ethyl-2-oxo-1-pyrrolidine acetamide, also known from European Patent No. 0 165 919 B1, completely lacks activity (Gower A. J. et al., Eur. J. Pharmacol. (1992), 222, 193-203).

Belavin I. Yu. et al. (Khimiko-Farmatsevticheskii Zhurnal (1992), 26 (9-10), 74-76) discloses 1-[1-(1H-benzimidazol-1-yl)ethyl]-2-pyrrolidinone and its anticonvulsant activity.

EP 172 096 discloses 3-imidazol-[1,2-a]pyridine derivatives for therapeutic applications.

U.S. Pat. No. 6,303,638 discloses 3-pyridine derivatives for treatment of CNS disorders responsive to the administration of a m-nAChR modulator.

EP 1 020 447 discloses 1H-pyrazol-5-yl derivatives as plant disease control agents.

It has now surprisingly been found that certain 2-oxo-1-pyrrolidine derivatives demonstrate markedly improved therapeutic properties.

U.S. Pat. No. 5,334,720 discloses 4-diphenylpyrrolidine-ones for the treatment of epilepsy.

WO 2005/054188 discloses imidazole derivatives having the formula A

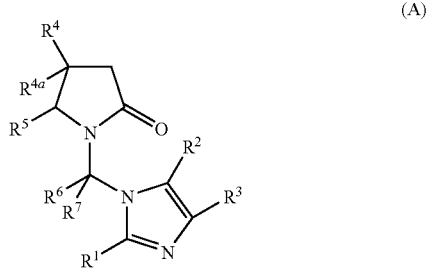

(A)

The imidazole or benzimidazole is attached by a nitrogen to the methylene linker of the pyrrolidinone.

SUMMARY OF THE INVENTION

The invention provides compounds having the formula (I) their geometrical isomers, enantiomers, diastereoisomers and mixtures, or a pharmaceutically acceptable salt thereof,

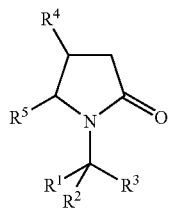

(I)

in particular for the manufacture of a medicament for the treatment or prevention of epilepsy, epileptogenesis, seizure disorders, convulsions, Parkinson's disease, dyskinesia induced by dopamine replacement therapy, tardive dyskinesia induced by administration of neuroleptic drugs, Huntington Chorea, and other neurological disorders including bipolar disorders, mania, depression, anxiety, attention deficit hyperactivity disorder (ADHD), migraine, trigeminal and other neuralgia, chronic pain, neuropathic pain, cerebral ischemia, cardiac arrhythmia, myotonia, cocaine abuse, stroke, myoclonus, tremor, essential tremor, simple or complex tics, Tourette syndrome, restless leg syndrome and other movement disorders, neonatal cerebral haemorrhage, amyotrophic lateral sclerosis, spasticity and degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

Further aspects of the invention will become apparent from the detailed description.

DETAILED DESCRIPTION OF THE INVENTION

The present invention relates to compounds having the formula I as well as their geometrical isomers, enantiomers, diastereoisomers and mixtures, or a pharmaceutically acceptable salt thereof,

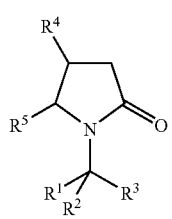

(I)

wherein
$R^1$ is hydrogen, $C_{1-12}$ alkyl, aryl or heterocycle;
$R^2$ is hydrogen; or $R^1$ and $R^2$ are linked together to form a $C_{3-6}$ cycloalkyl;
$R^3$ is either
a) an unsubstituted or substituted heterocycle linked to the rest of the molecule via one of its C atoms; or
b) an unsubstituted or substituted heterocycle linked to the rest of the molecule via one of its N atoms selected from the group consisting of
1H-1,2,3-benzotriazol-1-yl;
1H-imidazo[4,5-b]pyridin-1-yl;
3H-imidazo[4,5-b]pyridin-3-yl;
7H-imidazo[4,5-c]pyridazin-7-yl;
1H-indol-1-yl;
2,3-dihydro-1H-indol-1-yl;
9H-purin-9-yl;

1H-pyrazolo[3,4-b]pyridin-1-yl;
2H-pyrazolo[3,4-b]pyridin-2-yl;
1H-pyrrolo[2,3-b]pyridin-1-yl;
1H-pyrrolo[3,2-b]pyridin-1-yl;
3,4-dihydroquinolin-1(2H)-yl;
8H-isothiazolo[5,4-b]indol-8-yl;
1H-1,2,4-triazol-1-yl;
1H-1,2,3-triazol-1-yl;
1H-pyrrol-1-yl;
1H-tetrazol-1-yl;
2-chloro-1H-benzimidazol-1-yl.

$R^4$ is hydrogen; $C_{1-12}$ alkyl optionally substituted by halogen, $C_{1-4}$ alkoxy, $C_{1-4}$ alkylthio, azido, nitrooxy or aryl; $C_{2-12}$ alkenyl; $C_{2-12}$ alkynyl; aryl non-substituted by a cycloalkoxy; azido; alkoxy-carbonylamino; arylsulfonyloxy; or heterocycle;

$R^5$ is hydrogen;

or $R^4$ can form together with $R^5$ and the 2-oxo-1-pyrrolidine ring the following 1,3-dihydro-2H-indol-2-one cycle such as

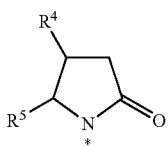

can represent a group of formula

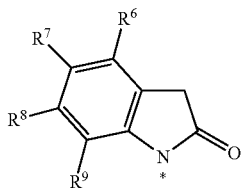

the asterisk * indicates the point of attachment of the substituents;

$R^6$ is hydrogen or halogen;

$R^7$ is hydrogen; nitro; halogen; heterocycle; amino; aryl; $C_{1-12}$ alkyl optionally substituted by at least one halogen; or $C_{1-12}$ alkoxy optionally substituted by at least one halogen;

$R^8$ is hydrogen, $C_{1-12}$ alkyl or halogen;
$R^9$ is hydrogen, $C_{1-12}$ alkyl or halogen;

Not comprised by formula (I) are those molecules wherein $R^4$ is not hydrogen when $R^1$, $R^2$ and $R^5$ are hydrogen, and $R^3$ is substituted or unsubstituted 3-pyridinyl; unsubstituted 4-pyridinyl; 2-(phenylamino)pyrimidin-4-yl; 2-trifluoropyrimidin-4-yl; isoxazol-5-yl 3-substituted by an aryl or an heterocycle; a substituted 1H-pyrazol-5-yl; a substituted 1H-pyrazol-3-yl; a 3-substituted 1,2,4-oxadiazol-5-yl; an unsubstituted or 1-substituted 1H-indol-3-yl; 2-[[4-[2-(1-methylethoxy)phenyl]-1-piperazinyl]methyl]thiazol-5-yl; (2-(4-chlorophenyl)-6-methylimidazo[1,2-a]pyridin-3-yl); 5-(4-methoxyphenyl)-7-trifluoromethyl-pyrazolo[1,5-a]pyrimidin-3-yl; substituted or unsubstituted 1,2,4-triazol-3-yl; substituted or unsubstituted 1,2,4-triazol-5-yl; 4,5,6,7-tetrahydro-2,1-benzisoxazol-3-yl; substituted 4,5-dihydroisoxazol-5-yl; substituted or unsubstituted 1H-1,2,3-benzotriazol-3-yl; 5-substituted 1,2,4-oxadiazol-3-yl; unsubstituted 1H-imidazo[4,5-c]pyridin-2-yl; 1,3-dimethyl-2,6-dioxo-1,2,3,6-tetrahydro-9H-purin-9-yl; substituted or unsubstituted 2-thienyl; substituted or unsubstituted 2-furyl; substituted or unsubstituted 2-pyrrolyl; substituted to unsubstituted 2-benzimidazol-2-yl; or 1-substituted 1H-indol-2-yl;

$R^4$ is not phenyl when $R^1$, $R^2$ and $R^5$ are hydrogen, and $R^3$ is a substituted 1,2,4-triazol-3-yl; a substituted 1,2,4-triazol-5-yl; or unsubstituted 1H-benzimidazol-2-yl;

$R^4$ is not hydrogen or phenyl when $R^1$ is hydrogen or $C_{1-12}$ alkyl, $R^2$ and $R^5$ are hydrogen, and $R^3$ is a substituted or unsubstituted non aromatic heterocycle;

$R^4$ is not hydrogen when $R^1$ is $C_{1-12}$ alkyl, $R^2$ and $R^5$ are hydrogen, and $R^3$ is a 3-substituted 1,2,4-oxadiazol-5-yl or unsubstituted 3-indolyl;

$R^4$ is not hydrogen when $R^1$ is phenyl, $C_{1-12}$ alkyl or heterocycle, $R^2$ and $R^5$ are hydrogen, and $R^3$ is unsubstituted 1,2,3-benzotriazol-1-yl or unsubstituted 1,2,4-triazol-1-yl;

$R^1$ is not 1-pyrrolidin-2-one when $R^2$, $R^4$ and $R^5$ are hydrogen, and $R^3$ is 2-furyl; and $R^1$ is not 4-(2-pyrimidinyl)-1-piperazinyl when $R^2$, $R^4$ and $R^5$ are hydrogen, and $R^3$ is 1-methyl-1H-pyrrol-2-yl.

In a specific embodiment, $R^3$ is a substituted or unsubstituted unsaturated heterocycle comprising at least one $sp^2$ hybridized nitrogen in the beta-, gamma- or delta-position of the carbon attached to the methylpyrrolidinone moiety; or a substituted or unsubstituted heterocycle linked to the rest of the molecule via one of its N atoms selected from the group consisting of 1H-1,2,3-benzotriazol-1-yl; 1H-imidazo[4,5-b]pyridin-1-yl; 3H-imidazo[4,5-b]pyridin-3-yl; 7H-imidazo[4,5-c]pyridazin-7-yl; 1H-indol-1-yl; 2,3-dihydro-1H-indol-1-yl; 9H-purin-9-yl; 1H-pyrazolo[3,4-b]pyridin-1-yl; 2H-pyrazolo[3,4-b]pyridin-2-yl; 1H-pyrrolo[2,3-b]pyridin-1-yl; 1H-pyrrolo[3,2-b]pyridin-1-yl; 3,4-dihydroquinolin-1(2H)-yl; 8H-isothiazolo[5,4-b]indol-8-yl; 1H-1,2,4-triazol-1-yl; 1H-1,2,3-triazol-1-yl; 1H-pyrrol-1-yl; 1H-tetrazol-1-yl; 2-chloro-1H-benzimidazol-1-yl.

In a further specific embodiment, $R^3$ is a substituted or unsubstituted aromatic heterocycle comprising at least one $sp^2$ hybridized nitrogen in the beta-, gamma- or delta-position of the carbon attached to the methylpyrrolidinone moiety; or a substituted or unsubstituted heterocycle linked to the rest of the molecule via one of its N atoms selected from the group consisting of 1H-1,2,3-benzotriazol-1-yl; 1H-imidazo[4,5-b]pyridin-1-yl; 3H-imidazo[4,5-b]pyridin-3-yl; 7H-imidazo[4,5-c]pyridazin-7-yl; 1H-indol-1-yl; 2,3-dihydro-1H-indol-1-yl; 9H-purin-9-yl; 1H-pyrazolo[3,4-b]pyridin-1-yl; 2H-pyrazolo[3,4-b]pyridin-2-yl; 1H-pyrrolo[2,3-b]pyridin-1-yl; 1H-pyrrolo[3,2-b]pyridin-1-yl; 3,4-dihydroquinolin-1(2H)-yl; 8H-isothiazolo[5,4-b]indol-8-yl; 1H-1,2,4-triazol-1-yl; 1H-pyrrol-1-yl; 2-chloro-1H-benzimidazol-1-yl.

More specifically, the compounds of the present invention are those covered by formula (I), their diastereomers and mixtures, or a pharmaceutically acceptable salt thereof.

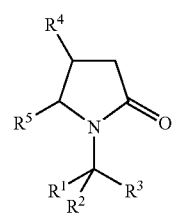

(I)

$R^1$ is hydrogen, substituted or unsubstituted $C_{1-12}$ alkyl, substituted or unsubstituted aryl or substituted or unsubstituted 3-8 membered heterocycle.

$R^2$ is hydrogen. Alternatively, $R^1$ and $R^2$ may be linked together in such a way to form a $C_{3-6}$ cycloalkyl.

$R^3$ is either (a) a substituted or unsubstituted heterocycle linked to the rest of the molecule via one of its C atoms, said heterocycle is selected from the group consisting of:
1H-benzimidazol-6-yl;
1H-benzimidazol-7-yl;
imidazo[1,2-a]pyridin-3-yl;
imidazo[1,2-a]pyrimidin-3-yl;
imidazo[1,2-b][1,2,4]triazin-7-yl;
imidazo[1,2-b]pyridazin-3-yl;
5,6,7,8-tetrahydroimidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
1H-indol-2-yl;
1H-indol-3-yl;
1H-indol-4-yl;
1H-indol-7-yl;
isoxazol-4-yl;
1H-pyrazol-4-yl;
1H-pyrazol-5-yl;
1H-pyrazolo[1,5-a]pyrimidin-3-yl;
1H-pyrazolo[3,4-b]pyridin-3-yl;
pyridazin-4-yl;
pyridin-2-yl;
pyridin-3-yl;
pyridin-4-yl;
1H-pyrrolo[2,3-b]pyridin-3-yl;
1H-pyrrolo[2,3-b]pyridin-4-yl;
1H-pyrrolo[2,3-b]pyridin-5-yl;
1H-pyrrolo[2,3-c]pyridin-2-yl;
1H-pyrrolo[2,3-c]pyridin-3-yl;
1H-pyrrolo[3,2-b]pyridin-3-yl;
1H-pyrrolo[3,2-c]pyridin-2-yl;
1H-pyrrolo[3,2-c]pyridin-3-yl;
1,3,4-thiadiazol-2-yl;
1,3-thiazol-5-yl;
[1,2,4]triazolo[4,3-b]pyridazin-7-yl;
[1,2,4]triazolo[4,3-b]pyridazin-8-yl;
indolizin-3-yl;

or $R^3$ is (b) a substituted or unsubstituted heterocycle linked to the rest of the molecule via one of its N atoms, said heterocycle is selected from the group consisting of:
1H-1,2,3-benzotriazol-1-yl;
1H-imidazo[4,5-b]pyridin-1-yl;
3H-imidazo[4,5-b]pyridin-3-yl;
7H-imidazo[4,5-c]pyridazin-7-yl;
1H-indol-1-yl;
2,3-dihydro-1H-indol-1-yl;
9H-purin-9-yl;
1H-pyrazolo[3,4-b]pyridin-1-yl;
2H-pyrazolo[3,4-b]pyridin-2-yl;
1H-pyrrolo[2,3-b]pyridin-1-yl;
1H-pyrrolo[3,2-b]pyridin-1-yl;
3,4-dihydroquinolin-1(2H)-yl;
8H-isothiazolo[5,4-b]indol-8-yl;
1H-1,2,4-triazol-1-yl;
1H-pyrrol-1-yl;
2-chloro-1H-benzimidazol-1-yl.

$R^4$ in formula (I) is selected from the group comprising or consisting of hydrogen; $C_{1-12}$ alkyl optionally substituted by halogen, $C_{1-4}$ alkoxy, $C_{1-4}$ alkylthio, azido, nitrooxy or an aryl; $C_{2-12}$ alkenyl optionally substituted by halogen; $C_{2-12}$ alkynyl optionally substituted by halogen; azido; alkoxycarbonylamino; arylsulfonyloxy; a substituted or unsubstituted aryl; or a 3-8 membered substituted or unsubstituted heterocycle;

In a specific embodiment $R^4$ is hydrogen; or $R^4$ is $C_{1-12}$ alkyl or a $C_{1-6}$ alkyl, optionally substituted by halogen, $C_{1-4}$ alkoxy, $C_{1-4}$ alkylthio, azido or nitrooxy; or $R^4$ is $C_{2-12}$ alkenyl or a $C_{1-6}$ alkenyl optionally substituted by halogen; or $R^4$ is $C_{2-12}$ alkynyl or a $C_{1-6}$ alkynyl optionally substituted by halogen; or $R^4$ is alkoxycarbonylamino.

$R^5$ is hydrogen;

Alternatively $R^4$ may form together with $R^5$ and the 2-oxo-1-pyrrolidine ring a 1,3-dihydro-2H-indol-2-one ring of the following structure:

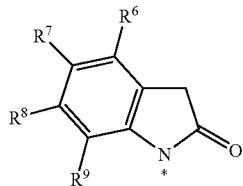

The asterisk * indicates the point of attachment of the substituents;

$R^6$ is hydrogen or halogen.

$R^7$ in formula (I) is selected from the group comprising or consisting of hydrogen; nitro; halogen; heterocycle; amino; aryl; $C_{1-12}$ alkyl optionally substituted by at least one halogen; or $C_{1-12}$ alkoxy optionally substituted by at least one halogen.

$R^8$ in formula (I) is selected from the group comprising or consisting of hydrogen, $C_{1-12}$ alkyl optionally substituted by halogen, or halogen.

$R^9$ in formula (I) is selected from the group comprising or consisting of hydrogen, $C_{1-12}$ alkyl optionally substituted by halogen, or halogen.

A further aspect of the present invention consists in compounds of formula (I) wherein
$R^1$ and $R^2$ are both hydrogen.
$R^3$ is:

(a) a substituted or unsubstituted heterocycle linked to the rest of the molecule via one of its C atoms selected from the group consisting of:
1H-benzimidazol-6-yl;
1H-benzimidazol-7-yl;
imidazo[1,2-a]pyridin-3-yl;
imidazo[1,2-a]pyrimidin-3-yl;
imidazo[1,2-b][1,2,4]triazin-7-yl;
imidazo[1,2-b]pyridazin-3-yl;
5,6,7,8-tetrahydroimidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
1H-indol-2-yl;
1H-indol-3-yl;
1H-indol-4-yl;
1H-indol-7-yl;
isoxazol-4-yl;

1H-pyrazol-4-yl;
1H-pyrazol-5-yl;
1H-pyrazolo[1,5-a]pyrimidin-3-yl;
1H-pyrazolo[3,4-b]pyridin-3-yl;
pyridazin-4-yl;
pyridin-2-yl;
pyridin-3-yl;
pyridin-4-yl;
1H-pyrrolo[2,3-b]pyridin-3-yl;
1H-pyrrolo[2,3-b]pyridin-4-yl;
1H-pyrrolo[2,3-b]pyridin-5-yl;
1H-pyrrolo[2,3-c]pyridin-2-yl;
1H-pyrrolo[2,3-c]pyridin-3-yl;
1H-pyrrolo[3,2-b]pyridin-3-yl;
1H-pyrrolo[3,2-c]pyridin-2-yl;
1H-pyrrolo[3,2-c]pyridin-3-yl;
1,3,4-thiadiazol-2-yl;
1,3-thiazol-5-yl;
[1,2,4]triazolo[4,3-b]pyridazin-7-yl;
[1,2,4]triazolo[4,3-b]pyridazin-8-yl;
indolizin-3-yl.
Alternatively R$^3$ is:
(b) a substituted or unsubstituted heterocycle linked to the rest of the molecule via one of its N atoms selected from the group consisting of:
1H-1,2,3-benzotriazol-1-yl;
1H-imidazo[4,5-b]pyridin-1-yl;
3H-imidazo[4,5-b]pyridin-3-yl;
7H-imidazo[4,5-c]pyridazin-7-yl;
1H-indol-1-yl;
2,3-dihydro-1H-indol-1-yl;
9H-purin-9-yl;
1H-pyrazolo[3,4-b]pyridin-1-yl;
2H-pyrazolo[3,4-b]pyridin-2-yl;
1H-pyrrolo[2,3-b]pyridin-1-yl;
1H-pyrrolo[3,2-b]pyridin-1-yl;
3,4-dihydroquinolin-1(2H)-yl;
8H-isothiazolo[5,4-b]indol-8-yl;
1H-1,2,4-triazol-1-yl;
1H-pyrrol-1-yl;
2-chloro-1H-benzimidazol-1-yl.
R$^4$ in formula (I) is selected from the group comprising or consisting of hydrogen; C$_{1-12}$ alkyl optionally substituted by halogen or C$_{1-4}$ alkoxy; C$_{2-12}$ alkenyl optionally substituted by halogen; C$_{2-12}$ alkynyl optionally substituted by halogen.
In a further specific embodiment R$^4$ is n-propyl, 2,2,2-trifluoroethyl, 2-chloro-2,2-difluoroethyl, 2 bromo-2,2-difluoroethyl, 2,2-difluorovinyl.
In another specific embodiment R$^4$ is phenyl, 2,3,5-trifluorophenyl or 3-chloro-4-fluorophenyl.
R$^5$ is hydrogen;
A further embodiment of the present invention consists in compounds of formula (I) wherein R$^4$ forms together with R$^5$ a 1,3-dihydro-2H-indol-2-one ring

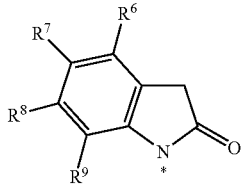

The asterisk * indicates the point of attachment of the heteroaryl alkylene substituent, and wherein
R$^6$ is hydrogen;
R$^7$ is chlorine;
R$^8$ is hydrogen;
R$^9$ is hydrogen.
A further embodiment of the present invention consists in compounds of formula (I) wherein R$^3$ is a substituted or unsubstituted heterocycle linked to the rest of the molecule via one of its C atoms and is selected from the group consisting of:
imidazo[1,2-a]pyrimidin-3-yl;
imidazo[1,2-b][1,2,4]triazin-7-yl;
imidazo[1,2-b]pyridazin-3-yl;
5,6,7,8-tetrahydroimidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
isoxazol-4-yl;
1H-pyrazol-4-yl;
1H-pyrazol-5-yl;
1H-pyrazolo[1,5-a]pyrimidin-3-yl;
1H-pyrazolo[3,4-b]pyridin-3-yl;
pyridin-3-yl;
1H-pyrrolo[2,3-b]pyridin-3-yl;
1H-pyrrolo[2,3-b]pyridin-4-yl;
1H-pyrrolo[2,3-b]pyridin-5-yl;
1H-pyrrolo[2,3-c]pyridin-2-yl;
1H-pyrrolo[2,3-c]pyridin-3-yl;
1,3-thiazol-5-yl;
[1,2,4]triazolo[4,3-b]pyridazin-8-yl;
indolizin-3-yl.
In a further specific embodiment R$^3$ is a heterocycle linked to the rest of the molecule via one of its C atoms and is selected from the group consisting of:
imidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
1H-pyrazol-4-yl;
1H-pyrazolo[1,5-a]pyrimidin-3-yl;
pyridin-3-yl;
1H-pyrrolo[2,3-b]pyridin-3-yl;
1H-pyrrolo[2,3-b]pyridin-4-yl;
1,3-thiazol-5-yl;
Said heterocycles are optionally substituted by e.g. a methyl, n-propyl, trifluoromethyl, cyclopropyl, bromine, chlorine, fluorine, iodine, methoxy, ethoxy, propoxy, isopropoxy, cyclopropyloxy, cyclopropylmethoxy, cyclobutylmethoxy, amino, methylamino, cyclopropylamino, cyclobutylamino, 1-pyrrolidinyl, cyano, phenyl, benzyl or 3-thienyl.
In a further specific embodiment R$^3$ is a heterocycle linked to the rest of the molecule via one of its C atoms and is selected from the group consisting of: 6-chloro-2-cyclopropylimidazo[1,2-b]pyridazin-3-yl, 6-(cyclopropyloxy)-2-(trifluoromethyl)imidazo[1,2-b]pyridazin-3-yl, 6-propoxy-2-(trifluoromethyl)imidazo[1,2-b]pyridazin-3-yl, 6-chloroimidazo[2,1-b][1,3]thiazol-5-yl, 2,6-dichloroimidazo[2,1-b][1,3]thiazol-5-yl, 5-chloro-1H-imidazol-4-yl, 5-bromo-1H-imidazol-4-yl, 4-bromo-1H-imidazol-5-yl, 4-chloro-1H-imidazol-5-yl, 1H-imidazol-5-yl, 1-methyl-1H-imidazol-5-yl, 4-chloro-1-methyl-1H-imidazol-5-yl, 1H-pyrazol-4-yl, 1H-pyrrolo[2,3-b]pyridin-3-yl.

A further embodiment of the present invention consists in compounds of formula (I) wherein $R^3$ is a heterocycle linked to the rest of the molecule via one of its C atoms and is a substituted or unsubstituted imidazo[1,2-a]pyridin-3-yl.

Said imidazo[1,2-a]pyridin-3-yl is optionally substituted by e.g. a methyl, cyclopropyl, bromine, chlorine, fluorine, iodine.

In a further specific embodiment $R^3$ is a heterocycle linked to the rest of the molecule via one of its C atoms and is selected from the group consisting of: imidazo[1,2-a]pyridin-3-yl, 6-methylimidazo[1,2-a]pyridin-3-yl, 2-chloroimidazo[1,2-a]pyridin-3-yl.

A further embodiment of the present invention consists in compounds of formula (I) wherein $R^3$ is a substituted or unsubstituted heterocycle linked to the rest of the molecule via one of its N atoms and is selected from the group consisting of:
3H-imidazo[4,5-b]pyridin-3-yl;
1H-indol-1-yl;
1H-pyrrolo[2,3-b]pyridin-1-yl;
1H-pyrrolo[3,2-b]pyridin-1-yl;
1H-pyrrol-1-yl;
2-chloro-1H-benzimidazol-1-yl.

A specific further embodiment of the present invention consists in compounds of formula (I) wherein $R^3$ is a heterocycle linked to the rest of the molecule via one of its N atoms and is selected from the group consisting of:
3H-imidazo[4,5-b]pyridin-3-yl;
1H-pyrrolo[3,2-b]pyridin-1-yl;
1H-pyrrol-1-yl;
2-chloro-1H-benzimidazol-1-yl;
Said heterocycles may optionally be substituted by trifluoromethyl, cyclopropyl, bromine, chlorine, fluorine, methoxy or cyano.

In a further specific embodiment $R^3$ is a heterocycle linked to the rest of the molecule via one of its C atoms and is selected from the group consisting of 6-bromo-2-chloro-3H-imidazo[4,5-b]pyridin-3-yl, 6-bromo-2-cyclopropyl-3H-imidazo[4,5-b]pyridin-3-yl, 1H-pyrrolo[3,2-b]pyridin-1-yl, 2,5-dichloro-1H-pyrrol-1-yl, 2-chloro-5-methoxy-1H-benzimidazol-1-yl, 5-bromo-2-chloro-1H-benzimidazol-1-yl or 2,5-dichloro-1H-benzimidazol-1-yl.

A further embodiment of the present invention consists in compounds of formula (I) wherein $R^1$, $R^2$ and $R^5$ are hydrogen.
$R^4$ is a $C_{1-6}$ alkyl optionally substituted by halogen, a $C_{2-6}$ alkenyl optionally substituted by halogen or $C_{2-12}$ alkynyl optionally substituted by halogen.
$R^3$ is selected from the group consisting of:
imidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
1H-pyrazol-4-yl;
1H-pyrazolo[1,5-a]pyrimidin-3-yl;
pyridin-3-yl;
1H-pyrrolo[2,3-b]pyridin-3-yl;
1H-pyrrolo[2,3-b]pyridin-4-yl;
1,3-thiazol-5-yl;
and optionally substituted by methyl, n-propyl, trifluoromethyl, cyclopropyl, bromine, chlorine, fluorine, iodine, methoxy, ethoxy, propoxy, isopropoxy, cyclopropyloxy, cyclopropylmethoxy, cyclobutylmethoxy, amino, methylamino, cyclopropylamino, cyclobutylamino, 1-pyrrolidinyl, cyano, phenyl, benzyl or 3-thienyl.

A further embodiment of the present invention consists in compounds of formula (I) wherein $R^1$, $R^2$ and $R^5$ are hydrogen.
$R^4$ is a $C_{1-6}$ alkyl optionally substituted by halogen, a $C_{2-6}$ alkenyl optionally substituted by halogen or $C_{2-12}$ alkynyl optionally substituted by halogen.
$R^3$ is selected from the group consisting of
3H-imidazo[4,5-b]pyridin-3-yl;
1H pyrrolo[3,2-b]pyridin-1-yl;
1H-pyrrol-1-yl;
2-chloro-1H-benzimidazol-1-yl;
optionally substituted by trifluoromethyl, cyclopropyl, bromine, chlorine, fluorine, methoxy or cyano.

A further embodiment of the invention consists in compounds of formula (I), their diastereomers and mixtures, or a pharmaceutically acceptable salt thereof.

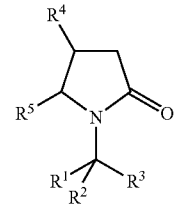

(I)

$R^1$, $R^2$ and $R^5$ are hydrogen.
$R^3$ is a substituted or unsubstituted heterocycle linked to the rest of the molecule via one of its C atoms, said heterocycle is selected from the group consisting of:
1H-benzimidazol-6-yl;
1H-benzimidazol-7-yl;
imidazo[1,2-a]pyridin-3-yl;
imidazo[1,2-a]pyrimidin-3-yl;
imidazo[1,2-b][1,2,4]triazin-7-yl;
imidazo[1,2-b]pyridazin-3-yl;
5,6,7,8-tetrahydroimidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
1H-indol-2-yl;
1H-indol-3-yl;
1H-indol-4-yl;
1H-indol-7-yl;
isoxazol-4-yl;
1H-pyrazol-4-yl;
1H-pyrazol-5-yl;
1H-pyrazolo[1,5-a]pyrimidin-3-yl;
1H-pyrazolo[3,4-b]pyridin-3-yl;
pyridazin-4-yl;
pyridin-2-yl;
pyridin-3-yl;
pyridin-4-yl;
1H-pyrrolo[2,3-b]pyridin-3-yl;
1H-pyrrolo[2,3-b]pyridin-4-yl;
1H-pyrrolo[2,3-b]pyridin-5-yl;
1H-pyrrolo[2,3-c]pyridin-2-yl;
1H-pyrrolo[2,3-c]pyridin-3-yl;
1H-pyrrolo[3,2-b]pyridin-3-yl;
1H-pyrrolo[3,2-c]pyridin-2-yl;
1H-pyrrolo[3,2-c]pyridin-3-yl;
1,3,4-thiadiazol-2-yl;
1,3-thiazol-5-yl;

[1,2,4]triazolo[4,3-b]pyridazin-7-yl;
[1,2,4]triazolo[4,3-b]pyridazin-8-yl;
indolizin-3-yl;

Particularly preferred are imidazo[1,2-a]pyridin-3-yl; imidazo[1,2-a]pyrimidin-3-yl; imidazo[1,2-b]pyridazin-3-yl; 1H-imidazol-4-yl; 1H-imidazol-5-yl;

$R^4$ is a substituted or unsubstituted phenyl moiety;

A further embodiment of the present invention consists in compounds of formula (I) wherein $R^1$ is hydrogen or $C_{1-12}$ alkyl;

$R^2$ is hydrogen;

$R^3$ is an aromatic 5-membered heterocycle linked to the rest of the molecule via one of its C atoms;

$R^4$ is hydrogen, $C_{1-12}$ alkyl or aryl;

$R^5$ is hydrogen;

Alternatively, $R^4$ can form together with $R^5$ and the 2-oxo-1-pyrrolidine ring the following 1,3-dihydro-2H-indol-2-one cycle

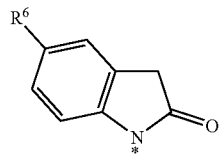

wherein the asterisk * indicates the point of attachment of the substituents;

$R^6$ is hydrogen or halogen;

In this embodiment $R^4$ may not be hydrogen when $R^3$ is substituted 1H-pyrazol-5-yl. Also this embodiment does not comprise 5-(2'-oxo-1'-pyrrolidinyl)methyl-1,3,4-tricarbomethoxy-pyrazole which is disclosed in A. Padwa et al *J. Org. Chem.* 2000, 65, 5223-5232 without any biological activity though.

In this embodiment wherein $R^3$ is an aromatic 5-membered heterocycle linked to the rest of the molecule via one of its C atoms, specific moieties $R^3$ may be selected from 1,3-thiazol-5-yl, 1H-imidazol-4-yl, 1H-imidazol-5-yl, 1H-pyrazol-4-yl, 1H-pyrazol-5-yl, 2-oxo-2,3-dihydro-1,3-thiazol-5-yl, each of them being optionally substituted by 1 to 3 substituents independently selected from methyl, chlorine, bromine, amino, methylamino, dimethylamino, (2-oxo-4-propyl-pyrrolidin-1-yl)methyl, 1-pyrrolidinyl, amido, cyano, methoxy, phenyl, 4-methylphenyl-sulfonyl, benzyl or 2-(benzylamino)-2-oxoethyl.

In this embodiment, more specific moieties $R^3$ are selected from 2-(methylamino)-1,3-thiazol-5-yl; 2-pyrrolidin-1-yl-1,3-thiazol-5-yl; 5-bromo-1H-imidazol-4-yl; 5-chloro-1H-imidazol-4-yl; 1H-imidazol-5-yl; 1-methyl-1H-imidazol-5-yl; 4-bromo-1-methyl-1H-imidazol-5-yl; 4-chloro-1H-imidazol-5-yl; 4-chloro-1-methyl-1H-imidazol-5-yl; 4-cyano-1-methyl-1H-imidazol-5-yl; 1H-pyrazol-4-yl; 3,5-dimethyl-1H-pyrazol-4-yl; 3-methyl-1H-pyrazol-4-yl.

In this embodiment, most specific moieties $R^3$ are selected from 5-bromo-1H-imidazol-4-yl; 5-chloro-1H-imidazol-4-yl; 1H-imidazol-5-yl; 4-bromo-1-methyl-1H-imidazol-5-yl; 4-chloro-1-methyl-1H-imidazol-5-yl; 1H-pyrazol-4-yl.

Still in this embodiment, a specific moiety $R^1$ is selected from hydrogen or ethyl.

Still in this embodiment, a specific moiety $R^4$ is selected from hydrogen, n-propyl, 2,3,5-trifluorophenyl or phenyl.

A further embodiment of the present invention consists in compounds having the specific formula (Ia).

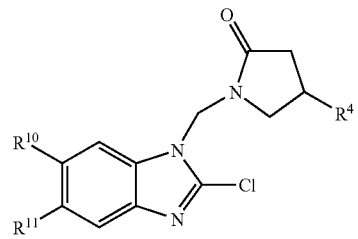

In formula (Ia) the substituent $R^{10}$ is hydrogen; halogen; $C_{1-4}$ alkyl optionally substituted by at least one halogen; $C_{1-4}$ alkoxy; methoxycarbonyl; nitro; amino; alkylamino; amido; or alkanoyl-amino. Preferably $R^{10}$ is hydrogen.

$R^{11}$ is hydrogen; halogen; $C_{1-4}$ alkyl optionally substituted by at least one halogen; $C_{1-4}$ alkoxy; methoxycarbonyl; nitro; amino; alkylamino; amido; or alkanoylamino. Preferably $R^{11}$ is hydrogen.

$R^4$ is $C_{1-4}$ alkyl optionally substituted by at least one halogen; or $C_{2-4}$ alkenyl optionally substituted by at least one halogen. Preferably $R^4$ is n-propyl.

Still in this aspect of the invention a specific embodiment relates to an embodiment wherein $R^{10}$ is selected from hydrogen; methyl; fluorine; chlorine; bromine; methoxy; methoxycarbonyl; nitro; or trifluoromethyl, while $R^{11}$ is selected from hydrogen; methyl; fluorine; chlorine; bromine; methoxy; methoxycarbonyl; nitro; or trifluoromethyl; and $R^3$ is n-propyl.

Specific compounds of the present invention are those selected from the group consisting of:

1-[(1-methyl-1H-benzimidazol-6-yl)methyl]-4-propylpyrrolidin-2-one;
1-(1H-benzimidazol-7-ylmethyl)-4-propylpyrrolidin-2-one;
1-(imidazo[1,2-a]pyridin-3-ylmethyl)-4-propylpyrrolidin-2-one;
1-{[6-chloro-2-(4-methylphenyl)imidazo[1,2-a]pyridin-3-yl]methyl}-4-propylpyrrolidin-2-one;
1-{[2-(4-chlorophenyl)-6-methylimidazo[1,2-a]pyridin-3-yl]methyl}-4-propylpyrrolidin-2-one;
1-[(5-methylimidazo[1,2-a]pyridin-3-yl)methyl]-4-phenylpyrrolidin-2-one;
1-(imidazo[1,2-a]pyridin-3-ylmethyl)-4-phenylpyrrolidin-2-one;
1-[(6-methylimidazo[1,2-a]pyridin-3-yl)methyl]-4-propylpyrrolidin-2-one;
1-[(6-bromoimidazo[1,2-a]pyridin-3-yl)methyl]-4-propylpyrrolidin-2-one;
1-[(8-methylimidazo[1,2-a]pyridin-3-yl)methyl]-4-propylpyrrolidin-2-one;
1-[(6-iodoimidazo[1,2-a]pyridin-3-yl)methyl]-4-propylpyrrolidin-2-one;
1-{[8-chloro-6-(trifluoromethyl)imidazo[1,2-a]pyridin-3-yl]methyl}-4-propylpyrrolidin-2-one;
1-[(7-methylimidazo[1,2-a]pyridin-3-yl)methyl]-4-propylpyrrolidin-2-one;
1-[(6,8-dibromoimidazo[1,2-a]pyridin-3-yl)methyl]-4-propylpyrrolidin-2-one;
1-[(6,8-dichloroimidazo[1,2-a]pyridin-3-yl)methyl]-4-propylpyrrolidin-2-one;
1-[(6-chloroimidazo[1,2-a]pyridin-3-yl)methyl]-4-propylpyrrolidin-2-one;
1-[(2-chloroimidazo[1,2-a]pyridin-3-yl)methyl]-4-propylpyrrolidin-2-one;
1-[(2-cyclopropyl-6-fluoroimidazo[1,2-a]pyridin-3-yl)methyl]-4-(2,2-difluorovinyl)pyrrolidin-2-one;

1-[(6-chloro-2-cyclopropylimidazo[1,2-a]pyridin-3-yl)methyl]-4-(2,2-difluorovinyl)pyrrolidin-2-one;
1-(imidazo[1,2-a]pyrimidin-3-ylmethyl)-4-propylpyrrolidin-2-one;
1-{[2-(4-chlorophenyl)imidazo[1,2-a]pyrimidin-3-yl]methyl}-4-propyl pyrrolidin-2-one;
1-(imidazo[1,2-a]pyrimidin-3-ylmethyl)-4-phenylpyrrolidin-2-one;
1-[(6-chloroimidazo[1,2-a]pyrimidin-3-yl)methyl]-4-propylpyrrolidin-2-one;
1-{[6-chloro-2-(trifluoromethyl)imidazo[1,2-a]pyrimidin-3-yl]methyl}-4-propylpyrrolidin-2-one;
1-[(6-phenylimidazo[1,2-b][1,2,4]triazin-7-yl)methyl]-4-propylpyrrolidin-2-one;
1-{[6-chloro-2-(4-methylphenyl)imidazo[1,2-b]pyridazin-3-yl]methyl}-4-propylpyrrolidin-2-one;
1-{[6-chloro-2-(4-chlorophenyl)imidazo[1,2-b]pyridazin-3-yl]methyl}-4-propylpyrrolidin-2-one;
1-[(6-chloroimidazo[1,2-b]pyridazin-3-yl)methyl]-4-propylpyrrolidin-2-one;
1-[(6-chloroimidazo[1,2-b]pyridazin-3-yl)methyl]-4-phenylpyrrolidin-2-one;
1-{[6-chloro-2-(trifluoromethyl)imidazo[1,2-b]pyridazin-3-yl]methyl}-4-propylpyrrolidin-2-one;
1-{[6-chloro-2-(trifluoromethyl)imidazo[1,2-b]pyridazin-3-yl]methyl}-4-(2,3,5-trifluorophenyl)pyrrolidin-2-one;
1-{[6-chloro-2-(trifluoromethyl)imidazo[1,2-b]pyridazin-3-yl]methyl}pyrrolidin-2-one;
1-{[6-chloro-2-(trifluoromethyl)imidazo[1,2-b]pyridazin-3-yl]methyl}-4-(2,2-difluorovinyl)pyrrolidin-2-one;
1-{[6-chloro-2-(trifluoromethyl)imidazo[1,2-b]pyridazin-3-yl]methyl}-4-phenylpyrrolidin-2-one;
5-chloro-1-{[6-chloro-2-(trifluoromethyl)imidazo[1,2-b]pyridazin-3-yl]methyl}-1,3-dihydro-2H-indol-2-one;
1-{[6-methoxy-2-(trifluoromethyl)imidazo[1,2-b]pyridazin-3-yl]methyl}-4-propylpyrrolidin-2-one;
1-[(6-chloro-2-cyclopropylimidazo[1,2-b]pyridazin-3-yl)methyl]-4-propylpyrrolidin-2-one;
1-{[6-isopropoxy-2-(trifluoromethyl)imidazo[1,2-b]pyridazin-3-yl]methyl}-4-propylpyrrolidin-2-one;
1-{[6-(benzyloxy)-2-(trifluoromethyl)imidazo[1,2-b]pyridazin-3-yl]methyl}-4-propylpyrrolidin-2-one;
1-{[6-cyclopropyl-2-(trifluoromethyl)imidazo[1,2-b]pyridazin-3-yl]methyl}-4-propylpyrrolidin-2-one;
1-{[6-(dimethylamino)-2-(trifluoromethyl)imidazo[1,2-b]pyridazin-3-yl]methyl}-4-propylpyrrolidin-2-one;
4-(2,2-difluorovinyl)-1-{[6-methoxy-2-(trifluoromethyl)imidazo[1,2-b]pyridazin-3-yl]methyl}pyrrolidin-2-one;
4-(2-chloro-2,2-difluoroethyl)-1-{[6-chloro-2-(trifluoromethyl)imidazo[1,2-b]pyridazin-3-yl]methyl}pyrrolidin-2-one;
1-{[6-(methylamino)-2-(trifluoromethyl)imidazo[1,2-b]pyridazin-3-yl]methyl}-4-propylpyrrolidin-2-one;
1-{[6-hydroxy-2-(trifluoromethyl)imidazo[1,2-b]pyridazin-3-yl]methyl}-4-propylpyrrolidin-2-one;
1-{[6-(methylthio)-2-(trifluoromethyl)imidazo[1,2-b]pyridazin-3-yl]methyl}-4-propylpyrrolidin-2-one;
4-(2-bromo-2,2-difluoroethyl)-1-{[6-chloro-2-(trifluoromethyl)imidazo[1,2-b]pyridazin-3-yl]methyl}pyrrolidin-2-one;
1-{[6-(methylsulfonyl)-2-(trifluoromethyl)imidazo[1,2-b]pyridazin-3-yl]methyl}-4-propylpyrrolidin-2-one;
1-{[6-(methylsulfinyl)-2-(trifluoromethyl)imidazo[1,2-b]pyridazin-3-yl]methyl}-4-propylpyrrolidin-2-one;
1-{[6-chloro-2-(trifluoromethyl)imidazo[1,2-b]pyridazin-3-yl]methyl}-4-(2,2,2-trifluoroethyl)pyrrolidin-2-one;
1-[(6-chloro-2-cyclobutylimidazo[1,2-b]pyridazin-3-yl)methyl]-4-propylpyrrolidin-2-one;
1-{[6-chloro-2-(4-methylphenyl)imidazo[1,2-b]pyridazin-3-yl]methyl}-4-(2,2-difluorovinyl)pyrrolidin-2-one;
1-{[6-amino-2-(trifluoromethyl)imidazo[1,2-b]pyridazin-3-yl]methyl}-4-propylpyrrolidin-2-one;
1-{[6-(ethylamino)-2-(trifluoromethyl)imidazo[1,2-b]pyridazin-3-yl]methyl}-4-propylpyrrolidin-2-one;
4-propyl-1-{[6-(propylamino)-2-(trifluoromethyl)imidazo[1,2-b]pyridazin-3-yl]methyl}pyrrolidin-2-one;
4-(2-bromo-2,2-difluoroethyl)-1-{[6-(propylamino)-2-(trifluoromethyl)imidazo[1,2-b]pyridazin-3-yl]methyl}pyrrolidin-2-one;
4-(2,2-difluorovinyl)-1-{[6-(propylamino)-2-(trifluoromethyl)imidazo[1,2-b]pyridazin-3-yl]methyl}pyrrolidin-2-one;
4-(2,2-difluorovinyl)-1-{[6-methoxy-2-(4-methylphenyl)imidazo[1,2-b]pyridazin-3-yl]methyl}pyrrolidin-2-one;
4-propyl-1-{[6-pyrrolidin-1-yl-2-(trifluoromethyl)imidazo[1,2-b]pyridazin-3-yl]methyl}pyrrolidin-2-one;
4-(2-bromo-2,2-difluoroethyl)-1-{[6-methoxy-2-(trifluoromethyl)imidazo[1,2-b]pyridazin-3-yl]methyl}pyrrolidin-2-one;
1-{[6-(cyclopropylamino)-2-(trifluoromethyl)imidazo[1,2-b]pyridazin-3-yl]methyl}-4-(2,2-difluorovinyl)pyrrolidin-2-one;
1-[(6-chloro-2-cyclopropylimidazo[1,2-b]pyridazin-3-yl)methyl]-4-(2,2-difluorovinyl)pyrrolidin-2-one;
4-(2,2-difluorovinyl)-1-{[6-(isopropylamino)-2-(trifluoromethyl)imidazo[1,2-b]pyridazin-3-yl]methyl}pyrrolidin-2-one;
4-(2,2-difluorovinyl)-1-{[2-(trifluoromethyl)imidazo[1,2-b]pyridazin-3-yl]methyl}pyrrolidin-2-one;
1-{[2-cyclopropyl-6-(propylamino)imidazo[1,2-b]pyridazin-3-yl]methyl}-4-(2,2-difluorovinyl)pyrrolidin-2-one;
1-({2-cyclopropyl-6-[(2-fluoroethyl)amino]imidazo[1,2-b]pyridazin-3-yl}methyl)-4-(2,2-difluorovinyl)pyrrolidin-2-one;
1-({2-cyclopropyl-6-[(2,2-difluoroethyl)amino]imidazo[1,2-b]pyridazin-3-yl}methyl)-4-(2,2-difluorovinyl)pyrrolidin-2-one;
1-({2-cyclopropyl-6-[(2,2,2-trifluoroethyl)amino]imidazo[1,2-b]pyridazin-3-yl}methyl)-4-(2,2-difluorovinyl)pyrrolidin-2-one;
4-(2,2-difluoroethyl)-1-{[2-(trifluoromethyl)imidazo[1,2-b]pyridazin-3-yl]methyl}pyrrolidin-2-one;
1-{[2-cyclopropyl-6-(cyclopropylamino)imidazo[1,2-b]pyridazin-3-yl]methyl}-4-(2,2-difluorovinyl)pyrrolidin-2-one;
1-[(6-chloro-2-cyclobutylimidazo[1,2-b]pyridazin-3-yl)methyl]-4-(2,2-difluorovinyl)pyrrolidin-2-one;
1-[(6-chloro-2-cyclopropylimidazo[1,2-b]pyridazin-3-yl)methyl]-4-(3-chloro-4-fluorophenyl)pyrrolidin-2-one;
1-{[6-(butylamino)-2-(trifluoromethyl)imidazo[1,2-b]pyridazin-3-yl]methyl}-4-(2,2-difluorovinyl)pyrrolidin-2-one;
1-{[6-(cyclobutylamino)-2-(trifluoromethyl)imidazo[1,2-b]pyridazin-3-yl]methyl}-4-(2,2-difluorovinyl)pyrrolidin-2-one;
1-[(2-cyclopropyl-6-methoxyimidazo[1,2-b]pyridazin-3-yl)methyl]-4-(2,2-difluorovinyl)pyrrolidin-2-one;
4-(2,2-difluorovinyl)-1-{[6-ethoxy-2-(trifluoromethyl)imidazo[1,2-b]pyridazin-3-yl]methyl}pyrrolidin-2-one;
4-(2,2-difluorovinyl)-1-{[6-isopropoxy-2-(trifluoromethyl)imidazo[1,2-b]pyridazin-3-yl]methyl}pyrrolidin-2-one;

1-{[6-(cyclopropylmethoxy)-2-(trifluoromethyl)imidazo[1,2-b]pyridazin-3-yl]methyl}-4-(2,2-difluorovinyl)pyrrolidin-2-one;
1-{[6-(cyclobutylmethoxy)-2-(trifluoromethyl)imidazo[1,2-b]pyridazin-3-yl]methyl}-4-(2,2-difluorovinyl)pyrrolidin-2-one;
1-{[6-(cyclopropyloxy)-2-(trifluoromethyl)imidazo[1,2-b]pyridazin-3-yl]methyl}-4-(2,2-difluorovinyl)pyrrolidin-2-one;
4-(2,2-difluorovinyl)-1-{[6-propoxy-2-(trifluoromethyl)imidazo[1,2-b]pyridazin-3-yl]methyl}pyrrolidin-2-one;
3-{[4-(2,2-difluorovinyl)-2-oxopyrrolidin-1-yl]methyl}-2-(trifluoromethyl)imidazo[1,2-b]pyridazine-6-carbonitrile;
4-(2,2-difluorovinyl)-1-{[6-thien-3-yl-2-(trifluoromethyl)imidazo[1,2-b]pyridazin-3-yl]methyl}pyrrolidin-2-one;
4-(2,2-difluorovinyl)-1-{[6-phenyl-2-(trifluoromethyl)imidazo[1,2-b]pyridazin-3-yl]methyl}pyrrolidin-2-one;
4-(2,2-difluorovinyl)-1-{[6-methyl-2-(trifluoromethyl)imidazo[1,2-b]pyridazin-3-yl]methyl}pyrrolidin-2-one;
4-(2,2-difluorovinyl)-1-{[6-pyridin-3-yl-2-(trifluoromethyl)imidazo[1,2-b]pyridazin-3-yl]methyl}pyrrolidin-2-one;
4-propyl-1-{[2-(trifluoromethyl)-5,6,7,8-tetrahydroimidazo[1,2-b]pyridazin-3-yl]methyl}pyrrolidin-2-one;
1-[(6-methylimidazo[2,1-b][1,3,4]thiadiazol-5-yl)methyl]-4-propylpyrrolidin-2-one;
1-{[6-(4-methylphenyl)imidazo[2,1-b][1,3,4]thiadiazol-5-yl]methyl}-4-propylpyrrolidin-2-one;
1-[(2-cyclopropyl-6-phenylimidazo[2,1-b][1,3,4]thiadiazol-5-yl)methyl]-4-propylpyrrolidin-2-one;
1-[(6-methylimidazo[2,1-b][1,3]thiazol-5-yl)methyl]-4-propylpyrrolidin-2-one;
1-[(6-chloroimidazo[2,1-b][1,3]thiazol-5-yl)methyl]-4-propylpyrrolidin-2-one;
1-[(2,6-dichloroimidazo[2,1-b][1,3]thiazol-5-yl)methyl]-4-propylpyrrolidin-2-one;
1-(3H-imidazo[4,5-b]pyridin-7-ylmethyl)-4-propylpyrrolidin-2-one;
1-(3H-imidazo[4,5-b]pyridin-7-ylmethyl)-4-phenylpyrrolidin-2-one;
4-phenyl-1-[(5-phenyl-3H-imidazo[4,5-b]pyridin-7-yl)methyl]pyrrolidin-2-one;
4-phenyl-1-{[5-(trifluoromethyl)-3H-imidazo[4,5-b]pyridin-7-yl]methyl}pyrrolidin-2-one;
1-[(6-bromo-3H-imidazo[4,5-b]pyridin-7-yl)methyl]-4-propylpyrrolidin-2-one;
1-[(2-phenyl-3H-imidazo[4,5-b]pyridin-7-yl)methyl]-4-propylpyrrolidin-2-one;
1-[(5-methyl-3H-imidazo[4,5-b]pyridin-7-yl)methyl]-4-propylpyrrolidin-2-one;
1-[(2-methyl-3H-imidazo[4,5-b]pyridin-7-yl)methyl]-4-propylpyrrolidin-2-one;
4-propyl-1-{[5-(trifluoromethyl)-3H-imidazo[4,5-b]pyridin-7-yl]methyl}pyrrolidin-2-one;
1-[(6-methyl-3H-imidazo[4,5-b]pyridin-7-yl)methyl]-4-propylpyrrolidin-2-one;
1-[(6-phenyl-3H-imidazo[4,5-b]pyridin-7-yl)methyl]-4-propylpyrrolidin-2-one;
1-[1-(1H-imidazol-4-yl)propyl]pyrrolidin-2-one;
1-[(5-methyl-1H-imidazol-4-yl)methyl]pyrrolidin-2-one;
1-[(2-methyl-1H-imidazol-4-yl)methyl]pyrrolidin-2-one;
1-(1H-imidazol-4-ylmethyl)-4-propylpyrrolidin-2-one;
1-({1-[(2-oxo-4-propylpyrrolidin-1-yl)methyl]-1H-imidazol-4-yl}methyl)-4-propylpyrrolidin-2-one;
1-[(5-chloro-1H-imidazol-4-yl)methyl]-4-(2,3,5-trifluorophenyl)pyrrolidin-2-one;
1-[(5-bromo-1H-imidazol-4-yl)methyl]-4-(2,3,5-trifluorophenyl)pyrrolidin-2-one;
1-[(5-bromo-1H-imidazol-4-yl)methyl]-5-chloro-1,3-dihydro-2H-indol-2-one;
1-(1H-imidazol-5-ylmethyl)pyrrolidin-2-one;
1-[(1-methyl-1H-imidazol-5-yl)methyl]pyrrolidin-2-one;
1-methyl-5-[(2-oxopyrrolidin-1-yl)methyl]-1H-imidazole-4-carbonitrile;
1-(1H-imidazol-5-ylmethyl)-4-phenylpyrrolidin-2-one;
1-[(1-methyl-1H-imidazol-5-yl)methyl]-4-phenylpyrrolidin-2-one;
1-[(4-methoxy-1-methyl-1H-imidazol-5-yl)methyl]pyrrolidin-2-one;
1-[(1-methyl-1H-imidazol-5-yl)methyl]-4-propylpyrrolidin-2-one;
1-methyl-5-[(2-oxo-4-propylpyrrolidin-1-yl)methyl]-1H-imidazole-4-carbonitrile;
1-methyl-5-[(2-oxo-4-propylpyrrolidin-1-yl)methyl]-1H-imidazole-4-carboxamide;
N-benzyl-2-{5-[(2-oxo-4-propylpyrrolidin-1-yl)methyl]-1H-imidazol-1-yl}acetamide;
1-methyl-5-[(2-oxo-4-propylpyrrolidin-1-yl)methyl]-1H-imidazole-2-carbonitrile;
1-[(4-chloro-1H-imidazol-5-yl)methyl]-4-propylpyrrolidin-2-one;
1-methyl-5-{[2-oxo-4-(2,3,5-trifluorophenyl)pyrrolidin-1-yl]methyl}-1H-imidazole-4-carbonitrile;
1-[(4-bromo-1-methyl-1H-imidazol-5-yl)methyl]-4-propylpyrrolidin-2-one;
1-[(2,4-dichloro-1-methyl-1H-imidazol-5-yl)methyl]-4-propylpyrrolidin-2-one; benzyl 1-methyl-5-[(2-oxo-4-propylpyrrolidin-1-yl)methyl]-1H-imidazol-2-ylcarbamate;
1-[(4-chloro-1-methyl-1H-imidazol-5-yl)methyl]-4-propylpyrrolidin-2-one;
1-[(2-bromo-1-methyl-1H-imidazol-5-yl)methyl]-4-propylpyrrolidin-2-one;
1-[(2-chloro-1-methyl-1H-imidazol-5-yl)methyl]-4-propylpyrrolidin-2-one;
5-chloro-1-(1H-imidazol-5-ylmethyl)-1,3-dihydro-2H-indol-2-one;
1-[(2,4-dichloro-1H-imidazol-5-yl)methyl]-4-(2,3,5-trifluorophenyl)pyrrolidin-2-one;
1-[(2,4-dichloro-1-methyl-1H-imidazol-5-yl)methyl]-4-(2,3,5-trifluorophenyl)pyrrolidin-2-one;
1-[(2-chloro-1-methyl-1H-imidazol-5-yl)methyl]-4-(2,3,5-trifluorophenyl)pyrrolidin-2-one;
1-[(4-bromo-1-methyl-1H-imidazol-5-yl)methyl]-4-(2,3,5-trifluorophenyl)pyrrolidin-2-one;
5-chloro-1-[(1-methyl-1H-imidazol-5-yl)methyl]-1,3-dihydro-2H-indol-2-one;
1-[(4-chloro-1-methyl-1H-imidazol-5-yl)methyl]-4-(2,3,5-trifluorophenyl)pyrrolidin-2-one;
1-(1H-indol-2-ylmethyl)-4-propylpyrrolidin-2-one;
1-(1H-indol-3-ylmethyl)-4-propylpyrrolidin-2-one;
3-[(2-oxo-4-propylpyrrolidin-1-yl)methyl]-1H-indole-5-carbonitrile;
1-[(2-methyl-1H-indol-3-yl)methyl]-4-propylpyrrolidin-2-one;
1-[(7-methoxy-1H-indol-3-yl)methyl]-4-propylpyrrolidin-2-one;
1-[(6-nitro-1H-indol-3-yl)methyl]-4-propylpyrrolidin-2-one;
4-propyl-1-{[6-(trifluoromethyl)-1H-indol-3-yl]methyl}pyrrolidin-2-one;
1-[(5-nitro-1H-indol-3-yl)methyl]-4-propylpyrrolidin-2-one;
1-[(7-fluoro-1H-indol-3-yl)methyl]-4-propylpyrrolidin-2-one;

1-[(5-chloro-2-methyl-1H-indol-3-yl)methyl]-4-propylpyr-rolidin-2-one;
1-[1H-indol-3-yl(phenyl)methyl]-4-propylpyrrolidin-2-one;
1-[1-(1H-indol-3-yl)propyl]-4-propylpyrrolidin-2-one;
1-[2-furyl(1H-indol-3-yl)methyl]-4-propylpyrrolidin-2-one;
3-[(2-oxo-4-propylpyrrolidin-1-yl)(phenyl)methyl]-1H-indole-5-carbonitrile;
1-(1H-indol-4-ylmethyl)-4-propylpyrrolidin-2-one;
1-(1H-indol-7-ylmethyl)-4-propylpyrrolidin-2-one;
1-(isoxazol-4-ylmethyl)-4-propylpyrrolidin-2-one;
1-[(1-phenyl-1H-pyrazol-4-yl)methyl]-4-(2,3,5-trifluorophenyl)pyrrolidin-2-one;
1-[(1-methyl-1H-pyrazol-4-yl)methyl]-4-(2,3,5-trifluorophenyl)pyrrolidin-2-one;
1-[(1-benzyl-1H-pyrazol-4-yl)methyl]-4-(2,3,5-trifluorophenyl)pyrrolidin-2-one;
4-(2,3,5-trifluorophenyl)-1-[(1,3,5-trimethyl-1H-pyrazol-4-yl)methyl]pyrrolidin-2-one;
4-phenyl-1-(1H-pyrazol-4-ylmethyl)pyrrolidin-2-one;
1-({1-[(4-methylphenyl)sulfonyl]-1H-pyrazol-4-yl}methyl)-4-(2,3,5-trifluorophenyl)pyrrolidin-2-one;
1-(1H-pyrazol-4-ylmethyl)-4-(2,3,5-trifluorophenyl)pyrrolidin-2-one;
1-[(5-chloro-1,3-dimethyl-1H-pyrazol-4-yl)methyl]-4-(2,3,5-trifluorophenyl)pyrrolidin-2-one;
1-[(1-chloro-1H-pyrazol-4-yl)methyl]-4-(2,3,5-trifluorophenyl)pyrrolidin-2-one;
1-[(3,5-dimethyl-1H-pyrazol-4-yl)methyl]-4-(2,3,5-trifluorophenyl)pyrrolidin-2-one;
1-[(3-methyl-1H-pyrazol-4-yl)methyl]-4-(2,3,5-trifluorophenyl)pyrrolidin-2-one;
1-[(5-amino-1,3-dimethyl-1H-pyrazol-4-yl)methyl]-4-(2,3,5-trifluorophenyl)pyrrolidin-2-one;
1-[(5-amino-1-methyl-1H-pyrazol-4-yl)methyl]-4-propylpyrrolidin-2-one;
(−)-1-(1H-pyrazol-4-ylmethyl)-4-(2,3,5-trifluorophenyl)pyrrolidin-2-one;
(+)-1-(1H-pyrazol-4-ylmethyl)-4-(2,3,5-trifluorophenyl)pyrrolidin-2-one;
1-(1H-pyrazol-4-ylmethyl)-1,3-dihydro-2H-indol-2-one;
5-chloro-1-(1H-pyrazol-4-ylmethyl)-1,3-dihydro-2H-indol-2-one;
5-chloro-1-({1-[(4-methylphenyl)sulfonyl]-1H-pyrazol-4-yl}methyl)-1,3-dihydro-2H-indol-2-one;
1-{[5-chloro-1-methyl-3-(trifluoromethyl)-1H-pyrazol-4-yl]methyl}-4-propylpyrrolidin-2-one;
1-[(5-amino-1H-pyrazol-4-yl)methyl]-4-(2,3,5-trifluorophenyl)pyrrolidin-2-one;
1-[(1-benzyl-5-chloro-1H-pyrazol-4-yl)methyl]-4-propylpyrrolidin-2-one;
1-[(1,3-dimethyl-1H-pyrazol-5-yl)methyl]-4-(2,3,5-trifluorophenyl)pyrrolidin-2-one;
1-(1H-pyrazol-5-ylmethyl)-4-(2,3,5-trifluorophenyl)pyrrolidin-2-one;
1-[(4-bromo-1-methyl-1H-pyrazol-5-yl)methyl]-4-(2,3,5-trifluorophenyl)pyrrolidin-2-one;
1-[(1-methyl-1H-pyrazol-5-yl)methyl]-4-(2,3,5-trifluorophenyl)pyrrolidin-2-one;
1-[(6-bromo-2-methylpyrazolo[1,5-a]pyrimidin-3-yl)methyl]-4-propylpyrrolidin-2-one;
1-[(2-methylpyrazolo[1,5-a]pyrimidin-3-yl)methyl]-4-propylpyrrolidin-2-one;
1-[(6-bromo-2-phenylpyrazolo[1,5-a]pyrimidin-3-yl)methyl]-4-propylpyrrolidin-2-one;
1-[(6-bromo-2-thien-2-ylpyrazolo[1,5-a]pyrimidin-3-yl)methyl]-4-propylpyrrolidin-2-one;
4-propyl-1-[(2-thien-2-ylpyrazolo[1,5-a]pyrimidin-3-yl)methyl]pyrrolidin-2-one;
1-[(6-bromo-2-cyclopropylpyrazolo[1,5-a]pyrimidin-3-yl)methyl]-4-propylpyrrolidin-2-one;
1-[(6-bromo-2-tert-butylpyrazolo[1,5-a]pyrimidin-3-yl)methyl]-4-propylpyrrolidin-2-one;
1-[(2-phenylpyrazolo[1,5-a]pyrimidin-3-yl)methyl]-4-propylpyrrolidin-2-one;
1-[(2-tert-butyl-6-cyclopropylpyrazolo[1,5-a]pyrimidin-3-yl)methyl]-4-propylpyrrolidin-2-one;
1-{[2-(2-furyl)pyrazolo[1,5-a]pyrimidin-3-yl]methyl}-4-propylpyrrolidin-2-one;
1-[(2-methyl-6-thien-2-ylpyrazolo[1,5-a]pyrimidin-3-yl)methyl]-4-propylpyrrolidin-2-one;
1-[(2-methyl-6-phenylpyrazolo[1,5-a]pyrimidin-3-yl)methyl]-4-propylpyrrolidin-2-one;
1-{[2-methyl-6-(1H-pyrrol-2-yl)pyrazolo[1,5-a]pyrimidin-3-yl]methyl}-4-propylpyrrolidin-2-one;
1-({6-[(1E)-hex-1-enyl]-2-methylpyrazolo[1,5-a]pyrimidin-3-yl}methyl)-4-propylpyrrolidin-2-one;
1-[(6-chloro-2-phenylpyrazolo[1,5-a]pyrimidin-3-yl)methyl]-4-propylpyrrolidin-2-one;
1-{[2-methyl-6-(phenylethynyl)pyrazolo[1,5-a]pyrimidin-3-yl]methyl}-4-propylpyrrolidin-2-one;
1-[(6-bromo-2-phenylpyrazolo[1,5-a]pyrimidin-3-yl)methyl]-4-(2,2-difluorovinyl)pyrrolidin-2-one;
1-[(6-hydroxy-2-methylpyrazolo[1,5-a]pyrimidin-3-yl)methyl]-4-propylpyrrolidin-2-one;
1-[(6-methyl-2-phenylpyrazolo[1,5-a]pyrimidin-3-yl)methyl]-4-propylpyrrolidin-2-one;
4-(2,2-difluorovinyl)-1-[(2-phenylpyrazolo[1,5-a]pyrimidin-3-yl)methyl]pyrrolidin-2-one;
1-[(6-methoxy-2-phenylpyrazolo[1,5-a]pyrimidin-3-yl)methyl]-4-propylpyrrolidin-2-one;
1-[(5-chloropyrazolo[1,5-a]pyrimidin-3-yl)methyl]-4-propylpyrrolidin-2-one;
4-(2,2-difluorovinyl)-1-[(5,6-dimethyl-2-phenylpyrazolo[1,5-a]pyrimidin-3-yl)methyl]pyrrolidin-2-one;
4-(2,2-difluorovinyl)-1-[(6-fluoro-5-methyl-2-phenylpyrazolo[1,5-a]pyrimidin-3-yl)methyl]pyrrolidin-2-one;
1-[(5-methoxypyrazolo[1,5-a]pyrimidin-3-yl)methyl]-4-propylpyrrolidin-2-one;
1-{[2-(4-bromophenyl)pyrazolo[1,5-a]pyrimidin-3-yl]methyl}-4-(2,2-difluorovinyl)pyrrolidin-2-one;
1-{[2-(4-fluorophenyl)pyrazolo[1,5-a]pyrimidin-3-yl]methyl}-4-propylpyrrolidin-2-one;
4-(2,2-difluorovinyl)-1-[(6-methyl-2-phenylpyrazolo[1,5-a]pyrimidin-3-yl)methyl]pyrrolidin-2-one;
4-(2,2-difluorovinyl)-1-[(5-methyl-2-phenylpyrazolo[1,5-a]pyrimidin-3-yl)methyl]pyrrolidin-2-one;
4-(2,2-difluorovinyl)-1-[(2-thien-2-ylpyrazolo[1,5-a]pyrimidin-3-yl)methyl]pyrrolidin-2-one;
1-{[2-(4-chlorophenyl)-6-methylpyrazolo[1,5-a]pyrimidin-3-yl]methyl}-4-propylpyrrolidin-2-one;
1-{[2-(4-chlorophenyl)pyrazolo[1,5-a]pyrimidin-3-yl]methyl}-4-(2,2-difluorovinyl)pyrrolidin-2-one;
1-[(6-chloro-2-phenylpyrazolo[1,5-a]pyrimidin-3-yl)methyl]-4-(2,2-difluorovinyl)pyrrolidin-2-one;
1-{[6-chloro-2-(4-chlorophenyl)pyrazolo[1,5-a]pyrimidin-3-yl]methyl}-4-(2,2-difluorovinyl)pyrrolidin-2-one;
1-[(2-cyclopropyl-5-methylpyrazolo[1,5-a]pyrimidin-3-yl)methyl]-4-(2,2-difluorovinyl)pyrrolidin-2-one;
1-[(5-chloro-2-cyclopropylpyrazolo[1,5-a]pyrimidin-3-yl)methyl]-4-(2,2-difluorovinyl)pyrrolidin-2-one;
1-[(5-chloro-2,6-dimethylpyrazolo[1,5-a]pyrimidin-3-yl)methyl]-4-(2,2-difluorovinyl)pyrrolidin-2-one;

1-[(5-bromo-1H-pyrazolo[3,4-b]pyridin-3-yl)methyl]-4-(2, 2-difluorovinyl)pyrrolidin-2-one;
4-propyl-1-(pyridin-3-ylmethyl)pyrrolidin-2-one;
(−)-1-(1-pyridin-3-ylpropyl)pyrrolidin-2-one;
5-chloro-1-[(2-fluoropyridin-3-yl)methyl]-1,3-dihydro-2H-indol-2-one;
1-[(6-chloropyridin-3-yl)methyl]-4-propylpyrrolidin-2-one;
1-{[6-(benzylamino)pyridin-3-yl]methyl}-4-propylpyrrolidin-2-one;
1-[(2-aminopyridin-3-yl)methyl]-4-propylpyrrolidin-2-one;
4-propyl-1-(1H-pyrrolo[2,3-b]pyridin-3-ylmethyl)pyrrolidin-2-one;
1-[(2-isopropyl-1H-pyrrolo[2,3-b]pyridin-3-yl)methyl]-4-propylpyrrolidin-2-one;
1-[(2-phenyl-1H-pyrrolo[2,3-b]pyridin-3-yl)methyl]-4-propylpyrrolidin-2-one;
4-propyl-1-[(2-propyl-1H-pyrrolo[2,3-b]pyridin-3-yl)methyl]pyrrolidin-2-one;
1-[(6-bromo-1H-pyrrolo[2,3-b]pyridin-3-yl)methyl]-4-propylpyrrolidin-2-one;
1-[(1-benzoyl-6-bromo-1H-pyrrolo[2,3-b]pyridin-3-yl)methyl]-4-propylpyrrolidin-2-one;
1-[(6-phenyl-1H-pyrrolo[2,3-b]pyridin-3-yl)methyl]-4-propylpyrrolidin-2-one;
1-[(5-bromo-1H-pyrrolo[2,3-b]pyridin-3-yl)methyl]-4-(2,2-difluorovinyl)pyrrolidin-2-one;
1-[(7-oxido-1H-pyrrolo[2,3-b]pyridin-3-yl)methyl]-4-propylpyrrolidin-2-one;
4-propyl-1-(1H-pyrrolo[2,3-b]pyridin-4-ylmethyl)pyrrolidin-2-one;
4-propyl-1-(1H-pyrrolo[2,3-b]pyridin-5-ylmethyl)pyrrolidin-2-one;
4-propyl-1-(1H-pyrrolo[2,3-c]pyridin-2-ylmethyl)pyrrolidin-2-one;
4-propyl-1-(1H-pyrrolo[2,3-c]pyridin-3-ylmethyl)pyrrolidin-2-one;
4-propyl-1-(1H-pyrrolo[3,2-b]pyridin-3-ylmethyl)pyrrolidin-2-one;
4-propyl-1-(1H-pyrrolo[3,2-c]pyridin-2-ylmethyl)pyrrolidin-2-one;
4-propyl-1-(1H-pyrrolo[3,2-c]pyridin-3-ylmethyl)pyrrolidin-2-one;
4-propyl-1-(1,3,4-thiadiazol-2-ylmethyl)pyrrolidin-2-one;
1-[(2-amino-1,3-thiazol-5-yl)methyl]pyrrolidin-2-one;
1-(1,3-thiazol-5-ylmethyl)pyrrolidin-2-one;
1-[(2-chloro-1,3-thiazol-5-yl)methyl]-4-(2,3,5-trifluorophenyl)pyrrolidin-2-one;
1-{[2-(dimethylamino)-1,3-thiazol-5-yl]methyl}-4-(2,3,5-trifluorophenyl)pyrrolidin-2-one;
1-{[2-(methylamino)-1,3-thiazol-5-yl]methyl}-4-(2,3,5-trifluorophenyl)pyrrolidin-2-one;
1-[(2-pyrrolidin-1-yl-1,3-thiazol-5-yl)methyl]-4-(2,3,5-trifluorophenyl)pyrrolidin-2-one;
5-{[2-oxo-4-(2,3,5-trifluorophenyl)pyrrolidin-1-yl]methyl}-1,3-thiazol-2(3H)-one;
4-phenyl-1-{[3-(trifluoromethyl)[1,2,4]triazolo[4,3-b]pyridazin-7-yl]methyl}pyrrolidin-2-one;
4-phenyl-1-[(3-phenyl[1,2,4]triazolo[4,3-b]pyridazin-7-yl)methyl]pyrrolidin-2-one;
4-phenyl-1-{[3-(trifluoromethyl)[1,2,4]triazolo[4,3-b]pyridazin-8-yl]methyl}pyrrolidin-2-one;
4-propyl-1-{[3-(trifluoromethyl)[1,2,4]triazolo[4,3-b]pyridazin-8-yl]methyl}pyrrolidin-2-one;
4-phenyl-1-[(3-phenyl[1,2,4]triazolo[4,3-b]pyridazin-8-yl)methyl]pyrrolidin-2-one;
1-[(6-chloro-3-phenyl[1,2,4]triazolo[4,3-b]pyridazin-8-yl)methyl]-4-propylpyrrolidin-2-one;
1-[(6-chloro[1,2,4]triazolo[4,3-b]pyridazin-8-yl)methyl]-4-phenylpyrrolidin-2-one;
1-{[6-chloro-3-(trifluoromethyl)[1,2,4]triazolo[4,3-b]pyridazin-8-yl]methyl}-4-phenylpyrrolidin-2-one;
1-[(6-chloro-3-phenyl[1,2,4]triazolo[4,3-b]pyridazin-8-yl)methyl]-4-phenylpyrrolidin-2-one;
1-[(2-fluoroindolizin-3-yl)methyl]-4-propylpyrrolidin-2-one;
1-(1H-1,2,3-benzotriazol-1-ylmethyl)-4-propylpyrrolidin-2-one;
1-[(6-bromo-2-chloro-1H-imidazo[4,5-b]pyridin-1-yl)methyl]-4-propylpyrrolidin-2-one;
1-[(6-bromo-2-phenyl-1H-imidazo[4,5-b]pyridin-1-yl)methyl]-4-propylpyrrolidin-2-one;
1-(3H-imidazo[4,5-b]pyridin-3-ylmethyl)-4-propylpyrrolidin-2-one;
1-[(6-bromo-3H-imidazo[4,5-b]pyridin-3-yl)methyl]-4-propylpyrrolidin-2-one;
1-[(6-bromo-2-chloro-3H-imidazo[4,5-b]pyridin-3-yl)methyl]-4-propylpyrrolidin-2-one;
1-[(6-bromo-2-phenyl-3H-imidazo[4,5-b]pyridin-3-yl)methyl]-4-propylpyrrolidin-2-one;
1-[(6-bromo-2-cyclopropyl-3H-imidazo[4,5-b]pyridin-3-yl)methyl]-4-(2,2-difluorovinyl)pyrrolidin-2-one;
1-[(3-chloro-7H-imidazo[4,5-c]pyridazin-7-yl)methyl]-4-propylpyrrolidin-2-one;
1-[(2-chloro-1H-indol-1-yl)methyl]-4-propylpyrrolidin-2-one;
1-[(5-methyl-1H-indol-1-yl)methyl]-4-propylpyrrolidin-2-one;
1-[(6-methyl-1H-indol-1-yl)methyl]-4-propylpyrrolidin-2-one;
1-[(2-phenyl-1H-indol-1-yl)methyl]-4-propylpyrrolidin-2-one;
1-[(5-fluoro-1H-indol-1-yl)methyl]-4-propylpyrrolidin-2-one;
1-[(5-bromo-1H-indol-1-yl)methyl]-4-propylpyrrolidin-2-one;
1-[(5-chloro-1H-indol-1-yl)methyl]-4-propylpyrrolidin-2-one;
1-(2,3-dihydro-1H-indol-1-ylmethyl)-4-propylpyrrolidin-2-one;
1-[(5-fluoro-2-phenyl-1H-indol-1-yl)methyl]-4-propylpyrrolidin-2-one;
1-[(2-oxo-4-propylpyrrolidin-1-yl)methyl]-1H-indole-2-carbonitrile;
1-[(2-bromo-1H-indol-1-yl)methyl]-4-propylpyrrolidin-2-one;
1-[(2,5-dichloro-1H-indol-1-yl)methyl]-4-propylpyrrolidin-2-one;
1-[(6-amino-9H-purin-9-yl)methyl]-4-propylpyrrolidin-2-one;
4-propyl-1-(9H-purin-9-ylmethyl)pyrrolidin-2-one;
1-{[6-(cyclopropylamino)-9H-purin-9-yl]methyl}-4-propylpyrrolidin-2-one;
1-{[6-(benzylamino)-9H-purin-9-yl]methyl}-4-propylpyrrolidin-2-one;
4-propyl-1-{[6-(propylamino)-9H-purin-9-yl]methyl}pyrrolidin-2-one;
1-({6-[(cyclopropylmethyl)amino]-9H-purin-9-yl}methyl)-4-propylpyrrolidin-2-one;
4-propyl-1-[(6-pyrrolidin-1-yl-9H-purin-9-yl)methyl]pyrrolidin-2-one;
1-[(5-bromo-3-phenyl-1H-pyrazolo[3,4-b]pyridin-1-yl)methyl]-4-propylpyrrolidin-2-one;
1-[(5-bromo-2H-pyrazolo[3,4-b]pyridin-2-yl)methyl]-4-propylpyrrolidin-2-one;

1-[(5-bromo-3-phenyl-2H-pyrazolo[3,4-b]pyridin-2-yl)methyl]-4-propylpyrrolidin-2-one;
1-[(2-chloro-1H-pyrrolo[2,3-b]pyridin-1-yl)methyl]-4-propylpyrrolidin-2-one;
4-propyl-1-(1H-pyrrolo[3,2-b]pyridin-1-ylmethyl)pyrrolidin-2-one;
1-(3,4-dihydroquinolin-1(2H)-ylmethyl)-4-propylpyrrolidin-2-one;
1-(8H-isothiazolo[5,4-b]indol-8-ylmethyl)-4-propylpyrrolidin-2-one;
1-(1H-1,2,4-triazol-1-ylmethyl)pyrrolidin-2-one;
1-[(2,5-dichloro-1H-pyrrol-1-yl)methyl]-4-propylpyrrolidin-2-one;
1-[(2-chloro-1H-pyrrol-1-yl)methyl]-4-propylpyrrolidin-2-one;
1-[(2-chloro-1H-benzimidazol-1-yl)methyl]-4-propylpyrrolidin-2-one;
1-[(2-chloro-1H-benzimidazol-1-yl)methyl]-4-phenylpyrrolidin-2-one;
2-chloro-1-[(2-oxo-4-propylpyrrolidin-1-yl)methyl]-1H-benzimidazole-5-carbonitrile;
2-chloro-1-[(2-oxo-4-propylpyrrolidin-1-yl)methyl]-1H-benzimidazole-6-carbonitrile;
4-propyl-1-[(2,5,6-trichloro-1H-benzimidazol-1-yl)methyl]pyrrolidin-2-one;
1-[(2-chloro-6-methoxy-1H-benzimidazol-1-yl)methyl]-4-propylpyrrolidin-2-one;
1-[(2-chloro-5-methoxy-1H-benzimidazol-1-yl)methyl]-4-propylpyrrolidin-2-one;
1-[(2-chloro-6-nitro-1H-benzimidazol-1-yl)methyl]-4-propylpyrrolidin-2-one;
1-[(2-chloro-5-nitro-1H-benzimidazol-1-yl)methyl]-4-propylpyrrolidin-2-one;
1-[(2-chloro-6-methyl-1H-benzimidazol-1-yl)methyl]-4-propylpyrrolidin-2-one;
1-[(2-chloro-1H-benzimidazol-1-yl)methyl]-4-(2,2-difluorovinyl)pyrrolidin-2-one;
1-[(6-bromo-2-chloro-1H-benzimidazol-1-yl)methyl]-4-propylpyrrolidin-2-one;
1-[(5-bromo-2-chloro-1H-benzimidazol-1-yl)methyl]-4-propylpyrrolidin-2-one;
1-[(2-chloro-6-fluoro-1H-benzimidazol-1-yl)methyl]-4-propylpyrrolidin-2-one;
1-[(2-chloro-5-fluoro-1H-benzimidazol-1-yl)methyl]-4-propylpyrrolidin-2-one;
1-[(2,6-dichloro-1H-benzimidazol-1-yl)methyl]-4-propylpyrrolidin-2-one;
1-[(2,5-dichloro-1H-benzimidazol-1-yl)methyl]-4-propylpyrrolidin-2-one;
1-{[2-chloro-6-(trifluoromethyl)-1H-benzimidazol-1-yl]methyl}-4-propylpyrrolidin-2-one;
1-{[2-chloro-5-(trifluoromethyl)-1H-benzimidazol-1-yl]methyl}-4-propylpyrrolidin-2-one;
1-[(2-chloro-1H-benzimidazol-1-yl)methyl]pyrrolidin-2-one;
1-[(2-chloro-6-hydroxy-1H-benzimidazol-1-yl)methyl]-4-propylpyrrolidin-2-one;
1-(pyridin-4-ylmethyl)pyrrolidin-2-one, and
1-[(2-chloro-5-hydroxy-1H-benzimidazol-1-yl)methyl]-4-propylpyrrolidin-2-one.

The compounds of the present invention are for use as a medicament, in particular for disorder is selected from the group consisting of epilepsy, epileptogenesis, seizure disorders, convulsions, Parkinson's disease, dyskinesia induced by dopamine replacement therapy, tardive dyskinesia induced by administration of neuroleptic drugs, Huntington Chorea, and other neurological disorders including bipolar disorders, mania, depression, anxiety, attention deficit hyperactivity disorder (ADHD), migraine, trigeminal and other neuralgia, chronic pain, neuropathic pain, cerebral ischemia, cardiac arrhythmia, myotonia, cocaine abuse, stroke, myoclonus, tremor, essential tremor, simple or complex tics, Tourette syndrome, restless leg syndrome and other movement disorders, neonatal cerebral haemorrhage, amyotrophic lateral sclerosis, spasticity and degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

Specific disorders are epilepsy, dyskinesia induced by dopamine replacement therapy, chronic pain, neuropathic pain.

A further aspect of the present invention relates to a pharmaceutical composition comprising an effective amount of a compound of formula (I) in combination with a pharmaceutically acceptable diluent or carrier.

The following paragraphs provide definitions of the various chemical moieties that make up the compounds according to the invention and are intended to apply uniformly through-out the specification and claims unless an otherwise expressly set out definition provides a broader definition.

"$C_{1-12}$ alkyl" or "$C_{1-6}$ alkyl" refers to alkyl groups having 1 to 12 or 1 to 6 carbon atoms. This term is exemplified by groups such as methyl, ethyl, n-propyl, isopropyl, n-butyl, isobutyl, tert-butyl, n-pentyl, n-hexyl, trifluoromethyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"Heterocycle" refers to a saturated or unsaturated ring system containing, in addition to carbon atoms, at least one hetero atom, such as nitrogen, oxygen and/or sulfur.

"Heterocycle" includes both "heteroaryl" and "heterocycloalkyl".

Specific heterocycles comprise the following

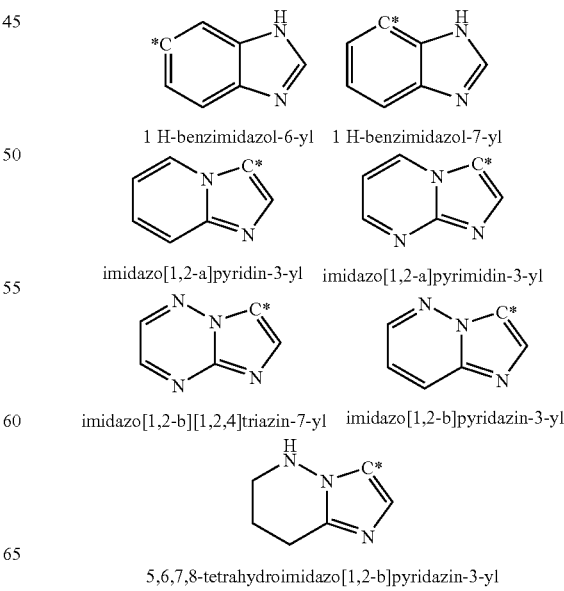

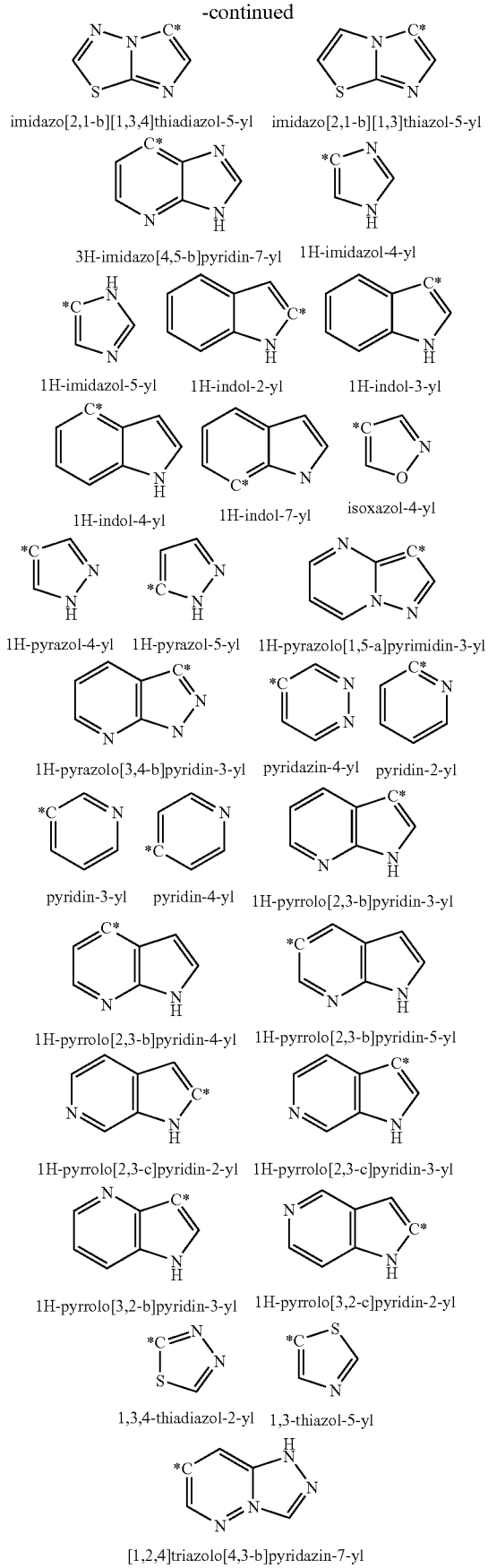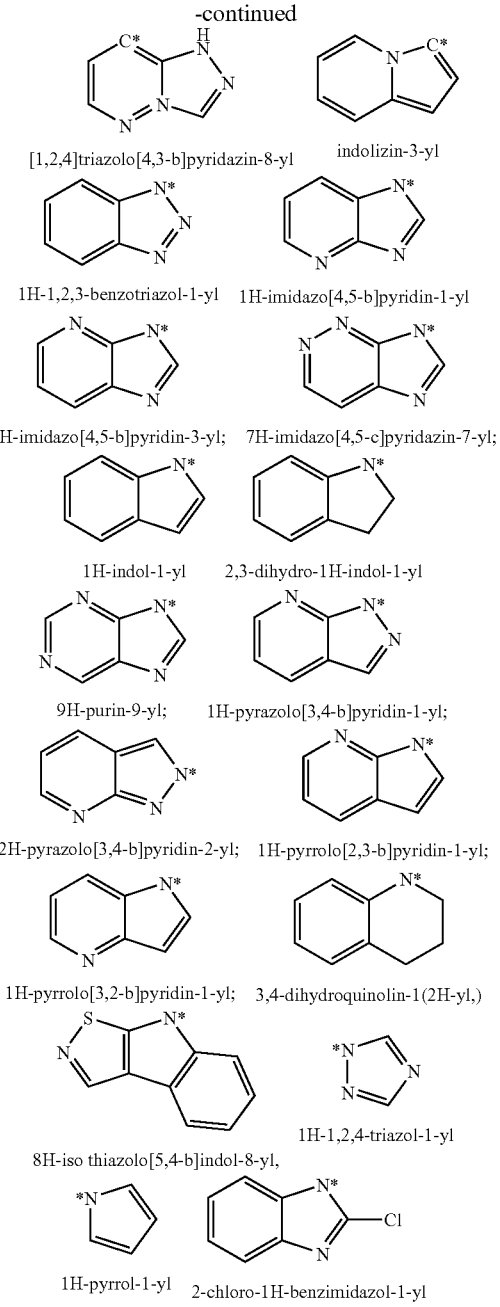

wherein the asterisk * indicates the point of attachment.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl, imidazopyrimidine, imidazopyridazine, imidazothiazole, imidazothiadiazole.

"$C_{2-6}$ alkenyl" refers to alkenyl groups preferably having from 2 to 6 carbon atoms and having at least 1 or 2 sites of alkenyl unsaturation. Preferable alkenyl groups include ethenyl (vinyl, —CH=CH$_2$), n-2-propenyl (allyl, —CH$_2$CH=CH$_2$) and the like.

"$C_{2-6}$ alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

"$C_{3-8}$ cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopropyl, cyclobutyl, cyclopentyl, cyclohexyl, norbornyl and the like.

"Heterocycloalkyl" refers to a $C_{3-8}$ cycloalkyl group according to the definition above, in which 1 to 3 carbon atoms are replaced by hetero atoms chosen from the group consisting of O, S, NR, R being defined as hydrogen or $C_{1-6}$ alkyl. Preferred heterocycloalkyl include pyrrolidine, piperidine, piperazine, 1-methylpiperazine, morpholine, and the like.

"Alkoxy" refers to the group —O—R where R includes "$C_{1-6}$ alkyl", "$C_{2-6}$ alkenyl", "$C_{2-6}$ alkynyl", "$C_{3-8}$ cycloalkyl", "heterocycloalkyl", "aryl", "heteroaryl".

"Amino" refers to the group —NRR' where each R, R' is independently hydrogen, "$C_{1-6}$ alkyl", "$C_{2-6}$ alkenyl", "$C_{2-6}$ alkynyl", "$C_{3-8}$ cycloalkyl", "heterocycloalkyl", "aryl", "heteroaryl", and where R and R', together with the nitrogen atom to which they are attached, can optionally form a 3-8-membered heterocycloalkyl ring.

"Amido" refers to the group —C(=O)NRR' where each R, R' is independently hydrogen, "$C_{1-6}$ alkyl", "$C_{2-6}$ alkenyl", "$C_{2-6}$ alkynyl", "$C_{3-8}$ cycloalkyl", "heterocycloalkyl", "aryl", "heteroaryl", and where R and R', together with the nitrogen atom to which they are attached, can optionally form a 3-8-membered heterocycloalkyl ring.

"Sulfanyl" refers to the group —SR where R is "$C_{1-6}$ alkyl", "$C_{2-6}$ alkenyl", "$C_{2-6}$ alkynyl", "$C_{3-8}$ cycloalkyl", "heterocycloalkyl", "aryl" or "heteroaryl".

"Sulfinyl" refers to the group —S(=O)R where R is "$C_{1-6}$ alkyl", "$C_{2-6}$ alkenyl", "$C_{2-6}$ alkynyl", "$C_{3-8}$ cycloalkyl", "heterocycloalkyl", "aryl" or "heteroaryl".

"Sulfonyl" refers to the group —S(=O)$_2$R where R is "$C_{1-6}$ alkyl", "$C_{2-6}$ alkenyl", "$C_{2-6}$ alkynyl", "$C_{3-8}$ cycloalkyl", "heterocycloalkyl", "aryl" or "heteroaryl".

"Halogen" refers to fluoro, chloro, bromo and iodo atoms.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_{1-6}$ alkyl", "$C_{2-6}$ alkenyl", "$C_{2-6}$ alkynyl", "cycloalkyl", "heterocycloalkyl", "amino", "aryl", "heteroaryl", "alkoxy", "halogen", cyano, hydroxy, mercapto, nitro, "amido", "sulfanyl", "sulfinyl", "sulfonyl" and the like.

The "pharmaceutically acceptable salts" according to the invention include therapeutically active, non-toxic acid or base salt forms which the compounds of formula I are able to form.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula I containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula I and their salts can be in the form of a solvate, which is included within the scope of the present invention. Such solvates include for example hydrates, alcoholates and the like.

Many of the compounds of formula I and some of their intermediates have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereoisomeric forms of the compounds of formula I or mixtures thereof (including all possible mixtures of stereoisomers).

With respect to the present invention reference to a compound or compounds is intended to encompass that compound in each of its possible isomeric forms and mixtures thereof, unless the particular isomeric form is referred to specifically.

Compounds according to the present invention may exist in different polymorphic forms. Although not explicitly indicated in the above formula, such forms are intended to be included within the scope of the present invention.

Some of the compounds of formula I may also exist in tautomeric forms. Such forms although not explicity indicated in the above formula are intended to be included within the scope of the present invention.

The invention also includes within its scope pro-drug forms of the compounds of formula I and its various subscopes and sub-groups.

The compounds of formula I according to the invention can be prepared analogously to conventional methods as understood by the person skilled in the art of synthetic organic chemistry.

A. According to one embodiment, compounds having the general formula I may be prepared by chlorination of a compound of formula II and reaction of the corresponding derivative of formula III with an heterocycle of formula R$^3$H, or by direct condensation of a compound of formula II with an heterocycle of formula R$^3$H, according to the equation:

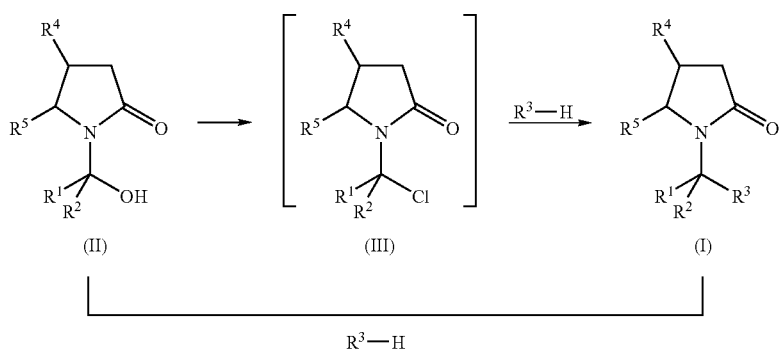

wherein $R^1$, $R^2$, $R^3$, $R^4$ and $R^5$ have the same definitions as defined above for compounds of formula I.

When $R^3$ is an heterocycle linked to the rest of the molecules via its N atom, this condensation is better performed under basic conditions using strong bases like LiH or NaH, in DMF, THF or the like.

The synthesis of intermediates of formula III may be carried out using thionyl chloride (or any other chlorination agent such as HCl, $POCl_3$, $PCl_5$ . . . ) neat or in toluene at a temperature ranging from 20° C. to 80° C.

The condensation of a compound of formula III with a compound of formula $R^3H$ can be performed in 1,1',2,2'-tetrachloroethane toluene, dioxane in the presence of a lewis acid such as $AlCl_3$ at a temperature ranging from 20° C. to 80° C.

The direct condensation of a compound of formula II with an heterocycle of formula $R^3H$ can be performed according to any method known to the person skilled in the art (eg PTSA/Toluene or TFA, or use of catalytic amount of N,N-diethylcarbamoyl chloride in acetonitrile under microwave irradiation).

Compounds of formula II may be prepared by hydroxyalkylation of a compound of formula V with a carbonyl derivative of formula IV according to the equation

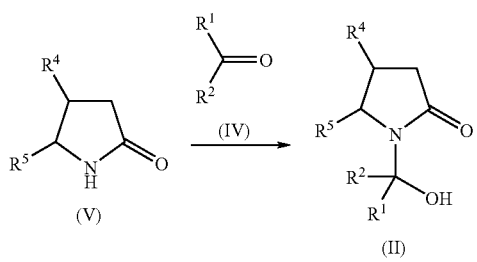

wherein $R^1$, $R^2$, $R^4$ and $R^5$ are defined as described above for compounds of formula I. This reaction may be carried out by heating the pyrrolidone derivative V with the aldehyde IV (or its synthetic equivalent such as paraformaldehyde in the case of formaldehyde) in the presence of an acid or a base such as $CF_3CO_2H$ or NaOH. Compounds of formula II may also be generated in situ using microwave technology.

B. According to another embodiment, some compounds having the general formula I wherein $R^2$ is H, may be prepared by reductive amination of the aldehyde of formula VI with an amino acid derivative of formula VII according to the equation:

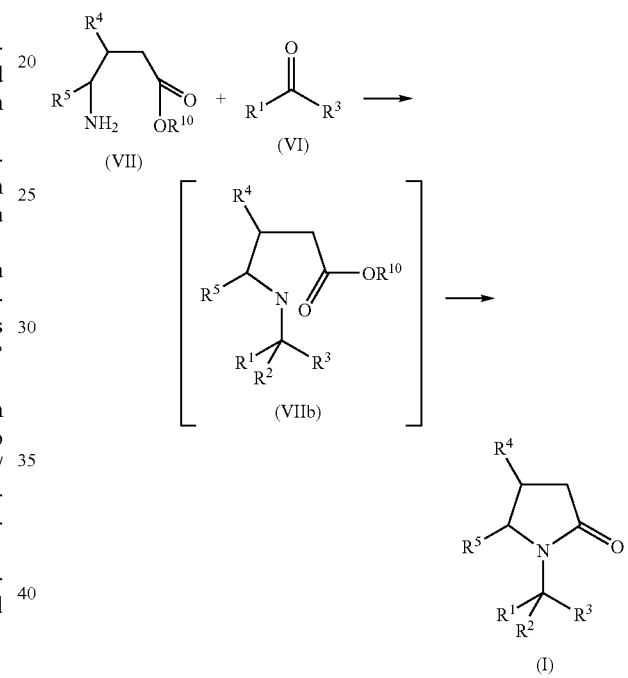

wherein $R^1$, $R^3$, $R^4$ and $R^5$ have the same definitions as described above, and $R^{10}$ represents hydrogen, a $C_{1-4}$ alkyl group or a metal atom (such as $Ba^{2+}$ or $Na^+$).

In compounds of formula VII, $R^4$ can form together with $R^5$ and the amino-butyrate side chain a cycle, leading to a derivative of formula (VIIa)

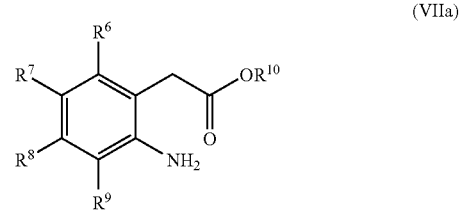

wherein $R^6$, $R^7$, $R^8$, $R^9$ and $R^{10}$ have the same definitions as described above. This reaction may be carried out using the conditions described in Abdel-Magid, A. F., Harris, B. D., Maryanoff, C. A., Synlett (1994), 81-83.

The synthesis of compounds of formula VI, VII and VIIa can be done using standard procedure described in the literature or known by the person skilled in the art.

C. Compounds of formula I may be prepared by alkylation of a compound of formula VIII with a compound of formula V according to the equation

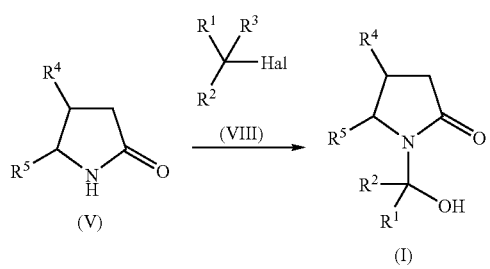

wherein Hal is a halogen atom, preferably Br or Cl; $R^1$, $R^2$, $R^3$, $R^4$ and $R^5$ have the same definitions as defined above for compounds of formula I.

This reaction may be carried out in the presence of a strong base, preferably sodium hydride, at a temperature comprised between 0 and 40° C., in an inert solvent, for example DMF, under an inert atmosphere, or as described in patent GB 1,309,692 (UCB). The synthesis of compounds of formula VIII can be done using standard procedure described in the literature or known by the person skilled in the art.

D. Compounds of formula I may be prepared by condensation of an amine of formula IX with a halogenated acid derivative of formula X, or by reductive amination of an hydroxylactone of formula XI or XII with an amine of formula IX, according to the following equation

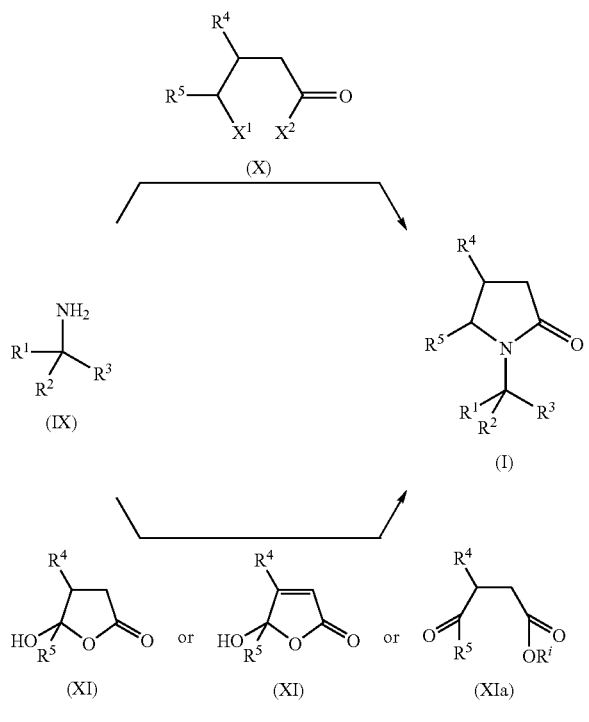

In compounds of formula X, $X^1$ represents a halogen atom, preferably a iodine or a chlorine atom, $X^2$ represents a halogen atom, preferably a chlorine atom. This reaction may be carried out as described in patent application GB 2225322 A, or according to any method known to the person skilled in the art.

The synthesis of compounds of formula IX can be done using standard procedure described in the literature or known by the person skilled in the art.

E. According to another embodiment, some compounds of formula I wherein $R^3$ is a group of formula

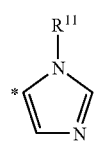

wherein $R^{11}$ is hydrogen or $C_{1-4}$ alkyl optionally substituted by amino group and the asterisk * indicates the point of attachment of the ring $R^3$ may be prepared from the corresponding compound of formula XIII by treatment respectively with an acidic aqueous solution or with an alkylating agent as follows:

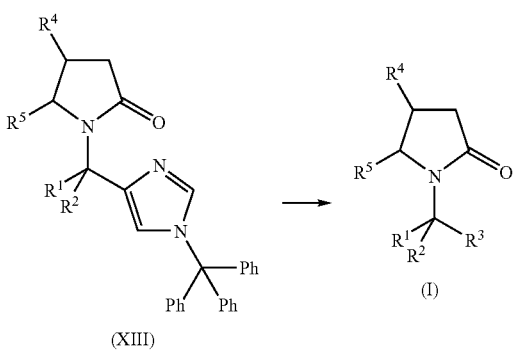

Compounds of formula XIII may be synthesized according to the method described in item B.

F. According to another embodiment, some compounds of formula I wherein $R^3$ is 1-[2-(benzylamino)-2-oxoethyl]-1H-imidazol-5-yl may be prepared from compounds of formula XIII according to the equation

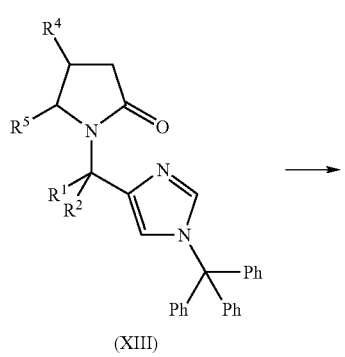

-continued

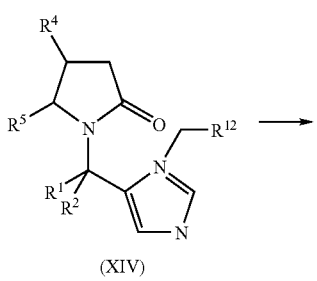

(XIV)

wherein R¹² = ester

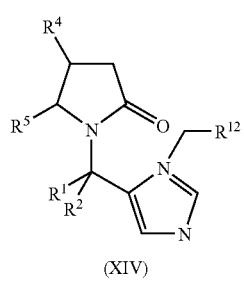

(XIV)

wherein R¹² = COOH

Basic hydrolysis and aminolysis of compounds of formula XIV are performed according to methods known to the person skilled in the art.

Compounds of formula XIV may be prepared from the corresponding compound of formula XIII by treatment with an alkylating agent as described above.

G. According to one embodiment, compounds of formula I wherein $R^3$ is

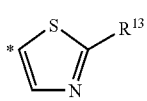

wherein $R^{13}$ is amino or an amino group and the asterisk * indicates the point of attachment of the ring $R^3$, may be prepared by reaction of a compound of formula II with dichloroethylene, followed by reaction of the such obtained aldehyde derivative of formula XV with a thiourea of formula XVI as follows:

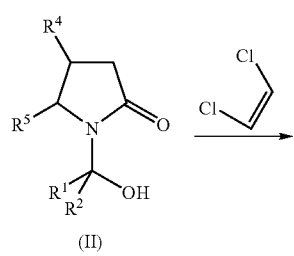

-continued

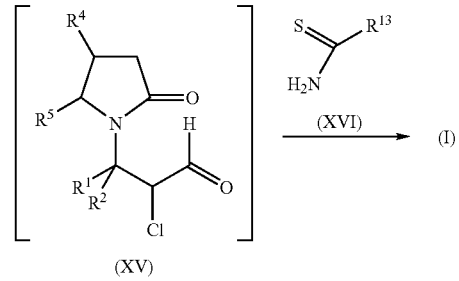

(XV)

wherein $R^1$, $R^2$, $R^4$ and $R^5$ are defined as described above for compounds of formula I. This reaction may be carried out in concentrated sulfuric acid by reacting II and a dichloroethylene at low temperature (such as 0° C.).

The condensation of the aldehyde XV with a thiourea derivative XVI is performed in an alcohol at reflux in the presence of an iodide salt (such as KI).

H. According to another embodiment, some compounds having the general formula I may be prepared by functional group transformation.

(a) compound of formula I wherein $R^3$ is

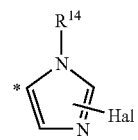

wherein $R^{14}$ is hydrogen or $C_{1-4}$ alkyl optionally substituted by amino group, Hal is an halogen atom and the asterisk * indicates the point of attachment of the ring $R^3$, may be prepared from the corresponding non-halogenated compound of formula I according to any method known to the person skilled in the art.

(b) compound of formula I wherein $R^3$ is a 1,3-thiazol-5-yl 2-substituted by amino or an amino group may be prepared by reaction of a compound of formula I wherein $R^3$ is a 2-halogeno-1,3-thiazol-5-yl with respectively concentrated HCl or an amine derivative according to any method known to the person skilled in the art.

(c) compound of formula I wherein $R^3$ is a 1,3-thiazol-5-yl may be prepared by reaction of a compound of formula I wherein $R^3$ is a 2-amino-1,3-thiazol-5-yl with iso-amyl nitrite according to any method known to the person skilled in the art.

(d) Compound of formula I bearing at least on halogen atom on to the core heteroaryl

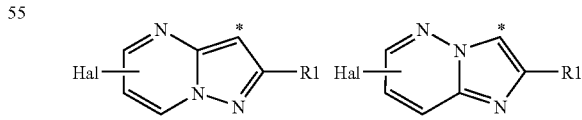

where $R^1$ are defined as described above, Hal is an halogen atom and the asterisk * indicates the point of attachment of the ring $R^3$, may be transformed to the corresponding compound (halogen substitution by hydrogen, alkyne, alkyl, aryl, heteroaryl, amino, alkylamino, hydroxy, alkoxy, cyano, alkylthio) compound of formula I according to any method known to the person skilled in the art.

(e) compounds bearing an alkylsulfonyl and alkyl sulfoxide moiety can be prepared from corresponding alkylthio substituted compound according to any method known to the person skilled in the art.

(f) Compound of formula I

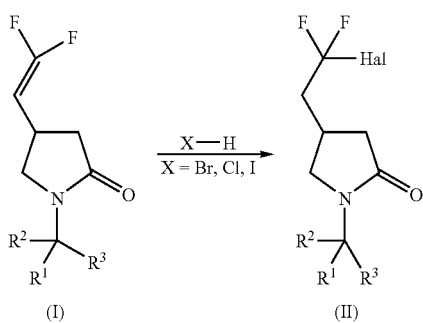

wherein $R^1$, $R^2$ and $R^3$ are defined as described above may be prepared from compound of formula I according to any method known to the person skilled in the art.

(g) compounds bearing an alkoxy substituent on position $R^3$ can be prepared from the corresponding hydroxy derivatives according to any method known to the person skilled in the art.

(h) compounds bearing N-oxide moiety on position $R^3$ can be prepared from the corresponding aza-derivatives according to any method known to the person skilled in the art.

In another embodiment, the present invention concerns the synthesis of the following intermediates:

methyl 3-(aminomethyl)hexanoate hydrochloride;
6-bromo-2-methylpyrazolo[1,5-a]pyrimidine;
6-bromo-2-(2-thienyl)pyrazolo[1,5-a]pyrimidine;
6-bromo-2-phenylpyrazolo[1,5-a]pyrimidine;
6-bromo-2-cyclopropylpyrazolo[1,5-a]pyrimidine;
6-bromo-2-tert-butylpyrazolo[1,5-a]pyrimidine;
6-chloro-2-phenylpyrazolo[1,5-a]pyrimidine;
6-bromo-2-methylpyrazolo[1,5-a]pyrimidine-3-carbaldehyde;
2-methylpyrazolo[1,5-a]pyrimidine-3-carbaldehyde;
6-bromo-2-(2-thienyl)pyrazolo[1,5-a]pyrimidine-3-carbaldehyde;
6-bromo-2-cyclopropylpyrazolo[1,5-a]pyrimidine-3-carbaldehyde;
2-(2-furyl)pyrazolo[1,5-a]pyrimidine-3-carbaldehyde;
6-methyl-2-phenylpyrazolo[1,5-a]pyrimidine-3-carbaldehyde;
5-methyl-2-phenylpyrazolo[1,5-a]pyrimidine-3-carbaldehyde;
2-(2-thienyl)pyrazolo[1,5-a]pyrimidine-3-carbaldehyde;
6-(4-methylphenyl)imidazo[2,1-b][1,3,4]thiadiazole-5-carbaldehyde;
ethyl 3-(aminomethyl)hexanoate hydrochloride;
6-chloro-3-methyl-2-(trifluoromethyl)imidazo[1,2-b]pyridazine;
3-(bromomethyl)-6-chloro-2-(trifluoromethyl)imidazo[1,2-b]pyridazine;
4-(2,3,5-trifluorophenyl)pyrrolidin-2-one;
1-[2-(aminooxy)-2-oxoethyl]-4-propylpyrrolidin-2-one;
2-(2-oxo-4-propylpyrrolidin-1-yl)acetohydrazide;
4-phenyl-1-[(1-trityl-1H-imidazol-4-yl)methyl]pyrrolidin-2-one;
4-propyl-1-[(1-trityl-1H-imidazol-4-yl)methyl]pyrrolidin-2-one;
1-[(1-trityl-1H-imidazol-4-yl)methyl]pyrrolidin-2-one;
4-(2,3,5-trifluorophenyl)-1-[(1-trityl-1H-imidazol-4-yl)methyl]pyrrolidin-2-one;
1-[(1-methyl-1H-imidazol-5-yl)methyl]-4-(2,3,5-trifluorophenyl)pyrrolidin-2-one;
ethyl {5-[(2-oxo-4-propylpyrrolidin-1-yl)methyl]-1H-imidazol-1-yl}acetate;
{5-[(2-oxo-4-propylpyrrolidin-1-yl)methyl]-1H-imidazol-1-yl}acetic acid;
4-iodo-3-methyl-1-[(4-methylphenyl)sulfonyl]-1H-pyrazole;
3,5-dimethyl-1-[(4-methylphenyl)sulfonyl]-1H-pyrazole-4-carbaldehyde;
3-methyl-1-[(4-methylphenyl)sulfonyl]-1H-pyrazole-4-carbaldehyde;
1-[(4-methylphenyl)sulfonyl]-1H-pyrazole-4-carbaldehyde;
1-[(4-methylphenyl)sulfonyl]-1H-pyrazole-5-carbaldehyde;
ethyl 4-amino-3-(2,3,5-trifluorophenyl)butanoate hydrochloride;
1-({3,5-dimethyl-1-[(4-methylphenyl)sulfonyl]-1H-pyrazol-4-yl}methyl)-4-(2,3,5-trifluorophenyl)pyrrolidin-2-one;
1-({3-methyl-1-[(4-methylphenyl)sulfonyl]-1H-pyrazol-4-yl}methyl)-4-(2,3,5-trifluorophenyl)pyrrolidin-2-one;
ethyl 4-[(pyridazin-4-ylmethylene)amino]butanoate;
ethyl 4-[(pyridazin-4-ylmethyl)amino]butanoate;
5-chloro-1-[(2-fluoropyridin-3-yl)methyl]-1H-indole;
3,3-dibromo-5-chloro-1-[(2-fluoropyridin-3-yl)methyl]-1,3-dihydro-2H-indol-2-one;
1-[(6-chloro-9H-purin-9-yl)methyl]-4-propylpyrrolidin-2-one;
1-{[(3-nitropyridin-2-yl)amino]methyl}-4-propylpyrrolidin-2-one;
1-{[(3-aminopyridin-2-yl)amino]methyl}-4-propylpyrrolidin-2-one;
5-bromo-1H-pyrazolo[3,4-b]pyridine;
2-chloro-3-(2-oxopyrrolidin-1-yl)propanal;
S-ethyl 4-cyano-1-methyl-1H-imidazole-5-carbothioate;
5-formyl-1-methyl-1H-imidazole-4-carbonitrile;
1-(1H-imidazol-4-ylmethyl)-4-(2,3,5-trifluorophenyl)pyrrolidin-2-one;
ethyl 4-{[1-(1-trityl-1H-imidazol-4-yl)propyl]amino}butanoate;
ethyl 3-{[(2-methyl-1-trityl-1H-imidazol-5-yl)methyl]amino}propanoate;
ethyl 3-{[(4-methyl-1-trityl-1H-imidazol-5-yl)methyl]amino}propanoate;
1-(4-methoxy-1-methyl-1H-imidazol-5-yl)methanamine;
barium bis[(2-amino-5-chlorophenyl)acetate];
5-hydroxy-4-(2,2,2-trifluoroethyl)furan-2(5H)-one;
1-benzyl-5-hydroxy-4-(2,2,2-trifluoroethyl)-1,5-dihydro-2H-pyrrol-2-one;
1-benzyl-4-(2,2,2-trifluoroethyl)pyrrolidin-2-one;
4-(2,2,2-trifluoroethyl)pyrrolidin-2-one;
6-chloro-2-cyclopropylimidazo[1,2-b]pyridazine;
6-chloro-2-cyclobutylimidazo[1,2-b]pyridazine;
2-cyclopropyl-6-fluoroimidazo[1,2-a]pyridine;
6-chloro-2-cyclopropylimidazo[1,2-b]pyridazine-3-carbaldehyde;
6-chloro-2-cyclobutylimidazo[1,2-b]pyridazine-3-carbaldehyde;
2-cyclopropyl-6-fluoroimidazo[1,2-a]pyridine-3-carbaldehyde;
6-chloro-2-cyclopropylimidazo[1,2-b]pyridazine-3-carbaldehyde;
(6-chloro-2-cyclopropylimidazo[1,2-b]pyridazin-3-yl)methanol;

[6-chloro-2-(4-methylphenyl)imidazo[1,2-b]pyridazin-3-yl]methanol;
(6-chloro-2-cyclobutylimidazo[1,2-b]pyridazin-3-yl)methanol;
(2-cyclopropyl-6-fluoroimidazo[1,2-a]pyridin-3-yl)methanol;
(2-cyclopropyl-6-chloroimidazo[1,2-a]pyridin-3-yl)methanol;
6-methyl-2-phenylpyrazolo[1,5-a]pyrimidine;
2-(2-thienyl)pyrazolo[1,5-a]pyrimidine;
2-(2-furyl)pyrazolo[1,5-a]pyrimidine;
2-(4-bromophenyl)pyrazolo[1,5-a]pyrimidine;
2-(4-fluorophenyl)pyrazolo[1,5-a]pyrimidine;
2-(4-chlorophenyl)-6-methylpyrazolo[1,5-a]pyrimidine;
2-(4-chlorophenyl)pyrazolo[1,5-a]pyrimidine;
6-chloro-2-(4-chlorophenyl)pyrazolo[1,5-a]pyrimidine;
6-fluoro-5-methyl-2-phenylpyrazolo[1,5-a]pyrimidin-7-ol;
2-cyclopropyl-5-methylpyrazolo[1,5-a]pyrimidin-7-ol;
7-chloro-6-fluoro-5-methyl-2-phenylpyrazolo[1,5-a]pyrimidine;
7-chloro-5,6-dimethyl-2-phenylpyrazolo[1,5-a]pyrimidine;
7-chloro-2-cyclopropyl-5-methylpyrazolo[1,5-a]pyrimidine;
6-fluoro-5-methyl-2-phenylpyrazolo[1,5-a]pyrimidine;
5,6-dimethyl-2-phenylpyrazolo[1,5-a]pyrimidine;
2-cyclopropyl-5-methylpyrazolo[1,5-a]pyrimidine;
4-(2,2-difluorovinyl)-1-(hydroxymethyl)pyrrolidin-2-one;
(6-methyl-2-phenylpyrazolo[1,5-a]pyrimidin-3-yl)methanol;
(5-methyl-2-phenylpyrazolo[1,5-a]pyrimidin-3-yl)methanol;
[2-(2-thienyl)pyrazolo[1,5-a]pyrimidin-3-yl]methanol;
3-(chloromethyl)-6-methyl-2-phenylpyrazolo[1,5-a]pyrimidine;
3-(chloromethyl)-5-methyl-2-phenylpyrazolo[1,5-a]pyrimidine;
3-(chloromethyl)-2-(2-thienyl)pyrazolo[1,5-a]pyrimidine;
1-[(6-hydroxy-2-phenylpyrazolo[1,5-a]pyrimidin-3-yl)methyl]-4-propylpyrrolidin-2-one;
5-bromo-3-phenyl-1H-pyrazolo[3,4-b]pyridine;
5-bromo-3-methyl-1H-pyrazolo[3,4-b]pyridine;
tert-butyl 5-bromo-3-methyl-1H-pyrazolo[3,4-b]pyridine-1-carboxylate;
tert-butyl 5-bromo-3-(bromomethyl)-1H-pyrazolo[3,4-b]pyridine-1-carboxylate;
1,3-dihydro-2H-pyrrolo[2,3-b]pyridin-2-one;
2,5-dichloro-1H-indole;
1-[(6-chloro-9H-purin-9-yl)methyl]-4-propylpyrrolidin-2-one;
6-bromo-2-cyclopropyl-1H-imidazo[4,5-b]pyridine;
(5-chloro-2-imino-1,3-thiazol-3(2H)-yl)acetic acid hydrobromide;
methyl 3-(4-methoxybenzyl)-3H-imidazo[4,5-b]pyridine-7-carboxylate;
methyl 1-(4-methoxybenzyl)-1H-imidazo[4,5-b]pyridine-7-carboxylate;
methyl 3-(4-methoxybenzyl)-2-methyl-3H-imidazo[4,5-b]pyridine-7-carboxylate;
1-(4-methoxybenzyl)-2-methyl-1H-imidazo[4,5-b]pyridine-7-carboxylate;
[3-(4-methoxybenzyl)-3H-imidazo[4,5-b]pyridin-7-yl]methanol;
[3-(4-methoxybenzyl)-2-methyl-3H-imidazo[4,5-b]pyridin-7-yl]methanol;
7-(chloromethyl)-3-(4-methoxybenzyl)-3H-imidazo[4,5-b]pyridine;
7-(chloromethyl)-3-(4-methoxybenzyl)-2-methyl-3H-imidazo[4,5-b]pyridine;
1-{[3-(4-methoxybenzyl)-3H-imidazo[4,5-b]pyridin-7-yl]methyl}-4-propylpyrrolidin-2-one;
1-{[3-(4-methoxybenzyl)-3H-imidazo[4,5-b]pyridin-7-yl]methyl}-4-phenylpyrrolidin-2-one;
1-{[3-(4-methoxybenzyl)-2-methyl-3H-imidazo[4,5-b]pyridin-7-yl]methyl}-4-propylpyrrolidin-2-one;
N-(4-methoxybenzyl)-2-nitroethylene-1,1-diamine;
ethyl 2-[(4-methoxybenzyl)amino]-3-nitro-6-(trifluoromethyl)isonicotinate;
ethyl 2-[(4-methoxybenzyl)amino]-3-nitro-6-phenylisonicotinate;
ethyl 2-[(4-methoxybenzyl)amino]-6-methyl-3-nitroisonicotinate;
ethyl 3-(4-methoxybenzyl)-5-(trifluoromethyl)-3H-imidazo[4,5-b]pyridine-7-carboxylate;
ethyl 3-(4-methoxybenzyl)-5-phenyl-3H-imidazo[4,5-b]pyridine-7-carboxylate;
ethyl 3-(4-methoxybenzyl)-5-methyl-3H-imidazo[4,5-b]pyridine-7-carboxylate;
[3-(4-methoxybenzyl)-5-(trifluoromethyl)-3H-imidazo[4,5-b]pyridin-7-yl]methanol;
[3-(4-methoxybenzyl)-5-phenyl-3H-imidazo[4,5-b]pyridin-7-yl]methanol;
[3-(4-methoxybenzyl)-5-methyl-3H-imidazo[4,5-b]pyridin-7-yl]methanol;
7-(chloromethyl)-3-(4-methoxybenzyl)-5-(trifluoromethyl)-3H-imidazo[4,5-b]pyridine;
7-(chloromethyl)-3-(4-methoxybenzyl)-5-phenyl-3H-imidazo[4,5-b]pyridine;
7-(chloromethyl)-3-(4-methoxybenzyl)-5-methyl-3H-imidazo[4,5-b]pyridine;
1-{[3-(4-methoxybenzyl)-5-(trifluoromethyl)-3H-imidazo[4,5-b]pyridin-7-yl]methyl}-4-propylpyrrolidin-2-one;
1-{[3-(4-methoxybenzyl)-5-phenyl-3H-imidazo[4,5-b]pyridin-7-yl]methyl}-4-propylpyrrolidin-2-one;
1-{[3-(4-methoxybenzyl)-5-methyl-3H-imidazo[4,5-b]pyridin-7-yl]methyl}-4-propylpyrrolidin-2-one;
methyl 6-bromo-1H-imidazo[4,5-b]pyridine-7-carboxylate;
methyl 6-bromo-3-(4-methoxybenzyl)-3H-imidazo[4,5-b]pyridine-7-carboxylate;
[6-bromo-3-(4-methoxybenzyl)-3H-imidazo[4,5-b]pyridin-7-yl]methanol;
6-bromo-7-(chloromethyl)-3-(4-methoxybenzyl)-3H-imidazo[4,5-b]pyridine;
1-{[6-bromo-3-(4-methoxybenzyl)-3H-imidazo[4,5-b]pyridin-7-yl]methyl}-4-propylpyrrolidin-2-one;
[3-(4-methoxybenzyl)-6-phenyl-3H-imidazo[4,5-b]pyridin-7-yl]methanol;
7-(chloromethyl)-3-(4-methoxybenzyl)-6-phenyl-3H-imidazo[4,5-b]pyridine;
1-{[3-(4-methoxybenzyl)-6-phenyl-3H-imidazo[4,5-b]pyridin-7-yl]methyl}-4-propylpyrrolidin-2-one;
[3-(4-methoxybenzyl)-6-methyl-3H-imidazo[4,5-b]pyridin-7-yl]methanol;
7-(chloromethyl)-3-(4-methoxybenzyl)-6-methyl-3H-imidazo[4,5-b]pyridine;
1-{[3-(4-methoxybenzyl)-6-methyl-3H-imidazo[4,5-b]pyridin-7-yl]methyl}-4-propylpyrrolidin-2-one;
3-(4-methoxybenzyl)-7-methyl-2-phenyl-3H-imidazo[4,5-b]pyridine;
2-[3-(4-methoxybenzyl)-2-phenyl-3H-imidazo[4,5-b]pyridin-7-yl]-N,N-dimethylethylenamine;
3-(4-methoxybenzyl)-2-phenyl-3H-imidazo[4,5-b]pyridine-7-carbaldehyde;

1-{[3-(4-methoxybenzyl)-2-phenyl-3H-imidazo[4,5-b]pyridin-7-yl]methyl}-4-propylpyrrolidin-2-one;
6-chloro-8-methyl-3-(trifluoromethyl)[1,2,4]triazolo[4,3-b]pyridazine;
6-chloro-7-methyl-3-(trifluoromethyl)[1,2,4]triazolo[4,3-b]pyridazine;
8-methyl-3-(trifluoromethyl)[1,2,4]triazolo[4,3-b]pyridazine;
7-methyl-3-(trifluoromethyl)[1,2,4]triazolo[4,3-b]pyridazine;
N,N-dimethyl-2-[3-(trifluoromethyl)[1,2,4]triazolo[4,3-b]pyridazin-7-yl]ethylenamine;
N,N-dimethyl-2-(3-phenyl[1,2,4]triazolo[4,3-b]pyridazin-7-yl)ethylenamine;
3-(trifluoromethyl)[1,2,4]triazolo[4,3-b]pyridazine-7-carbaldehyde;
3-phenyl[1,2,4]triazolo[4,3-b]pyridazine-7-carbaldehyde;
N,N-dimethyl-2-[3-(trifluoromethyl)[1,2,4]triazolo[4,3-b]pyridazin-8-yl]ethylenamine;
2-[6-chloro-3-(trifluoromethyl)[1,2,4]triazolo[4,3-b]pyridazin-8-yl]-N,N-dimethylethylenamine;
3-(trifluoromethyl)[1,2,4]triazolo[4,3-b]pyridazine-8-carbaldehyde;
N,N-dimethyl-2-(3-phenyl[1,2,4]triazolo[4,3-b]pyridazin-8-yl)ethylenamine;
2-(6-chloro-3-phenyl[1,2,4]triazolo[4,3-b]pyridazin-8-yl)-N,N-dimethylethylenamine;
2-(6-chloro[1,2,4]triazolo[4,3-b]pyridazin-8-yl)-N,N-dimethylethylenamine;
3-phenyl[1,2,4]triazolo[4,3-b]pyridazine-8-carbaldehyde;
methyl 3-phenyl[1,2,4]triazolo[4,3-b]pyridazine-8-carboxylate;
6-chloro[1,2,4]triazolo[4,3-b]pyridazine-8-carbaldehyde;
methyl 6-chloro[1,2,4]triazolo[4,3-b]pyridazine-8-carboxylate;
(6-chloro-3-phenyl[1,2,4]triazolo[4,3-b]pyridazin-8-yl)(methoxy)methanol;
[6-chloro-3-(trifluoromethyl)[1,2,4]triazolo[4,3-b]pyridazin-8-yl](methoxy)methanol;
1-(triisopropylsilyl)-1H-pyrrolo[2,3-b]pyridine-5-carbaldehyde;
4-propyl-1-{[1-(triisopropylsilyl)-1H-pyrrolo[2,3-b]pyridin-5-yl]methyl}pyrrolidin-2-one;
1-(triisopropylsilyl)-1H-pyrrolo[2,3-b]pyridine-4-carbaldehyde;
4-propyl-1-{[1-(triisopropylsilyl)-1H-pyrrolo[2,3-b]pyridin-4-yl]methyl}pyrrolidin-2-one;
1-(2-fluoroindolizin-3-yl)methanamine;
4-propyl-1-(1H-pyrrol-1-ylmethyl)pyrrolidin-2-one;
1-{[6-[(2,4-dimethoxybenzyl)amino]-2-(trifluoromethyl)imidazo[1,2-b]pyridazin-3-yl]methyl}-4-propylpyrrolidin-2-one;
2-cyclopropyl-7-hydroxypyrazolo[1,5-a]pyrimidin-5(4H)-one;
5,7-dichloro-2-cyclopropylpyrazolo[1,5-a]pyrimidine;
5,7-dichloro-2-cyclopropyl-6-methylpyrazolo[1,5-a]pyrimidine;
5-chloro-2-cyclopropylpyrazolo[1,5-a]pyrimidine;
5-chloro-2-cyclopropyl-6-methylpyrazolo[1,5-a]pyrimidine;
1-(chloromethyl)-4-(2,2-difluorovinyl)pyrrolidin-2-one;
1-methyl-5-[(2-oxo-4-propylpyrrolidin-1-yl)methyl]-1H-imidazole-2-carboxylic acid;
ethyl 3-hydroxy-2-[(2-oxo-4-propylpyrrolidin-1-yl)methyl]propanoate;
ethyl 2-formyl-3-(2-oxo-4-propylpyrrolidin-1-yl)propanoate;
2-benzyl-4-[(2-oxo-4-propylpyrrolidin-1-yl)methyl]-2,4-dihydro-3H-pyrazol-3-one.

In a further aspect, the present invention concerns also the use of a compound of formula I or a pharmaceutically acceptable salt thereof for the manufacture of a medicament for the treatment of neurological and other disorders such as mentioned above.

In particular, the present invention concerns the use of a compound of formula I or a pharmaceutically acceptable salt thereof for the manufacture of a medicament for the treatment of epilepsy, Parkinson's disease, dyskinesia, migraine, tremor, essential tremor, bipolar disorders, chronic pain, neuropathic pain, or bronchial, asthmatic or allergic conditions.

The methods of the invention comprise administration to a mammal (preferably human) suffering from above mentioned conditions or disorders, of a compound according to the invention in an amount sufficient to alleviate or prevent the disorder or condition.

The compound is conveniently administered in any suitable unit dosage form, including but not limited to one containing 3 to 3000 mg, preferably 25 to 500 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The term "epilepsy" as used herein refers to a chronic neurologic condition characterised by unprovoked, recurrent epileptic seizures. An epileptic seizure is the manisfestation of an abnormal and excessive synchronised discharge of a set of cerebral neurons; its clinical manifestations are sudden and transient. The term "epilepsy" as used herein can also refer to a disorder of brain function characterised by the periodic occurrence of seizures. Seizures can be "nonepileptic" when evoked in a normal brain by conditions such as high fever or exposure to toxins or "epileptic" when evoked without evident provocation.

The term "seizure" as used herein refers to a transient alteration of behaviour due to the disordered, synchronous, and rhythmic firing of populations of brain neurones.

The term "Parkinsonian symptoms" relates to a syndrome characterised by slowlyness of movement (bradykinesia), rigidity and/or tremor. Parkinsonian symptoms are seen in a variety of conditions, most commonly in idiopathic parkinsonism (i.e. Parkinson's Disease) but also following treatment of schizophrenia, exposure to toxins/drugs and head injury. It is widely appreciated that the primary pathology underlying Parkinson's disease is degeneration, in the brain, of the dopaminergic projection from the substantia nigra to the striatum. This has led to the widespread use of dopamine-replacing agents (e.g. L-3,4-dihydroxyphenylalanine (L-DOPA) and dopamine agonists) as symptomatic treatments for Parkinson's disease and such treatments have been successful in increasing the quality of life of patients suffering from Parkinson's disease. However, dopamine-replacement treatments do have limitations, especially following long-term treatment. Problems can include a wearing-off of the anti-parkinsonian efficacy of the treatment and the appearance of a range of side-effects which manifest as abnormal involuntary movements, such as dyskinesias.

The term "dyskinesia" is defined as the development in a subject of abnormal involuntary movements. This appears in patients with Huntington's disease, in Parkinson's disease patients exposed to chronic dopamine replacement therapy, and in Schizophrenia patients exposed to chronic treatment with neuroleptics. Dyskinesias, as a whole, are characterised by the development in a subject of abnormal involuntary movements. One way in which dyskinesias may arise is as a side effect of dopamine replacement therapy for parkinsonism or other basal ganglia-related movement disorders.

The term "migraine" as used herein means a disorder characterised by recurrent attacks of headache that vary widely in intensity, frequency, and duration. The attacks are commonly unilateral and are usually associated with anorexia, nausea, vomiting, phonophobia, and/or photophobia. In some cases they are preceded by, or associated with, neurological and mood disturbances. Migraine headache may last from 4 hours to about 72 hours. The International Headache Society (IHS, 1988) classifies migraine with aura (classical migraine) and migraine without aura (common migraine) as the major types of migraine. Migraine with aura consists of a headache phase preceded by characteristic visual, sensory, speech, or motor symptoms. In the absence of such symptoms, the headache is called migraine without aura.

The term "bipolar disorders" as used herein refers to those disorders classified as Mood Disorders according to the Diagnostic and Statistical Manual of Mental Disorders, 4th edition (Diagnostic and Statistical Manual of Mental Disorders (DSM-IV™), American Psychiatry Association, Washington, D.C., 1994). Bipolar disorders are generally characterised by spontaneously triggered repeated (i.e. at least two) episodes in which the patient's hyperexcitability, activity and mood are significantly disturbed, this disturbance consisting on some occasions of an elevation of mood and increased energy and activity (mania or hypomania), and in other occasions a lowering of mood and decreased energy and activity (depression). Bipolar disorders are separated into four main categories in the DSM-IV (bipolar I disorder, bipolar II disorder, cyclothymia, and bipolar disorders not otherwise specified).

The term "manic episode", as used herein refers to a distinct period during which there is an abnormally and persistently elevated, expansive, or irritable mood with signs of pressured speech and psychomotor agitation.

The term "hypomania", as used herein refers to a less extreme manic episode, with lower grade of severity.

The term "major depressive episode", as used herein refers to a period of at least 2 weeks during which there is either depressed mood or the loss of interest or pleasure in nearly all activities with signs of impaired concentration and psychomotor retardation.

The term "mixed episode", as used herein refers to a period of time (lasting at least 1 week) in which the criteria are met both for a manic episode and for a major depressive episode nearly every day.

The term "chronic pain" as used herein refers to the condition gradually being recognised as a disease process distinct from acute pain. Conventionally defined as pain that persists beyond the normal time of healing, pain can also be considered chronic at the point when the individual realises that the pain is going to be a persistent part of their lives for the foreseeable future. It is likely that a majority of chronic pain syndromes involves a neuropathic component, which is usually harder to treat than acute somatic pain.

The term "neuropathic pain" as used herein refers to pain initiated by a pathological change in a nerve which signals the presence of a noxious stimulus when no such recognisable stimulus exists, giving rise to a false sensation of pain. In other words, it appears that the pain system has been turned on and cannot turn itself off.

The term "tics" refers to common and often disabling neurological disorders. They are frequently associated with behaviour difficulties, including obsessive-compulsive disorder, attention deficit hyperactivity disorder and impulse control. Tics are involuntary, sudden, rapid, repetitive, nonrhythmic stereotype movements or vocalizations. Tics are manifested in a variety of forms, with different durations and degrees of complexity. Simple motor tics are brief rapid movements that often involve only one muscle group. Complex motor tics are abrupt movements that involve either a cluster of simple movements or a more coordinated sequence of movements. Simple vocal tics include sounds such as grunting, barking, yelping, and that clearing. Complex vocal tics include syllables, phrases, repeating other people's words and repeating one's own words.

The activity of the compounds of formula I, or their pharmaceutically acceptable salts, as anticonvulsants can be determined in the audiogenic seizure model. The objective of this test is to evaluate the anticonvulsant potential of a compound by means of audiogenic seizures induced in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. & Schmidt D., Epilepsy Res. (1998), 2, 145-181; Buchhalter J. R., Epilepsia (1993), 34, S31-S41). Results obtained with compounds of formula I are indicative of a strong pharmacological effect.

Another assay indicative of potential anticonvulsant activity is binding to levetiracetam binding site (LBS) as hereinafter described. As set forth in U.S. patent application Ser. Nos. 10/308,163 and 60/430,372 LBS has been identified as belonging to the family of SV2 proteins. As used herein reference to "LBS" is to be understood as including reference to SV2.

Activity in any of the above-mentioned indications can of course be determined by carrying out suitable clinical trials in a manner known to a person skilled in the relevant art for the particular indication and/or in the design of clinical trials in general.

For treating diseases, compounds of formula I or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula I or a pharmaceutically acceptable salt thereof in combination with a pharmaceutically acceptable diluent or carrier.

To prepare a pharmaceutical composition according to the invention, one or more of the compounds of formula I or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula I in compositions for oral administration is at least 0.5% by weight and can be up to 80% by weight with respect to the total weight of the composition.

In accordance with the invention it has also been found that the compounds of formula I or the pharmaceutically acceptable salts thereof can be administered alone or in combination with other pharmaceutically active ingredients. Non-limiting examples of such additional compounds which can be cited for use in combination with the compounds according to the invention are antivirals, antispastics (e.g. baclofen), antiemetics, antimanic mood stabilizing agents, analgesics (e.g. aspirin, ibuprofen, paracetamol), narcotic analgesics, topical anesthetics, opioid analgesics, lithium salts, antidepressants (e.g. mianserin, fluoxetine, trazodone), tricyclic antidepressants (e.g. imipramine, desipramine), anticonvulsants (e.g. valproic acid, carbamazepine, phenyloin), antipsychotics (e.g. risperidone, haloperidol), neuroleptics, benzodiazepines (e.g. diazepam, clonazepam), phenothiazines (e.g. chlorpromazine), calcium channel blockers, amphetamine, clonidine, lidocaine, mexiletine, capsaicin, caffeine, quetiapine, serotonin antagonists, β-blockers, antiarrhythmics, triptans, ergot derivatives and amantadine.

Of particular interest in accordance with the present invention are combinations of at least one compound of formula I or a pharmaceutically acceptable salt thereof and at least one compound inducing neural inhibition mediated by $GABA_A$ receptors. The compounds of formula I exhibit a potentiating effect on the compounds inducing neural inhibition mediated by $GABA_A$ receptors enabling, in many cases, effective treatment of conditions and disorders under reduced risk of adverse effects.

Examples of compounds inducing neural inhibition mediated by $GABA_A$ receptors include the following: benzodiazepines, barbiturates, steroids, and anticonvulsants such as valproate, viagabatrine, tiagabine or pharmaceutical acceptable salts thereof.

Benzodiazepines include the 1,4-benzodiazepines, such as diazepam and clonazepam, and the 1,5-benzodiazepines, such as clobazam. Preferred compound is clonazepam.

Barbiturates include phenobarbital and pentobarbital. Preferred compound is phenobarbital.

Steroids include adrenocorticotropic hormones such as tetracosactide acetate, etc.

Anticonvulsants include hydantoins (phenyloin, ethotoin, etc), oxazolidines (trimethadione, etc.), succinimides (ethosuximide, etc.), phenacemides (phenacemide, acetylpheneturide, etc.), sulfonamides (sulthiame, acetoazolamide, etc.), aminobutyric acids (e.g. gamma-amino-beta-hydroxybutyric acid, etc.), sodium valproate and derivatives, carbamazepine and so on.

Preferred compounds include valproic acid, valpromide, valproate pivoxil, sodium valproate, semi-sodium valproate, divalproex, clonazepam, phenobarbital, vigabatrine, tiagabine, amantadine.

For the preferred oral compositions, the daily dosage is in the range 3 to 3000 milligrams (mg) of compounds of formula I.

In compositions for parenteral administration, the quantity of compound of formula I present is at least 0.5% by weight and can be up to 33% by weight with respect to the total weight of the composition. For the preferred parenteral compositions, the dosage unit is in the range 3 mg to 3000 mg of compounds of formula I.

The daily dose can fall within a wide range of dosage units of compound of formula I and is generally in the range 3 to 3000 mg. However, it should be understood that the specific doses can be adapted to particular cases depending on the individual requirements, at the physician's discretion.

The LBS binding compounds provided by this invention and labeled derivatives thereof may be useful as standards and reagents in determining the ability of tested compounds (e.g., a potential pharmaceutical) to bind to the LBS receptor.

Labeled derivatives of LBS ligands provided by this invention may also be useful as radiotracers for positron emission tomography (PET) imaging or for single photon emission computerized tomography (SPECT).

The present invention therefore further provides labelled ligands as tools to screen chemical libraries for the discovery of potential pharmaceutical agents, in particular for treatment and prevention of the conditions set forth herein, on the basis of more potent binding to LBS/SV2 proteins, for localizing SV2 proteins in tissues, and for characterizing purified SV2 proteins. SV2 proteins include SV2A, SV2B, and SV2C whereby SV2A is the binding site for the anti-seizure drug levetiracetam and its analogs. The SV2 isoforms SV2A, SV2B, or SV2C can be derived from tissues, especially brain, from any mammal species, including human, rat or mice. Alternately the isoforms may be cloned versions of any mammalian species, including human, rat, and mice, heterologously expressed and used for assays. The screening method comprises exposing brain membranes, such as mammalian or human brain membranes, or cell lines expressing SV2 proteins or fragments thereof, especially SV2A, but including SV2B and SV2C, to a putative agent and incubating the membranes or proteins or fragments and the agent with labelled compound of formula I. The method further comprises determining if the binding of the compound of formula I to the protein is inhibited by the putative agent, thereby identifying binding partners for the protein. Thus, the screening assays enable the identification of new drugs or compounds that interact with LBS/SV2. The present invention also provides photoactivable ligands of SV2/LBS.

The labelled-ligands can also be used as tools to assess the conformation state of SV2 proteins after solubilization, purification and chromatography. The labelled-ligands may be directly or indirectly labeled. Examples of suitable labels include a radiolabel, such as $^3$H, a fluorescent label, an enzyme, europium, biotin and other conventional labels for assays of this type.

Screening assays of the present invention include methods of identifying agents or compounds that compete for binding to the LBS (especially SV2A). Labelled compounds of formula I are useful in the methods of the invention as probes in assays to screen for new compounds or agents that bind to the LBS (especially SV2A). In such assay embodiments, ligands can be used without modification or can be modified in a variety of ways; for example, by labelling, such as covalently or non-covalently joining a moiety which directly or indirectly provides a detectable signal. In any of these assays, the materials can be labelled either directly or indirectly. Possibilities for direct labelling include label groups such as: radiolabels including, but not limited to, [$^3$H], [$^{14}$C], [$^{32}$P], [$^{35}$S] or [$^{125}$I], enzymes such as peroxidase and alkaline phosphatase, and fluorescent labels capable of monitoring the change in fluorescence intensity, wavelength shift, or fluorescence polarization, including, but not limited to, fluorescein or rhodamine. Possibilities for indirect labelling include biotinylation of one constituent followed by binding to avidin coupled to one of the above label groups or the use of anti-ligand antibodies. The compounds may also include spacers or linkers in cases where the compounds are to be attached to a solid support. To identify agents or compounds which compete or interact with labelled ligands according to the invention for binding to the LBS (especially SV2A), intact cells, cellular or membrane fragments containing SV2A or the entire SV2 protein or a fragment comprising the LBS of the SV2 protein can be used. The agent or compound may be incubated with the cells, membranes, SV2 protein or fragment prior to, at the same time as, or after incubation with L059 or an analog or derivative thereof. Assays of the invention may be modified or prepared in any available format, including high-throughput screening (HTS) assays that monitor the binding of L059 or the binding of derivatives or analogs thereof to SV2 or to the LBS of the SV2 protein. In many drug screening programs which test libraries of compounds, high throughput assays are desirable in order to maximize the number of compounds surveyed in a given period of time. Such screening assays may use intact cells, cellular or membrane fragments containing SV2 as well as cell-free or membrane-free systems, such as may be derived with purified or semi-purified proteins. The advantage of the assay with membrane fragment containing SV2 or purified SV2 proteins and peptides is that the effects of cellular toxicity and/or bioavailability of the test compound can be generally ignored, the assay instead being focused primarily on the effect of the drug on the molecular target as may be manifest in an inhibition of, for instance, binding between two molecules. The assay can be formulated to detect the ability of a test agent or compound to inhibit binding of labeled ligand according to the invention to SV2 or a fragment of SV2 comprising the LBS or of L059, or derivatives or analogs thereof, to SV2 or a fragment of SV2 comprising the LBS. The inhibition of complex formation may be detected by a variety of techniques such as filtration assays, Flashplates (Perkin Elmer, scintillation proximity assays (SPA, Amersham Biosciences). For high-throughput screenings (HTS), scintillation proximity assay is a powerful method which uses microspheres coated with biological membranes and requires no separation or washing steps.

Labelled ligands are also useful for assessing the conformational state of SV2 after solubilization, purification, and chromatography. Moreover, the present invention provides photoactivable versions of the ligands for labelling and detection in biological samples. The photoactivable ligands may also be used to localize and purify SV2 from tissues, isolated cells, subcellular fractions and membranes. The photoactivable could also be used for SV2 cross-linking and identification of binding domains of LBS ligands.

EXAMPLES

The following examples are provided for illustrative purposes. Unless specified otherwise in the examples, characterization of the compounds is performed according to the following methods:

NMR spectra are recorded on a BRUKER AC 250 Fourier Transform NMR Spectrometer fitted with an Aspect 3000 computer and a 5 mm $^1$H/$^{13}$C dual probehead or BRUKER DRX 400 FT NMR fitted with a SG Indigo$^2$ computer and a 5 mm inverse geometry $^1$H/$^{13}$C/$^{15}$N triple probehead. The compound is studied in DMSO-d$_6$ (or CDCl$_3$) solution at a probe temperature of 313 K or 300 K and at a concentration of 20 mg/ml. The instrument is locked on the deuterium signal of DMSO-d$_6$ (or CDCl$_3$). Chemical shifts are given in ppm downfield from TMS taken as internal standard.

HPLC analyses are performed using one of the following systems:

an Agilent 1100 series HPLC system mounted with an INERTSIL ODS 3 C18, DP 5 µm, 250×4.6 mm column. The gradient ran from 100% solvent A (acetonitrile, water, H$_3$PO$_4$ (5/95/0.001, v/v/v)) to 100% solvent B (acetonitrile, water, H$_3$PO$_4$ (95/5/0.001, v/v/v)) in 6 min with a hold at 100% B of 4 min. The flow rate is set at 2.5 ml/min. The chromatography is carried out at 35° C.

a HP 1090 series HPLC system mounted with a HPLC Waters Symmetry C18, 250×4.6 mm column. The gradient ran from 100% solvent A (MeOH, water, H$_3$PO$_4$ (15/85/0.001M, v/v/M)) to 100% solvent B (MeOH, water, H$_3$PO$_4$ (85/15/0.001 M, v/v/M)) in 10 min with a hold at 100% B of 10 min. The flow rate is set at 1 ml/min. The chromatography is carried out at 40° C.

Mass Spectrometric Measurements in LC/MS Mode are Performed as Follows:

HPLC Conditions

Analyses are performed using a WATERS Alliance HPLC system mounted with an INERTSIL ODS 3, DP 5 µm, 250× 4.6 mm column.

The gradient ran from 100% solvent A (acetonitrile, water, TFA (10/90/0.1, v/v/v)) to 100% solvent B (acetonitrile, water, TFA (90/10/0.1, v/v/v)) in 7 min with a hold at 100% B of 4 min. The flow rate is set at 2.5 ml/min and a split of ⅕ is used just before API source.

MS Conditions

Samples are dissolved in acetonitrile/water, 70/30, v/v at the concentration of about 250 µgr/ml. API spectra (+ or −) are performed using a FINNIGAN (San Jose, Calif., USA) LCQ ion trap mass spectrometer. APCI source operated at 450° C. and the capillary heater at 160° C. ESI source operated at 3.5 kV and the capillary heater at 210° C. Mass spectrometric measurements in DIP/EI mode are performed as follows: samples are vaporized by heating the probe from 50° C. to 250° C. in 5 min. EI (Electron Impact) spectra are recorded using a FINNIGAN (San Jose, Calif., USA) TSQ 700 tandem quadrupole mass spectrometer. The source temperature is set at 150° C.

Mass spectrometric measurements on a TSQ 700 tandem quadrupole mass spectrometer (Finnigan MAT, San Jose, Calif., USA) in GC/MS mode are performed with a gas chromatograph model 3400 (Varian, Walnut Creek, Calif., USA) fitted with a split/splitless injector and a DB-5MS fused-silica column (15 m×0.25 mm I.D., 1 μm) from J&W Scientific (Folsom, Calif., USA). Helium (purity 99.999%) is used as carrier gas. The injector (CTC A200S autosampler) and the transfer line operate at 290 and 250° C., respectively. Sample (1 μl) is injected in splitless mode and the oven temperature is programmed as follows: 50° C. for 5 min., increasing to 280° C. (23° C./min) and holding for 10 min. The TSQ 700 spectrometer operates in electron impact (EI) or chemical ionization (CI/CH$_4$) mode (mass range 33-800, scan time 1.00 sec). The source temperature is set at 150° C. Also used is a 1100 LCMSD VL series, single quadrupole, APCI or API-ES ionization (Agilent Technologies, USA) equipped with the following HPLC columns: Luna C18 5 um 100×4.6 mm (Phenomenex, USA) or Hi-Q C18 5 um 100×4.6 mm (Peeke Scientific, USA) or Betasil C18 10 um 150×4.6 mm (ThermoHypersil, USA). GC/MS are also done with GC 6890 equipped with FID and 5973 MSD, single quadrupole, EI ionization (Agilent Technologies, USA) equipped with column: HP-5MS 30m×0.25 mm×0.25 um (Agilent Technologies, USA).

Specific rotation is recorded on a Perkin-Elmer 341 polarimeter. The angle of rotation is recorded at 25° C. on 1% solutions in MeOH. For some molecules, the solvent is CH$_2$Cl$_2$ or DMSO, due to solubility problems.

Melting points are determined on a Büchi 535 or 545 Tottoli-type fusionometer, and are not corrected, or by the onset temperature on a Perkin Elmer DSC 7.

Preparative chromatographic separations are performed on silicagel 60 Merck, particle size 15-40 μm, reference 1.15111.9025, using Novasep axial compression columns (80 mm i.d.), flow rates between 70 and 150 ml/min. Amount of silicagel and solvent mixtures as described in individual procedures.

Preparative Chiral Chromatographic separations are performed on a DAICEL Chiralpak AD 20 μm, 100*500 mm column using an in-house build instrument with various mixtures of lower alcohols and C5 to C8 linear, branched or cyclic alkanes at ±350 ml/min. Solvent mixtures as described in individual procedures.

The following abbreviations are used in the examples:

| | |
|---|---|
| AcOEt | Ethyl acetate |
| BINAP | (+/−)-2,2'-bis(diphenylphosphino)-1,1'-binaphthyl |
| CH$_3$CN | Acetonitrile |
| CH$_2$Cl$_2$ | Dichloromethane |
| DCE | 1,2-dichloroethane |
| DMF | N,N-Dimethylformamide |
| MTBE | Methyl tert-butyl ether |
| NBS | N-bromosuccinimide |
| NCS | N-chlorosuccinimide |
| NIS | N-iodosuccinimide |
| STAB | NaBH(OAc)$_3$ |
| TFA | Trifluoroacetic acid |
| THF | Tetrahydrofuran |

The following examples illustrate how the compounds covered by formula (I) can be synthesized.

Example 1

Synthesis of 1-[(5-nitro-1H-indol-3-yl)methyl]-4-propylpyrrolidin-2-one 148

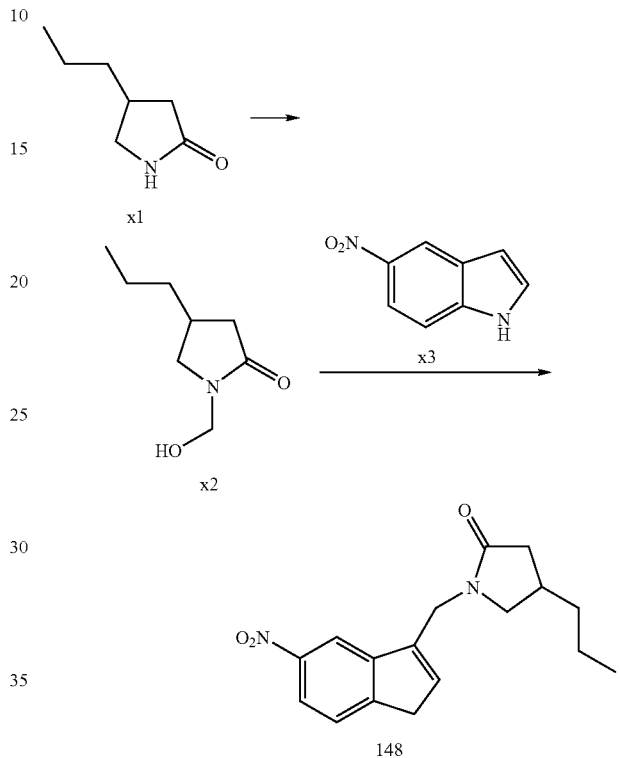

1.1. Synthesis of 1-(hydroxymethyl)-4-propylpyrrolidin-2-one x2

A solution of 4-propylpyrrolidin-2-one x1 (30 g, 0.236 mol), aqueous formaldehyde (37%, 3.5 eq, 0.826 mol, 71 ml), and potassium hydroxyde (0.05 eq, 0.012 mol, 0.662 g) in 150 ml of ethanol is refluxed for 24 hours. After evaporation of the solvent under reduced pressure, the crude product is poured in saturated NaHCO$_3$ aqueous solution and then extracted with CH$_2$Cl$_2$. The cumulated organic layers are dried over MgSO$_4$, filtered and evaporated under reduced pressure to yield compound 1-(hydroxymethyl)-4-propylpyrrolidin-2-one x2 as a colorless oil.

Yield: 100%.

LC-MS (MH$^+$): 158.

1.2. Synthesis of 1-[(5-nitro-1H-indol-3-yl)methyl]-4-propylpyrrolidin-2-one 148

A solution of 5-nitro-1H-indole x3 (100 mg, 1 eq, 0.62 mmol), 1-(hydroxymethyl)-4-propylpyrrolidin-2-one x2 (108.27 mg, 1 eq, 0.62 mmol), paratoluenesulfonic acid (11 mg, 0.1 eq, 0.062 mmol) in 5 ml of toluene is refluxed for 4 hours. After cooling to room temperature, the solvent is removed under reduced pressure and the crude product is purified by preparative chromatography on reverse phase (gradient: H$_2$O/CH$_3$CN/TFA: 95/5/0.1 (v/v/v) to 5/95/0.1

(v/v/v)) affording 1-[(5-nitro-1H-indol-3-yl)methyl]-4-propylpyrrolidin-2-one 148 as a colorless oil.

Yield: 44%.

LC-MS (MH$^+$): 302.

Compounds 142, 143, 144, 145, 146, 147, 149 and 150 may be synthesized according to the same method.

Example 2

Synthesis of 1-[2-furyl(1H-indol-3-yl)methyl]-4-propylpyrrolidin-2-one 153

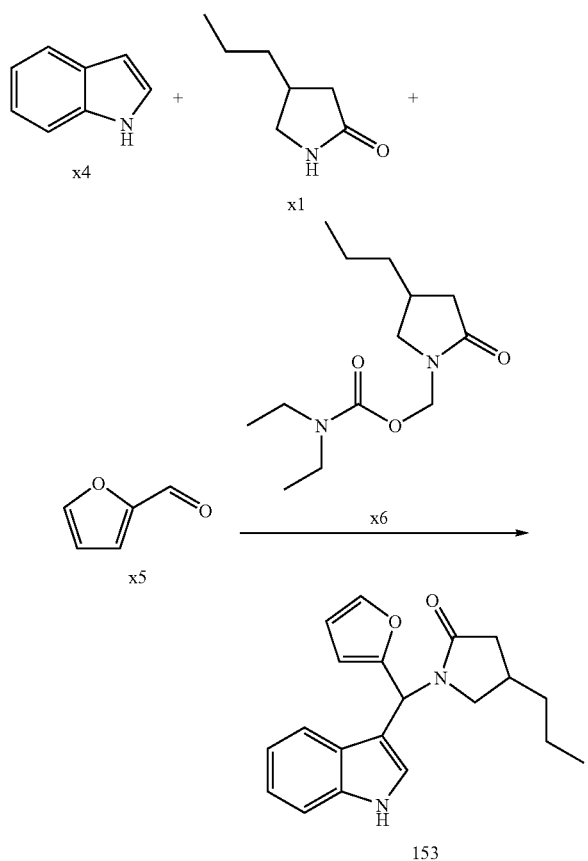

2.1. Synthesis of (2-oxo-4-propylpyrrolidin-1-yl)methyl diethylcarbamate x6

To a solution of 1-(hydroxymethyl)-4-propylpyrrolidin-2-one x2 (4 g, 25.44 mmol) and triethylamine (1.2 eq, 30.53 mmol, 3.089 g, 4.26 ml) in CH$_2$Cl$_2$ (25 ml) is added dropwise a solution of diethylcarbamyl chloride (1.1 eq, 27.99 mmol, 3.795 g, 3.55 ml) in CH$_2$Cl$_2$ (5 ml) at room temperature. The reaction mixture is allowed to react under agitation and inert atmosphere overnight. Hydrolysis (15 ml of water), extraction (CH$_2$Cl$_2$), drying of the combinated organic layers (MgSO$_4$), filtration and solvent evaporation under reduced pressure gives (2-oxo-4-propylpyrrolidin-1-yl)methyl diethylcarbamate x6 (100%) which is used without any further purification.

$^1$H NMR $\delta_H$ (250 MHz, CDCl$_3$): 0.93 (3H, t), 1.22 (6H, q), 1.4 (4H, m), 2.10 (1H, dd), 2.34 (1H, quint), 2.53 (1H, dd), 3.20 (1H, dd), 3.45 (4H, m), 3.65 (1H, dd), 4.78 (2H, q).

2.2. Synthesis of 1-[2-furyl(1H-indol-3-yl)methyl]-4-propylpyrrolidin-2-one 153

A solution of indole x4 (117 mg, 1 eq, 1 mmol), 4-propylpyrrolidin-2-one x1 (127 mg, 1 eq, 1 mmol), 2-furaldehyde x5 (0.33 ml, 4 eq, 4 mmol) and (2-oxo-4-propylpyrrolidin-1-yl)methyl diethylcarbamate x6 (25 mg, 0.1 eq, 0.1 mmol) in acetonitrile (3 ml) is heated 30 minutes in a microwave apparatus (Biotage, 150 W, 130° C.). After cooling to room temperature, the solvent is removed under reduced pressure, and the crude mixture is purified by preparative chromatography on silicagel (CH$_2$Cl$_2$) leading to 1-[2-furyl(1H-indol-3-yl)methyl]-4-propylpyrrolidin-2-one 153 as a brown solid.

Yield: 28%.

LC-MS (MH$^+$): 323.

Compounds 151, 152 and 154 may be synthesized according to the same method.

Example 3

Synthesis of 4-propyl-1-(1H-pyrrolo[2,3-b]pyridin-3-ylmethyl)pyrrolidin-2-one 231

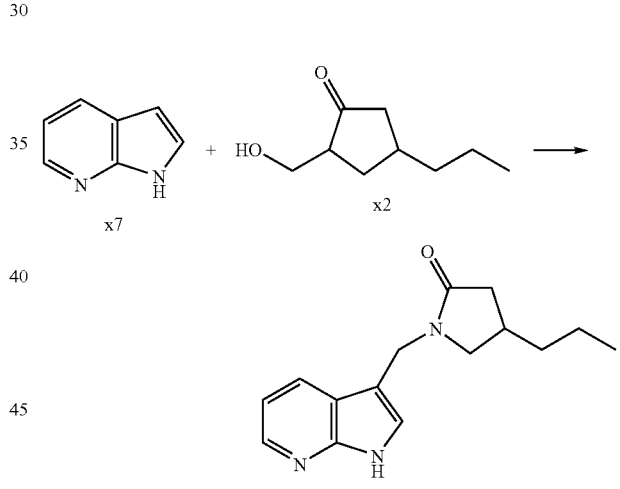

To a solution of commercially available 1H-pyrrolo[2,3-b]pyridine x7 (20.31 mmol, 1.2 eq, 3.19 g) dissolved TFA (25 ml) is added 1-(hydroxymethyl)-4-propylpyrrolidin-2-one x2 (16.93 mmol, 1 eq, 2 g). The mixture is heated at 70° C. overnight. The solvent is then evaporated under reduce pressure. CH$_2$Cl$_2$ (600 ml) is then added to the residue, and the resulting organic solution is washed with a saturated aqueous solution of sodium carbonate (200 ml). The organic phase is then dried over MgSO$_4$ and the volatiles are removed under reduced pressure. The product is purified by chromatography on silicagel (CH$_2$Cl$_2$/MeOH/NH$_4$OH: 97/3/0.3 (v/v/v)) and recristallized in acetonitrile. 4-propyl-1-(1H-pyrrolo[2,3-b]pyridin-3-ylmethyl)pyrrolidin-2-one 231 is obtained as a white solid.

Yield: 13%.

LC-MS (MH$^+$): 258.

Compounds 232, 233, 234, 244 and 246 may be synthesized according to the same method.

Example 4

Synthesis of 1-(imidazo[1,2-a]pyridin-3-ylmethyl)-4-phenylpyrrolidin-2-one 7

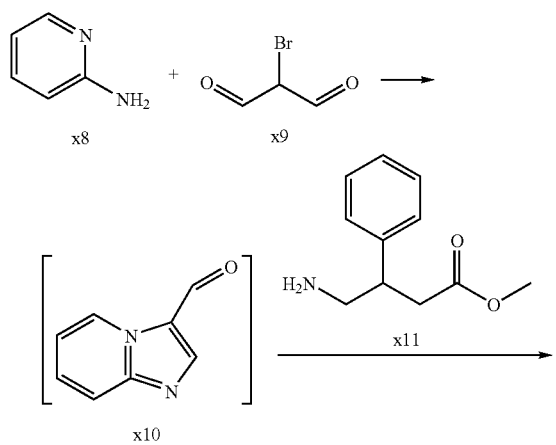

A solution of 2-aminopyridine x8 (1 g, 1 eq, 10.6 mmol) and bromomalonaldehyde x9 (1.6 g, 1 eq, 10.6 mmol) in 1.4-dioxane (20 ml) is refluxed for 3 days (Imidazo[1,2-a]pyridine-3-carbaldehyde x10 is formed in situ and not isolated). After cooling to room temperature, triethylamine (2.96 ml, 2 eq, 21.25 mmol), methyl 4-amino-3-phenylbutanoate hydrochloride x1 (2.44 g, 1 eq, 10.6 mmol) and ethanol (10 ml) are successively added. The mixture is then allowed to react during 3 days at room temperature. The reaction mixture is poured on ice, and organic solvents are removed under reduced pressure. The resulting aqueous layer is extracted by CH$_2$Cl$_2$ and the cumulated organic layers are dried over MgSO$_4$, filtered, and condensed under reduced pressure. The crude product is purified by preparative chromatography on silicagel (CH$_2$Cl$_2$/iPrOH: 97/3 (v/v)), then recristallized in ethyl acetate leading to 1-(imidazol-[1,2-a]pyridin-3-ylmethyl)-4-phenylpyrrolidin-2-one 7 as a white powder.

Yield: 8%.

LC-MS (MH$^+$): 292.

Methyl 3-(aminomethyl)hexanoate hydrochloride x12, useful for example for the synthesis of compound 3, may be prepared by esterification of the corresponding acid according to any method known to the person skilled in the art.

Compounds 3, 6, 8, 9, 10, 11, 12, 13, 14, 15, 16, 20, 22, 23, 28, 29, 155 and 156 may be synthesized as described for compound 7.

Example 5

Synthesis of 1-[(6-bromo-2-methylpyrazolo[1,5-a]pyrimidin-3-yl)methyl]-4-propylpyrrolidin-2-one 184

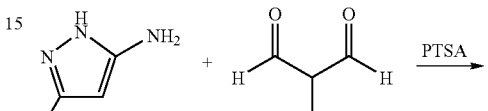

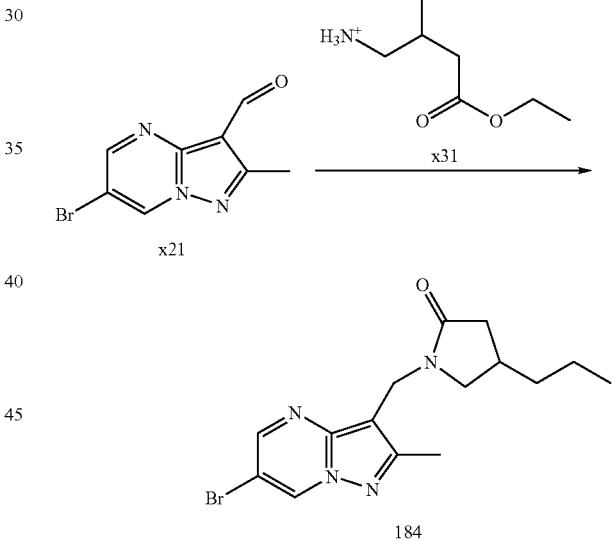

5.1. Synthesis of 6-bromo-2-methylpyrazolo[1,5-a]pyrimidine x14

To a solution of 3-methyl-1H-pyrazol-5-amine a12 (64.8 mmol, 1 eq, 6.3 g) in EtOH (100 ml), in the presence of PTSA, is added bromomalonaldehyde x9 (64.8 mmol, 1 eq, 9.79 g). The mixture is heated at 80° C. for 12 hours. The solvent is evaporated under reduce pressure and the residue purified by chromatography on silicagel (hexane/AcOEt: 93/7 (v/v)). 6-bromo-2-methylpyrazolo[1,5-a]pyrimidine x14 is obtained as a white solid (4.04 g).

Yield: 30%.

LC-MS (MH$^+$): 212/214.

The following compounds may be synthesized according to the same method:

| x15 | 2-methylpyrazolo[1,5-a]-pyrimidine | LC-MS (MH$^+$): 134 |
| --- | --- | --- |
| x16 | 6-bromo-2-(2-thienyl)pyrazolo[1,5-a]pyrimidine | LC-MS (MH$^+$): 280/282 |
| x17 | 6-bromo-2-phenylpyrazolo[1,5-a]pyrimidine | LC-MS (MH$^+$): 274/276 |
| x18 | 6-bromo-2-cyclopropylpyrazolo[1,5-a]pyrimidine | LC-MS (MH$^+$): 238/240 |
| x19 | 6-bromo-2-tert-butylpyrazolo[1,5-a]pyrimidine | LC-MS (MH$^+$): 254/256 |
| x20 | 6-chloro-2-phenylpyrazolo[1,5-a]pyrimidine | LC-MS (MH$^+$): 230/232 |

5.2. Synthesis of 6-bromo-2-methylpyrazolo[1,5-a]pyrimidine-3-carbaldehyde x21

POCl$_3$ (1.84 mmol, 1.3 eq, 172 µl) is added dropwise to DMF (1 ml) at 0° C. and the resulting solution is stirred at 0° C. during 30 minutes. Then, a solution of 6-bromo-2-methylpyrazolo[1,5-a]pyrimidine x14 (1.415 mmol, 1 eq, 300 mg) in DMF (1 ml) is added and the mixture is stirred for 30 minutes at room temperature. The reaction is quenched with water (100 ml). The resulting solid is filtered and washed with water to give 200 mg of 6-bromo-2-methylpyrazolo[1,5-a]pyrimidine-3-carbaldehyde x21 as a solid.

Yield: 59%.
LC-MS (MH$^+$): 240/242.

The following compounds may be synthesized according to the same method:

| x22 | 2-methylpyrazolo[1,5-a]pyrimidine-3-carbaldehyde | LC-MS (MH$^+$): 162 |
| --- | --- | --- |
| x23 | 6-bromo-2-(2-thienyl)pyrazolo[1,5-a]pyrimidine-3-carbaldehyde | LC-MS (MH$^+$): 308/310 |
| x24 | 6-bromo-2-cyclopropylpyrazolo[1,5-a]pyrimidine-3-carbaldehyde | LC-MS (MH$^+$): 266/268 |
| x25 | 2-(2-furyl)pyrazolo[1,5-a]pyrimidine-3-carbaldehyde | LC-MS (MH$^+$): 214 |
| x26 | 6-methyl-2-phenylpyrazolo[1,5-a]pyrimidine-3-carbaldehyde | LC-MS (MH$^+$): 238 |
| x27 | 5-methyl-2-phenylpyrazolo[1,5-a]pyrimidine-3-carbaldehyde | LC-MS (MH$^+$): 238 |
| x28 | 2-(2-thienyl)pyrazolo[1,5-a]pyrimidine-3-carbaldehyde | LC-MS (MH$^+$): 230 |
| x29 | 6-methylimidazo[2,1-b][1,3,4]thiadiazole-5-carbaldehyde | |
| x30 | 6-(4-methylphenyl)imidazo[2,1-b][1,3,4]thiadiazole-5-carbaldehyde | LC-MS (MH$^+$): 244 |

5.3. Synthesis of 1-[(6-bromo-2-methylpyrazolo[1,5-a]pyrimidin-3-yl)methyl]-4-propylpyrrolidin-2-one 184

Ethyl 3-(aminomethyl)hexanoate hydrochloride x31 is obtained by esterification of the corresponding carboxylic acid according to any method known to the person skilled in the art.

To a solution of 6-bromo-2-methylpyrazolo[1,5-a]pyrimidine-3-carbaldehyde x21 (0.83 mmol, 1 eq, 200 mg) in MeOH (10 ml), is added ethyl 3-(aminomethyl)hexanoate hydrochloride x31 (0.916 mmol, 1.1 eq, 192 mg) and the resulting solution is stirred at room temperature for 5 minutes. Triethylamine (0.916 mmol, 1.1 eq, 128 µl) is then added and the mixture is heated at 65° C. for 1 hour. After this time 1 hour, sodium borohydride is added (0.916 mmol, 1.1 eq, 34 mg). The reaction mixture is then heated at 65° C. for 2 hours. Water (100 ml) is added and the resulting mixture is extracted with CH$_2$Cl$_2$ (3×100 ml). The combined organic layers are combined, washed with brine (100 ml) and dried over MgSO$_4$. Volatiles are removed under reduce pressure and purified by chromatography on silicagel (CH$_2$Cl$_2$/MeOH/NH$_4$OH: 97/3/0.3) to give 130 mg of 1-[(6-bromo-2-methylpyrazolo[1,5-a]pyrimidin-3-yl)methyl]-4-propylpyrrolidin-2-one 184 as a solid.

Yield: 45%.
LC-MS (MH$^+$): 351/353.

Compounds 88, 89, 91, 92, 185, 187 and 193 may be synthesized as described for compound 184.

Example 6

Synthesis of 5-chloro-1-{[6-chloro-2-(trifluoromethyl)imidazo[1,2-b]pyridazin-3-yl]methyl}-1,3-dihydro-2H-indol-2-one 35

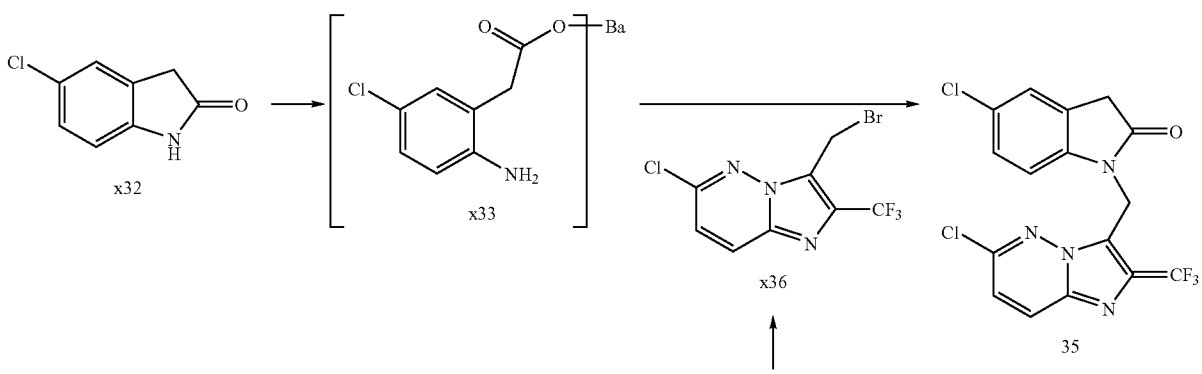

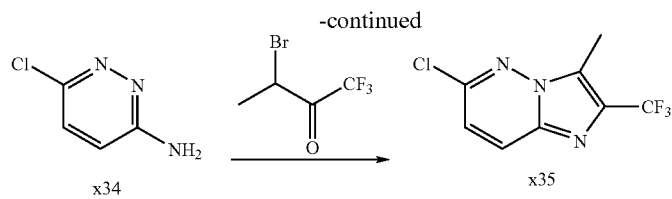

6.1. Synthesis of 6-chloro-3-methyl-2-(trifluoromethyl)imidazo[1,2-b]pyridazine x35

A solution of 6-chloro-3-aminopyridazine x34 (3.16 g, 1 eq, 24.2 mmol) and 3-bromo-1,1,1-trifluorobutan-2-one (5 g, 1 eq, 24.4 mmol) in 1,2-dimethoxyethane (100 ml) is refluxed during 17 hours. After cooling to room temperature and filtration, the solvent is removed under reduced pressure and the crude mixture is purified by preparative chromatography on silicagel ($CH_2Cl_2$/MeOH/$NH_4OH$: 98/2/0.2 (v/v/v)) leading to 6-chloro-3-methyl-2-(trifluoromethyl)imidazo[1,2-b]pyridazine x35.
Yield: 60%.
LC-MS ($MH^+$): 236/238.

6.2. Synthesis of 3-(bromomethyl)-6-chloro-2-(trifluoromethyl)imidazo[1,2-b]pyridazine x36

A mixture of 6-chloro-3-methyl-2-(trifluoromethyl)imidazo[1,2-b]pyridazine x35 (3.45 g, 1 eq, 14.64 mmol), N-bromosuccinimide (NBS; 2.87 g, 1.1 eq, 16.11 mmol) and azo-bis-iso-butyronitrile (AIBN; 240 mg, 0.1 eq, 1.5 mmol) in acetonitrile (50 ml) is refluxed for 2 hours. After cooling to room temperature, the solvent is removed under reduced pressure and the crude product is purified by preparative chromatography on silicagel ($CH_2Cl_2$) affording 3-(bromomethyl)-6-chloro-2-(trifluoromethyl)imidazo[1,2-b]pyridazine x36.
Yield: 35%.
LC-MS ($MH^+$): 315/317.

6.3. Synthesis of 5-chloro-1-{[6-chloro-2-(trifluoromethyl)imidazo[1,2-b]pyridazin-3-yl]methyl}-1,3-dihydro-2H-indol-2-one 35

To a suspension of 5-chloro-1,3-dihydro-2H-indol-2-one x32 (30 g, 1 eq, 0.1754 mol) in water (240 ml), is added barium hydroxyde (75.15 g, 2.5 eq, 0.4385 mol) at room temperature. The resulting suspension is heated at reflux for 17 hours, cooled to 0° C. and a 6 N hydrochloric acid solution (113 ml) is added (until pH 8). The resulting solution is heated at reflux for 30 minutes, cooled to 70° C. in 2 hours and then to 50° C. for 15 hours. The resulting suspension is progressively cooled to 0° C. and the solid collected by filtration. Subsequent washing of the solid by water (2×90 ml) and drying in vacuum oven (70° C.) furnished barium bis[(2-amino-5-chlorophenyl)acetate] x33 as a colorless powder (yield: 73%).

A mixture of barium bis[(2-amino-5-chlorophenyl)acetate] x33 (1.13 g, 1.5 eq, 3.34 mmol) and 3-(bromomethyl)-6-chloro-2-(trifluoromethyl)imidazo[1,2-b]pyridazine x36 (0.7 g, 1 eq, 2.22 mmol) in tetrahydrofuran (50 ml) is refluxed for 9 days. After cooling to room temperature, the reaction mixture is filtered over celite and concentrated under reduced pressure, the crude product is purified by preparative chromatography on silicagel ($CH_2Cl_2$/MeOH/$NH_4OH$: 99/1/0.1 (v/v/v)) and recristallized in toluene to yield 5-chloro-1-{[6-chloro-2-(trifluoromethyl)imidazo[1,2-b]pyridazin-3-yl]methyl}-1,3-dihydro-2H-indol-2-one 35 as a white powder.
Yield: 25%.
LC-MS ($MH^+$): 401/403/405.

Example 7

Synthesis of 1-{[6-(benzylamino)pyridin-3-yl]methyl}-4-propylpyrrolidin-2-one 229

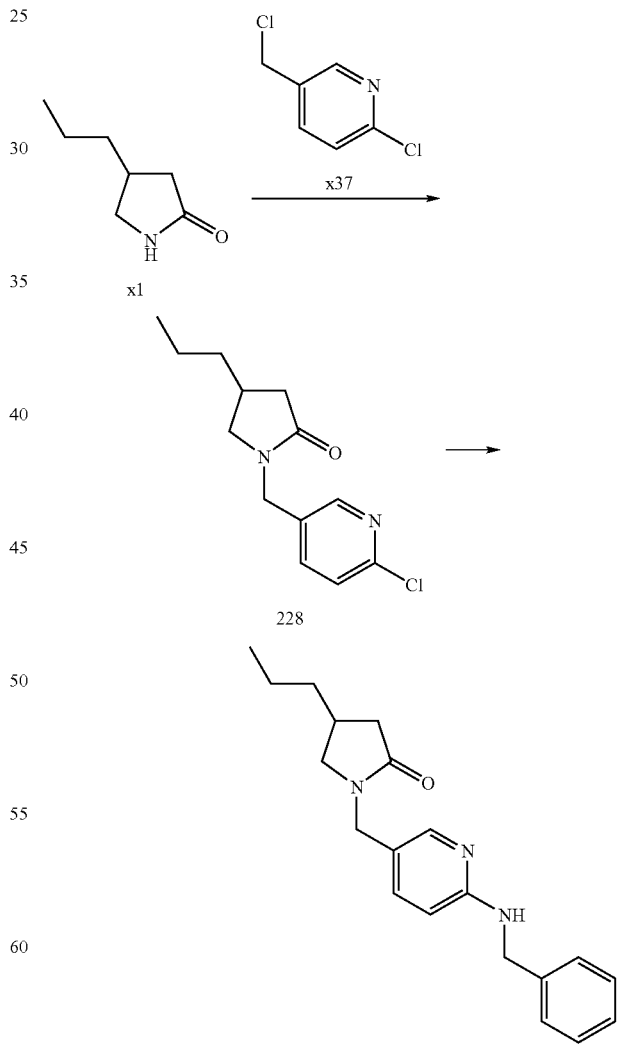

7.1 Synthesis of 1-[(6-chloropyridin-3-yl)methyl]-4-propylpyrrolidin-2-one 228

A solution of 4-propylpyrrolidin-2-one x1 (0.50 g, 3.93 mmol, 1 eq) and 2-chloro-5-(chloromethyl)pyridine x37 (0.64 g, 3.93 mmol, 1 eq) in acetonitrile (3 ml) is heated at 50° C. NaH (60% dispersion in oil, 158 mg, 3.93 mmol, 1 eq) and acetonitrile (5 ml) are added and the solution is stirred for 8 h at 50° C. The mixture is then poured on ice/water and the aqueous phase is extracted with $CH_2Cl_2$. The combined organic phases are dried over $MgSO_4$, filtered and concentrated to dryness. The crude product is purified by chromatography on silicagel ($CH_2Cl_2$/MeOH/$NH_4OH$: 99/1/0.1 (v/v/v)) to afford 790 mg of 1-[(6-chloropyridin-3-yl)methyl]-4-propylpyrrolidin-2-one 228.

Yield: 80%.

LC-MS (MH$^+$): 253/255.

Compound 224 and racemic 1-(1-pyridin-3-ylpropyl)pyrrolidin-2-one may be synthesized as described for compound 228.

Enantiomers 225 and 226 may be prepared from racemic 1-(1-pyridin-3-ylpropyl)pyrrolidin-2-one by separation by chiral chromatography.

7.2. Synthesis of 1-{[6-(benzylamino)pyridin-3-yl]methyl}-4-propylpyrrolidin-2-one 229

To a solution of 1-[(6-chloropyridin-3-yl)methyl]-4-propylpyrrolidin-2-one 228 (100 mg, 0.396 mmol, 1 eq), benzylamine (65 µl, 0.61 mmol, 1.6 eq) and potassium carbonate (274 mg, 1.98 mmol, 5 eq) is added a stirred solution of $Pd_2(dba)_3$ (Tris(dibenzylideneacetone)dipalladium(0), 18 mg, 0.02 mol, 0.05 eq) and BINAP (13 mg, 0.02 mol, 0.05 eq) in 2 ml of 1,4-dioxane. The mixture is heated at reflux for 36 h, filtered and concentrated. The crude product is dissolved in water and extracted three times with $CH_2Cl_2$. The organic phase is dried over $MgSO_4$, filtered and evaporated to dryness. The crude is purified by chromatography on silicagel ($CH_2Cl_2$/MeOH/$NH_4OH$: 97/3/0.3 (v/v/v)) to afford 14 mg of 1-{[6-(benzylamino)pyridin-3-yl]methyl}-4-propylpyrrolidin-2-one 229.

Yield: 11%.

LC-MS (MH$^+$): 324.

Example 8

Synthesis of 1-{[2-(methylamino)-1,3-thiazol-5-yl]methyl}-4-(2,3,5-trifluorophenyl)pyrrolidin-2-one 252

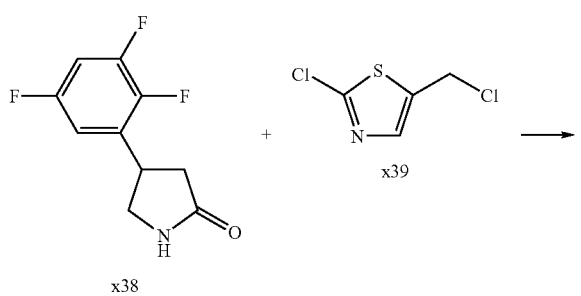

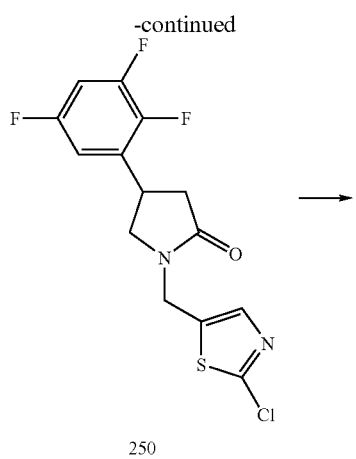

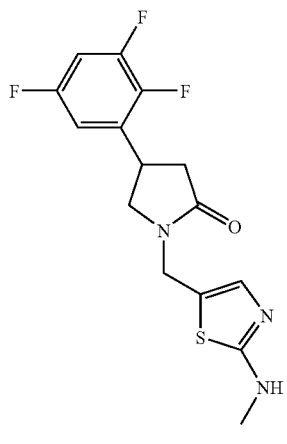

252

8.1. Synthesis of 4-(2,3,5-trifluorophenyl)pyrrolidin-2-one x38

4-(2,3,5-trifluorophenyl)pyrrolidin-2-one x38 is synthesized from nitromethane and ethyl 3-(2,3,5-trifluorophenyl)acrylate according to the methodology described in Kenda B. et al., J. Med. Chem. (2004), 47, 530-549.

8.2. Synthesis of 1-[(2-chloro-1,3-thiazol-5-yl)methyl]-4-(2,3,5-trifluorophenyl)pyrrolidin-2-one 250

In a 250 ml three-necked flask fitted with a magnetic stirrer and an addition funnel, under inert atmosphere, 1.04 g (0.026 mol) of sodium hydride (60% dispersion in oil, washed with hexane) is suspended in THF (80 ml) at 0° C. Compound x38 (4 g, 0.0183 mol), dissolved in THF, is added dropwise and the resulting mixture is stirred at room temperature for 0.5 h. A solution of 2-chloro-5-(chloromethyl)-1,3-thiazole x39 (3.12 g, 0.0186 mol) in THF is added and the solution is stirred at 50° C. overnight. The mixture is concentrated to dryness, dissolved in $CH_2Cl_2$, brine is added and the aqueous is extracted twice with $CH_2Cl_2$. The combined organic phases are dried over $MgSO_4$, filtered and evaporated. The crude product is purified by preparative chromatography on silicagel ($CH_2Cl_2$/MeOH/$NH_4OH$: 99.5/0.45/0.05 (v/v/v)) to afford 3.7 g of pure 1-[(2-chloro-1,3-thiazol-5-yl)methyl]-4-(2,3,5-trifluorophenyl)pyrrolidin-2-one 250.

Yield: 57%.

LC-MS (MH$^+$): 347/349.

8.3. Synthesis of 1-{[2-(methylamino)-1,3-thiazol-5-yl]methyl}-4-(2,3,5-trifluorophenyl)pyrrolidin-2-one 252

In a 50 ml sealed vessel, 1-[(2-chloro-1,3-thiazol-5-yl)methyl]-4-(2,3,5-trifluorophenyl)pyrrolidin-2-one 250 (0.1 g, 0.3 mmol) is dissolved in MeOH (3 ml). Sodium methoxide (3 mg, 0.06 mmol) and a solution of methylamine (0.09 g, 3 mmol) in MeOH are added. The vessel is closed and heated to 95° C. for 48 h. The reaction mixture is cooled to room temperature, the solvent is evaporated and the residue is taken up in $CH_2Cl_2$ and water. The aqueous phase is extracted twice with $CH_2Cl_2$, the combined organic phases are washed with brine, dried over $MgSO_4$, filtered and concentrated in vacuo. The crude product is recrystallized from AcOEt to afford 185 mg of 1-{[2-(methylamino)-1,3-thiazol-5-yl]methyl}-4-(2,3,5-trifluorophenyl)pyrrolidin-2-one 252.

Yield: 57%.

LC-MS ($MH^+$): 342.

Example 9

Synthesis of 4-propyl-1-(1,3,4-thiadiazol-2-ylmethyl)pyrrolidin-2-one 247

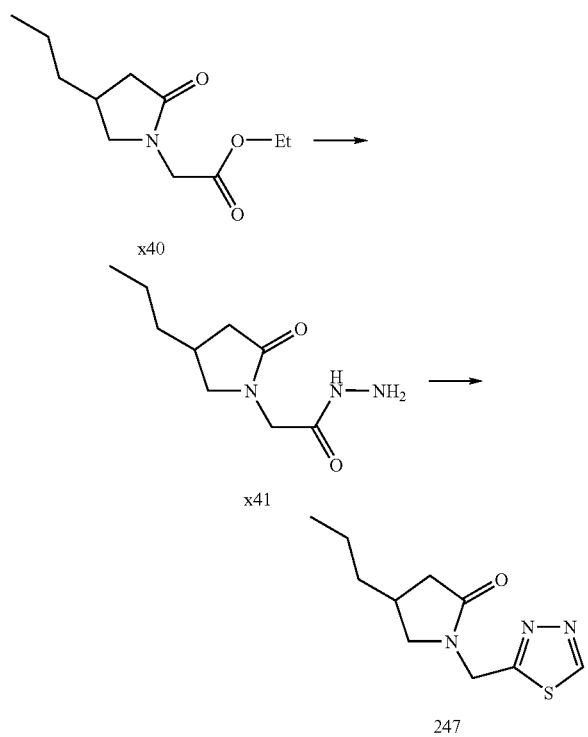

9.1. Synthesis of 1-[2-(aminooxy)-2-oxoethyl]-4-propylpyrrolidin-2-one x40

1-[2-(aminooxy)-2-oxoethyl]-4-propylpyrrolidin-2-one x40 is synthesized from ethyl bromoacetate and 4-propylpyrrolidin-2-one according to the methodology described in Kenda B. et al. (J. Med. Chem. (2004), 47, 530-49).

9.2. Synthesis of 2-(2-oxo-4-propylpyrrolidin-1-yl)acetohydrazide x41

In a 250 ml three necked flask fitted with a magnetic stirrer, hydrazine hydrate (5.78 g, 0.18 mol, 3 eq) is added to a solution of 1-[2-(aminooxy)-2-oxoethyl]-4-propylpyrrolidin-2-one x40 (11.99 g, 60.29 mmol) in EtOH (125 ml). The mixture is heated 4 h at reflux, cooled down to room temperature, diluted with brine and extracted with $CH_2Cl_2$. The combined organic phases are dried over $MgSO_4$, filtered and evaporated to afford 11.0 g of 2-(2-oxo-4-propylpyrrolidin-1-yl)acetohydrazide x41.

Yield: 83%.

LC-MS ($MH^+$): 200.

9.3. Synthesis of 4-propyl-1-(1,3,4-thiadiazol-2-ylmethyl)pyrrolidin-2-one 247

In a 25 ml vessel, a mixture of 2-(2-oxo-4-propylpyrrolidin-1-yl)acetohydrazide x41 (0.5 g, 2.5 mmol) and acetic acid (5 ml) is stirred overnight at room temperature and concentrated to dryness. The residue is dissolved in AcOEt, washed with a saturated solution of $NaHCO_3$, water and brine. The aqueous phase is saturated with NaCl, extracted with a mixture of $CH_2Cl_2$ and MeOH (9/1 (v/v)), resaturated with $Na_2CO_3$ and re-extracted with $CH_2Cl_2$. The combined organic phases are dried over $MgSO_4$, filtered and evaporated. The crude intermediate (2.3 mmol) is dissolved in 40 ml of dioxane, $P_2S_5$ (0.51 g, 2.3 mmol) is added at 0° C. and the mixture is stirred at room temperature during 9.5 h. The solvent is evaporated and the crude product is purified by column chromatography on silicagel ($CH_2Cl_2$/MeOH/$NH_4OH$: 95/4.5/0.5 (v/v/v)) to give 88 mg of 4-propyl-1-(1,3,4-thiadiazol-2-ylmethyl)pyrrolidin-2-one 247.

Yield: 16%.

LC-MS ($MH^+$): 226.

Example 10

Synthesis of 1-[(1-methyl-1H-imidazol-5-yl)methyl]-4-phenylpyrrolidin-2-one hydrochloride 119

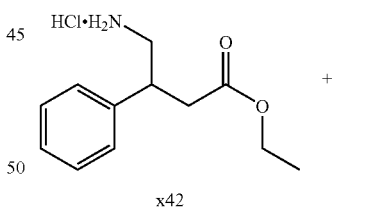

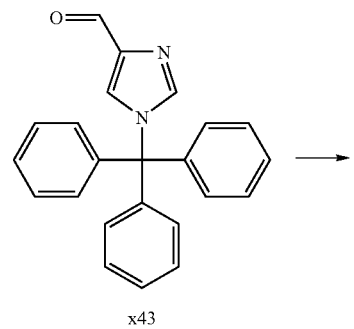

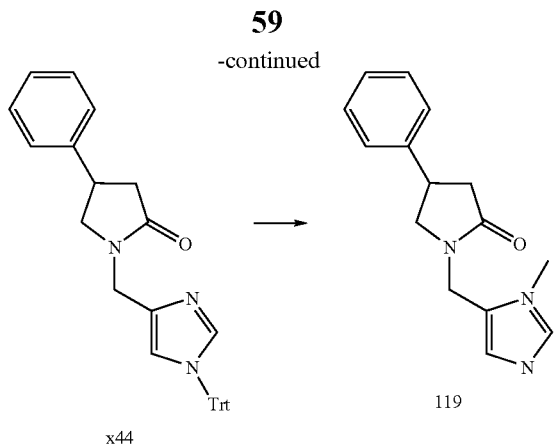
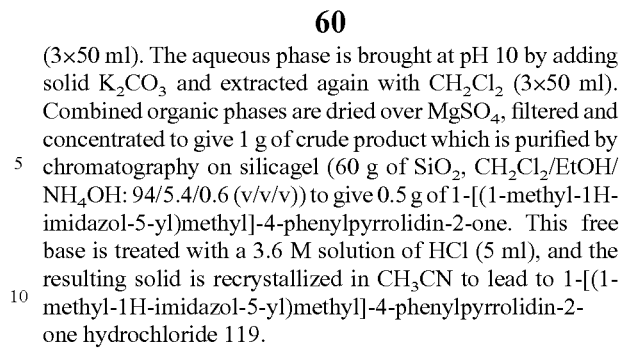

10.1. Synthesis of 4-phenyl-1-[(1-trityl-1H-imidazol-4-yl)methyl]pyrrolidin-2-one x44

In a 500 ml, three-necked flask fitted with a magnetic stirrer and a reflux condenser under inert atmosphere, ethyl 4-amino-3-phenylbutanoate hydrochloride x42 (synthesized as described in patent application EP1265862, 6.2 g, 38 mmol), 1-trityl-1H-imidazole-4-carbaldehyde x43 (Dolensky B., Kirk K. L., Collect. Czech. Chem. Commun. (2002), 67, 1335-1344; 8.2 g, 36.1 mmol) and MeOH (150 ml) are stirred at room temperature. Triethylamine (3.9 ml, 41.85 mmol) and NaBH$_4$ (1.06 g, 41.8 mmol) are added by portions. The mixture is stirred at 45° C. for 3 h, then at room temperature overnight. CH$_2$Cl$_2$ (300 ml) and water (300 ml) are added, the aqueous phase is extracted with CH$_2$Cl$_2$ (2×200 ml). The combined organic phases are washed with a saturated solution of NH$_4$Cl (2×150 ml), dried, filtered and concentrated in vacuo. The crude product is recrystallized from AcOEt to afford 4-phenyl-1-[(1-trityl-1H-imidazol-4-yl)methyl]pyrrolidin-2-one x44.

Yield: 36%.
LC-MS (MH$^+$): 484.

The following compounds may be synthesized according to the same method:

| | | |
|---|---|---|
| x45 | 4-propyl-1-[(1-trityl-1H-imidazol-4-yl)methyl]-pyrrolidin-2-one | LC-MS (MH$^+$): 450 |
| x46 | 1-[(1-trityl-1H-imidazol-4-yl)methyl]pyrrolidin-2-one | LC-MS (MH$^+$): 408 |
| x47 | 4-(2,3,5-trifluorophenyl)-1-[(1-trityl-1H-imidazol-4-yl)methyl]pyrrolidin-2-one | LC-MS (MH$^+$): 538 |

10.2. Synthesis of 1-[(1-methyl-1H-imidazol-5-yl)methyl]-4-phenylpyrrolidin-2-one hydrochloride 119

In a 50 ml, three-necked flask fitted with a magnetic stirrer, under inert atmosphere, 4-phenyl-1-[(1-trityl-1H-imidazol-4-yl)methyl]pyrrolidin-2-one x44 (2 g, 4.1 mmol) is dissolved in CH$_3$CN (20 ml) and MeI (283 µL, 4.5 mmol) is added. The mixture is stirred at room temperature and two additional portions of MeI (283 µl and 500 µl) are added after 40 h and 46 h. After stirring for 16 h at room temperature, the mixture is concentrated and dissolved in a 1/1 mixture of AcOH and water. After stirring at room temperature for 48 h, the mixture is filtered and evaporated to dryness (by azeotropic distillation with toluene). The residue is dissolved in a solution of HCl at pH 1 (25 ml) and extracted with CH$_2$Cl$_2$ (3×50 ml). The aqueous phase is brought at pH 10 by adding solid K$_2$CO$_3$ and extracted again with CH$_2$Cl$_2$ (3×50 ml). Combined organic phases are dried over MgSO$_4$, filtered and concentrated to give 1 g of crude product which is purified by chromatography on silicagel (60 g of SiO$_2$, CH$_2$Cl$_2$/EtOH/NH$_4$OH: 94/5.4/0.6 (v/v/v)) to give 0.5 g of 1-[(1-methyl-1H-imidazol-5-yl)methyl]-4-phenylpyrrolidin-2-one. This free base is treated with a 3.6 M solution of HCl (5 ml), and the resulting solid is recrystallized in CH$_3$CN to lead to 1-[(1-methyl-1H-imidazol-5-yl)methyl]-4-phenylpyrrolidin-2-one hydrochloride 119.

Yield: 33%.
LC-MS (MH$^+$): 256.

Compounds 116, 121 and 1-[(1-methyl-1H-imidazol-5-yl)methyl]-4-(2,3,5-trifluorophenyl)pyrrolidin-2-one x48 may be synthesized as described for compound 119.

Example 11

Synthesis of 1-[(2,4-dichloro-1-methyl-1H-imidazol-5-yl)methyl]-4-propylpyrrolidin-2-one 129

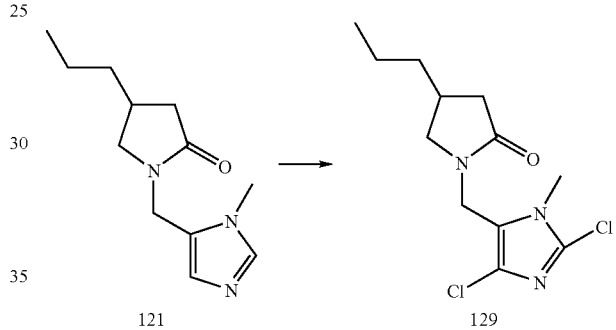

Synthesis of 1-[(2,4-dichloro-1-methyl-1H-imidazol-5-yl)methyl]-4-propylpyrrolidin-2-one 129 is performed by chlorination of 1-[(1-methyl-1H-imidazol-5-yl)methyl]-4-propylpyrrolidin-2-one 121 with 2 equivalents of N-chlorosuccinimide under standard conditions known by the person skilled in the art.

LC-MS (MH$^+$): 290/292/294.

Example 12

Synthesis of N-benzyl-2-{5-[(2-oxo-4-propylpyrrolidin-1-yl)methyl]-1H-imidazol-1-yl}acetamide 124

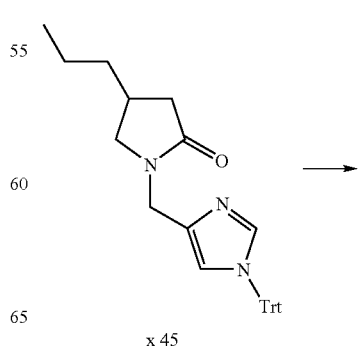

61

-continued

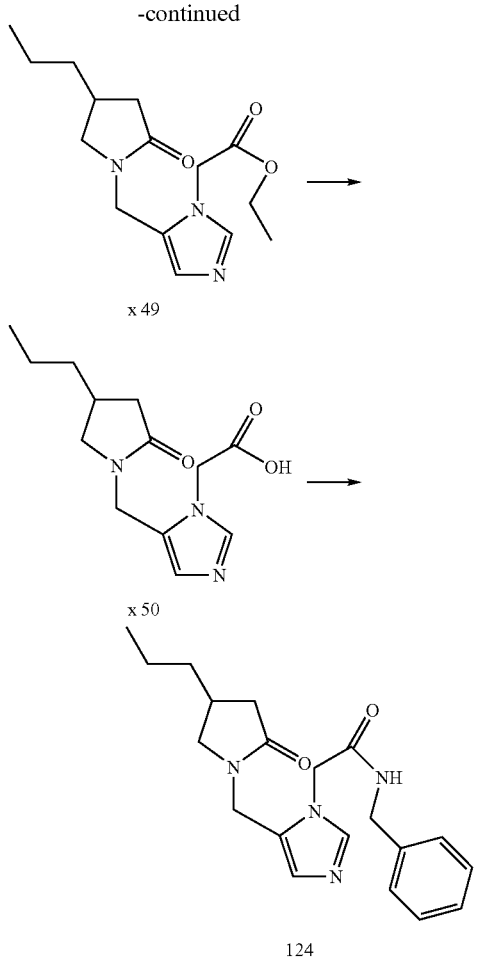

12.1. Synthesis of ethyl {5-[(2-oxo-4-propylpyrroli-din-1-yl)methyl]-1H-imidazol-1-yl}acetate hydrochloride x49

In a 50 ml, three-necked flask fitted with a magnetic stirrer under inert atmosphere, ethylbromoacetate (560 μl, 4.95 mmol) is added to a solution of 4-propyl-1-[(1-trityl-1H-imidazol-4-yl)methyl]pyrrolidin-2-one x45 (1.5 g, 3.3 mmol) in 10 ml of acetonitrile. The mixture is stirred at 40° C. for 3 h, 1.65 mmol of ethylbromoacetate is added and stirring is pursued for 48 h at room temperature. The mixture is concentrated in vacuo, 20 ml of a 1/1 mixture of acetic acid and water is added and the mixture is stirred at room temperature overnight. The mixture is filtered, the solvent is evaporated and the residue is dissolved in 25 ml of diluted HCl (pH 1). The aqueous phase is washed with $CH_2Cl_2$, basified to pH 10 by addition of solid $Na_2CO_3$ and extracted three times with $CH_2Cl_2$. The combined organic phases are dried over $MgSO_4$, filtered and concentrated to dryness. The crude product is purified by tin layer chromatography on preparative plates ($CH_2Cl_2$/EtOH: 90/10 (v/v)) to give 275 mg of ethyl {5-[(2-oxo-4-propylpyrrolidin-1-yl)methyl]-1H-imidazol-1-yl}acetate (30%). Ethyl {5-[(2-oxo-4-propylpyrrolidin-1-yl)methyl]-1H-imidazol-1-yl}acetate hydrochloride x49 is obtained by treatment with a solution of HCl in $Et_2O$ and recrystallization from $CH_3CN$/AcOEt.

Yield: 16%.
LC-MS ($MH^+$): 294.

62

12.2. Synthesis of {5-[(2-oxo-4-propylpyrrolidin-1-yl)methyl]-1H-imidazol-1-yl}acetic acid x50

In a 250 ml, three necked flask fitted with a magnetic stirrer, ethyl {5-[(2-oxo-4-propylpyrrolidin-1-yl)methyl]-1H-imidazol-1-yl}acetate hydrochloride x49 (5.19 g, 0.018 mol) is dissolved in 2M HCl (150 ml) and heated at 40° C. for 20 h. The reaction mixture is evaporated to dryness to afford the crude acid x50 (6.19 g) that is used as such in the next step.

LC-MS ($MH^+$): 266.

12.3. Synthesis of N-benzyl-2-{5-[(2-oxo-4-propylpyrrolidin-1-yl)methyl]-1H-imidazol-1-yl}acetamide 124

In a 10 ml, three necked flask fitted with a magnetic stirrer, under inert atmosphere, {5-[(2-oxo-4-propylpyrrolidin-1-yl)methyl]-1H-imidazol-1-yl}acetic acid x50 (0.1 g, 0.33 mmol) is dissolved in DMF (1 ml). Triethylamine (0.1 ml, 0.66 mmol), benzylamine (37 μl, 0.33 mmol) and TBTU (0.16 g, 0.33 mmol) are added and the mixture is stirred for 0.5 h at room temperature. An additional amount of benzylamine (0.0165 mmol) is added and stirring is continued overnight. The solvent is evaporated and the residue is purified by chromatography on silicagel (AcOEt/MeOH/$NH_4OH$: 90/9/1 (v/v/v)). The product is treated with a methanolic solution of HCl and the obtained solid is recrystallized from acetonitrile to afford N-benzyl-2-{5-[(2-oxo-4-propylpyrrolidin-1-yl)methyl]-1H-imidazol-1-yl}acetamide 124.

Yield: 43%.
LC/MS ($MH^+$): 355.

Example 13

Synthesis of 1-[(3,5-dimethyl-1H-pyrazol-4-yl)methyl]-4-(2,3,5-trifluorophenyl)pyrrolidin-2-one 167

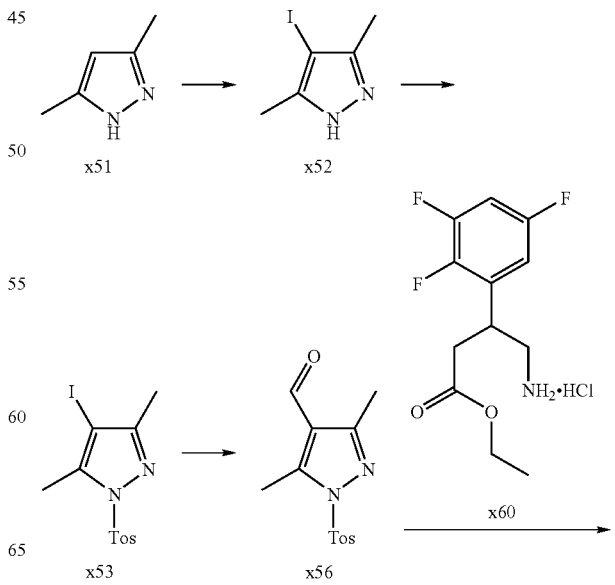

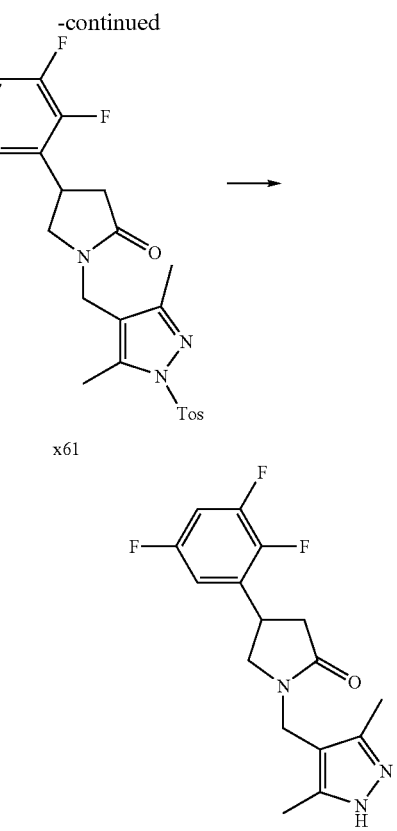

x61

167

13.1. Synthesis of 4-iodo-3,5-dimethyl-1H-pyrazole x52

In a 250 ml reaction vessel, 3,5-dimethyl-1H-pyrazole x51 (0.5 g, 5 mmol), $I_2$ (0.79 g, 30 mmol) and CAN (1.71 g, 3 mmol) are dissolved in 70 ml of $CH_3CN$ and stirred at room temperature for 16 h. The solvent is evaporated, the residue dissolved in AcOEt and washed with a 10% aqueous solution of $Na_2S_2O_3$ and brine. The aqueous phase is re-extracted with AcOEt and the combined organic phases are dried over $Na_2SO_4$, filtered and concentrated to dryness to afford 1.15 g (100%) of crude 4-iodo-3,5-dimethyl-1H-pyrazole x52, which is used in the next step without further purification.

LC-MS (MH$^+$): 223.

13.2. Synthesis of 4-iodo-3,5-dimethyl-1-[(4-methylphenyl)sulfonyl]-1H-pyrazole x53

In a 50 ml reaction vessel under argon, a solution of crude 4-iodo-3,5-dimethyl-1H-pyrazole x52 (1.15 g, 5.2 mmol) in 25 ml of dry $CH_2Cl_2$ is added to 4-methylbenzenesulfonyl chloride (1.18 g, 6.2 mmol). Pyridine (0.42 ml, 5.2 mmol) is added and the mixture is stirred for 16 h at room temperature. The organic phase is washed with water, dried over $MgSO_4$, filtered and concentrated. The residue is purified by column chromatography on silicagel ($CH_2Cl_2$/hexane: 70/30 (v/v)) to afford 4-iodo-3,5-dimethyl-1-[(4-methylphenyl)sulfonyl]-1H-pyrazole x53 (1.44 g).

Yield: 74%.

LC-MS (MH$^+$): 377.

The following compounds may be synthesized according to the same method:

| | | |
|---|---|---|
| x54 | 4-iodo-3-methyl-1-[(4-methylphenyl)sulfonyl]-1H-pyrazole | LC-MS (MH$^+$): 363 |
| x55 | 4-iodo-1-[(4-methylphenyl)sulfonyl]-1H-pyrazole | LC-MS (MH$^+$): 349 |

13.3. Synthesis of 3,5-dimethyl-1-[(4-methylphenyl)sulfonyl]-1H-pyrazole-4-carbaldehyde x56

In a reaction vessel under inert atmosphere, 4-iodo-3,5-dimethyl-1-[(4-methylphenyl)sulfonyl]-1H-pyrazole x53 (1.44 g, 3.8 mmol) is dissolved in dry THF (10 ml) and cooled down to −73° C. A 2M solution of isopropylmagnesiumchloride in THF (9.6 mmol, 4.8 ml) is added dropwise and the mixture is stirred at −73° C. for 1 h. Then 0.44 ml of DMF (5.7 mmol) are added and the solution stirred at room temperature overnight. DMF (1.9 mmol) is further added and stirring is continued for 16 h. The reaction mixture is quenched with a saturated solution of $NH_4Cl$, extracted three times with $CH_2Cl_2$, the organic phase is washed with brine, dried over $MgSO_4$, filtered and concentrated in vacuo to give 0.88 g of crude 3,5-dimethyl-1-[(4-methylphenyl)sulfonyl]-1H-pyrazole-4-carbaldehyde x56, which is used in the next step without any further purification.

Yield: 82%.

LC-MS (MH$^+$): 279.

The following compounds may be synthesized according to the same method:

| | | |
|---|---|---|
| x57 | 3-methyl-1-[(4-methylphenyl)sulfonyl]-1H-pyrazole-4-carbaldehyde | LC-MS (MH$^+$): 265 |
| x58 | 1-[(4-methylphenyl)sulfonyl]-1H-pyrazole-4-carbaldehyde | LC-MS (MH$^+$): 251 |
| x59 | 1-[(4-methylphenyl)sulfonyl]-1H-pyrazole-5-carbaldehyde | LC-MS (MH$^+$): 251 |

13.4. Synthesis of 1-({3,5-dimethyl-1-[(4-methylphenyl)sulfonyl]-1H-pyrazol-4-yl}methyl)-4-(2,3,5-trifluorophenyl)pyrrolidin-2-one x61

In a 100 ml three-necked flask fitted with a magnetic stirrer, under inert atmosphere, 3,5-dimethyl-1-[(4-methylphenyl)sulfonyl]-1H-pyrazole-4-carbaldehyde x56 (0.87 g, 3.1 mmol) and ethyl 4-amino-3-(2,3,5-trifluorophenyl)butanoate hydrochloride x60 (synthesized from nitromethane and ethyl 3-(2,3,5-trifluorophenyl)acrylate by the same methodology as described in Kenda et al., J. Med. Chem. (2004), 47, 530-49; 0.94 g, 3.1 mmol) are dissolved in $CH_2Cl_2$ (30 ml). Triethylamine (0.86 ml, 6.3 mmol) and NaBH(OAc)$_3$ (1.33 g, 6.3 mmol) are added and the heterogeneous mixture became a solution. After 16 h at room temperature, two additional portions of NaBH(OAc)$_3$ are added (1.6 mmol after 16 h and 3.2 mmol after 48 h) and 1.6 mmol of triethylamine are added after 24 h stirring at room temperature. The reaction is quenched with water and the aqueous phase is extracted three times with diethylether. The combined organic phases are washed with brine, dried over $MgSO_4$, filtered and concentrated to dryness. The crude product is purified by column chromatography on silicagel ($CH_2Cl_2$/MeOH/NH$_4$OH: 95/4.5/0.5 (v/v/v)) to afford 0.83 g of 1-({3,5-dimethyl-1-[(4-methylphenyl)sulfonyl]-1H-pyrazol-4-yl}methyl)-4-(2,3,5-trifluorophenyl)pyrrolidin-2-one x61.

Yield: 55%.

LC-MS (MH+): 478.

Compounds 158, 159, 160, 161, 163, 165, 169, 175, 176, 179, 180 and 1-({3-methyl-1-[(4-methylphenyl)sulfonyl]-1H-pyrazol-4-yl}methyl)-4-(2,3,5-trifluorophenyl)pyrrolidin-2-one x62 may be synthesized as described for compound x61.

13.5. Synthesis of 1-[(3,5-dimethyl-1H-pyrazol-4-yl)methyl]-4-(2,3,5-trifluorophenyl)pyrrolidin-2-one 167

In a 100 ml flask fitted with a magnetic stirrer and a reflux condenser under inert atmosphere, 1-({3,5-dimethyl-1-[(4-methylphenyl)sulfonyl]-1H-pyrazol-4-yl}methyl)-4-(2,3,5-trifluorophenyl)pyrrolidin-2-one x61 (0.83 g, 1.7 mmol) is dissolved in THF (40 ml). A 1 M solution of tetrabutylammonium fluoride in THF (1.7 ml, 1.7 mmol) is added and the mixture is heated at 85° C. for 48 h. The solvent is evaporated and the residue is dissolved in water. The aqueous phase is extracted six times with diethylether and the combined organic phases are dried over MgSO$_4$, filtered and concentrated in vacuo. The crude product is purified by preparative chromatography on silicagel and recrystallized from AcOEt to give 77 mg of 1-[(3,5-dimethyl-1H-pyrazol-4-yl)methyl]-4-(2,3,5-trifluorophenyl)pyrrolidin-2-one 167.

Yield: 14%.

LC-MS (MH+): 324.

Compounds 164, 168 and 181 may be synthesized as described for compound x61.

Enantiomers 171 and 172 may be obtained after separation by chiral chromatography (Chiralpak AD; hexane/iPrOH/Et$_2$NH: 90/10/01 (v/v/v)) of racemic compound 164.

Example 14

Synthesis of 1-[(5-amino-1-methyl-1H-pyrazol-4-yl)methyl]-4-propylpyrrolidin-2-one 170

In a 25 ml, three-necked flask fitted with a magnetic stirrer, under inert atmosphere, 1-(chloromethyl)-4-propylpyrrolidin-2-one x63 (0.136 g, 0.77 mmol) is added dropwise to a suspension of AlCl$_3$ (0.033 g, 0.25 mmol) in TCE at 0° C. In another 25 ml, three-necked flask fitted with a magnetic stirrer and reflux condenser under inert atmosphere, 1-methyl-1H-pyrazol-5-amine x64 (0.05 g, 0.51 mmol) is dissolved in TCE (10 ml) and the mixture is heated at 65° C. At this temperature, the solution containing compound x63 and AlCl$_3$ is added dropwise and the mixture is heated at 80° C. for 16 h. Water and CH$_2$Cl$_2$ are added, the pH is brought up to 8 with sodium bicarbonate and the aqueous phase is extracted with CH$_2$Cl$_2$. The combined organic phases are washed with brine, dried over MgSO$_4$, filtered and concentrated. The crude product is purified by preparative chromatography on silicagel, then by preparative chromatography on reverse phase to afford 19 mg of 1-[(5-amino-1-methyl-1H-pyrazol-4-yl)methyl]-4-propylpyrrolidin-2-one 170.

Yield: 16%.

LC-MS (MH+): 237.

Example 15

Synthesis of 1-[(1-methyl-1H-pyrazol-5-yl)methyl]-4-(2,3,5-trifluorophenyl)pyrrolidin-2-one 183

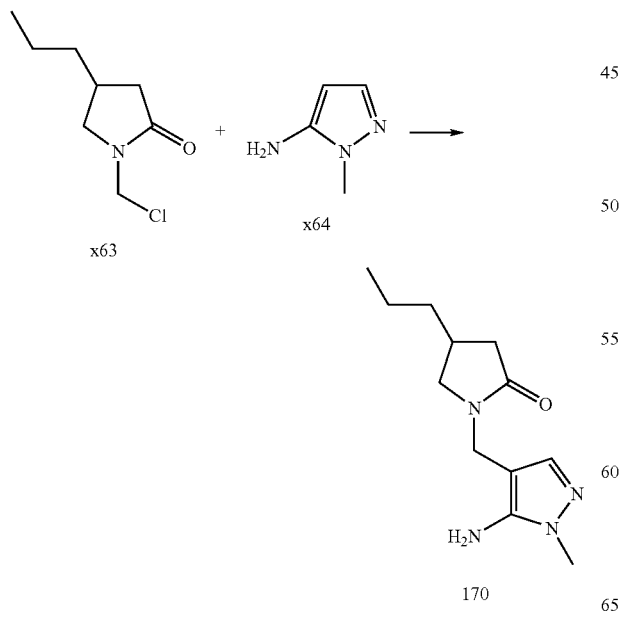

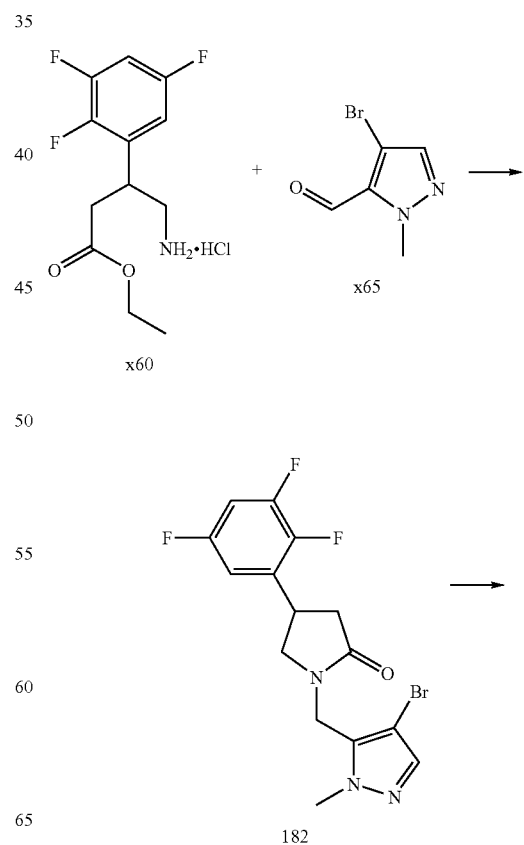

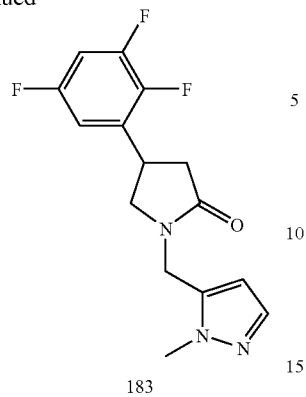

183

15.1. Synthesis of 1-[(4-bromo-1-methyl-1H-pyrazol-5-yl)methyl]-4-(2,3,5-trifluorophenyl)pyrrolidin-2-one 182

1-[(4-bromo-1-methyl-1H-pyrazol-5-yl)methyl]-4-(2,3,5-trifluorophenyl)pyrrolidin-2-one 182 is prepared as for compound x61 starting from ethyl 4-amino-3-(2,3,5-trifluorophenyl)butanoate hydrochloride x60 and 4-bromo-1-methyl-1H-pyrazole-5-carbaldehyde x65.

LC-MS (MH+): 388/390.

15.2. Synthesis of 1-[(1-methyl-1H-pyrazol-5-yl)methyl]-4-(2,3,5-trifluorophenyl)pyrrolidin-2-one 183

In a 250 ml pressure jar, under inert atmosphere, 1-[(4-bromo-1-methyl-1H-pyrazol-5-yl)methyl]-4-(2,3,5-trifluorophenyl)pyrrolidin-2-one 182 (0.41 g, 1 mmol) is dissolved in MeOH (50 ml). Pd on charcoal (82 mg, 20% w/w) is added and the mixture is hydrogenated under a pressure of 40 psi at room temperature for 3 h. The mixture is filtered on Celite and concentrated to dryness. The residue is purified by column chromatography on silicagel (CH$_2$Cl$_2$/MeOH/NH$_4$OH: 98/1.8/0.2 (v/v/v)) and recrystallized from diisopropylether to afford 0.18 g of 1-[(1-methyl-1H-pyrazol-5-yl)methyl]-4-(2,3,5-trifluorophenyl)pyrrolidin-2-one 183.

Yield: 58%.
LC-MS (MH+): 310.

Example 16

Synthesis of 1-(pyridazin-4-ylmethyl)pyrrolidin-2-one 222

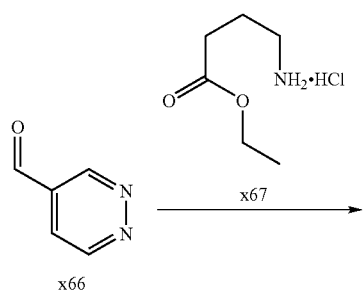

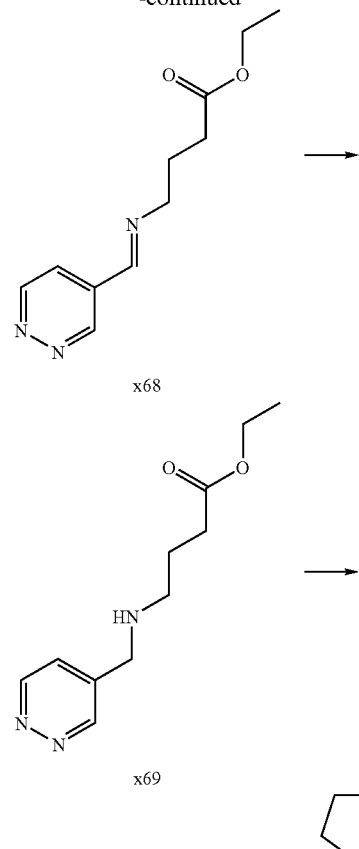

16.1. Synthesis of ethyl 4-[(pyridazin-4-ylmethylene)amino]butanoate x68

In a 25 ml, three-necked flask fitted with a magnetic stirrer under inert atmosphere, pyridazine-4-carbaldehyde x66 (0.93 g, 8.6 mmol) and ethyl 4-aminobutanoate hydrochloride x67 (1.58 g, 9.5 mmol) are dissolved in CHCl$_3$ (15 ml). Triethylamine (1.3 ml, 9.5 mmol) and MgSO$_4$ (2 g) are added and the mixture is stirred at room temperature for 4 h. The mixture is filtered, washed with water, dried over MgSO$_4$ and concentrated to give 1.92 g (100%) of crude ethyl 4-[(pyridazin-4-ylmethylene)amino]butanoate x68, which is used in the next step without further purification.

$^1$H NMR (250 MHz, DMSO): 1.16 (t, 3H), 1.9 (qt, 2H), 2.38 (t, 2H), 3.67 (t, 2H), 4.05 (q, 2H), 7.89 (m, 1H), 8.44 (s, 1H), 9.34 (m, 1H), 9.47 (s, 1H).

16.2. Synthesis of ethyl 4-[(pyridazin-4-ylmethyl)amino]butanoate x69

In a 50 ml, three-necked flask fitted with a magnetic stirrer, under inert atmosphere, ethyl 4-[(pyridazin-4-ylmethylene)amino]butanoate x68 (1.92 g, 8.7 mmol) is dissolved in MeOH (20 ml). Acetic acid (1.1 ml, 8.7 mmol), sodium acetate (0.71 g, 8.7 mmol) and NaCNBH$_3$ (1.1 g, 17.4 mmol)

are added and the reaction temperature rises to 47° C. The mixture is stirred for 1.25 h at room temperature, evaporated and the resulting residue is purified by column chromatography on silicagel (CH$_2$Cl$_2$/EtOH/NH$_4$OH: 96/5.4/0.6 (v/v/v)) to afford 0.72 g as a mixture of ethyl 4-[(pyridazin-4-ylmethyl)amino]butanoate x69 and 1-(pyridazin-4-ylmethyl)pyrrolidin-2-one 47 in a 75/25 ratio, which is used as such in the next step.

LC-MS (MH$^+$): 224.

16.3. Synthesis of 1-(pyridazin-4-ylmethyl)pyrrolidin-2-one 222

In a 25 ml, three-necked flask fitted with a magnetic stirrer and a reflux condenser under inert atmosphere, the mixture described in 16.2 (0.72 g, 75/25 (w/w), 3.4 mmol)) is dissolved in acetic acid (10 ml) and brought to reflux for 4.5 h. The solvent is removed by azeotropic distillation with toluene, the crude product is purified by chromatography on silicagel (CH$_2$Cl$_2$/MeOH: 92/8 (v/v)) and recrystallized from toluene to give 127 mg of 1-(pyridazin-4-ylmethyl)pyrrolidin-2-one 222.

Yield: 21%.

LC-MS (MH$^+$): 178.

Example 17

Synthesis of 5-chloro-1-[(2-fluoropyridin-3-yl)methyl]-1,3-dihydro-2H-indol-2-one 227

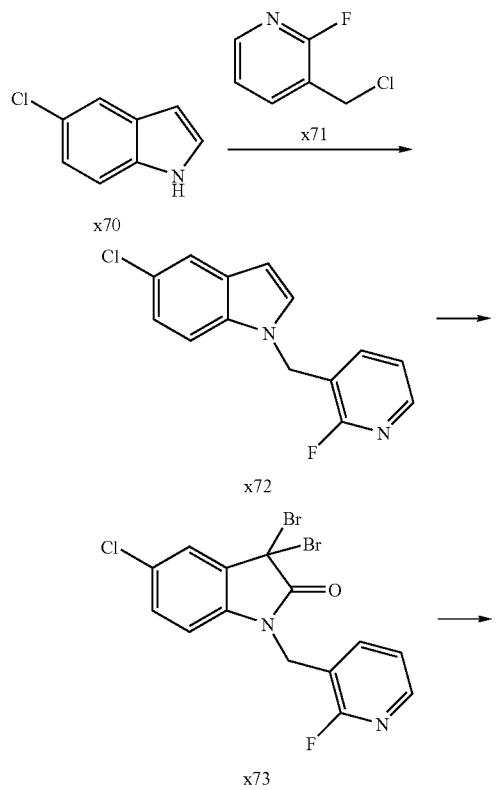

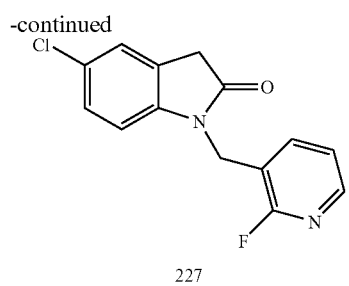

17.1. Synthesis of 5-chloro-1-[(2-fluoropyridin-3-yl)methyl]-1H-indole x72

In a 50 ml, three-necked flask fitted with a magnetic stirrer under inert atmosphere, 5-chloro-1H-indole x70 (1.13 g, 7.43 mmol) is dissolved in dry DMF (20 ml). At 0° C., NaH (327 mg, 8.18 mmol, 60% in mineral oil) is added and the mixture is stirred at this temperature for 0.3 h. A solution of 3-(chloromethyl)-2-fluoropyridine x71 (obtained from (2-fluoropyridin-3-yl)methanol and SOCl$_2$ (1.3 g, 8.92 mmol)) in DMF (5 ml) is then added and stirring is continued for 0.5 h at 0° C. The reaction mixture is poured on ice and the aqueous phase is extracted three times with AcOEt. The combined organic phases are dried over MgSO$_4$, filtered and concentrated. Purification by chromatography on silicagel (Hexane/AcOEt:9/1 (v/v)) affords 5-chloro-1-[(2-fluoropyridin-3-yl)methyl]-1H-indole x72 as a solid (1.13 g).

Yield: 59%.

$^1$H NMR (250 MHz, DMSO): 5.5 (s, 2H), 6.5 (s, 1H), 7.1 (dd, 1H), 7.3 (m, 1H), 7.4-7.6 (m, 3H), 7.6 (d, 1H), 8.1 (d, 1H).

17.2. Synthesis of 3,3-dibromo-5-chloro-1-[(2-fluoropyridin-3-yl)methyl]-1,3-dihydro-2H-indol-2-one x73

In a 100 ml, three-necked flask fitted with a magnetic stirrer under inert atmosphere, pyridine hydrobromide perbromide (4.04 g, 12.65 mmol) is added to a suspension of 5-chloro-1-[(2-fluoropyridin-3-yl)methyl]-1H-indole x72 (1.10 g, 4.22 mmol) in t-BuOH. The mixture is stirred at room temperature for 0.5 h. Water is added and the aqueous phase is extracted three times with AcOEt. The combined organic phases are dried over MgSO$_4$, filtered and concentrated to dryness to afford 1.79 g of 3,3-dibromo-5-chloro-1-[(2-fluoropyridin-3-yl)methyl]-1,3-dihydro-2H-indol-2-one x73, which is used in the next step without further purification.

Yield: 98%.

$^1$H NMR (250 MHz, DMSO): 5.15 (s, 2H), 7.20 (d, 1H), 7.50 (m, 1H), 7.56 (dd, 1H), 7.90-7.97 (m, 2H), 8.30 (d, 1H).

17.3. Synthesis of 5-chloro-1-[(2-fluoropyridin-3-yl)methyl]-1,3-dihydro-2H-indol-2-one 227

In a 50 ml, three-necked flask fitted with a magnetic stirrer under inert atmosphere, 3,3-dibromo-5-chloro-1-[(2-fluoropyridin-3-yl)methyl]-1,3-dihydro-2H-indol-2-one x73 (1.79 g, 4.12 mmol) is dissolved in AcOH (20 ml) and, at 0° C., powdered zinc (2.7 g, 41.2 mmol) is added. The mixture is stirred for 10 min at room temperature, filtered on Celite and concentrated to dryness. The residue is purified by chromatography on silicagel (Hexane/AcOEt:6/4 (v/v)) to give 104 mg of 5-chloro-1-[(2-fluoropyridin-3-yl)methyl]-1,3-dihydro-2H-indol-2-one 227.

Yield: 35%.
LC-MS (DIP) (M+1): 276/278.

Example 18

Synthesis of 1-[(6-amino-9H-purin-9-yl)methyl]-4-propylpyrrolidin-2-one 283

18.1. Synthesis of 1-[(6-chloro-9H-purin-9-yl)methyl]-4-propylpyrrolidin-2-one x75

A solution of commercially available 6-chloro-7H-purine x74 (0.5 g, 3.23 mmol), 1-(hydroxymethyl)-4-propylpyrrolidin-2-one x2 (1 eq, 3.23 mmol, 0.508 g), and (2-oxo-4-propylpyrrolidin-1-yl)methyl diethylcarbamate x6 (0.1 eq, 83 mg, 0.32 mmol) in acetonitrile (5 ml) is heated 30 minutes in a microwave apparatus (Biotage, 150 W, 130° C.). After cooling to room temperature, the solvent is removed under reduced pressure and the crude product is purified by preparative chromatography leading to 600 mg of pure 1-[(6-chloro-9H-purin-9-yl)methyl]-4-propylpyrrolidin-2-one x75.

Yield: 63%.
LC-MS (MH+): 294/296.

18.2. Synthesis of 1-[(6-amino-9H-purin-9-yl)methyl]-4-propylpyrrolidin-2-one 283

A solution of intermediate x75 (600 mg, 2.04 mmol), ammonium formiate (644 mg, 5 eq, 10.21 mmol) and palladium on charcoal (10% wt, 109 mg, 0.1 mmol) in a 1 to 1 mixture of THF and methanol (20 ml) is allowed to react at ambient temperature for 16 hours. After filtration on celite and solvent evaporation, the crude product is purified using preparative chromatography on silicagel to furnish a crude compound which is recristallized in a mixture of $CH_2Cl_2$ and hexane to furnish 1-[(6-amino-9H-purin-9-yl)methyl]-4-propylpyrrolidin-2-one 283 as a white crystalline product (320 mg).

Yield: 60%.
LC-MS (MH+): 260.

Example 19

Synthesis of 1-(3H-imidazo[4,5-b]pyridin-3-ylmethyl)-4-propylpyrrolidin-2-one 268

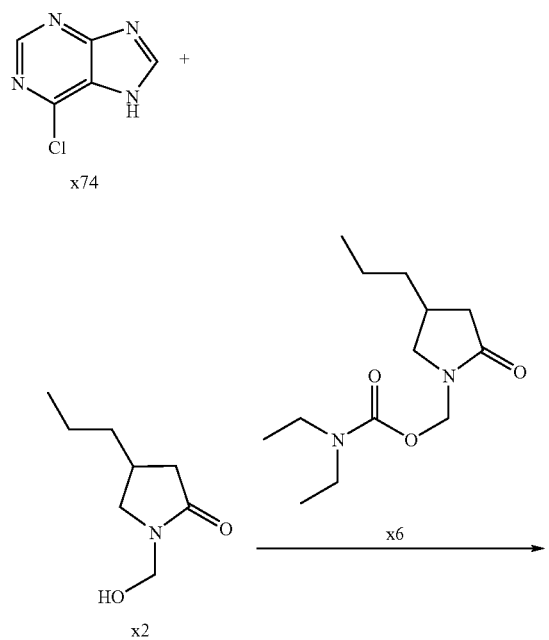

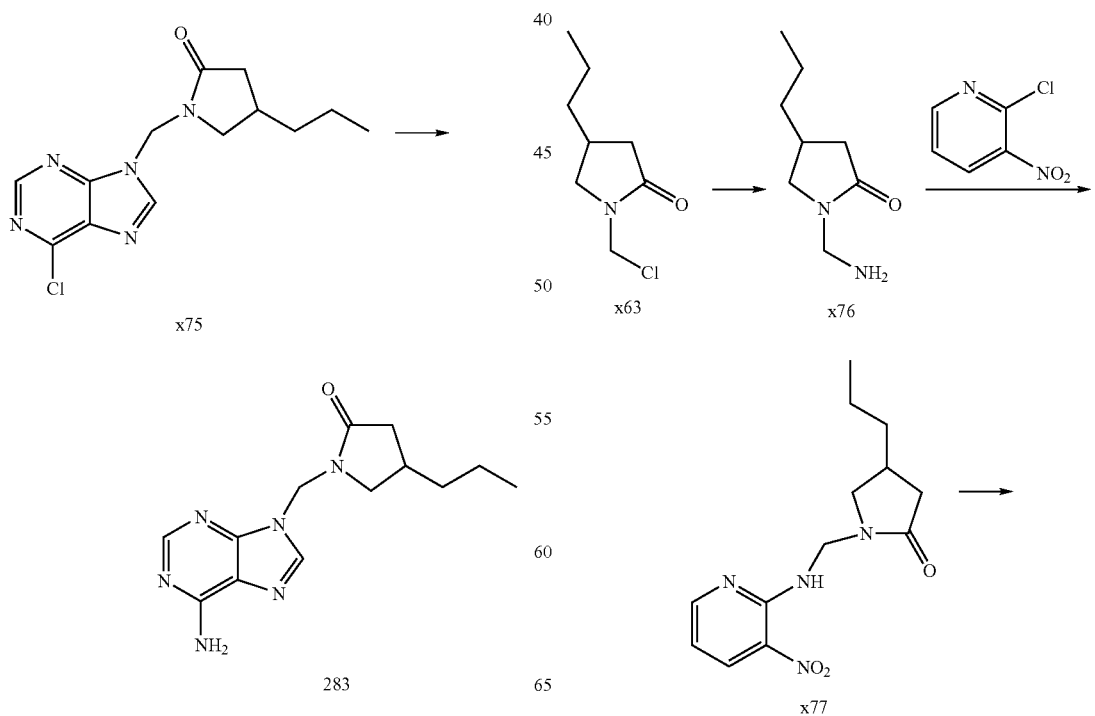

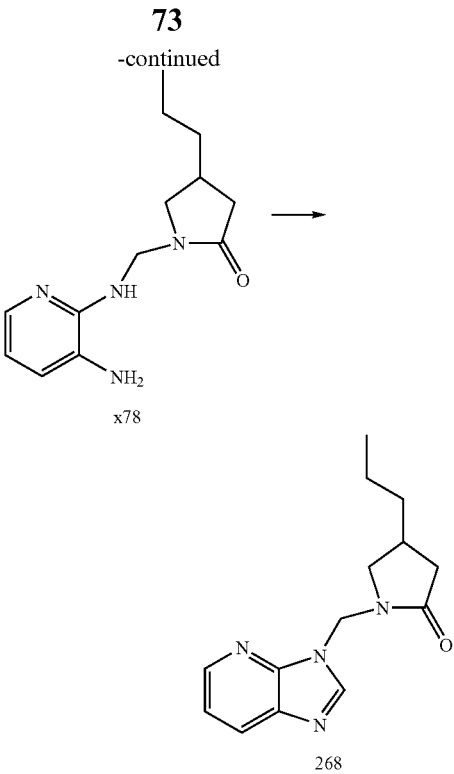

19.1. Synthesis of 1-(aminomethyl)-4-propylpyrrolidin-2-one x76

A solution of 1-(chloromethyl)-4-propylpyrrolidin-2-one x63 (41.34 g, 0.235 mol) in toluene (350 ml) is added dropwise at −78° C. to liquid ammonia (300 ml). At the end of the addition, the temperature is raised slowly to room temperature, and ammonia of the crude mixture is allowed to distille at room temperature overnight. Filtration of the reaction mixture and subsequent evaporation lead to 55 g of the crude 1-(aminomethyl)-4-propylpyrrolidin-2-one x76 which is used without further purification.

LC-MS (MH$^+$): 157.

19.2. Synthesis of 1-{[(3-nitropyridin-2-yl)amino]methyl}-4-propylpyrrolidin-2-one x77

A mixture of 1-(aminomethyl)-4-propylpyrrolidin-2-one x76 (1 eq, 17.09 mmol, 2.67 g), 2-chloro-3-nitropyridine (1 eq, 17.09 mmol, 2.709 g) and triethylamine (1.1 eq, 18.8 mmol, 1.902 g, 2.62 ml) in dioxane (20 ml) is refluxed 48 h. After cooling, the crude mixture is filtrated and the dioxane is distilled under vacuum. The residue is purified by preparative chromatography to afford 2.5 g of 1-{[(3-nitropyridin-2-yl)amino]methyl}-4-propylpyrrolidin-2-one x77.

Yield: 53%.
LC-MS (MH$^+$): 279.

19.3. Synthesis of 1-{[(3-aminopyridin-2-yl)amino]methyl}-4-propylpyrrolidin-2-one x78

Palladium on charcoal (10% wt, 0.478 g) is added to a solution of 1-{[(3-nitropyridin-2-yl)amino]methyl}-4-propylpyrrolidin-2-one x77 (1 eq, 2.5 g, 8.983 mmol) and NH$_4$CO$_2$H (5 eq, 44.9 mmol, 2.832 g) in water and methanol (1/1 (v/v), 35 ml). The resulting slurry is kept under agitation during 16 hours at room temperature, then filtration over celite and evaporation of the crude mixture afford 2.524 g of 1-{[(3-aminopyridin-2-yl)amino]methyl}-4-propylpyrrolidin-2-one x78.

Yield: 100%.
$^1$H NMR (250 MHz, CDCl$_3$) δ ppm: 0.88 (3H, t); 1.26-1.38 (4H, m); 2.02 (1H, dd); 2.28 (1H, quint); 2.47 (1H, dd); 3.22 (1H, dd), 3.37 (2H, s, broad); 3.73 (1H, dd); 5.02 (2H, d), 5.40 (1H, m, broad); 6.55 (1H, dd), 6.85 (1H, dd), 7.67 (1H, dd).

19.4. 1-(3H-imidazo[4,5-b]pyridin-3-ylmethyl)-4-propylpyrrolidin-2-one 268

A solution of 1-{[(3-aminopyridin-2-yl)amino]methyl}-4-propylpyrrolidin-2-one x78 (1 eq, 1.6 mmol, 300 mg), and para-toluenesulfonic acid (0.32 mmol, 0.2 eq, 42 mg) in trimethyl orthoformate (15 ml) is allowed to react at room temperature for 3 days. After hydrolysis (20 ml of saturated NaHCO$_3$), extraction with AcOEt (2×10 ml), drying of the cumulated organic layers over MgSO$_4$, and filtration, the volatiles are removed under reduced pressure and the crude material is purified by preparative chromatography affording 250 mg of 1-(3H-imidazo[4,5-b]pyridin-3-ylmethyl)-4-propylpyrrolidin-2-one 268.

Yield: 61%.
LC-MS (MH$^+$): 259.

Example 20

Synthesis of 1-[(5-bromo-2H-pyrazolo[3,4-b]pyridin-2-yl)methyl]-4-propylpyrrolidin-2-one 291

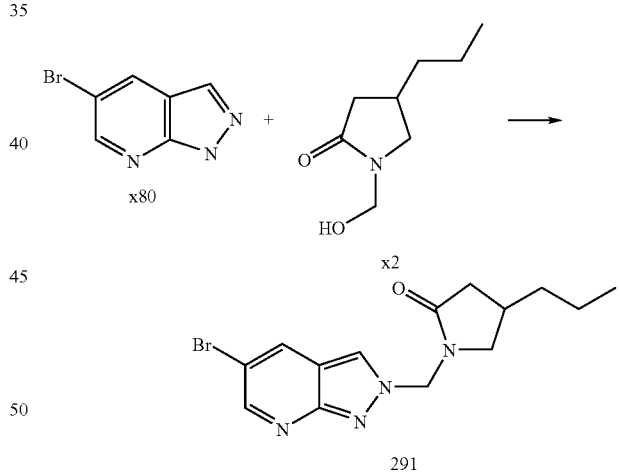

20.1. Synthesis of 5-bromo-1H-pyrazolo[3,4-b]pyridine x80

-continued

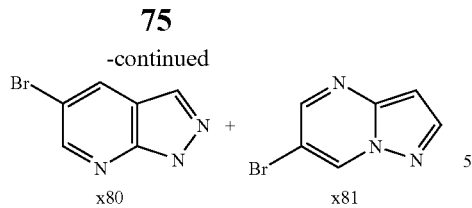
x80    x81

A solution of 1H-pyrazol-5-amine x79 (25 g, 1 eq, 0.3 mol) and bromomalonaldehyde x9 (45.4 g, 1 eq, 0.3 mol) ethanol (250 ml) is refluxed for 2 hours. After cooling, the reaction mixture is stirred at room temperature overnight. The solvent is removed under reduced pressure and the crude is purified using chiral chromatography affording 5-bromo-1H-pyrazolo[3,4-b]pyridine x80 (yield: 2.1%; LC-MS (MH$^+$): 198/200) and 6-bromopyrazolo[1,5-a]pyrimidine x81 (yield: 13.8%; LC-MS (MH$^+$): 198/200).

20.2. Synthesis of 1-[(5-bromo-2H-pyrazolo[3,4-b]pyridin-2-yl)methyl]-4-propylpyrrolidin-2-one 291

A solution of 5-bromo-1H-pyrazolo[3,4-b]pyridine x80 (1 g, 1 eq, 5.04 mmol) and 1-(hydroxymethyl)-4-propylpyrrolidin-2-one x2 (1.58 g, 2 eq, 10.08 mmol) in trifluoroacetic acid (20 ml) is refluxed for 4 hours. The reaction mixture is poured on crushed ice, on saturated NaHCO$_3$ aqueous solution, and the aqueous phase is extracted with dichloromethane. The cumulated organic layers are dried over MgSO$_4$, filtered, evaporated under reduced pressure. The crude product is purified by preparative chromatography on silicagel affording 1-[(5-bromo-2H-pyrazolo[3,4-b]pyridin-2-yl)methyl]-4-propylpyrrolidin-2-one 291 as a white solid.

Yield: 7.8%.

LC-MS (MH$^+$): 337/339.

Compound 265 may be synthesized according to the same method.

Example 21

Synthesis of 1-(1H-1,2,4-triazol-1-ylmethyl)pyrrolidin-2-one 297

In a three-necked flask fitted with a reflux condenser, a magnetic stirrer, and under inert atmosphere, triazole (1.0 g, 14.5 mmol) is dissolved in THF (10 ml) at room temperature. Sodium hydride (0.64 g, 16 mmol) is added by portions under efficient stirring. The temperature raises to 31° C. The resulting mixture is refluxed, 1-(chloromethyl)pyrrolidin-2-one (1.93 g, 14.5 mmol) is added, and further stirring is applied for 2 hours. The mixture is cooled down to room temperature, diluted with CH$_2$Cl$_2$ and water, and concentrated to dryness. The crude mixture is purified by chromatography on silicagel (CH$_2$Cl$_2$/MeOH/NH$_4$OH: 96/4/0.4) and recrystallized from toluene to afford 0.59 g of 1-(1H-1,2,4-triazol-1-ylmethyl)pyrrolidin-2-one 297.

Yield: 24.5%.

LC-MS (MH$^+$): 167.

Example 22

Synthesis of 1-{[2-(dimethylamino)-1,3-thiazol-5-yl]methyl}-4-(2,3,5-trifluorophenyl)pyrrolidin-2-one 251

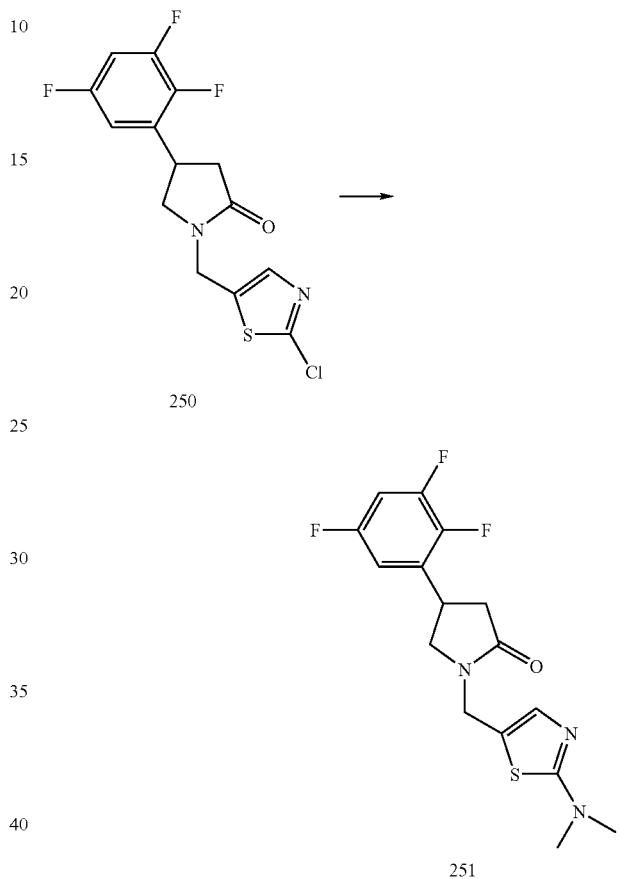

In a sealed tube fitted with a magnetic stirrer, 1-[(2-chloro-1,3-thiazol-5-yl)methyl]-4-(2,3,5-trifluorophenyl)pyrrolidin-2-one 250 (0.3 g, 0.87 mmol) is dissolved in a mixture of THF (4 ml) and H$_2$O (0.1 ml). Dimethylamine (0.85 ml, 1.7 mmol) and LiOH.H$_2$O (0.043 g, 1 mmol) are added and the mixture is stirred at room temperature for 12 h and heated at 50° C. overnight. Dimethylamine (3×3.4 mmol, then 1×5.1 mmol) is added after 24 h, 48 h, 72 h and 96 h heating. THF is evaporated, the residue is dissolved in water and CH$_2$Cl$_2$, the pH of the aqueous phase is brought to 9 and the aqueous phase is extracted with CH$_2$Cl$_2$. The combined organic phases are dried over MgSO$_4$, filtered and concentrated. The crude product is purified by chromatography on silicagel and recrystallized from diisopropylether to afford 0.1 g of 1-{[2-(dimethylamino)-1,3-thiazol-5-yl]methyl}-4-(2,3,5-trifluorophenyl)pyrrolidin-2-one 251.

Yield: 32%.

LC-MS (MH$^+$): 356.

Compound 253 may be synthesized according to the same method.

Example 23

Synthesis of 5-{[2-oxo-4-(2,3,5-trifluorophenyl)pyrrolidin-1-yl]methyl}-1,3-thiazol-2(3H)-one 254

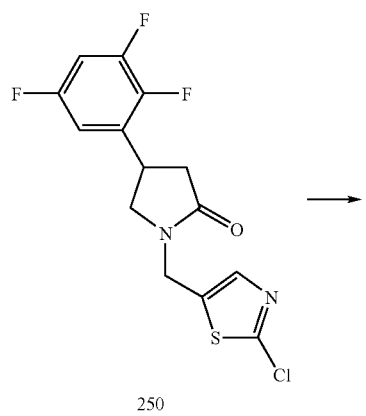

250

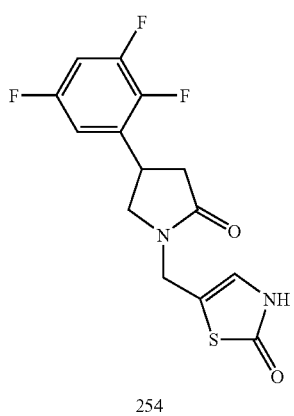

254

Synthesis of 5-{[2-oxo-4-(2,3,5-trifluorophenyl)pyrrolidin-1-yl]methyl}-1,3-thiazol-2(3H)-one 250 is performed by hydrolysis of 1-[(2-chloro-1,3-thiazol-5-yl)methyl]-4-(2,3,5-trifluorophenyl)pyrrolidin-2-one 254 with concentrated HCl (37% w/w) in classical conditions know by the person skilled in the art.

Yield: 5%.

LC-MS (MH⁺): 329.

Example 24

Synthesis of 1-[(2-amino-1,3-thiazol-5-yl)methyl]pyrrolidin-2-one 6 and 1-(1,3-thiazol-5-ylmethyl)pyrrolidin-2-one 249

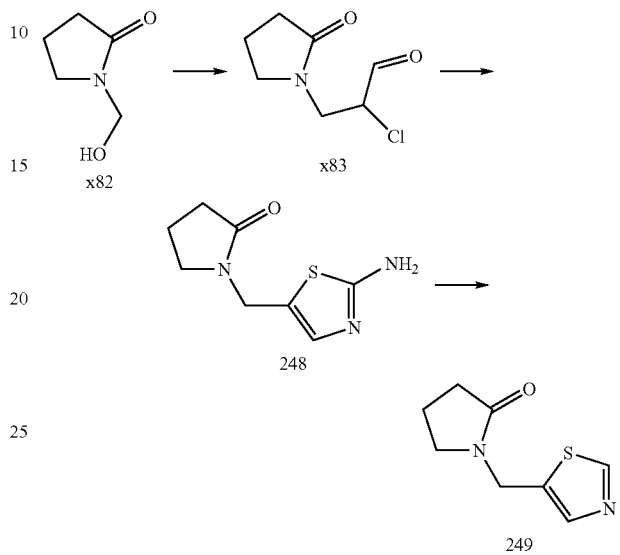

24.1. Synthesis of 2-chloro-3-(2-oxopyrrolidin-1-yl)propanal x83

In a 250 ml, three-necked flask fitted with a magnetic stirrer, 1-(hydroxymethyl)pyrrolidin-2-one x82 (15 g, 0.13 mol) is cooled to −10° C. Cold concentrated sulfuric acid (150 ml) is added dropwise. At this temperature, 1,2-dichloroethene (46.73 g, 0.482 mol) is added while the temperature is kept below 0° C. At the end of the addition the mixture is stirred at 40° C. for 2 h. Water is added and the pH is adjusted with $K_2CO_3$. The aqueous phase is extracted with $CH_2Cl_2$, the combined organic phases are dried over $MgSO_4$, filtered and concentrated. The crude 2-chloro-3-(2-oxopyrrolidin-1-yl)propanal x83 is used in the next step without any further purification.

24.2. Synthesis of 1-[(2-amino-1,3-thiazol-5-yl)methyl]pyrrolidin-2-one 248

In a 500 ml, three-necked flask fitted with a magnetic stirrer and reflux condenser under inert atmosphere, crude 2-chloro-3-(2-oxopyrrolidin-1-yl)propanal x83 (14.13 g, 0.08 mol) is dissolved in MeOH (150 ml). Thiourea (6.12 g, 0.08 mol) and potassium iodide (catalytic amount) are added and the mixture is stirred at reflux for 48 h. Thiourea (3.04 g, 0.04 mol) is added and the mixture is heated for another 72 h. The solvent is evaporated, the residue is purified by chromatography on silicagel ($CH_2Cl_2$/MeOH: 95/5 (v/v)) to afford three fractions of respectively 3.11 g (A), 0.470 g (B) and 2.45 g (C). Fraction B is recrystallized from EtOH to afford 143 mg of 1-[(2-amino-1,3-thiazol-5-yl)methyl]pyrrolidin-2-one 248.

Yield: 9%.

LC-MS (MH⁺): 198.

24.3. Synthesis of 1-(1,3-thiazol-5-ylmethyl)pyrrolidin-2-one 249

In a 250 ml, three-necked flask fitted with a magnetic stirrer and reflux condenser under inert atmosphere, 1-[(2-amino-1,3-thiazol-5-yl)methyl]pyrrolidin-2-one 248 (1.04 g, 6.8 mmol) is dissolved in THF 20 ml). Isoamylnitrite (1.59 g, 13.6 mmol) is added and the mixture is heated at reflux for 3 h. The solvent is evaporated and the residue is purified by chromatography on silicagel (CH$_2$Cl$_2$/MeOH: 95/5 (v/v)) to give 405 mg of 1-(1,3-thiazol-5-ylmethyl)pyrrolidin-2-one 249.

Yield: 31%.

GC-MS (M+1): 182.

Example 25

Synthesis of 1-methyl-5-{[2-oxo-4-(2,3,5-trifluorophenyl)pyrrolidin-1-yl]methyl}-1H-imidazole-4-carbonitrile 127

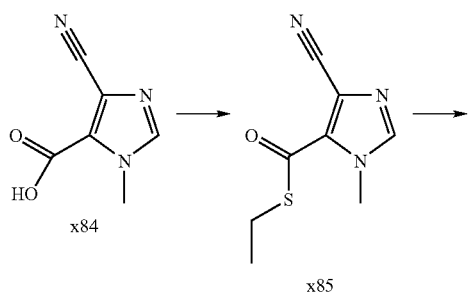

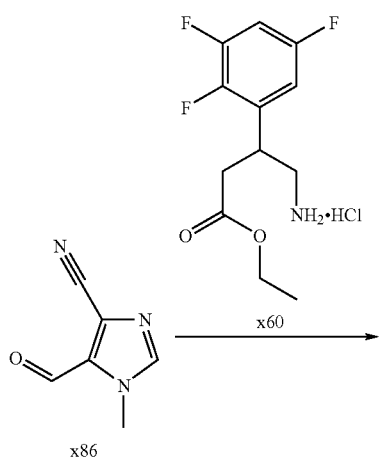

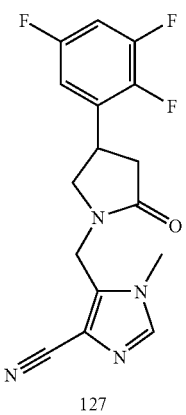

25.1. Synthesis of S-ethyl 4-cyano-1-methyl-1H-imidazole-5-carbothioate x85

In a 1 l, three-necked flask fitted with a magnetic stirrer and a reflux condenser under inert atmosphere, 4-cyano-1-methyl-1H-imidazole-5-carboxylic acid x84 (24.5 g, 0.162 mol) and CH$_2$Cl$_2$ (500 ml) are stirred at room temperature. To this suspension, ethanethiol (13.2 ml, 0.178 mol) and DMAP (1.98 g, 0.016 mol) are added, followed by DCC (36.77 g, 0.178 mol) in two portions. The temperature rises to 35° C. and the mixture is stirred at room temperature for 16 h. Ethanethiol (0.0324 mol) is further added and stirring is continued overnight. The mixture is filtered and the solvent is evaporated. The residue is purified by chromatography on silicagel (Hexane/AcOEt:6/4 (v/v)) to give 29.5 g of S-ethyl 4-cyano-1-methyl-1H-imidazole-5-carbothioate x85.

Yield: 93%.

$^1$H RMN (250 MHz, DMSO): 1.37 (t, 3H), 3.13 (q, 2H), 3.91 (s, 3H), 7.56 (s, 1H).

25.2. Synthesis of 5-formyl-1-methyl-1H-imidazole-4-carbonitrile x86

In a 750 ml, three-necked flask fitted with a magnetic stirrer under inert atmosphere, S-ethyl 4-cyano-1-methyl-1H-imidazole-5-carbothioate x85 (8 g, 0.041 mol) is dissolved in 400 ml of acetone. Pd on charcoal (1.6 g) is added and the mixture is cooled to 0° C. Triethylsilane (13.1 ml, 0.082 mol) is added dropwise and the mixture is stirred at 0° C. for 0.5 h. The reaction is monitored by NMR. Three additional portions of triethylsilane (0.041 mol, 0.041 mol and 0.0205 mol) are added over a period of 14 h, 17 h and 19 h respectively while stirring at 0° C. The mixture is filtered on Celite after complete consumption of starting product. The solvent is evaporated and the residue is purified twice by chromatography on silicagel (Hexane/AcOEt:6/4 (v/v)) to afford 3 g of 5-formyl-1-methyl-1H-imidazole-4-carbonitrile x86.

Yield: 54%.

GC-MS (M+1): 135.

25.3. Synthesis of 1-methyl-5-{[2-oxo-4-(2,3,5-trifluorophenyl)pyrrolidin-1-yl]methyl}-1H-imidazole-4-carbonitrile 127

1-methyl-5-{[2-oxo-4-(2,3,5-trifluorophenyl)pyrrolidin-1-yl]methyl}-1H-imidazole-4-carbonitrile 127 is prepared according to the method described in 10.1 starting from 5-formyl-1-methyl-1H-imidazole-4-carbonitrile x86 and ethyl 4-amino-3-(2,3,5-trifluorophenyl)butanoate hydrochloride x60.

Yield: 25.8%.

LC-MS (MH$^+$): 335.

Compounds 117 and racemic 122 may be synthesized as described for compound 127.

Example 26

Synthesis of 1-({1-[(2-oxo-4-propylpyrrolidin-1-yl)methyl]-1H-imidazol-4-yl}methyl)-4-propylpyrrolidin-2-one trifluoroacetate 111

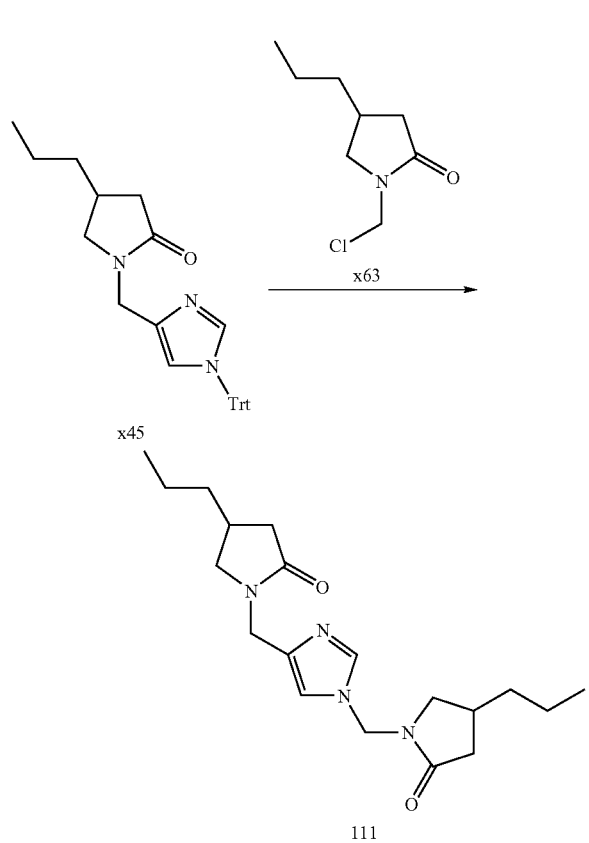

In a 50 ml, three-necked flask fitted with a magnetic stirrer, a reflux condenser and a dropping funnel under inert atmosphere, 1.56 g (3.5 mmol) of 4-propyl-1-[(1-trityl-1H-imidazol-4-yl)methyl]pyrrolidin-2-one x45 is dissolved in acetonitrile (9 ml). To this solution is added dropwise a mixture of 1-(chloromethyl)-4-propylpyrrolidin-2-one x63 (0.98 g, 5 mmol) in 9 ml of acetonitrile that is first brought to pH 8 by adding triethylamine. The mixture is warmed to 75-80° C. during 32 h, the solvent is evaporated and the residue dissolved in acetic acid (10 ml) and water (10 ml). The mixture is stirred overnight at room temperature, filtered and concentrated. The residue taken up with a HCl solution (pH 2) and extracted with diethyl ether. The aqueous phase is brought to pH 8 with solid Na$_2$CO$_3$ and extracted with CH$_2$Cl$_2$. The combined organic phases are dried over MgSO$_4$, filtered and concentrated to dryness. After purification by chromatography on silicagel (MTBE/CH$_2$Cl$_2$/MeOH/NH$_4$OH: 45/45/9/1 (v/v/v/v)), the compound (0.4 g) is dissolved in CH$_2$Cl$_2$ (10 ml), treated with trifluoroacetic acid (80 µl), concentrated and recrystallized from THF/isopropanol to afford 0.23 g of 1-({1-[(2-oxo-4-propylpyrrolidin-1-yl)methyl]-1H-imidazol-4-yl}methyl)-4-propylpyrrolidin-2-one trifluoroacetate 111.

Yield: 11%.

LC-MS (MH$^+$): 347.

Example 27

Synthesis of 1-methyl-5-[(2-oxo-4-propylpyrrolidin-1-yl)methyl]-1H-imidazole-4-carboxamide 123

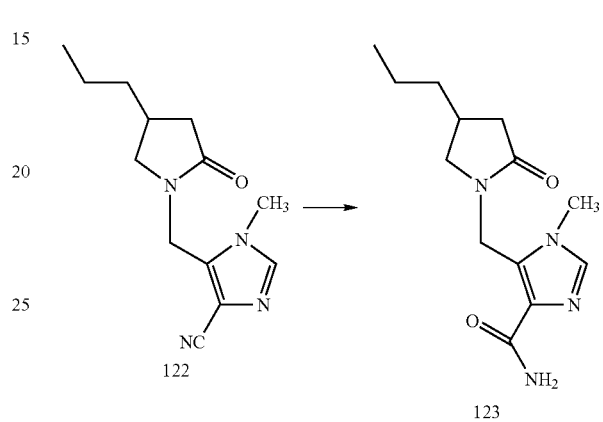

In a 25 ml, three-necked flask fitted with a magnetic stirrer, a reflux condenser and a dropping funnel under inert atmosphere, 150 mg (0.61 mmol) of 1-methyl-5-[(2-oxo-4-propylpyrrolidin-1-yl)methyl]-1H-imidazole-4-carbonitrile 122 is dissolved in MeOH (9 ml) with water (3 ml) and aqueous NaOH (35% w/w, 30 µl). The reaction mixture is refluxed 72 h, cooled down to room temperature and the solvent is evaporated to dryness. The crude reaction mixture is purified by preparative chromatography on silicagel (CH$_2$Cl$_2$/MeOH/NH$_4$OH: 96/3.6/0.4 (v/v/v/v)) and recrystallized in CH$_2$Cl$_2$/hexane to afford 1-methyl-5-[(2-oxo-4-propylpyrrolidin-1-yl)methyl]-1H-imidazole-4-carboxamide 123 (0.07 g).

Yield: 43%.

LC-MS (MH$^+$): 247.

Example 28

Synthesis of 1-[(4-chloro-1H-imidazol-5-yl)methyl]-4-propylpyrrolidin-2-one 126

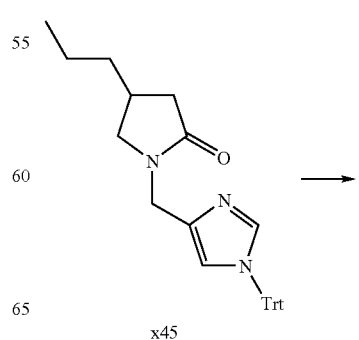

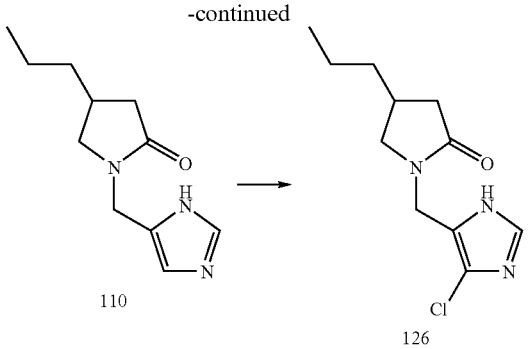

28.1. Synthesis of 1-(1H-imidazol-4-ylmethyl)-4-propylpyrrolidin-2-one 110

In a 50 ml reaction flask fitted with a magnetic stirrer, 4-propyl-1-[(1-trityl-1H-imidazol-4-yl)methyl]pyrrolidin-2-one x45 (1.8 g, 4 mmol) is dissolved in a 1/1 mixture of $CH_3CO_2H/H_2O$ (30 ml) and the solution is stirred for 36 h at room temperature. Most of the solvents are removed under vacuum and the residue is dissolved in 1N HCl and diluted with $CH_2Cl_2$. The first organic phase is removed and pH of the aqueous phase is adjusted to 9 by addition of solid $Na_2CO_3$. Then $CH_2Cl_2$ is added and the second organic phase is separated, dried over $MgSO_4$ and concentrated to dryness, affording 730 mg of 1-(1H-imidazol-4-ylmethyl)-4-propylpyrrolidin-2-one 110.

Yield: 88%.

LC-MS (MH+): 208.

Compounds 115, 118 and 1-(1H-imidazol-4-ylmethyl)-4-(2,3,5-trifluorophenyl)pyrrolidin-2-one x87 (LC-MS (MH+): 226) may be synthesized according to the same method.

Compound 139 is obtained in two steps following the experimental procedure of example 34 followed by reaction with MeI as described in example 28.1.

28.2. Synthesis of 1-[(4-chloro-1H-imidazol-5-yl)methyl]-4-propylpyrrolidin-2-one 126

In a 100 ml, three-necked flask fitted with a magnetic stirrer and under inert atmosphere, 1-(1H-imidazol-4-ylmethyl)-4-propylpyrrolidin-2-one 110 (500 mg, 2.4 mmol) is dissolved in a 1/1 mixture of $CH_3CN/THF$ (40 ml) and the solution is cooled to 0° C. N-chlorosuccinimide (410 mg, 3.1 mmol) is added by portions while the temperature is maintained at 0° C. The mixture is stirred for 18 h at this temperature. Most of the solvents are removed under vacuum and the residue is dissolved in 1N HCl and diluted with $CH_2Cl_2$. The first organic phase is removed and pH of the aqueous phase is adjusted to 9 by addition of solid $Na_2CO_3$. Then $CH_2Cl_2$ is added and the second organic phase is separated, dried over $MgSO_4$ and concentrated to dryness. Purification by preparative chromatography on silicagel (eluent: $CH_2Cl_2/MeOH/NH_4OH$: 95/05/0.5 (v/v/v)) affords 440 mg of 1-[(4-chloro-1H-imidazol-5-yl)methyl]-4-propylpyrrolidin-2-one 126.

Yield: 76%.

LC-MS (MH+): 242/244.

Compounds 112, 131, 133, 135, 136, 137 and 140 may be synthesized according to the same method.

1-[(4-bromo-1-methyl-1H-imidazol-5-yl)methyl]-4-propylpyrrolidin-2-one 128 is obtained by bromination of 1-[(1-methyl-1H-imidazol-5-yl)methyl]-4-propylpyrrolidin-2-one 121 with N-bromosuccinimide using standard procedures known by any person skilled in the art.

Yield: 70%.

LC-MS (MH+): 300/302.

Compounds 113, 114, 132 and 138 may be synthesized according to the same method.

Example 29

Synthesis of 1-methyl-5-[(2-oxo-4-propylpyrrolidin-1-yl)methyl]-1H-imidazole-2-carbonitrile 125

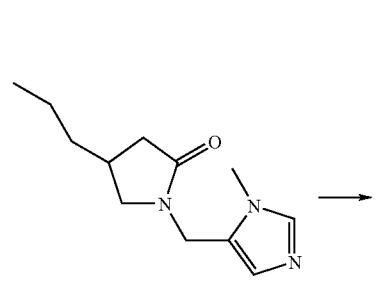

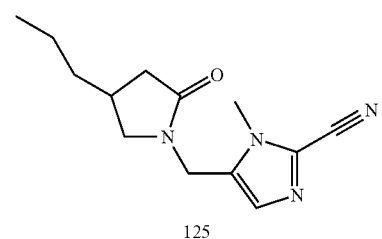

In a 2 l, three-necked flask fitted with a magnetic stirrer and reflux condenser under inert atmosphere, DMAP (60.4 g, 0.495 mol) is dissolved in DMF (900 ml) and the solution is cooled to 0° C. Cyanogen bromide (54.4 g, 0.495 mol) is added by portions while the temperature is maintained between 0 and 10° C. The mixture is stirred for 0.5 h at this temperature and a solution of 1-[(1-methyl-1H-imidazol-5-yl)methyl]-4-propylpyrrolidin-2-one 121 (36.5 g, 0.165 mol) in DMF (500 ml) is added. The mixture is heated at 40° C. overnight. The DMAP-BrCN complex (0.165 mol) in 350 ml of DMF is added at 5° C. (after being stirred for 1 h) and the mixture is heated at 45° C. overnight. One equivalent of the DMAP-BrCN complex in DMF (150 ml) is prepared again and added to the mixture at a temperature comprised between 0° C. and 10° C. The mixture is stirred at 45° C. overnight. The solvent is evaporated, the residue is dissolved in AcOEt, then the organic phase is washed with a saturated solution of $NaHCO_3$ and brine, dried over $MgSO_4$ and concentrated to dryness. Purification by preparative chromatography on silicagel affords 13.5 g 1-methyl-5-[(2-oxo-4-propylpyrrolidin-1-yl)methyl]-1H-imidazole-2-carbonitrile 125.

Yield: 33%.

LC-MS (MH+): 247.

Example 30

Synthesis of the two enantiomers of 1-[1-(1H-imidazol-4-yl)propyl]pyrrolidine-2-one 106 and 107

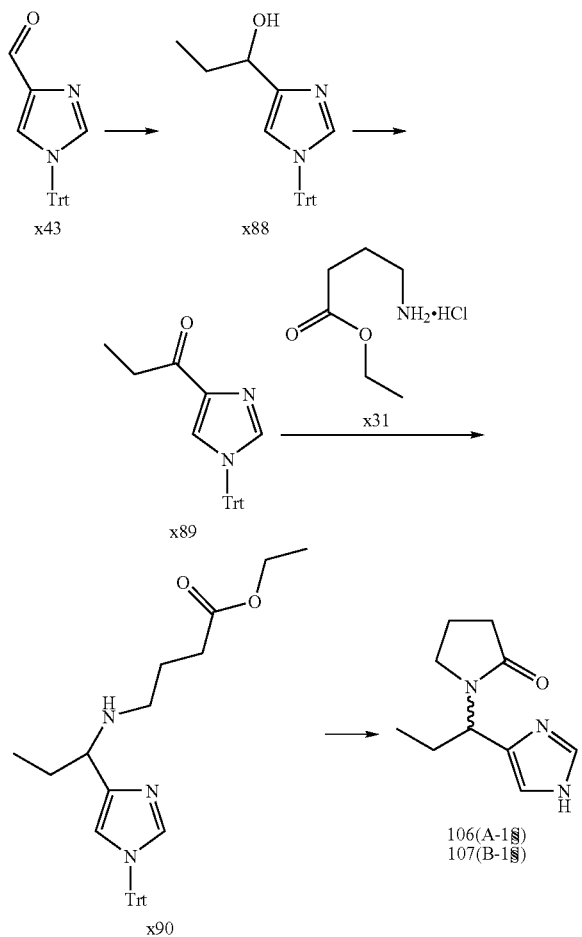

30.1. Synthesis of 1-(1-trityl-1H-imidazol-4-yl)propan-1-ol x88

In a 100 ml, three-necked flask fitted with a magnetic stirrer, under inert atmosphere, ethyl iodide (1.1 ml, 0.0136 mol) is dissolved in Et$_2$O (25 ml). At −70° C., a 1.5 M solution of t-BuLi in pentane (17 ml, 0.026 mol) is added dropwise. The mixture is stirred 0.3 h at this temperature and 0.75 h at room temperature. A solution of 1-trityl-1H-imidazole-4-carbaldehyde x43 (2 g, 0.00591 mole) in THF (25 ml) is added dropwise at 0° C. The mixture is stirred for 1 h and poured onto ice. HCl is added until the pH is slightly acid (pH: 3-5) and the aqueous phase is extracted twice with Et$_2$O. The combined organic phases are dried over MgSO$_4$, filtered and concentrated to dryness. The crude product is purified by chromatography on silicagel (CH$_2$Cl$_2$/MeOH/NH$_4$OH: 95/4.5/0.5 (v/v/v)) to afford 1.21 g of 1-(1-trityl-1H-imidazol-4-yl)propan-1-ol x88.

Yield: 56%.

LC-MS (MH$^+$): 369.

30.2. Synthesis of 1-(1-trityl-1H-imidazol-4-yl)propan-1-one x89

In a 50 ml three-necked flask fitted with a magnetic stirrer and a reflux condenser under inert atmosphere, 1-(1-trityl-1H-imidazol-4-yl)propan-1-ol x88 (1.21 g, 3.3 mmol) and MnO$_2$ (2.85 g, 33 mmol) are dissolved in 20 ml of dioxane and the mixture is brought to reflux for 1 h. The mixture is filtered on Celite and the solvent is evaporated. Purification by chromatography on silicagel (CH$_2$Cl$_2$/MeOH/NH$_4$OH: 90/9/1 (v/v/v)) affords 0.96 g of pure 1-(1-trityl-1H-imidazol-4-yl)propan-1-one x89.

Yield: 80%.

$^1$H RMN (250 MHz, DMSO): 1.05 (t, 3H), 2.9 (q, 2H), 7.25 (m, 6H), 7.5 (m, 10), 7.6 (s, 1H).

30.3. Synthesis of ethyl 4-{[1-(1-trityl-1H-imidazol-4-yl)propyl]amino}butanoate x90

In a 100 ml, three-necked flask fitted with a magnetic stirrer, under inert atmosphere, ethyl 4-aminobutanoate hydrochloride a17 (1.75 g, 0.0104 mol) is dissolved in MeOH (30 ml). Sodium acetate (1.28 g, 0.0156 mol), a solution of 1-(1-trityl-1H-imidazol-4-yl)propan-1-one x89 (0.96 g, 2.6 mmol) in a mixture of MeOH (7 ml) and Et$_2$O (20 ml), NaBH$_3$CN (0.15 g, 2.34 mmol) and finally Na$_2$SO$_4$ are added. After stirring for 48 h at room temperature, the mixture is poured on Et$_2$O/H$_2$O. The organic phase is washed with water and brine, dried over Na$_2$SO$_4$, filtered and concentrated in vacuo. The crude ethyl 4-{[1-(1-trityl-H-imidazol-4-yl)propyl]amino}butanoate x90 (0.814 g) is used in the next step without any further purification.

Yield: 65%.

LC-MS (MH$^+$): 482.

The following compounds may be synthesized according to the same method:

| x91 | ethyl 3-{[(2-methyl-1-trityl-1H-imidazol-5-yl)methyl]amino}propanoate | LC-MS (MH$^+$): 468 |
| --- | --- | --- |
| x92 | ethyl 3-{[(4-methyl-1-trityl-1H-imidazol-5-yl)methyl]amino}propanoate | LC-MS (MH$^+$): 468 |

30.4. Synthesis of the two enantiomers of 1-[1-(1H-imidazol-4-yl)propyl]pyrrolidin-2-one 106 and 107

In a 25 ml, three-necked flask fitted with a magnetic stirrer and a reflux condenser under inert atmosphere, a solution of ethyl 4-{[1-(1-trityl-1H-imidazol-4-yl)propyl]amino}butanoate x90 (0.81 g, 1.68 mmol) in acetic acid (10 ml) is brought to reflux for 48 h. The solvent is evaporated and the residue is purified by chromatography on silicagel (CH$_2$Cl$_2$/MeOH/NH$_4$OH: 95/4.5/0.5 to 92/7.2/0.8 (v/v/v)). The enantiomers are separated by chiral chromatography and recrystallized from AcOEt to afford 106 (A-1§, 33 mg, yield: 48%) and 107 (B-1§, 37 mg, yield: 54%).

LC-MS (MH$^+$): 194.

Example 31

Synthesis of 1-[(4-methoxy-1-methyl-1H-imidazol-5-yl)methyl]pyrrolidin-2-one 120

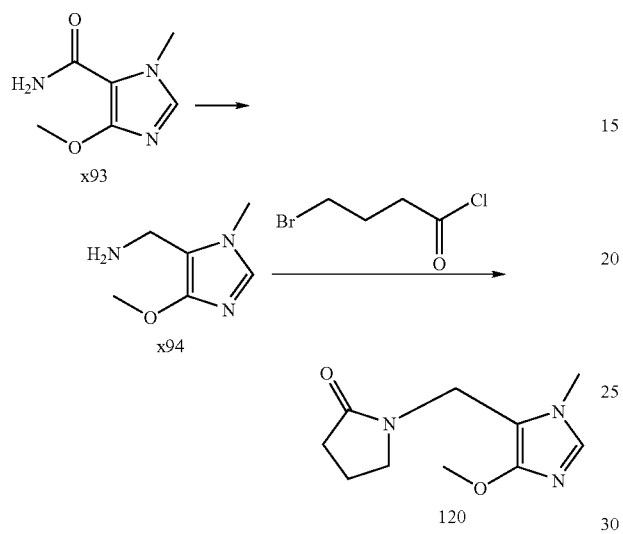

Compounds 108 and 109 may be synthesized according to the same method.

31.1 Synthesis of 1-(4-methoxy-1-methyl-1H-imidazol-5-yl)methanamine x94

In a 250 ml, three-necked flask fitted with a magnetic stirrer, a reflux condenser and under inert atmosphere, 4-methoxy-1-methyl-1H-imidazole-5-carboxamide x93 (1.45 g, 9.5 mmol) is dissolved at room temperature in anhydrous THF (80 ml). Lithium aluminium hydride (685 mg, 18 mmol) is added by portions while the temperature is rising to 30° C. The mixture is stirred for 7 h at 60° C. and cooled down to room temperature. Then isopropanol is added and the mixture is stirred for a further 16 hours at room temperature. First HCl 37% (W/W) is added to the rectional mixture to reach pH 1, then 5 N KOH to adjust pH to 10. The solvents are removed under vacuum. The residue is dissolved in a mixture of $CH_2Cl_2$/MeOH (80/20), filtered through a celite pad and concentrated to dryness. Purification by preparative chromatography on silicagel (conditions: $CH_2Cl_2$/MeOH/$NH_4OH$: 90/10/1 (v/v/v)) affords 500 mg of 1-(4-methoxy-1-methyl-1H-imidazol-5-yl)methanamine x94.

Yield: 38%.
DIP (MH+): 141.

31.2. Synthesis of 1-[(4-methoxy-1-methyl-1H-imidazol-5-yl)methyl]pyrrolidin-2-one 120

In a 50 ml, three-necked flask fitted with a magnetic stirrer, under inert atmosphere, 1-(4-methoxy-1-methyl-1H-imidazol-5-yl)methanamine x94 (0.37 g, 2.62 mmol), $Na_2SO_4$ (0.37 g, 2.62 mmol) and powdered molecular sieves are stirred in $CH_2Cl_2$ (25 ml) at 0° C. At this temperature, powdered KOH (0.53 g, 9.44 mmol) and a solution of tetra-n-butyl ammonium bromide (48 mg, 0.13 mmol) in $CH_2Cl_2$ (5 ml) are added. The mixture is stirred for 0.25 h at 0° C. and 4-bromobutanoyl chloride (366 µl, 3.14 mmol) is added dropwise. Stirring is continued for 2 h. The mixture is filtered on Celite and evaporated in vacuo. The residue is dissolved in DMF (25 ml) and NaH (60% dispersion in oil, 0.12 g, 3.14 mmol) is added. The mixture is stirred at room temperature for 16 h. An additional portion of NaH (0.52 mmol) is added and the mixture is stirred for 4 more hours at room temperature. The mixture is then diluted with 30 ml of $CH_2Cl_2$, filtered on Celite and concentrated to dryness. The residue is purified by chromatography on silicagel ($CH_2Cl_2$/MeOH/$NH_4OH$: 95/4.5/0.5 (v/v/v)) and recrystallized from diisopropyl ether to afford 150 mg of 1-[(4-methoxy-1-methyl-1H-imidazol-5-yl)methyl]pyrrolidin-2-one 120.

Yield: 27%.
LC-MS (MH+): 210.

Example 32

Synthesis of 4-phenyl-1-(1H-pyrazol-4-ylmethyl)pyrrolidin-2-one 162

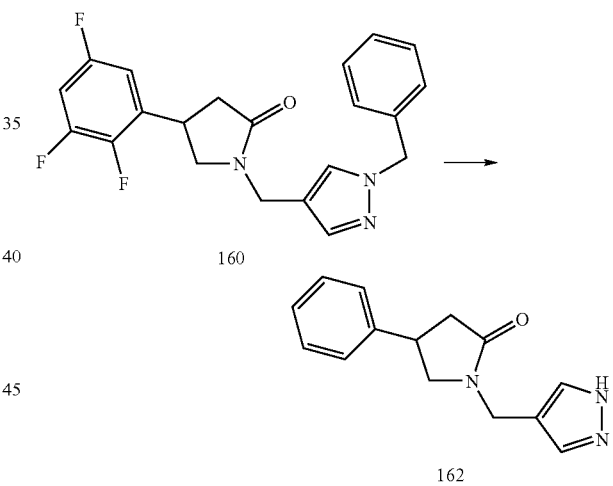

In a 250 ml, three-necked flask fitted with a magnetic stirrer under inert atmosphere, 20 ml of liquid ammonia is condensed and sodium is added until the solution turns blue. A solution of 1-[(1-benzyl-1H-pyrazol-4-yl)methyl]-4-(2,3,5-trifluorophenyl)pyrrolidin-2-one 160 (1 g, 2.6 mmol) in THF (5 ml) is added and the mixture is stirred at −78° C. for 5 minutes. $NH_4Cl$ and water are added, ammonia is evaporated in vacuo and the aqueous phase is extracted with $CH_2Cl_2$. The combined organic phases are washed with brine, dried over $MgSO_4$, filtered and concentrated to dryness. The residue is purified by preparative chromatography on C18 reversed phase ($CH_3CN$/$H_2O$/$NH_4HCO_3$, gradient) to afford 73 mg of 4-phenyl-1-(1H-pyrazol-4-ylmethyl)pyrrolidin-2-one 162.

Yield: 12%.
LC-MS (MH+): 242.

Example 33

Synthesis of 1-(1H-pyrazol-4-ylmethyl)-1,3-dihydro-2H-indol-2-one 173

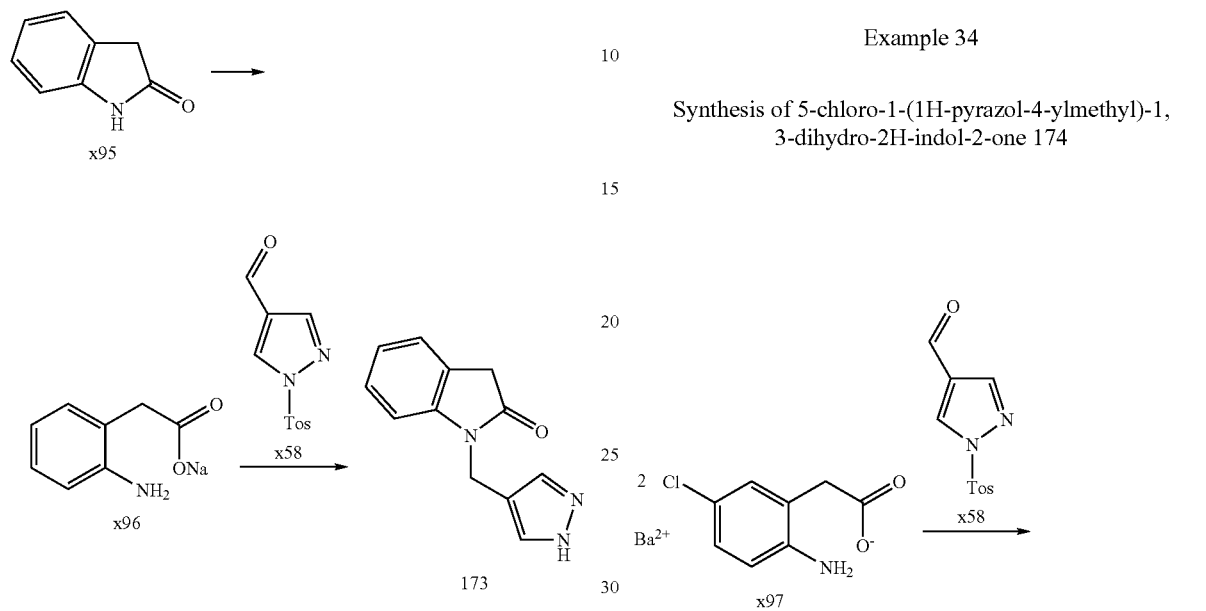

33.1. Synthesis of sodium (2-aminophenyl)acetate x96

In a 25 ml, three-necked flask fitted with a magnetic stirrer and a reflux condenser, oxindole x95 (1 g, 7.5 mmol) and 15 ml of 4N NaOH (37.5 mmol) are heated at 100° C. overnight. This solution containing (2-aminophenyl)acetic acid x96 is used as such in the next step without further purification.

LC-MS (MH$^+$): 152.

Barium bis[(2-amino-5-chlorophenyl)acetate] x97 is synthesized according to the same procedure (LC-MS (MH$^+$): 186/188 and (M-H)$^-$:184/186) starting from 5-chloro-1,3-dihydro-2H-indol-2-one.

33.2. Synthesis of 1-(1H-pyrazol-4-ylmethyl)-1,3-dihydro-2H-indol-2-one hydrate 173

In a 100 ml, three-necked flask fitted with a magnetic stirrer, 1-[(4-methylphenyl)sulfonyl]-1H-pyrazole-4-carbaldehyde x58 (1.65 g, 6.6 mmol) is dissolved in a 1/1 mixture of THF/H$_2$O (50 ml) and the solution containing (2-aminophenyl)acetic acid x96 (1 g, 66 mmol) is added. The pH is adjusted to 5 with acetic acid and the mixture is cooled to 0° C. Sodium triacetoxyborohydride (2.10 g, 10 mmol) is added and the mixture is stirred overnight at room temperature. Water is added and the aqueous phase is extracted three times with CH$_2$Cl$_2$. The combined organic phases are washed with brine, dried over MgSO$_4$ and evaporated. Purification of the residue by preparative chromatography on silicagel and recrystallization from AcOEt affords 106 mg of pure 1-(1H-pyrazol-4-ylmethyl)-1,3-dihydro-2H-indol-2-one hydrate 173.

Yield: 8%.

LC-MS (MH$^+$): 214.

Example 34

Synthesis of 5-chloro-1-(1H-pyrazol-4-ylmethyl)-1,3-dihydro-2H-indol-2-one 174

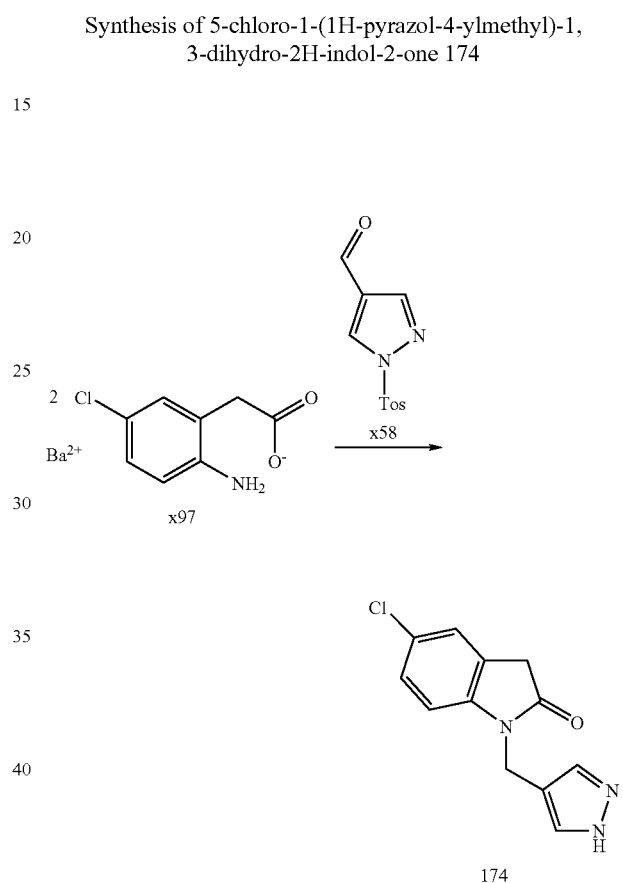

In a 50 ml, three-necked flask fitted with a magnetic stirrer, under inert atmosphere, 1-[(4-methylphenyl)sulfonyl]-1H-pyrazole-4-carbaldehyde x58 (0.4 g, 1.6 mmol) and barium bis[(2-amino-5-chlorophenyl)acetate] x97 (0.2 g, 0.4 mmol) are dissolved in a 1/1 mixture of TFA and CH$_2$Cl$_2$ (10 ml) and Et$_3$SiH (0.26 ml, 1.6 mmol) is added. The mixture is stirred at room temperature for 1 h and 3.2 mmol of Et$_3$SiH are added. At the end of the reaction, the mixture is diluted with water and CH$_2$Cl$_2$, extracted three times with CH$_2$Cl$_2$ and the combined organic phases are washed with water, dried over MgSO$_4$, filtered and concentrated. The residue is purified by preparative chromatography and recrystallized from AcOEt and Et$_2$O to afford 9.3 mg of 5-chloro-1-(1H-pyrazol-4-ylmethyl)-1,3-dihydro-2H-indol-2-one 174.

Yield: 6%.

LC-MS (MH$^+$): 248/250.

Compound 134 may be synthesized as described for compound 174.

Example 35

Synthesis of {[6-chloro-2-(trifluoromethyl)imidazo[1,2-b]pyridazin-3-yl]methyl}-4-(2,2-difluoro-vinyl)-pyrrolidin-2-one 33

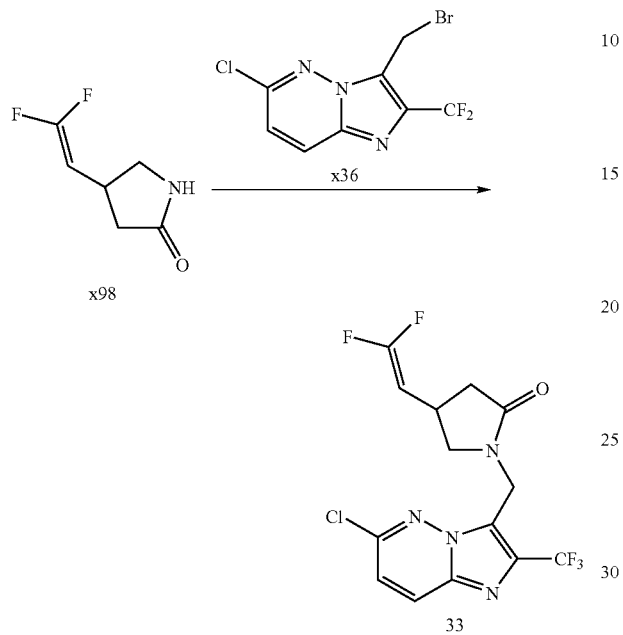

Sodium hydride (60% wt mineral oil dispersion, 0.82 g, 1.3 eq, 20.5 mmol) is washed three times by hexane (15 ml). THF (15 ml) is added at room temperature to this clean sodium hydride, a solution of 4-(2,2-difluorovinyl)pyrrolidin-2-one x98 (3.42 g, 23 mmol, 1.4 eq) and 3-(bromomethyl)-6-chloro-2-(trifluoromethyl)imidazo[1,2-b]pyridazine x36 (4.97 mg, 15.8 mmol, 1 eq) in THF (15 ml). After 3 hours of stirring at room temperature, a small amount of sodium hydride is added in order to complete the reaction and stirring is pursue overnight. Water (25 ml) is then added to the mixture and THF is removed evaporation under reduced pressure. The aqueous layer is extracted by ethyl acetate (2×50 ml), the resulting organic layer is dried over MgSO$_4$, filtered and concentrated to dryness. The residue is purified by preparative chromatography (benzine/AcOEt:50/50) to afford 4.33 g of {[6-chloro-2-(trifluoromethyl)imidazo[1,2-b]pyridazin-3-yl]methyl}-4-(2,2-difluoro-vinyl)-pyrrolidin-2-one 33.

Yield: 72%.
LC-MS (MH$^+$): 381/383.

Compounds 30, 31, 32, 34 and 50 may be synthesized as described for compound 33.

4-(2,2-trifluoroethyl)pyrrolidin-2-one x103, used in the synthesis of compound 50, may be prepared according to the following scheme:

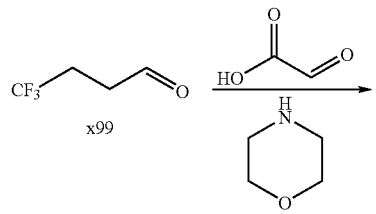

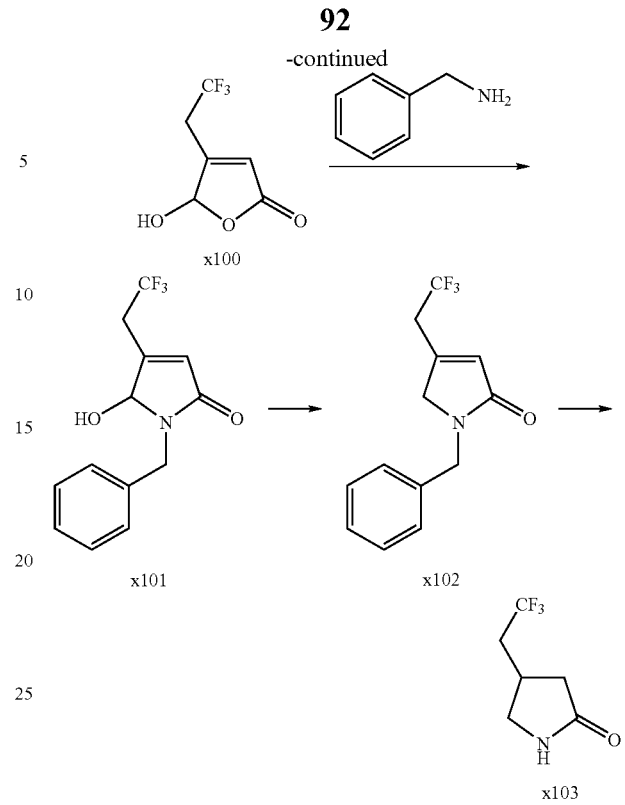

(i) 5-hydroxy-4-(2,2,2-trifluoroethyl)furan-2(5H)-one x100

Glyoxylic acid monohydrate (2.43 g, 26.4 mmol), morpholine hydrochloride (3.59 g, 29 mmol) and dioxane (10.5 ml) are stirred together at room temperature. Water (14 ml) is added and the reaction mixture is stirred for a few minutes until it becomes homogeneous. 4,4,4-trifluorobutyraldehyde x99 (3.16 g, 25.1 mmol) is added and the mixture is stirred for 1 h at room temperature and under reflux conditions overnight. The mixture is diluted in tert-butylmethylether and washed with water. The aqueous phase is re-extracted with tert-butylmethylether. The organic extracts are combined, dried over magnesium sulphate, filtered and concentrated in vacuo to obtain 5-hydroxy-4-(2,2,2-trifluoroethyl)furan-2(5H)-one x100 as a yellow oil (3.76 g, 81%). The product is used in the next reaction without further purification.

(ii) 1-benzyl-5-hydroxy-4-(2,2,2-trifluoroethyl)-1,5-dihydro-2H-pyrrol-2-one x101

A solution of 5-hydroxy-4-(2,2,2-trifluoroethyl)furan-2-one x100 (3.76 g, 20.4 mmol) in isopropyl alcohol (20 ml) is added to a solution of benzylamine (2.7 ml, 25.0 mmol) in isopropylalcohol (20 ml) with stirring at room temperature. The reaction mixture is heated at 30° C. overnight until completion. The solution containing crude 1-benzyl-5-hydroxy-4-(2,2,2-trifluoroethyl)-1,5-dihydro-2H-pyrrol-2-one x10 is used as such in the next step.

(iii) 1-benzyl-4-(2,2,2-trifluoroethyl)pyrrolidin-2-one x102

The crude solution of 1-benzyl-5-hydroxy-4-(2,2,2-trifluoroethyl)-1,5-dihydro-2H-pyrrol-2-one x101 in isopropyl alcohol (40 ml) is added to a suspension of Pd(C) (10%) (0.53 g) in isopropylalcohol (40 ml) and the resulting solution is degassed 3 times with nitrogen. The reaction mixture is stirred under hydrogen (balloon) for 1 day. The Pd(C) is removed by filtration through celite, and the filtrates are concentrated under reduced pressure. Purification by chromatography on silicagel (petroleum ether/ethyl acetate 10/50) affords 1.67 g of 1-benzyl-4-(2,2,2-trifluoroethyl)pyrrolidin-2-one x102.

RMN $^1$H(CDCl$_3$): 2.16 (3H, m); 2.59 (2H, m); 2.92 (1H, t; J=9.6 Hz); 3.36 (1H, t, J=9.6 Hz); 4.38 (2H, dd, J=14.4 & 24 Hz); 7.17 (2H, m); 7.27 (3H, m).

(iv) 4-(2,2,2-trifluoroethyl)pyrrolidin-2-one x103

1-Benzyl-4-(2,2,2-trifluoroethyl)pyrrolidin-2-one x102 (1.67 g, 6.5 mmol) is dissolved in diethyl ether (17 ml) and anhydrous tert-butanol (7 ml). The solution is cooled to −78° C. and ammonia (33 ml) is condensed into the flask. Sodium (0.373 g, 16.2 mmol) is added to the solution portionwise at −78° C., followed by the anhydrous tert-butanol (7 ml). The reaction mixture is stirred at −78° C. for 2-3 h. Ethanol (50 ml) is slowly added. The mixture is warmed to room temperature and stirred overnight. Saturated ammonium chloride is added and the mixture is extracted with ether (3 times). The organic layers are combined, dried over magnesium sulphate, filtered and concentrated in vacuo to obtain 4-(2,2,2-trifluoroethyl)pyrrolidin-2-one x103 as an orange solid (0.61 g).

Yield: 56%.

RMN $^1$H(CDCl$_3$): 2.10 (1H, m); 2.21 (2H, m); 2.45 (1H, dd, J=2.4 & 8.4 Hz); 2.75 (1H, m); 3.10 (1H, t; J=8.8 Hz); 3.52 (1H, t, J=8.8 Hz), 6.11 (H, s broad).

Example 36

Synthesis of 1-[(6-chloro-2-cyclopropylimidazo[1,2-b]pyridazin-3-yl)methyl]-4-(2,2-difluorovinyl)pyrrolidin-2-one 62

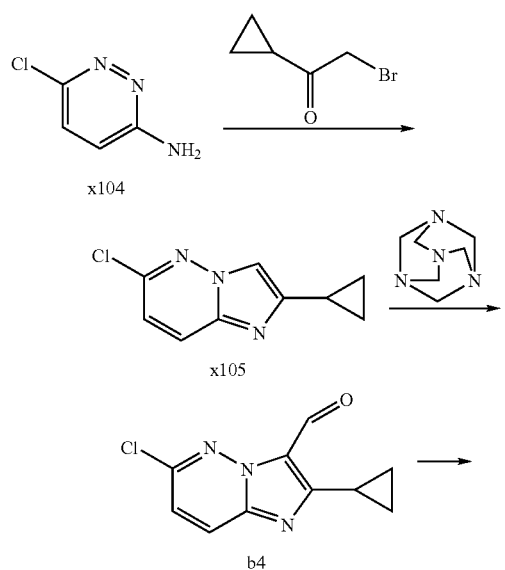

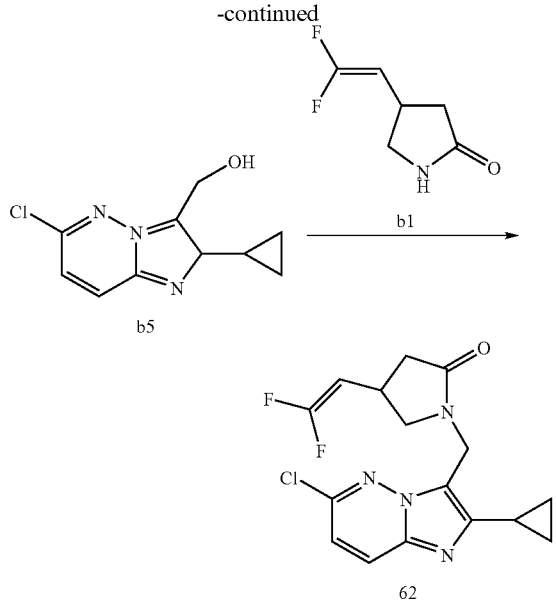

36.1. Synthesis of 6-chloro-2-cyclopropylimidazo[1,2-b]pyridazine x105

A mixture of 6-chloropyridazin-3-amine x104 (24.63 g, 0.19 mol) and 2-bromo-1-cyclopropylethanone (31 g, 0.190 mol, 1 eq) in dimethoxyethane (400 ml) is refluxed under inert atmosphere for 2 days. After cooling to room temperature, the solvent is removed under reduced pressure, the crude is taken up in water (100 ml) and extracted with ethyl acetate (2×300 ml). The cumulated organic layers are dried over MgSO$_4$, filtered and condensed under reduced pressure to furnish 6-chloro-2-cyclopropylimidazo[1,2-b]pyridazine x105 (Yield: 42%) which is used as such in the next step. Note that further title compound x105 can be extracted from aqueous layer after neutralization to pH 5 by addition of sodium hydroxyde, extraction with dichloromethane, drying (MgSO$_4$), filtration and condensation under reduced pressure (additional 11.13 g are then collected).

Overall yield: 73% (26.85 g).

LC-MS (MH$^+$): 194/196.

The following compounds may be synthesized according to the same method:

| x106 | 6-chloro-2-(4-methylphenyl)imidazo[1,2-b]pyridazine | RMN $^1$H (DMSO): 2.36 (s, 3H), 7.31 (d, 2H), 7.51 (d, 1H), 7.92 (d, 2H), 8.27 (d, 2H), 8.94 (s, 1H) |
|---|---|---|
| x107 | 6-chloro-2-cyclobutylimidazo[1,2-b]pyridazine | LC-MS (MH$^+$): 208/210 |
| x108 | 2-cyclopropyl-6-fluoroimidazo[1,2-a]-pyridine | LC-MS (MH$^+$): 177 |
| x109 | 6-chloro-2-cyclopropylimidazo[1,2-a]-pyridine | LC-MS (MH$^+$): 193/195 |

36.2. Synthesis of 6-chloro-2-cyclopropylimidazo[1,2-b]pyridazine-3-carbaldehyde x110

6-chloro-2-cyclopropylimidazo[1,2-b]pyridazine x105 (1.88 g, 9.71 mmol) and hexamethyltetramine (HMTE, 13.61 g, 97.09 mmol, 10 eq) in trifluoroacetic acid (75 ml) are heated at 60° C. during 6 days. After cooling and solvent evaporation under reduced pressure, the crude product is dissolved in dichloromethane (150 ml). The organic layer is washed with water (150 ml) and the resulting aqueous layer is extracted with dichloromethane (150 ml). The cumulated organic layers are dried over MgSO$_4$, filtered and the solvent is removed by evaporation under reduced pressure. The resulting crude compound is purified by preparative chromatography (benzine/AcOEt:80/20) affording 0.82 g of 6-chloro-2-cyclopropylimidazo[1,2-b]pyridazine-3-carbaldehyde x110.

Yield: 45%.

LC-MS (MH$^+$): 222/224.

$^1$H NMR (CDCl$_3$) δ 1.20 (m, 4H), 2.89 (m, 1H), 7.26 (m, 1H), 7.80 (m, 1H), 10.49 (m, 1H).

The following compounds may be synthesized according to the same method:

| x111 | 6-chloro-2-(4-methylphenyl)imidazo[1,2-b]pyridazine-3-carbaldehyde | LC-MS (MH$^+$): 272/274 |
|---|---|---|
| x112 | 6-chloro-2-cyclobutylimidazo[1,2-b]pyridazine-3-carbaldehyde | NMR $^1$H (CDCl$_3$) δ 2.15 (m, 1H), 2.42-2.51 (m, 5H), 4.29 (m, 1H), 7.29 (d, 1H), 7.99 (d, 1H), 10.42 (s, 1H) |
| x113 | 2-cyclopropyl-6-fluoroimidazo[1,2-b]pyridazine-3-carbaldehyde | LC-MS (MH$^+$): 205 |
| x114 | 6-chloro-2-cyclopropylimidazo[1,2-b]pyridazine-3-carbaldehyde | LC-MS (MH$^+$): 221/223 |

36.3. Synthesis of (6-chloro-2-cyclopropylimidazo[1,2-b]pyridazin-3-yl)methanol x115

Sodium borohydride (5.62 mg, 6.62 mmol, 1.3 eq) is added dropwised, at room temperature, to a solution of 6-chloro-2-cyclopropylimidazo[1,2-b]pyridazine-3-carbaldehyde x110 (958 mg, 4.32 mmol) in methanol (100 ml). After 1 hour, the reaction is quenched by water (100 ml) and the crude product is extracted by dichloromethane (2×100 ml). The organic layers are dried over MgSO$_4$, filtered and condensed under reduced pressure to afford (6-chloro-2-cyclopropylimidazo[1,2-b]pyridazin-3-yl)methanol x115 which is used without any further purification.

Yield: 93%.

$^1$H NMR δ 0.95 (m, 4H), 2.24 (m, 1H), 4.84 (m, 2H), 5.21 (m, 1H), 7.28 (d, 9.35 Hz, 1H), 8.04 (d, 9.35 Hz, 1H).

The following compounds may be synthesized according to the same method:

| x116 | [6-chloro-2-(4-methylphenyl)imidazo[1,2-b]pyridazin-3-yl]methanol | LC-MS (MH$^+$): 274/276 |
|---|---|---|
| x117 | (6-chloro-2-cyclobutylimidazo[1,2-b]pyridazin-3-yl)methanol | NMR $^1$H (CDCl$_3$) δ 2.10 (m, 1H), 2.34-2.56 (m, 5H), 3.81 (m, 1H), 4.99 (m, 1H), 7.04 (d, 1H), 7.86 (d, 1H) |
| x118 | (2-cyclopropyl-6-fluoroimidazo[1,2-a]pyridin-3-yl)methanol | LC-MS (MH$^+$): 207 |
| x119 | (2-cyclopropyl-6-chloroimidazo[1,2-a]pyridin-3-yl)methanol | LC-MS (MH$^+$): 223/225 |

36.4. Synthesis of 1-[(6-chloro-2-cyclopropylimidazo[1,2-b]pyridazin-3-yl)methyl]-4-(2,2-difluorovinyl)pyrrolidin-2-one 62

A solution of (6-chloro-2-cyclopropylimidazo[1,2-b]pyridazin-3-yl)methanol x115 (889 mg, 3.97 mmol), 4-(2,2-difluorovinyl)pyrrolidin-2-one (643 mg, 4.37 mmol, 1.1 eq) and paratoluenesulfonic acid (76 mg, 0.40 mmol, 0.1 eq) in toluene (20 ml) is heated under reflux for 16 h. After cooling, the solvent is removed under reduced pressure, the crude product is dissolved in dichloromethane (100 ml). The organic layer is washed by water (150 ml). The aqueous layer is extracted by dichloromethane (100 ml). The cumulated organic layers are dried over MgSO$_4$, filtered and evaporated under reduced pressure. The residue is purified by preparative chromatography over silicagel (benzine/AcOEt:60/40) to afford 1-[(6-chloro-2-cyclopropylimidazo[1,2-b]pyridazin-3-yl)methyl]-4-(2,2-difluorovinyl)pyrrolidin-2-one 62 after recrystallization in diisopropylether.

Yield: 28%.

LC-MS (MH$^+$): 353/355.

Compounds 18, 19, 51, 52, 71 and 72 may be prepared as described for compound 62.

Example 37

Synthesis of 1-{[2-cyclopropyl-6-(propylamino)imidazo[1,2-b]pyridazin-3-yl]methyl}-4-(2,2-difluorovinyl)pyrrolidin-2-one 65

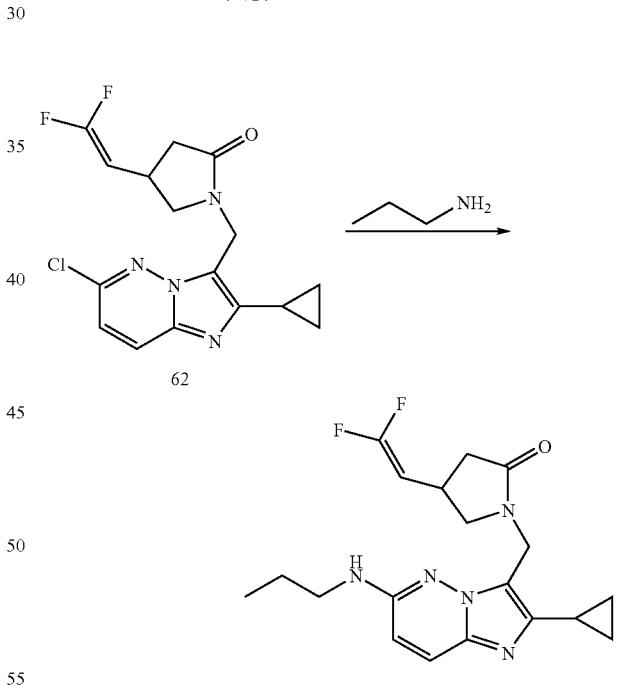

A solution of 1-[(6-chloro-2-cyclopropylimidazo[1,2-b]pyridazin-3-yl)methyl]-4-(2,2-difluorovinyl)pyrrolidin-2-one 62 (340 mg, 0.964 mmol), sodium terbutoxide (11.2 mg, 1.16 mmol, 1.2 eq), palladium (II) acetate (21.6 mg, 0.093 mmol, 0.1 eq) and BINAP (120 mg, 0.193 mmol, 0.2 eq) in toluene (20 ml) is heated during 1.5 h under reflux. After cooling to room temperature, the crude reaction mixture is filtered. The organic layer is washed with water (2×30 ml) and dried over MgSO$_4$. The solvent is evaporated under reduced pressure and the crude product is purified by preparative chromatography (CH$_2$Cl$_2$/MeOH/NH$_4$OH: 97/3/0.3 (v/v/v)). 1-{[2-cyclopropyl-6-(propylamino)imidazo[1,2-b]pyridazin-3-yl]methyl}-4-(2,2-difluorovinyl)pyrrolidin-2-one 65 is obtained after recrystallization in dichloromethane/hexane.

Yield: 55%.

LC-MS (MH$^+$): 376.

Compounds 66, 67, 68 and 70 may be prepared as described for compound 65.

Example 38

Synthesis of 4-(2,2-difluorovinyl)-1-{[6-methoxy-2-(trifluoromethyl)imidazo[1,2-b]pyridazin-3-yl]methyl}pyrrolidin-2-one 42

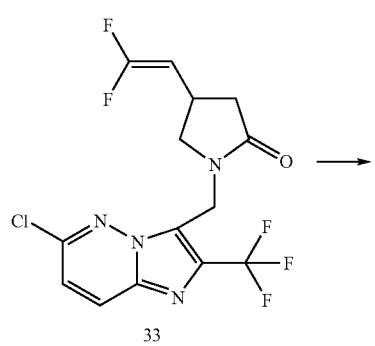

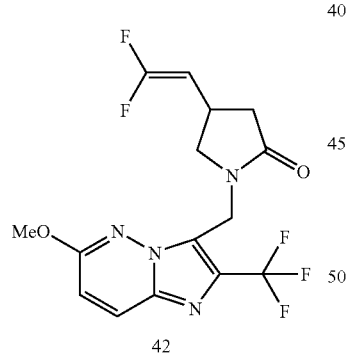

A solution of {[6-chloro-2-(trifluoromethyl)imidazo[1,2-b]pyridazin-3-yl]methyl}-4-(2,2-difluoro-vinyl)-pyrrolidin-2-one 33 (500 mg, 1.31 mmol, 1 eq) and sodium methoxide (142 mg, 2.63 mmol, 2 eq) in methanol (5 ml) is heated in microwave apparatus (300 W, T 150° C.) until complete conversion (0.5 h). After cooling to room temperature, water (10 ml) is added and the methanol is removed under reduced pressure. Subsequent extraction with dichloromethane (2×20 ml), drying of cumulated organic layers over MgSO$_4$, filtration and solvent evaporation under reduced pressure affords the crude reaction mixture which is recristallized in AcOEt/iPr$_2$O to yield 0.46 g of 4-(2,2-difluorovinyl)-1-{[6-methoxy-2-(trifluoromethyl)imidazo[1,2-b]pyridazin-3-yl]methyl}pyrrolidin-2-one 42.

Yield: 93%.

LC-MS (MH$^+$): 377.

Compounds 36, 38, 39, 58, 60, 75, 76, 77, 78, 79, 80 and 81 may be prepared as described for compound 42.

Example 39

Synthesis of 1-{[6-(butylamino)-2-(trifluoromethyl)imidazo[1,2-b]pyridazin-3-yl]methyl}-4-(2,2-difluorovinyl)pyrrolidin-2-one 73

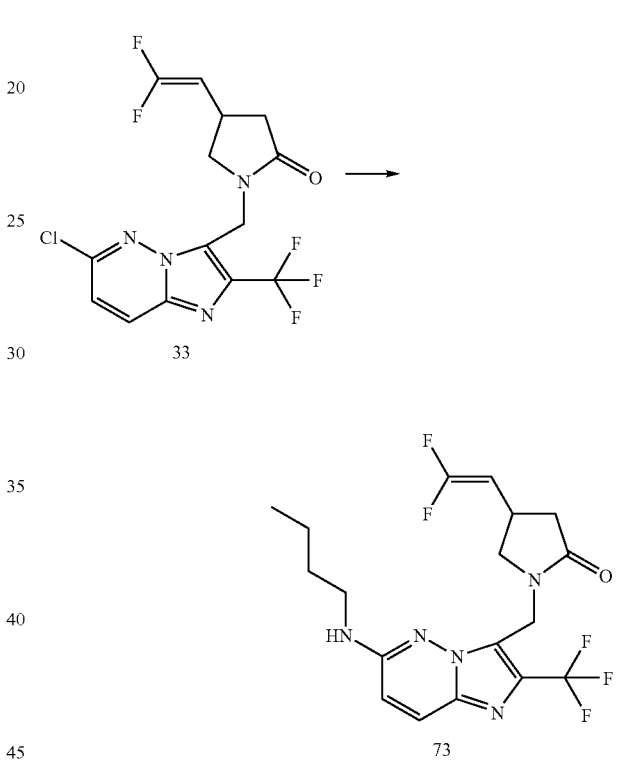

A solution of 1-{[6-chloro-2-(trifluoromethyl)imidazo[1,2-b]pyridazin-3-yl]methyl}-4-(2,2-difluorovinyl)pyrrolidin-2-one 33 (200 mg, 0.48 mmol, 1 eq) and n-butylamine (0.14 g, 0.96 mmol, 2 eq) in acetonitrile (2 ml) is heated in microwave apparatus (300 W, Tmax 150° C.) until complete conversion (2 h). After cooling to room temperature, a potassium carbonate aqueous saturated solution (10 ml) is added and the crude reaction mixture is extracted with dichloromethane (3×20 ml). Subsequent drying of cumulated organic layers over MgSO$_4$, filtration and solvent evaporation under reduced pressure furnished the crude reaction mixture which is purified by preparative chromatography over silicagel (CH$_2$Cl$_2$/MeOH/NH$_4$OH: 95/5/0.5) to afford 1-{[6-(butylamino)-2-(trifluoromethyl)imidazo[1,2-b]pyridazin-3-yl]methyl}-4-(2,2-difluorovinyl)pyrrolidin-2-one 73.

Yield: 80%.

LC-MS (MH$^+$): 418.

Compounds 41, 44, 54, 55, 57, 59, 61, 63 and 74 may be prepared as described for compound 73.

Example 40

Synthesis of 1-{[6-(methylthio)-2-(trifluoromethyl)imidazo[1,2-b]pyridazin-3-yl]methyl}-4-propylpyrrolidin-2-one 46

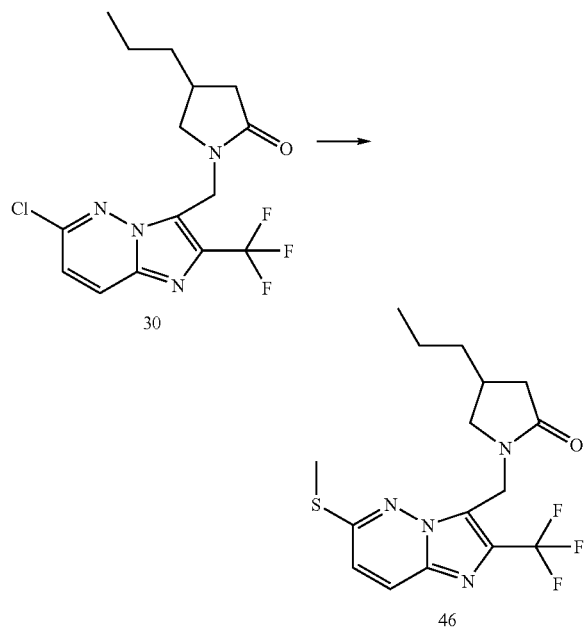

A mixture of 1-{[6-chloro-2-(trifluoromethyl)imidazo[1,2-b]pyridazin-3-yl]methyl}-4-propylpyrrolidin-2-one 30 (400 mg, 1.11 mmol) and sodium methanethiolate (155 mg, 2.22 mmol, 2.2 eq) in THF is heated in a microwave apparatus (300 W, Tmax 150° C.) during 15 minutes. After cooling to room temperature, hydrolysis (15 ml of water), extraction (ethyl acetate, 3×15 ml), the cumulated organic layers are dried over MgSO$_4$, filtered and condensed under reduce pressure to afford an oil which is purified under preparative chromatography over silicagel (Gradient: CH$_2$Cl$_2$ to CH$_2$Cl$_2$/MeOH/NH$_4$OH 99/1/0.1 (v/v/v)). Recrystallization in diisopropyl ether affords 1-{[6-(methylthio)-2-(trifluoromethyl)imidazo[1,2-b]pyridazin-3-yl]methyl}-4-propylpyrrolidin-2-one 46.

Yield: 26%.
LC-MS (MH$^+$): 373.

Example 41

Synthesis of 1-[{6-(methylsulfonyl)-2-(trifluoromethyl)imidazo[1,2-b]pyridazin-3-yl]methyl}-4-propylpyrrolidin-2-one 48

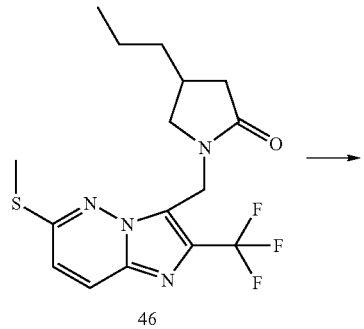

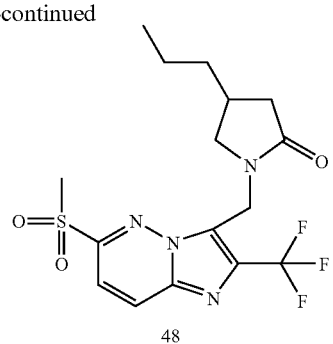

To 1-{[6-(methylthio)-2-(trifluoromethyl)imidazo[1,2-b]pyridazin-3-yl]methyl}-4-propylpyrrolidin-2-one 46 (100 mg, 0.27 mmol) in chloroform (5 ml) is added 4-chloroperbenzoic acid (93 mg, 0.54 mmol, 2 eq) at −30° C. After 15 minutes, the mixture is warmed to room temperature then stirred for additional 16 hours. Then is added further 4-chloroperbenzoic acid (46 mg, 0.27 mmol, 1 eq) and stirring is pursued during additional 16 h. The organic layer is washed with a saturated aqueous Na$_2$CO$_3$ solution (3 ml), then with a saturated aqueous Na$_2$S$_2$O$_5$ solution (3 ml). After drying over MgSO$_4$ and filtration, the organic layer is condensed under reduced pressure. The resulting crude product is purified by chromatography (CH$_2$Cl$_2$/MeOH/NH$_4$OH 99/1/0.1) to yield 1-{[6-(methylsulfonyl)-2-(trifluoromethyl)imidazo[1,2-b]pyridazin-3-yl]methyl}-4-propylpyrrolidin-2-one 48.

Yield: 55%.
LC-MS (MH$^+$): 405.

Example 42

Synthesis of 1-{[6-(methylsulfinyl)-2-(trifluoromethyl)imidazo[1,2-b]pyridazin-3-yl]methyl}-4-propylpyrrolidin-2-one 49

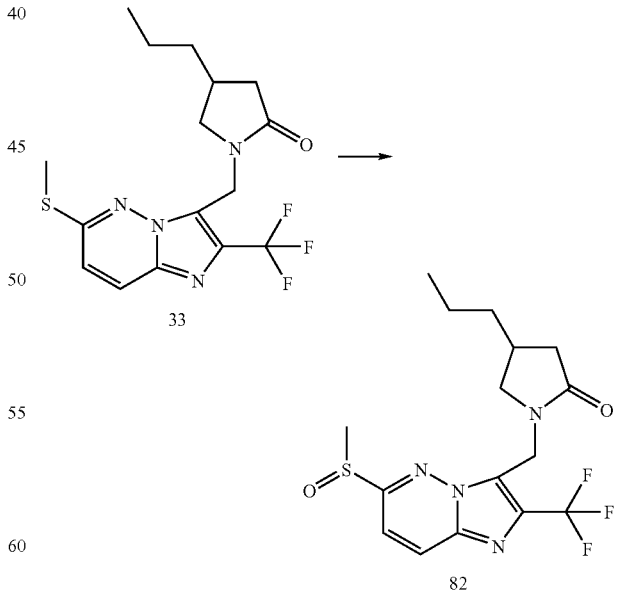

4-chloroperbenzoic acid (36 mg, 0.134 mmol, 1 eq) is added to a solution of 1-{[6-(methylthio)-2-(trifluoromethyl)imidazo[1,2-b]pyridazin-3-yl]methyl}-4-propylpyrrolidin-2-one 33 (50 mg, 0.134 mmol) in chloroform (2 ml) at −30° C.

After 30 minutes, the mixture is warmed to room temperature then stirred for additional 16 hours. After hydrolysis with a saturated aqueous NaHCO₃ solution (2 ml) and extraction with CHCl₃ (2 ml), the cumulated organic layers are dried over MgSO₄ and condensed under reduced pressure. The resulting crude product is purified by reverse phase liquid chromatography (gradient acetonitrile/water/TFA) to yield 1-{[6-(methylsulfinyl)-2-(trifluoromethyl)imidazo[1,2-b]pyridazin-3-yl]methyl}-4-propylpyrrolidin-2-one 82.

Yield: 38%.

LC-MS (MH⁺): 389.

Example 43

Synthesis of 3-{[4-(2,2-difluorovinyl)-2-oxopyrrolidin-1-yl]methyl}-2-(trifluoromethyl)imidazo[1,2-b]pyridazine-6-carbonitrile 82

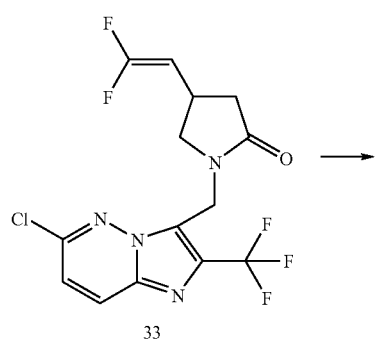

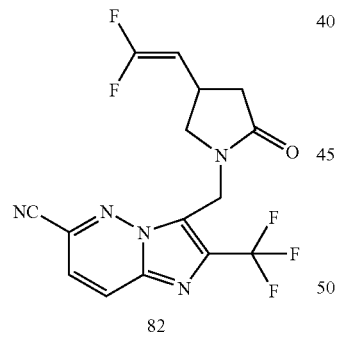

A solution of 1-{[6-chloro-2-(trifluoromethyl)imidazo[1,2-b]pyridazin-3-yl]methyl}-4-(2,2-difluorovinyl)pyrrolidin-2-one 33 (1 g, 2.63 mmol), nickel (II) bromide (579 mg, 2.63 mmol, 1 eq) and sodium cyanide (257 mg, 5.25 mmol, 2 eq) in N-methylpyrrolidin-2-one (15 ml) is heated at 200° C. in microwave apparatus for 30 minutes. After cooling to room temperature, ethyl ether (100 ml) is added, and the resulting solution is washed three time by 50 ml of water. The resulting organic layer is dried over magnesium sulfate, filtrated and condensed under reduced pressure. The resulting crude oil is purified by preparative chromatography over silicagel (CH₂Cl₂/MeOH/NH₄OH: 99/1/0.1), then recrystallized in ethyl acetate and diisopropyl ether to afford 3-{[4-(2,2-difluorovinyl)-2-oxopyrrolidin-1-yl]methyl}-2-(trifluoromethyl)imidazo[1,2-b]pyridazine-6-carbonitrile 82.

Yield: 23%.

LC-MS (MH⁺): 372.

Example 44

Synthesis of 4-(2,2-difluorovinyl)-1-{[6-phenyl-2-(trifluoromethyl)imidazo[1,2-b]pyridazin-3-yl]methyl}pyrrolidin-2-one 84

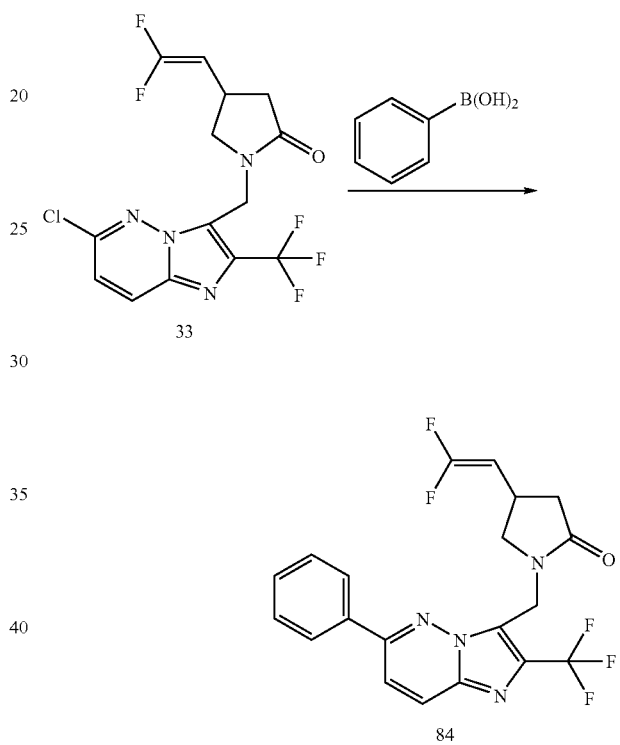

A solution of sodium carbonate (28 mg, 0.26 mmol, 2 eq in 0.25 ml of water) is added to a solution of 1-{[6-chloro-2-(trifluoromethyl)imidazo[1,2-b]pyridazin-3-yl]methyl}-4-(2,2-difluorovinyl)pyrrolidin-2-one 33 (50 mg, 0.13 mmol), phenylboronic acid (18 mg, 0.144 mmol, 1.1 eq) and tetrakis(triphenylphosphine) palladium (8 mg, 0.007 mol, 0.05 eq) in dimethoxyethane (2 ml) at 75° C. The reaction mixture is stirred overnight. The reaction mixture is filtered, condensed under reduced pressure, the residue is taken in 2 ml of water and extracted with ethyl acetate (2×2 ml). The cumulated organic layers are dried over MgSO₄, filtered and condensed under reduced pressure to afford the crude product which is purified by preparative chromatography (CH₂Cl₂/MeOH/NH₄OH: 99/1/0.1 (v/v/v)) yielding the 4-(2,2-difluorovinyl)-1-{[6-phenyl-2-(trifluoromethyl)imidazo[1,2-b]pyridazin-3-yl]methyl}pyrrolidin-2-one 84.

Yield: 58%.

LC-MS (MH⁺): 423.

Compounds 83, 85 and 86 may be prepared as described for compound 84.

Example 45

Synthesis of 1-{[6-cyclopropyl-2-(trifluoromethyl)imidazo[1,2-b]pyridazin-3-yl]methyl}-4-propylpyrrolidin-2-one 40

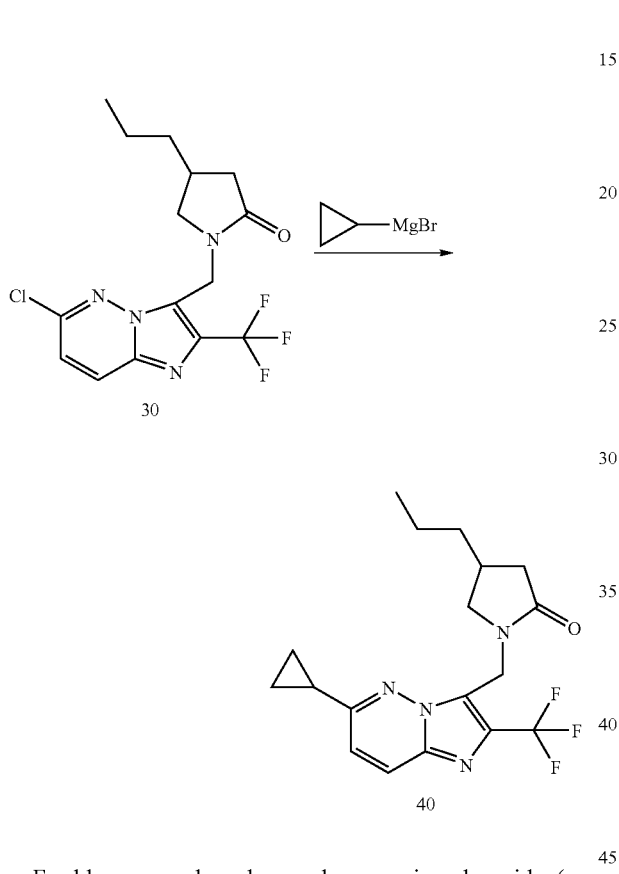

Freshly prepared cyclopropyl magnesium bromide (as described in J. Am. Chem. Soc. (2002), 124, 13856-63; with cyclopropylbromide (48 mg, 0.4 mmol, 1.2 eq) and magnesium powder (10 mg) in 5 ml of THF) is added slowly and dropwise to a mixture of 1-{[6-chloro-2-(trifluoromethyl)imidazo[1,2-b]pyridazin-3-yl]methyl}-4-propylpyrrolidin-2-one 30 (120 mg, 0.33 mmol) and iron (III) acetylacetone (3 mg, 0.0165 mmol, 0.05 eq) in THF (5 ml) at room temperature. The reaction is kept at room temperature for 16 h, then hydrolyzed (10 ml of 1 N HCl), neutralized with a saturated solution of $NaHCO_3$ until alkaline pH. The crude product is extracted with ethyl acetate (3×20 ml). The cumulated organic layers are dried over $MgSO_4$, filtered and condensed under reduced pressure. The residue is purified by preparative chromatography ($CH_2Cl_2$/MeOH/$NH_4OH$: 98/2/0.2 (v/v/v)) to afford 1-{[6-cyclopropyl-2-(trifluoromethyl)imidazo[1,2-b]pyridazin-3-yl]methyl}-4-propylpyrrolidin-2-one 40.

Yield 25%

LC-MS (MH+): 367.

Example 46

Synthesis of 1-[(6-methyl-2-phenylpyrazolo[1,5-a]pyrimidin-3-yl)methyl]-4-propylpyrrolidin-2-one 202

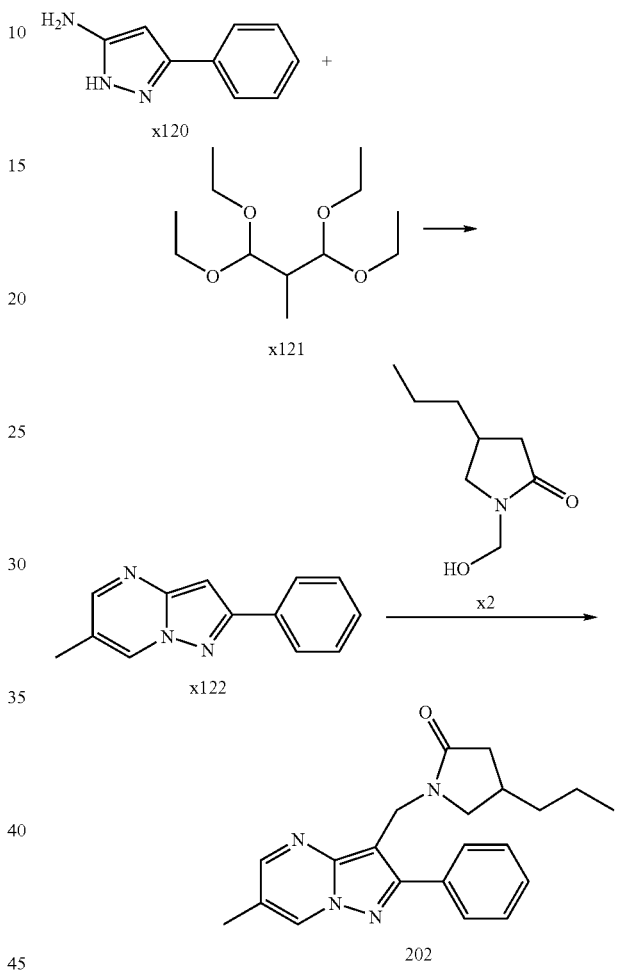

46.1. Synthesis 6-methyl-2-phenylpyrazolo[1,5-a]pyrimidine x122

To a solution of 3-phenyl-1H-pyrazol-5-amine x120 (31.4 mmol, 1 eq, 5 g) in AcOH (30 ml) is added 1,1,3,3-tetraethoxy-2-methylpropane x121 (31.4 mmol, 1 eq, 7.36 g). The mixture is heated at 100° C. during 4 hours. After evaporation of the solvent under reduced pressure, the crude product is poured in saturated $NaHCO_3$ aqueous solution and then extracted with AcOEt. The cumulated organic layers are dried over $MgSO_4$, filtered and evaporated under reduce pressure. The crude mixture is recristallized in AcOEt to afford 6-methyl-2-phenylpyrazolo[1,5-a]pyrimidine x122 as a solid (3 g).

Yield: 45%.

LC-MS (MH+): 210.

The following compounds may be synthesized according to the same method:

| | | |
|---|---|---|
| x123 | 2-(2-thienyl)pyrazolo[1,5-a]pyrimidine | LC-MS (MH+): 202 |
| x124 | 2-phenylpyrazolo[1,5-a]pyrimidine | LC-MS (MH+): 196 |
| x125 | 2-(2-furyl)pyrazolo[1,5-a]pyrimidine | LC-MS (MH+): 186 |
| x126 | 2-(4-bromophenyl)pyrazolo[1,5-a]pyrimidine | LC-MS (MH+): 274/276 |
| x127 | 2-(4-fluorophenyl)pyrazolo[1,5-a]pyrimidine | LC-MS (MH+): 214 |
| x128 | 2-(4-chlorophenyl)-6-methylpyrazolo[1,5-a]pyrimidine | LC-MS (MH+): 244/246 |
| x129 | 2-(4-chlorophenyl)pyrazolo[1,5-a]pyrimidine | LC-MS (MH+): 230/232 |
| x130 | 6-chloro-2-(4-chlorophenyl)pyrazolo[1,5-a]pyrimidine | LC-MS (MH+): 264/266/268 |

46.2. Synthesis of 1-[(6-methyl-2-phenylpyrazolo[1,5-a]pyrimidin-3-yl)methyl]-4-propylpyrrolidin-2-one 202

To a solution of 1-(hydroxymethyl)-4-propylpyrrolidin-2-one x2 (3.18 mmol, 1 eq, 0.5 g) in toluene (20 ml) is added thionyl chloride (3.5 mmol, 1.1 eq, 0.416 g). The mixture is stirred vigorously overnight at 80° C. After this time, 6-methyl-2-phenylpyrazolo[1,5-a]pyrimidine x122 (3.18 mmol, 1 eq, 0.665 g) and $AlCl_3$ (3.18 mmol, 1 eq, 0.424 g) are successively added. The mixture is stirred at 80° C. for 2 hours. After evaporation of the solvent under reduced pressure, the crude mixture is poured to water and extracted with dichloromethane. The cumulated organic layers are dried over $MgSO_4$, filtered over celite and evaporated under reduced pressure. The crude reaction mixture is purified by chromatography on silicagel ($CH_2Cl_2$/MeOH/$NH_4OH$ 98/2/0.2 (v/v/v)) and crystallized with AcOEt to afford 0.5 g of 1-[(6-methyl-2-phenylpyrazolo[1,5-a]pyrimidin-3-yl)methyl]-4-propylpyrrolidin-2-one 202.

Yield: 50%.

LC-MS (MH+): 349.

Compounds 205 and 210 may be prepared as described for compound 202.

Example 47

Synthesis of 4-(2,2-difluorovinyl)-1-[(6-fluoro-5-methyl-2-phenylpyrazolo[1,5-a]pyrimidin-3-yl)methyl]pyrrolidin-2-one 207

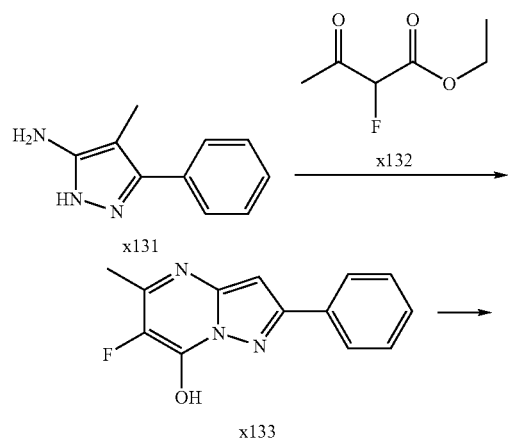

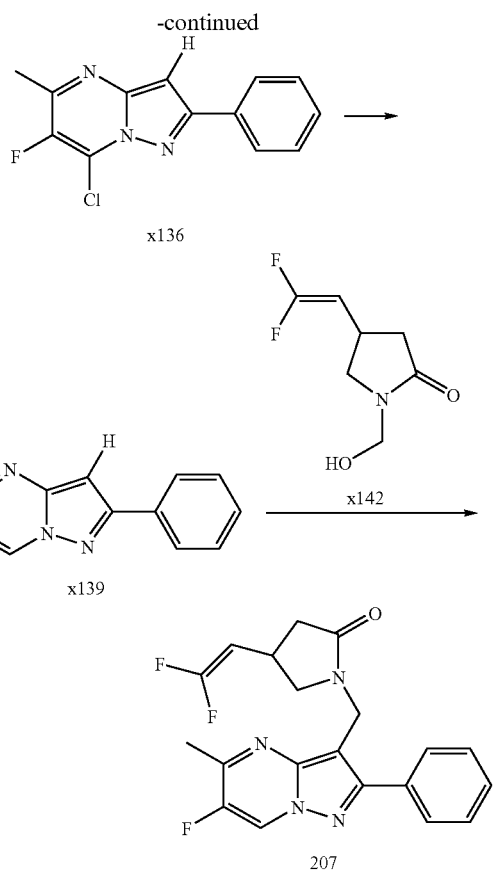

47.1. Synthesis of 6-fluoro-5-methyl-2-phenylpyrazolo[1,5-a]pyrimidin-7-ol x133

To a solution of 3-phenyl-1H-pyrazol-5-amine x131 (52 mmol, 1 eq, 8.3 g) in 50 ml of AcOH, is added ethyl 2-fluoro-3-oxobutanoate x132 (57 mmol, 1.2 eq, 8.5 g). The mixture is heated at 100° C. for 0.5 hour. After cooling to room temperature, the resulting product is filtered, washed with EtOH and dried to afford 8.1 g of 6-fluoro-5-methyl-2-phenylpyrazolo[1,5-a]pyrimidin-7-ol x133.

Yield: 55%

LC-MS (MH+): 244.

The following compounds may be synthesized according to the same method:

| | | |
|---|---|---|
| x134 | 5,6-dimethyl-2-phenylpyrazolo[1,5-a]pyrimidin-7-ol | LC-MS (MH+): 240 |
| x135 | 2-cyclopropyl-5-methylpyrazolo[1,5-a]pyrimidin-7-ol | LC-MS (MH+): 190 |

47.2. Synthesis of 7-chloro-6-fluoro-5-methyl-2-phenylpyrazolo[1,5-a]pyrimidine x136

A solution of 6-fluoro-5-methyl-2-phenylpyrazolo[1,5-a]pyrimidin-7-ol x133 (25 mmol, 1 eq, 6.2 g) in $POCl_3$ (150 ml) is heated at 125° C. overnight. After cooling to room temperature, the solution is diluted in dichloromethane and quenched on ice (temperature must be kept under 25° C.). After separation of the organic layer, the aqueous phase is extracted twice with dichloromethane. The cumulated organic-layers are dried over MgSO$_4$, filtered, evaporated under reduced pressure and the residue purified by chromatography on silicagel (CH$_2$Cl$_2$) to afford 6.6 g of 7-chloro-6-fluoro-5-methyl-2-phenylpyrazolo[1,5-a]pyrimidine x136.

Yield: 89%.

LC-MS (MH$^+$): 262/264.

The following compounds may be synthesized according to the same method:

| x137 | 7-chloro-5,6-dimethyl-2-phenylpyrazolo[1,5-a]pyrimidine | LC-MS (MH$^+$): 258/260 |
|---|---|---|
| x138 | 7-chloro-2-cyclopropyl-5-methylpyrazolo[1,5-a]pyrimidine | LC-MS (MH$^+$): 208/210 |

47.3. Synthesis 6-fluoro-5-methyl-2-phenylpyrazolo[1,5-a]pyrimidine x139

To a solution of 7-chloro-6-fluoro-5-methyl-2-phenylpyrazolo[1,5-a]pyrimidine x136 (22.9 mmol, 1 eq, 6 g) in 150 ml of AcOH at 0° C., is added zinc dust (68 mmol, 3 eq, 4.5 g). The mixture is stirred at 25° C. overnight. After evaporation of the solvent under reduced pressure, the crude product is poured on ice and quenched with a saturated aqueous NaHCO$_3$ solution and extracted with AcOEt. The cumulated organic layers are washed with brine, dried over MgSO$_4$, filtered and evaporated under reduced pressure to yield 6-fluoro-5-methyl-2-phenylpyrazolo[1,5-a]pyrimidine x139.

Yield: 90%.

LC-MS (MH$^+$): 228.

The following compounds may be synthesized according to the same method:

| x140 | 5,6-dimethyl-2-phenylpyrazolo[1,5-a]pyrimidine | LC-MS (MH$^+$): 224 |
|---|---|---|
| x141 | 2-cyclopropyl-5-methylpyrazolo[1,5-a]pyrimidine | LC-MS (MH$^+$): 174 |

47.4. Synthesis of 4-(2,2-difluorovinyl)-1-[(6-fluoro-5-methyl-2-phenylpyrazolo[1,5-a]pyrimidin-3-yl)methyl]pyrrolidin-2-one 207

4-(2,2-difluorovinyl)-1-(hydroxymethyl)pyrrolidin-2-one x142 is prepared as described in example 1.1 from 4-(2,2-difluorovinyl)pyrrolidin-2-one x98.

To a solution of 6-fluoro-5-methyl-2-phenylpyrazolo[1,5-a]pyrimidine x139 (5.6 mmol, 1 eq, 1.28 g) in 60 ml of toluene is added successively 1-(hydroxymethyl)-4-propylpyrrolidin-2-one (5.6 mmol, 1 eq, 1 g) and paratoluene sulfonic acid (0.56 mmol, 0.1 eq, 0.107 g). The mixture is stirred vigorously overnight at 100° C. The solvent is removed under reduce pressure. The residue is poured in water and extracted with toluene. The cumulated organic layers are dried over MgSO$_4$, filtered and evaporated under reduced pressure. The crude product purified by chromatography on silicagel (CH$_2$Cl$_2$/MeOH/NH$_4$OH 98/2/0.2) to afford 237 mg of 4-(2,2-difluorovinyl)-1-[(6-fluoro-5-methyl-2-phenylpyrazolo[1,5-a]pyrimidin-3-yl)methyl]pyrrolidin-2-one 207 as a solid.

Yield: 11%.

LC-MS (MH$^+$): 387.

Compounds 186, 188, 190, 198, 200, 206, 209, 210, 214, 215, 216, 217 and 218 may be prepared as described for compound 207.

Example 48

Synthesis of 1-[(2-phenylpyrazolo[1,5-a]pyrimidin-3-yl)methyl]-4-propylpyrrolidin-2-one 191

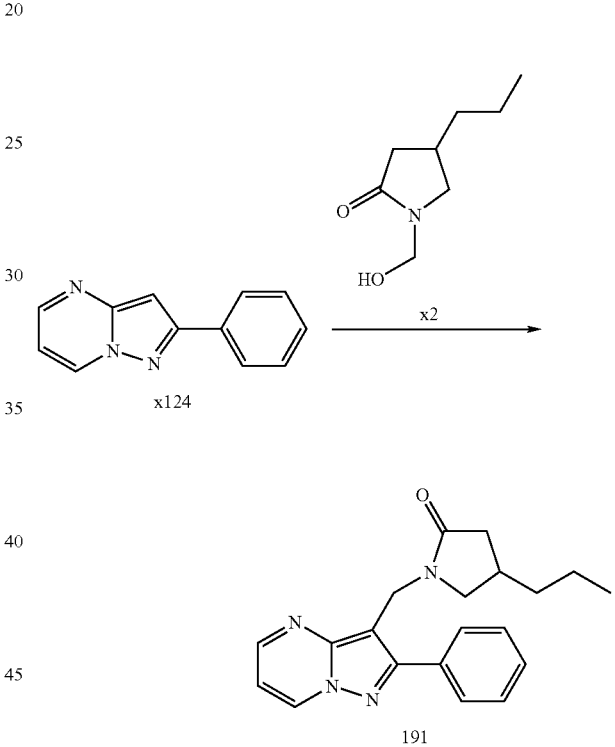

To a solution of 2-phenylpyrazolo[1,5-a]pyrimidine x124 (25.6 mmol, 1 eq, 5 g) in trifluoroacetic acid (150 ml) is added 1-(hydroxymethyl)-4-propylpyrrolidin-2-one x2 (38.4 mmol, 1.5 eq, 6 g). The resulting solution is stirred at room temperature for three days. The solvent is removed under reduce pressure, ice is added and the mixture is alkalinized by solid NaHCO$_3$. The mixture is extracted by AcOEt, the organic layers are washed with brine and dried over Na$_2$SO$_4$. The solvent is removed under reduce pressure and the crude reaction mixture purified by chromatography on silicagel (AcOEt/hexane 40/60). After crystallisation in AcOEt/hexane, to afford 2.06 g of 1-[(2-phenylpyrazolo[1,5-a]pyrimidin-3-yl)methyl]-4-propylpyrrolidin-2-one 191 are obtained.

Yield: 24%.

LC-MS (MH$^+$): 335.

Compounds 21, 25, 26, 27, 203, 243 and 245 may be prepared as described for compound 191.

Example 49

Synthesis of 4-(2,2-difluorovinyl)-1-[(6-methyl-2-phenylpyrazolo[1,5-a]pyrimidin-3-yl)methyl]pyrrolidin-2-one 211

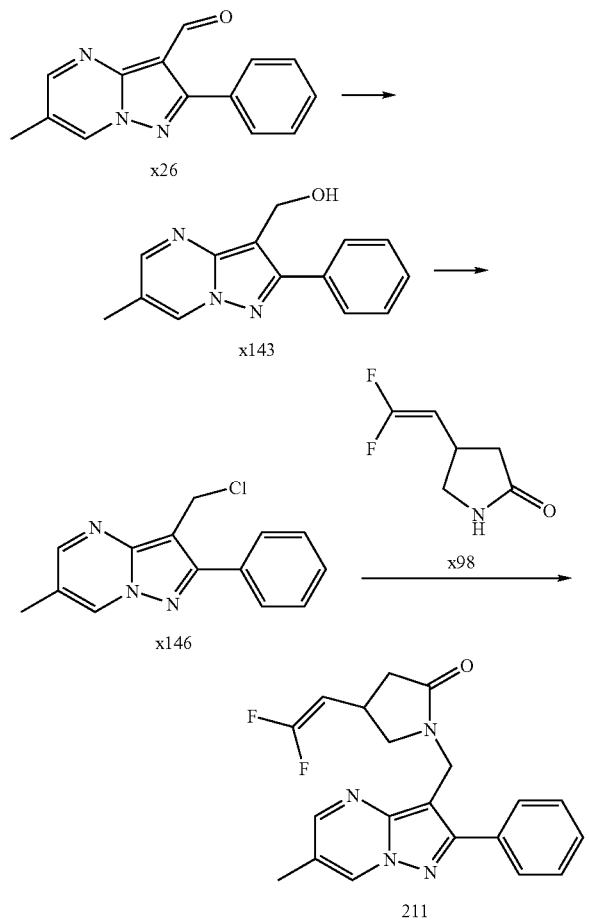

49.1. Synthesis of (6-methyl-2-phenylpyrazolo[1,5-a]pyrimidin-3-yl)methanol x143

To a solution of 6-methyl-2-phenylpyrazolo[1,5-a]pyrimidine-3-carbaldehyde x26 (3.37 mmol, 1 eq, 0.8 g) in MeOH (20 ml) maintained at 0° C. is added sodium borohydride (3.7 mmol, 1.1 eq, 0.14 g) and the resulting solution is stirred at room temperature during 0.5 hour. After this time, the solvent is removed under reduced pressure. The solid residue is washed with water, filtered and dried (under vacuum) to give 0.58 g of pure (6-methyl-2-phenylpyrazolo[1,5-a]pyrimidin-3-yl)methanol x143.

Yield: 72%.

LC-MS (MH+): 240.

The following compounds may be synthesized according to the same method:

| x144 | (5-methyl-2-phenylpyrazolo[1,5-a]pyrimidin-3-yl)methanol | LC-MS (MH+): 240 |
|---|---|---|
| x145 | [2-(2-thienyl)pyrazolo[1,5-a]pyrimidin-3-yl]methanol | LC-MS (MH+): 232 |

49.2. Synthesis of 4-(2,2-difluorovinyl)-1-[(6-methyl-2-phenylpyrazolo[1,5-a]pyrimidin-3-yl)methyl]pyrrolidin-2-one 211

To a solution of (6-methyl-2-phenylpyrazolo[1,5-a]pyrimidin-3-yl)methanol x143 (2.4 mmol, 1 eq, 0.58 g) in toluene (20 ml) is added thionyl chloride (4.8 mmol, 2 eq, 353 µl). The mixture is heated at 80° C. for 2 hours. The resulting mixture is cooled down to room temperature and the solvent removed under reduced pressure to afford 3-(chloromethyl)-6-methyl-2-phenylpyrazolo[1,5-a]pyrimidine x146, to which 5 ml of dry DMF are added.

3-(chloromethyl)-5-methyl-2-phenylpyrazolo[1,5-a]pyrimidine x147 and 3-(chloromethyl)-2-(2-thienyl)pyrazolo[1,5-a]pyrimidine x148 may be synthesized according to the same method The above mentioned solution of intermediate x146 is added to a solution containing 4-(2,2-difluorovinyl)pyrrolidin-2-one x98 (2.64 mmol, 1.1 eq, 0.356 g), 6 ml of dry DMF and sodium hydride (60% dispersion in oil, 2.64 mmol, 1.1 eq, 0.1 g) that have been stirred at room temperature for 0.5 hour. The resulting mixture is heated up at 80° C. for 1 hour. The mixture is poured in water and extracted with AcOEt. The cumulated organic layers are washed with brine, dried over MgSO4, filtered and evaporated under reduced pressure. The residue is crystallized in AcOEt to afford 0.443 g of 4-(2,2-difluorovinyl)-1-[(6-methyl-2-phenylpyrazolo[1,5-a]pyrimidin-3-yl)methyl]pyrrolidin-2-one 211.

Yield: 50%.

LC-MS (MH+): 369.

Compounds 212 and 213 may be prepared as described for compound 211.

Example 50

Synthesis of 1-[(2-tert-butyl-6-cyclopropylpyrazolo[1,5-a]pyrimidin-3-yl)methyl]-4-propylpyrrolidin-2-one 192

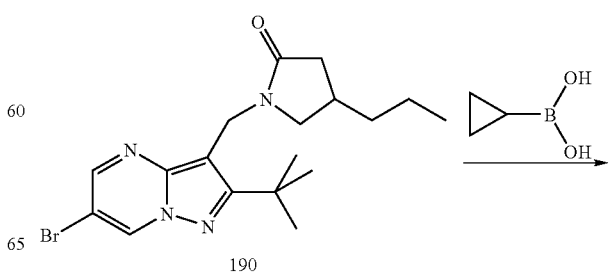

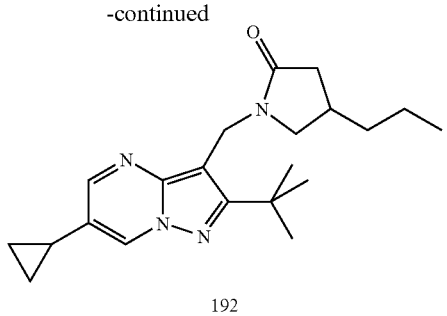

192

To a solution of 1-[(6-bromo-2-tertbutylpyrazolo(1,5-a)pyrimidin-3-yl)methyl]-4-propylpyrrolidin-2-one 190 (0.56 mmol, 1 eq, 0.2 g) in 5 ml of DME is added successively palladium-tetrakis-triphenylphosphine (0.019 mmol, 0.03 eq, 22 mg), cyclopropyl-boronic acid (0.727 mmol, 1.1 eq, 62 mg), and K₃PO₄ (1.98 mmol, 3 eq, 0.42 g) dissolved in 4 ml of water. The mixture is degassed and stirred vigorously at 90° C. for 4 hours. The solvent is removed under reduce pressure, water is added and the resulting mixture is extracted with dichloromethane. The organic phases are combined, washed with brine and dried over MgSO₄. Volatiles are removed under reduce pressure. The crude product is purified by chromatography on silicagel (CH₂Cl₂/MeOH/NH₄OH: 99/1/0.1) to afford 58 mg of pure 1-[(2-tert-butyl-6-cyclopropylpyrazolo[1,5-a]pyrimidin-3-yl)methyl]-4-propylpyrrolidin-2-one 192 the compound in pure form.

Yield: 25%.

LC-MS (MH⁺): 355.

Compounds 194, 195, 196 and 197 may be prepared as described for compound 192.

Example 51

Synthesis of 1-{[2-methyl-6-(phenylethynyl)pyrazolo[1,5-a]pyrimidin-3-yl]methyl}-4-propylpyrrolidin-2-one 199

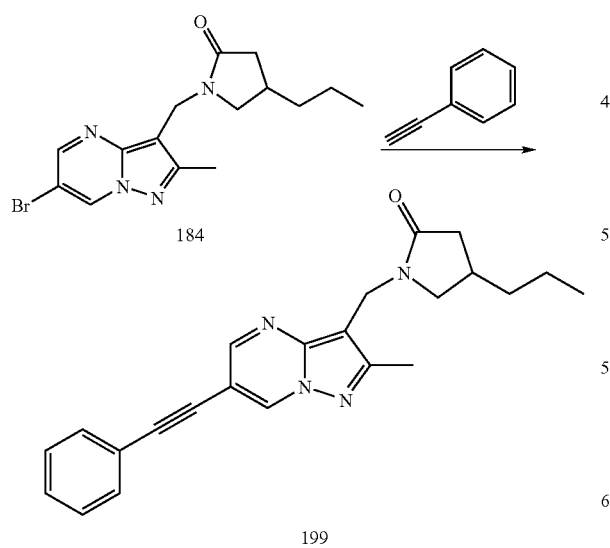

To a solution of 1-[(6-bromo-2-methylpyrazolo[1,5-a]pyrimidin-3-yl)methyl]-4-propylpyrrolidin-2-one 184 (0.66 mmol, 1 eq, 0.26 g) in 2 ml of water and 2 ml of isopropyl alcohol are added successively palladium on activated carbon (10%, 0.284 mmol, 0.5 eq, 30 mg), phenyl acetylene (0.68 mmol, 1.2 eq, 70 mg), and K₃PO₄ (1.13 mmol, 2 eq, 0.24 g) dissolved in 2 ml of water. The mixture is degassed and stirred vigorously overnight at 100° C. The solvent is removed under reduce pressure. The crude product is purified by chromatography on silicagel (AcOEt/hexane: 4/6) to afford 25 mg of 1-{[2-methyl-6-(phenylethynyl)pyrazolo[1,5-a]pyrimidin-3-yl]methyl}-4-propylpyrrolidin-2-one 199.

Yield: 11%.

LC-MS (MH⁺): 373.

Example 52

Synthesis of 1-{[2-methyl-6-(phenylethynyl)pyrazolo[1,5-a]pyrimidin-3-yl]methyl}-4-propylpyrrolidin-2-one 204

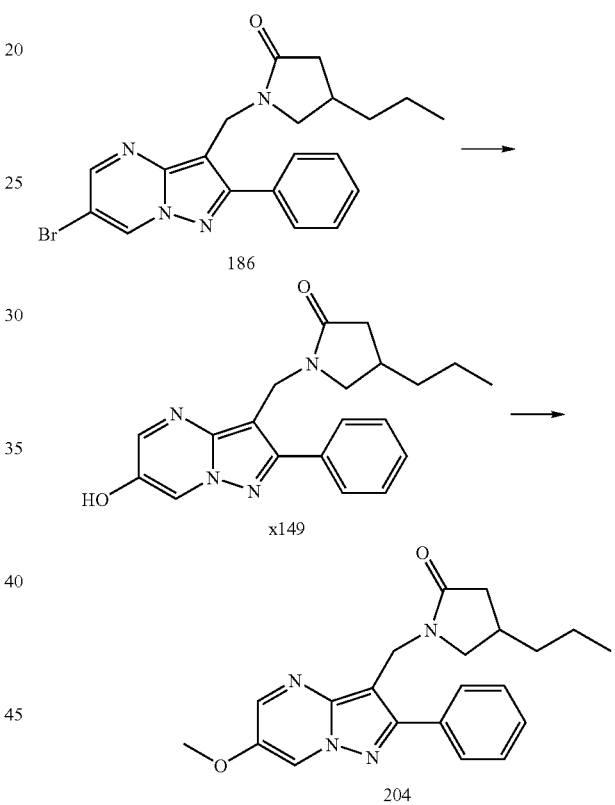

52.1. Synthesis of 1-[(6-hydroxy-2-phenylpyrazolo[1,5-a]pyrimidin-3-yl)methyl]-4-propylpyrrolidin-2-one x149

To a solution of 1-[(6-bromo-2-phenylpyrazolo[1,5-a]pyrimidin-3-yl)methyl]-4-propylpyrrolidin-2-one 186 (24 mmol, 1 eq, 10 g) in 100 ml of water are added successively palladium on activated carbon (10%, 1.2 mmol, 0.05 eq, 1.2 g) and K₃PO₄ (48 mmol, 2 eq, 10.25 g). The mixture is degassed and stirred vigorously at 130° C. for 8 hours. After cooling to room temperature, the reaction mixture is filtered on celite and a 5 N hydrochloric acid solution (10 ml) is added (until pH 7). The water is removed under reduce pressure and the crude is triturated with hot THF. After filtration and evaporation of THF, 1-[(6-hydroxy-2-phenylpyrazolo[1,5-a]pyrimidin-3-yl)methyl]-4-propylpyrrolidin-2-one x149 is obtained (1.9 g).

Yield: 22%.

LC-MS (MH⁺): 351.

Compound 201 may be prepared according to the same method.

52.2. Synthesis of 1-[(6-methoxy-2-phenylpyrazolo[1,5-a]pyrimidin-3-yl)methyl]-4-propylpyrrolidin-2-one 204

To a solution of 1-[(6-hydroxy-2-phenylpyrazolo[1,5-a]pyrimidin-3-yl)methyl]-4-propylpyrrolidin-2-one x149 (1.71 mmol, 1 eq, 0.6 g) in acetone (100 ml) is added iodomethane (17.1 mmol, 10 eq, 1.065 ml) and K₂CO₃ (17.1 mmol, 10 eq, 2.36 g). The mixture is refluxed for 5 minutes. Solvent is evaporated under reduced pressure. The crude product is purified by chromatography on silicagel (AcOEt/hexane: 1/1) and recrystallized in AcOEt to afford 0.19 g of 1-[(6-methoxy-2-phenylpyrazolo[1,5-a]pyrimidin-3-yl)methyl]-4-propylpyrrolidin-2-one 204.

Yield: 30%.

LC-MS (MH⁺): 365.

Example 53

Synthesis of 1-[(5-methoxypyrazolo[1,5-a]pyrimidin-3-yl)methyl]-4-propylpyrrolidin-2-one 208

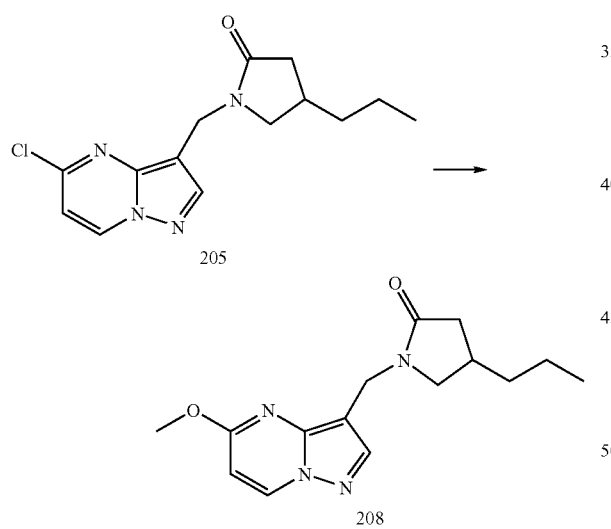

To a solution of 1-[(5-chloropyrazolo[1,5-a]pyrimidin-3-yl)methyl]-4-propylpyrrolidin-2-one 205 (0.575 mmol, 1 eq, 0.22 g) in MeOH (10 ml) is added sodium methoxide (5.75 mmol, 10 eq, 0.4 g). The mixture is heated at 80° C. for 2 hours. The solvent is removed under reduce pressure, water is added and the resulting mixture is extracted with CH₂Cl₂. The organic phases are combined, and dried over MgSO₄. Volatiles are removed under reduced pressure to afford 89 mg of 1-[(5-methoxypyrazolo[1,5-a]pyrimidin-3-yl)methyl]-4-propylpyrrolidin-2-one 208.

Yield: 33%.

LC-MS (MH⁺): 289.

Example 54

Synthesis of 1-[(5-bromo-3-phenyl-2H-pyrazolo[3,4-b]pyridin-2-yl)methyl]-4-propylpyrrolidin-2-one 292 and 1-[(5-bromo-3-phenyl-1H-pyrazolo[3,4-b]pyridin-1-yl)methyl]-4-propylpyrrolidin-2-one 290

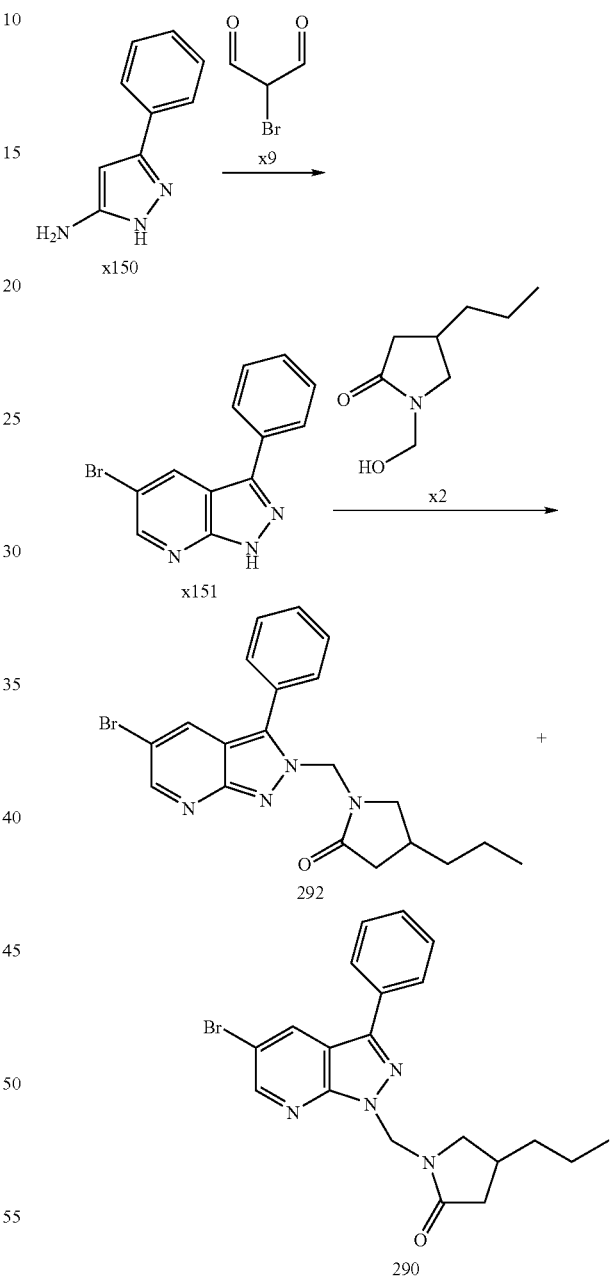

54.1. Synthesis of 5-bromo-3-phenyl-1H-pyrazolo[3,4-b]pyridine x151

5-bromo-3-phenyl-1H-pyrazolo[3,4-b]pyridine x151 is synthesized according to the method described in example 20.1 using 3-phenyl-1H-pyrazol-5-amine x150 and bromomalonaldehyde x9.

Yield: 13%.
LC-MS (MH+): 274/276.

54.2. Synthesis of 1-[(5-bromo-3-phenyl-2H-pyrazolo[3,4-b]pyridin-2-yl)methyl]-4-propylpyrrolidin-2-one 292 and 1-[(5-bromo-3-phenyl-1H-pyrazolo[3,4-b]pyridin-1-yl)methyl]-4-propylpyrrolidin-2-one 290

To a solution of 5-bromo-3-phenyl-1H-pyrazolo[3,4-b]pyridine x151 (14.6 mmol, 1 eq, 4 g) dissolved in TFA (100 ml) is added 1-(hydroxymethyl)-4-propylpyrrolidin-2-one x2 (21.8 mmol, 1.5 eq, 3.44 g). The mixture is heated at 100° C. for 2 hours. After evaporation of the solvent under reduced pressure, the crude reaction mixture is poured on ice and a saturated NaHCO₃ aqueous solution is added until pH 7. The mixture is extracted with CH₂Cl₂. The cumulated organic layers are dried over MgSO₄, filtered and evaporated under reduced. The products are purified by chromatography on silicagel (Hexane/AcOEt 6/4).

Yield: 50% for compound 292 and 21% for compound 290.
LC-MS (MH+): 413/415 for these two compounds.

Example 55

Synthesis of 1-[(5-bromo-1H-pyrazolo[3,4-b]pyridin-3-yl)methyl]-4-(2,2-difluorovinyl)pyrrolidin-2-one 221

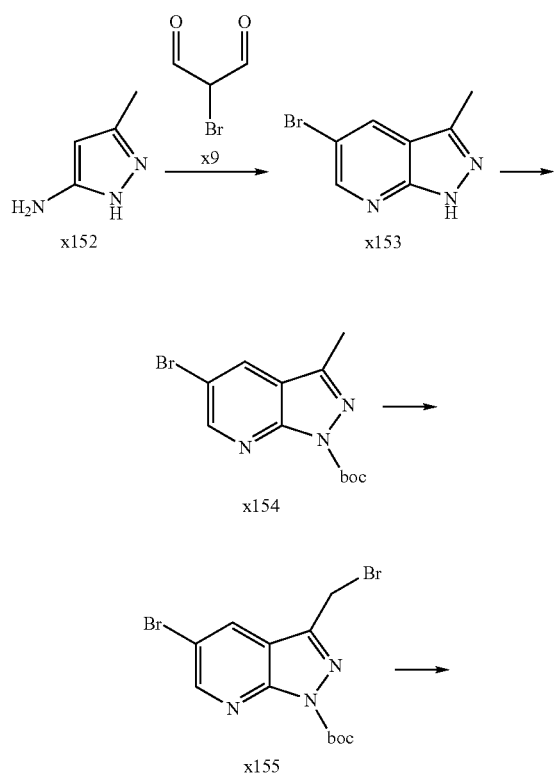

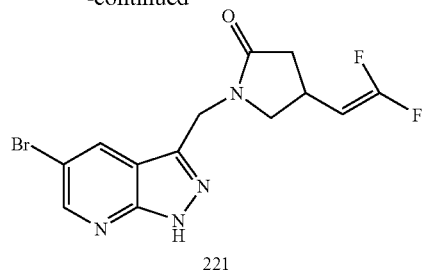
221

55.1. Synthesis of 5-bromo-3-methyl-1H-pyrazolo[3,4-b]pyridine x153

5-bromo-3-methyl-1H-pyrazolo[3,4-b]pyridine x153 is synthesized according to the method described in example 20.1 using 3-methyl-1H-pyrazol-5-amine b40 and bromomalonaldehyde a9.
Yield: 10%.
LC-MS (MH+): 212/214.

55.2. Synthesis of tert-butyl 5-bromo-3-methyl-1H-pyrazolo[3,4-b]pyridine-1-carboxylate x154

To a solution of 5-bromo-3-methyl-1H-pyrazolo[3,4-b]pyridine x153 (13.4 mmol, 1 eq, 2.86 g) in acetonitrile (10 ml) is added di(tert-butyl)dicarbonate (13.4 mmol, 1 eq, 2.94 g) and N,N-dimethyl aminopyridine (DMAP) (13.4 mmol, 1 eq, 1.64 g). The resulting mixture is refluxed during 1 minute. After cooling to room temperature, the solvent is evaporated under reduce pressure, and the residue washed with water, filtered and dried under vacuum to afford 3.62 g of tert-butyl 5-bromo-3-methyl-1H-pyrazolo[3,4-b]pyridine-1-carboxylate x154 as a solid.
Yield: 86%.
LC-MS (MH+): 312/314.

55.3. Synthesis of tert-butyl 5-bromo-3-(bromomethyl)-1H-pyrazolo[3,4-b]pyridine-1-carboxylate x155

A mixture of tert-butyl 5-bromo-3-methyl-1H-pyrazolo[3,4-b]pyridine-1-carboxylate x154 (10.8 mmol, 1 eq, 3.37 g), N-bromosuccinimide (1.92 g, 1 eq, 10.8 mmol) and azobisiso-butyronitrile (AIBN) (10.8 mmol, 1 eq, 1.77 g) in CCl₄ (50 ml) is heated for 2 hours at 80° C. The solvent is removed under reduce pressure, water is added and the resulting mixture is extracted with dichloromethane. The combined organic phases are dried over MgSO₄, filtered and volatiles removed under reduced pressure. The product is purified by chromatography on silicagel (hexane/AcOEt 8/2) and recristallized in AcOEt to afford 0.28 g of pure tert-butyl 5-bromo-3-(bromomethyl)-1H-pyrazolo[3,4-b]pyridine-1-carboxylate x155.
Yield: 6.6%.
LC-MS (MH+): 390/392/394.

55.4. Synthesis of 1-[(5-bromo-1H-pyrazolo[3,4-b]pyridin-3-yl)methyl]-4-(2,2-difluorovinyl)pyrrolidin-2-one 221

To a solution of 4-(2,2-difluorovinyl)pyrrolidin-2-one x98 (2.86 mmol, 2 eq, 0.42 g) in dry DMF (5 ml) maintained at 0° C. is added natrium hydride (60% dispersion in oil; 2.86 mmol, 2 eq, 0.114 g). The resulting mixture is stirred at room temperature for 0.5 hour and tert-butyl 5-bromo-3-(bromomethyl)-1H-pyrazolo[3,4-b]pyridine-1-carboxylate x155 (1.43 mmol, 1 eq, 0.56 g) dissolved in DMF (2 ml) is added. The resulting mixture is stirred overnight at room temperature. The mixture is poured in water and extracted with AcOEt. The cumulated organic layers are dried over MgSO$_4$, filtered and evaporated under reduced pressure. The crude mixture is purified twice by chromatography on silicagel (CH$_2$Cl$_2$/MeOH/NH$_4$OH 98/2/0.2) to afford pure 1-[(5-bromo-1H-pyrazolo[3,4-b]pyridin-3-yl)methyl]-4-(2,2-difluorovinyl)pyrrolidin-2-one 221 (0.025 g).

Yield: 4.9%.

LC-MS (MH$^+$): 357/359.

Example 56

Synthesis of 1-[(6-bromo-1H-pyrrolo[2,3-b]pyridin-3-yl)methyl]-4-propylpyrrolidin-2-one 235

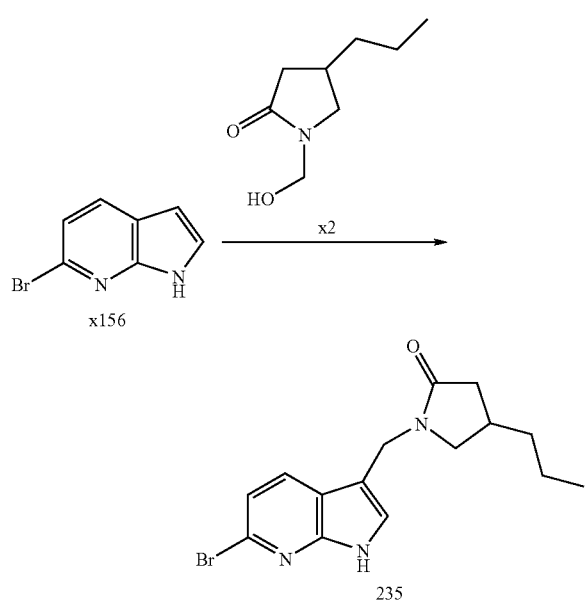

To a solution of 6-bromo-1H-pyrrolo[2,3-b]pyridine x156 (2.5 mmol, 1.06 eq, 0.49 g) in 15 ml of toluene is added successively 1-(hydroxymethyl)-4-propylpyrrolidin-2-one x2 (2.35 mmol, 1 eq, 0.37 g) and paratoluene sulfonic acid (1.25 mmol, 0.5 eq, 0.24 g). The mixture is stirred at reflux for 1 hour. The reaction mixture is quenched with a saturated NaHCO$_3$ aqueous solution and then extracted with AcOEt. The combined organic layers are dried over MgSO$_4$, filtered and evaporated under reduced pressure. The crude product is purified by chromatography on silicagel (CH$_2$Cl$_2$/MeOH/NH$_4$OH 95/5/0.5), then by chromatography on a reverse phase (Sunfire Prep MS C18 ODB column (5 µm, 19×50 mm); eluent: gradient of water/acetonitrile/TFA; 25° C.) to afford 224 mg of 1-[(6-bromo-1H-pyrrolo[2,3-b]pyridin-3-yl)methyl]-4-propylpyrrolidin-2-one 235 as a solid.

Yield: 28%.

LC-MS (MH$^+$): 336/338.

Compounds 236, 237, 238 and 239 may be prepared as described for compound 235.

Example 57

Synthesis of 1-[(7-oxido-1H-pyrrolo[2,3-b]pyridin-3-yl)methyl]-4-propylpyrrolidin-2-one 239

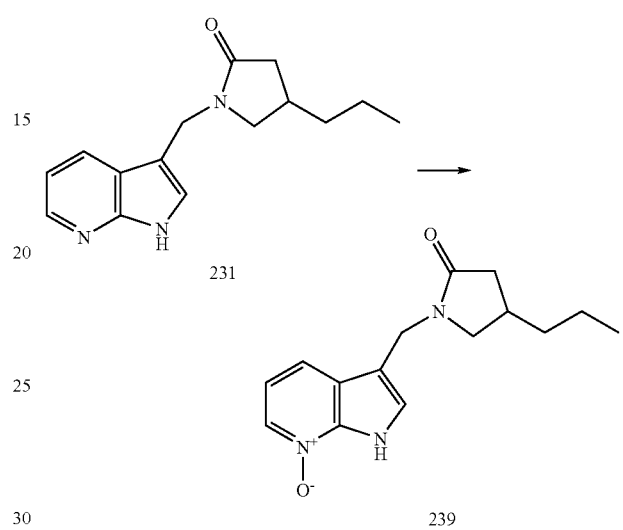

To 4-propyl-1-(1H-pyrrolo[2,3-b]pyridin-3-ylmethyl)pyrrolidin-2-one 231 (100 mg, 1 eq, 0.39 mmol) dissolved in 1,2-dimethoxyethane (3 ml) is added m-chloroperoxybenzoic acid (111 mg, 1.6 eq, 0.64 mmol). The resulting solution is stirred at room temperature for 20 hours. Hexane (10 ml) is added to the reaction mixture, and the decanted syrup is washed twice with hexane by decantation and dried under vacuum. To the residual solid are added 3 ml of water and a saturated solution of K$_2$CO$_3$ until pH 9. The resulting mixture is extracted with CH$_2$Cl$_2$ and the organic phase is dried over MgSO$_4$. Volatiles are removed under reduced pressure and the residue is purified twice by chromatography on silicagel (CH$_2$Cl$_2$/MeOH/NH$_4$OH 95/5/05) to give 50 mg of 1-[(7-oxido-1H-pyrrolo[2,3-b]pyridin-3-yl)methyl]-4-propylpyrrolidin-2-one 239.

Yield: 47%.

LC-MS (MH$^+$): 274.

Example 58

Synthesis of 1-[(5-fluoro-1H-indol-1-yl)methyl]-4-propylpyrrolidin-2-one 278

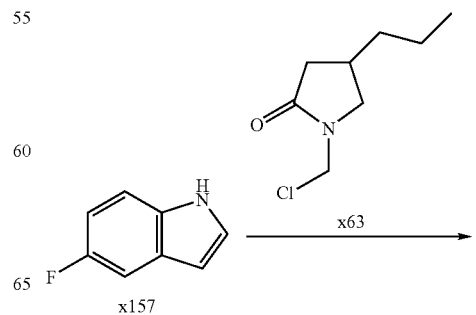

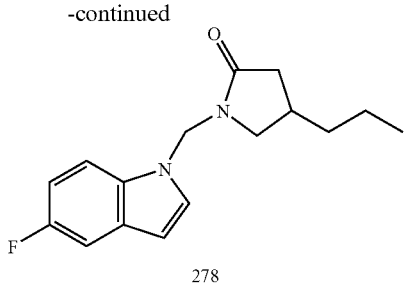

278

To a solution of 5-fluoroindole x157 (405 mg, 3 mmol, 1 eq) of in DMF (7 ml) maintained under argon is added NaH (60% in mineral oil; 120 mg, 3 mmol, 1 eq). The resulting mixture is stirred for three hours at room temperature, then a solution of 1-(chloromethyl)-4-propylpyrrolidin-2-one x63 in DMF (1 M, 3 ml, 3 mmol, 1 eq) is added. The reaction mixture is stirred for 20 hours at room temperature. Water (70 ml) is added and the resulting mixture is extracted with ethyl acetate (30 ml). The organic phase is washed twice with water and dried over $Na_2SO_4$. After filtration and evaporation of volatiles, the crude product is purified by two consecutive chromatographies on silicagel ($CH_2Cl_2$/MeOH gradient, then $CH_2Cl_2$). Pure 1-[(7-oxido-1H-pyrrolo[2,3-b]pyridin-3-yl)methyl]-4-propylpyrrolidin-2-one 278 is obtained as syrup (274 mg).

Yield: 33%.
LC-MS (MH$^+$): 275.

Compounds 275, 276, 277, 279, 280, 281 and 282 may be synthesized as described for compound 278.

Example 59

Synthesis of 1-(3,4-dihydroquinolin-1(2H)-ylmethyl)-4-propylpyrrolidin-2-one 295

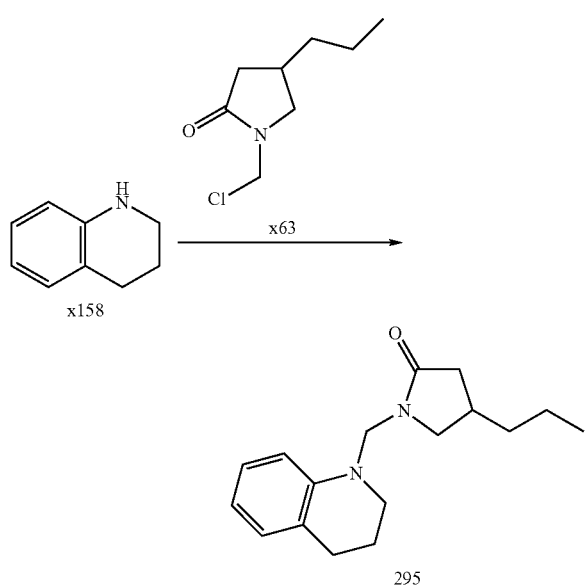

To a solution of 1,2,3,4-tetrahydroquinoline x158 (400 mg, 3 mmol, 1 eq) in DMF (7 ml) maintained under argon is added NaH (60% in mineral oil; 120 mg, 3 mmol, 1 eq). The reaction mixture is stirred for three hour at room temperature, then a solution of 1-(chloromethyl)-4-propylpyrrolidin-2-one x63 in DMF (1 M, 3 ml, 3 mmol, 1 eq) is added. The reaction mixture is stirred for 20 hours at the same temperature. Water (70 ml) is added and the resulting mixture is extracted with ethyl acetate (30 ml). The organic phase is washed twice with water and dried over $Na_2SO_4$. After filtration and evaporation, the crude product is purified by two consecutive chromatographies on silicagel ($CH_2Cl_2$/MeOH gradient, then $CH_2Cl_2$). Pure 1-(3,4-dihydroquinolin-1(2H)-ylmethyl)-4-propylpyrrolidin-2-one 295 is obtained as syrup (231 mg).

Yield: 28%.
LC-MS (MH$^+$): 273.

Example 60

Synthesis of 1-[(2-chloro-1H-indol-1-yl)methyl]-4-propylpyrrolidin-2-one 274

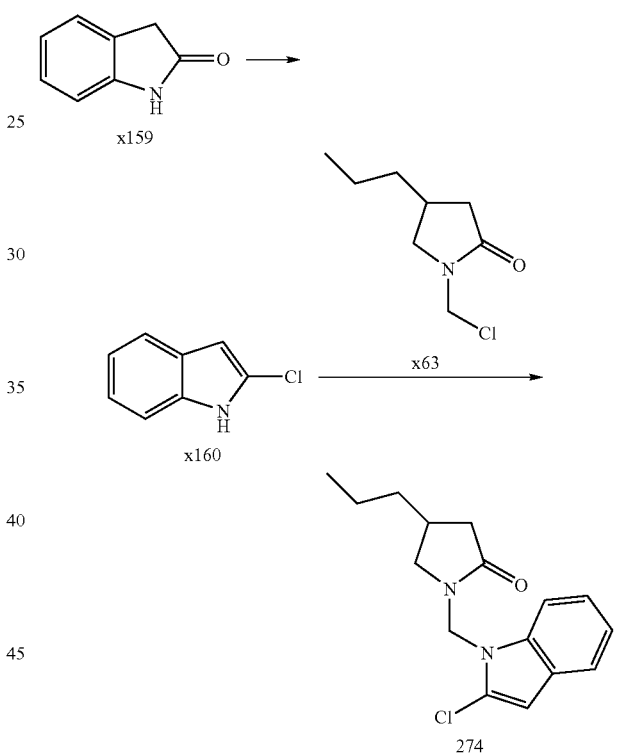

60.1. Synthesis of 2-chloro-1H-indole x160

At room temperature, $POCl_3$ (1 ml, 10.82 mmol, 2 eq) is added to a well stirred suspension of N,N-diethylaniline (1 ml, 5.41 mmol, 1 eq) and 1,3-dihydro-2H-indol-2-one x159 (0.72 g, 5.41 mmol, 1 eq) in dry toluene (15 ml). The mixture is heated at reflux during 3 hours. After cooling, water (15 ml) is carefully added and the organic layer is washed with water (3×25 ml). The organic layer is dried on anhydrous $MgSO_4$, filtered off and concentrated under reduced pressure to obtain 0.76 g of 2-chloro-1H-indole x160 as an orange solid (0.76 g, 93%).

Yield: 93%.
LC-MS (MH$^-$): 150/152.
Due to relative instability of the product, it is directly used in the following step.

1,3-dihydro-2H-pyrrolo[2,3-b]pyridin-2-one x161 (LC-MS (MH+): 153/155) and 2,5-dichloro-1H-indole x162 (¹H NMR (CDCl₃): δ 6.37 (s, 1H); 7.12-7.24 (m, 2H overlapped with solvent), 7.49 (s, 1H), 8.10 (s broad, 1H)) may be synthesized according to the same method.

60.2. Synthesis of 1-[(2-chloro-1H-indol-1-yl)methyl]-4-propylpyrrolidin-2-one 274

At −78° C., NaH (60% in mineral oil; 220 mg, 5.52 mmol, 1.1 eq) is added to a solution of 2-chloro-1H-indole x160 (0.76 g, 5.02 mmol, 1 eq) in dry DMF (50 ml). The temperature is raised to −20° C. during 20 minutes, then 1-(chloromethyl)-4-propylpyrrolidin-2-one x63 (0.76 g, 5.02 mmol, 1 eq) dissolved in DMF (10 ml) is added drop wise. After 2 hours at room temperature, water (50 ml) is added. The aqueous layer is extracted with CH₂Cl₂ (3×30 ml). The combined organic layers are dried on anhydrous MgSO₄, filtered off and concentrated under reduced pressure to obtain a liquid that is purified on silicagel (AcOEt/Benzine 1/9) yielding 1-[(2-chloro-1H-indol-1-yl)methyl]-4-propylpyrrolidin-2-one 274 as a colorless liquid (605 mg).

Yield: 42%.

LC-MS (MH+): 291/293.

Compounds 293, 294, 296, 322, 323 and 324 may be synthesized according to the same method.

Example 61

Synthesis of 1-[(2-chloro-1H-benzimidazol-1-yl)methyl]-4-propyl-pyrrolidin-2-one 300

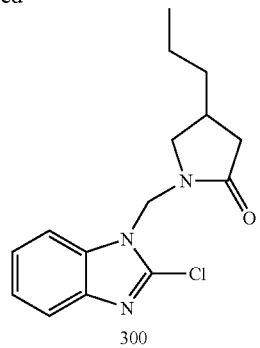

A solution of 1-(hydroxymethyl)-4-propylpyrrolidin-2-one x2 (0.472 g, 1 eq, 3 mmol), (2-oxo-4-propylpyrrolidin-1-yl)methyl diethylcarbamate x6 (38.5 mg, 5 mol %, 0.15 mmol) and 2-chloro-1H-benzimidazole x163 (1.2 eq, 3.3 mmol, 0.504 g) in acetonitrile (3 ml) is irradiated in a microwave apparatus (CEM discover) during 0.75 h (100 w). After cooling, evaporation of the solvent under reduce pressure and purification by preparative chromatography on reverse phase, 1-[(2-chloro-1H-benzimidazol-1-yl)methyl]-4-propyl-pyrrolidin-2-one 300 is isolated as a clear oil (0.42 g).

Yield: 49.2%.

LC-MS (MH+): 292/294.

Compounds 301, 304, 310 and 319 may be synthesized according to the same method.

Example 62

Synthesis of 1-[(2-chloro-6-methoxy-1H-benzimidazol-1-yl)methyl]-4-propylpyrrolidin-2-one 305 and 1-[(2-chloro-5-methoxy-1H-benzimidazol-1-yl)methyl]-4-propylpyrrolidin-2-one 306

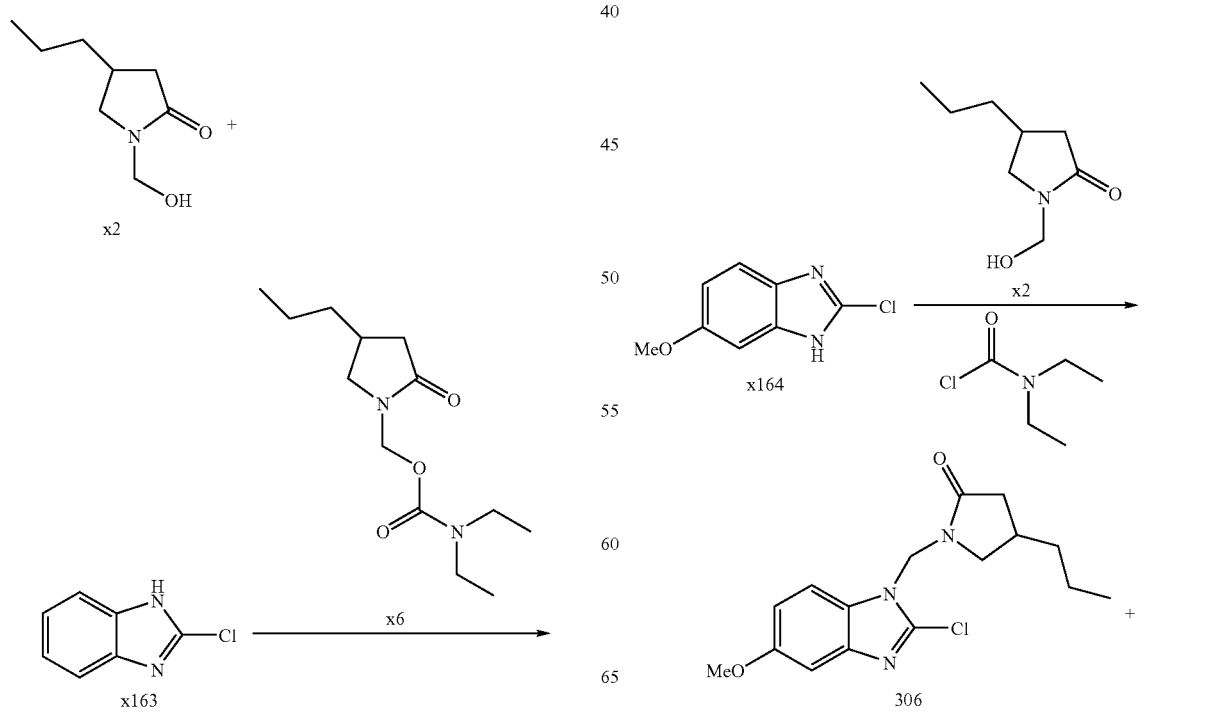

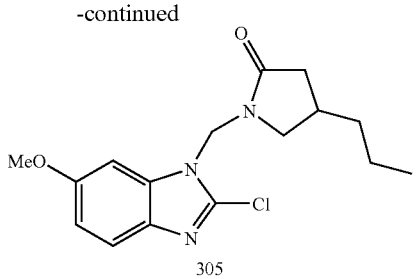

A mixture of the two compounds is synthesized according to the procedure described in example 61 using 2-chloro-5-methoxy-1H-benzimidazole x164 and 1-(hydroxymethyl)-4-propylpyrrolidin-2-one x2. Compounds are separated by preparative chiral chromatography (EtOH/heptane: 10/90, 30° C., 300 ml/min).

Yield: 27% for compound 305 and 18% for compound 306.
LC-MS (MH$^+$): 322/324.

Compounds 302, 303, 307, 308, 309, 311, 312, 313, 314, 315, 316, 317 and 318 may be synthesized according to the same method.

Example 63

Synthesis of 1-[(2-chloro-6-hydroxy-1H-benzimidazol-1-yl)methyl]-4-propylpyrrolidin-2-one 320

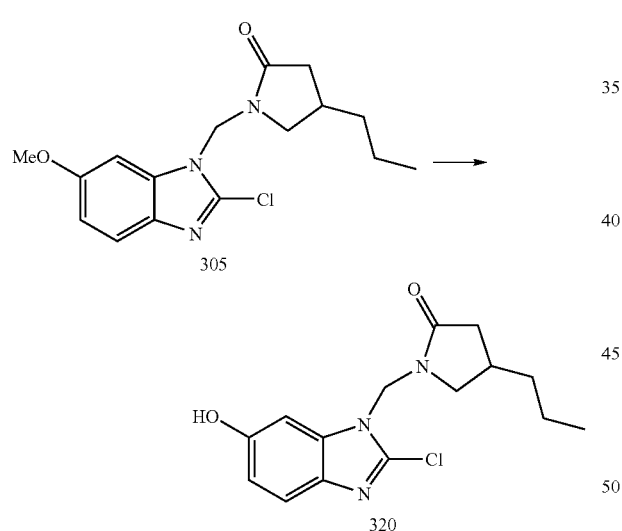

Under argon, BBr$_3$ (1 M in CH$_2$Cl$_2$) (1.86 ml, 1.8645 mmol, 2 eq) is added drop wise to a solution of 1-[(2-chloro-6-methoxy-1H-benzimidazol-1-yl)methyl]-4-propylpyrrolidin-2-one 305 (0.3 g, 0.9322 mmol, 1 eq) in dry CH$_2$Cl$_2$ (20 ml). After 48 hours at room temperature, saturated aqueous solution of NaHCO$_3$ (20 ml) is added. The aqueous layer is extracted with CH$_2$Cl$_2$ (3×20 ml) then the combined organic layers are dried on anhydrous MgSO$_4$, filtered off and evaporated under reduced pressure. The remaining pale yellow solid is recrystallized in MeCN/H$_2$O (9/1) to yield 102 mg of 1-[(2-chloro-6-hydroxy-1H-benzimidazol-1-yl)methyl]-4-propylpyrrolidin-2-one 320 as a white solid.

Yield: 35%.
LC-MS (MH$^+$): 308/310.

Compound 321 may be synthesized according to the same method.

Example 64

Synthesis of 1-{[6-(cyclopropylamino)-9H-purin-9-yl]methyl}-4-propylpyrrolidin-2-one 285

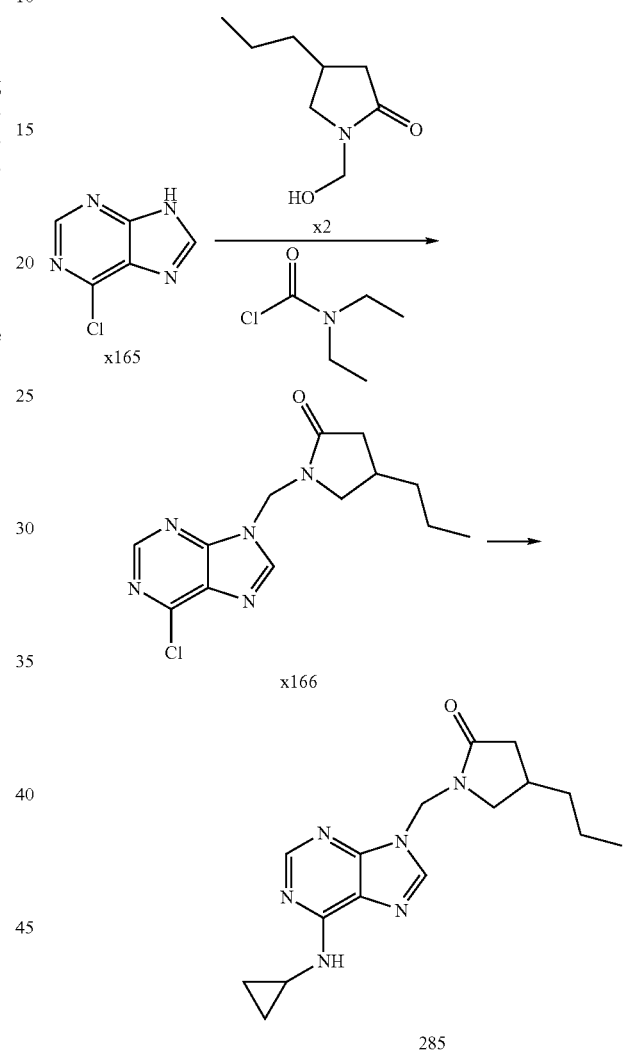

64.1. Synthesis of 1-[(6-chloro-9H-purin-9-yl)methyl]-4-propylpyrrolidin-2-one x166

A mixture of 6-chloro-1H-purine x165 (2 g, 12.93 mmol, 1 eq), 1-(hydroxymethyl)-4-propylpyrrolidin-2-one x2 (2.44 g, 15.53 mmol, 1.2 eq) and N,N-diethylcarbamoylchloride (332 mg, 1.293 mmol, 0.1 eq) in MeCN (30 ml) is heated at 100° C. in microwave apparatus during 5 hours. After cooling, the solvent is evaporated and the crude is purified on silicagel (CH$_2$Cl$_2$/MeOH (+NH$_4$OH 10%) 95/5) to yield 3.8 g of 1-[(6-chloro-9H-purin-9-yl)methyl]-4-propylpyrrolidin-2-one x166 as a pale yellow solid.

Yield: 99%.
$^1$H NMR (400 MHz, CDCl$_3$) δ 0.89 (t, 7.18 Hz, 3 H), 1.33 (m, 4 H), 2.07 (dd, 17.12, 8.18 Hz, 1 H), 2.36 (m, 1 H), 2.53

(dd, 17.12, 8.56 Hz, 1 H), 3.15 (dd, 9.32, 7.05 Hz, 1 H), 3.68 (dd, 9.32, 8.06 Hz, 1 H), 5.70 (m, 2 H), 8.37 (s, 1 H), 8.78 (s, 1 H).

64.2. Synthesis of 1-{[6-(cyclopropylamino)-9H-purin-9-yl]methyl}-4-propylpyrrolidin-2-one 285

A mixture of 1-[(6-chloro-9H-purin-9-yl)methyl]-4-propylpyrrolidin-2-one x166 (250 mg, 0.85 mmol, 1 eq) and cyclopropylamine (1 ml) is heated at 50° C. during 24 hours in THF. After cooling, a saturated aqueous solution of NaHCO$_3$ is added and the aqueous phase is extracted with AcOEt. The combined organic layers are dried on anhydrous MgSO$_4$, filtered of and evaporated under reduced pressure. The crude mixture is purified by preparative HPLC to yield 1-{[6-(cyclopropylamino)-9H-purin-9-yl]methyl}-4-propylpyrrolidin-2-one 285.

Yield: 54%.

LC-MS (MH$^+$): 315.

Compounds 286, 287, 288 and 289 may be synthesized according to the same method.

Example 65

Synthesis of 1-[(6-bromo-2-cyclopropyl-3H-imidazo[4,5-b]pyridin-3-yl)methyl]-4-(2,2-difluorovinyl)pyrrolidin-2-one 272

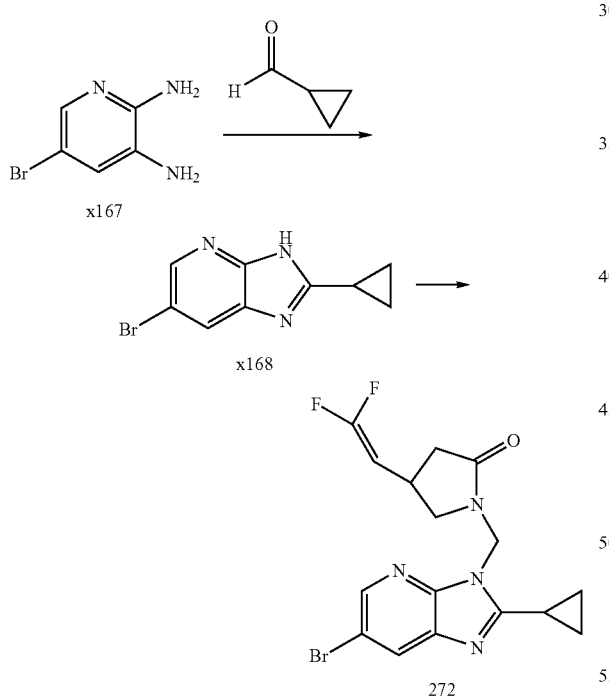

65.1. Synthesis of 6-bromo-2-cyclopropyl-1H-imidazo[4,5-b]pyridine x168

A solution of cyclopropanecarbaldehyde (0.89 g, 12.76 mmol, 1.2 eq), 5-bromopyridine-2,3-diamine x167 (2 g, 10.63 mmol, 1 eq) in AcOH (20 ml) and 1,4-dioxane (40 ml) is heated at 110° C. during 24 hours. After cooling, the solvents are evaporated under reduced pressure. The resulting brown solid is recrystallized in CH$_2$Cl$_2$/hexane (1/1) to yield 0.53 g of 6-bromo-2-cyclopropyl-1H-imidazo[4,5-b]pyridine x168 as an orange solid.

Yield: 21%.

LC-MS (MH$^+$): 238/240.

6-bromo-2-phenyl-1H-imidazo[4,5-b]pyridine x169 may be synthesized according to the same method (LC-MS (MH$^+$): 274/276).

65.2. Synthesis of 1-[(6-bromo-2-cyclopropyl-3H-imidazo[4,5-b]pyridin-3-yl)methyl]-4-(2,2-difluorovinyl)pyrrolidin-2-one 272

1-[(6-bromo-2-cyclopropyl-3H-imidazo[4,5-b]pyridin-3-yl)methyl]-4-(2,2-difluorovinyl)pyrrolidin-2-one 272 is synthesized according to the procedure described in example 61 using 6-bromo-2-cyclopropyl-1H-imidazo[4,5-b]pyridine x168 and 4-(2,2-difluorovinyl)-1-(hydroxymethyl)pyrrolidin-2-one x142.

Yield: 25%.

LC-MS (MH$^+$): 238/240.

Compounds 266, 267, 269, 270 and 271 may be synthesized according to the same method.

Example 66

Synthesis of 1-[(2,6-dichloroimidazo[2,1-b][1,3]thiazol-5-yl)methyl]-4-propylpyrrolidin-2-one 93

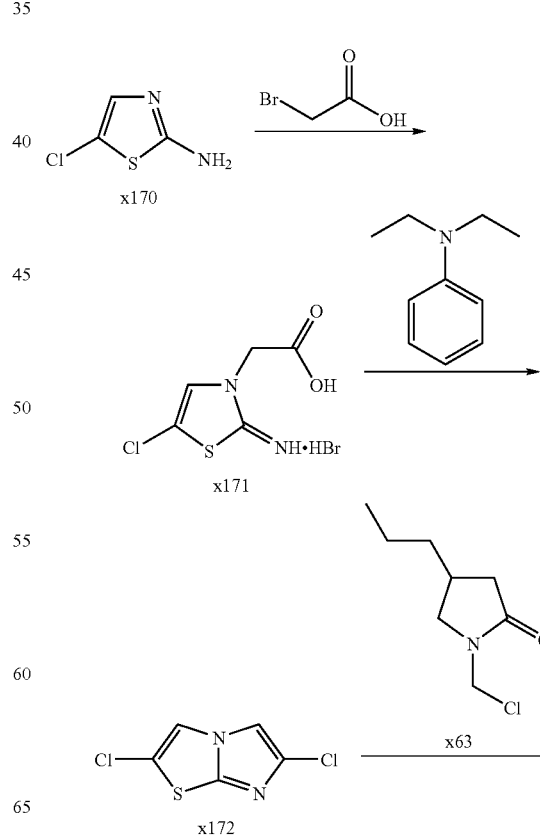

127

-continued

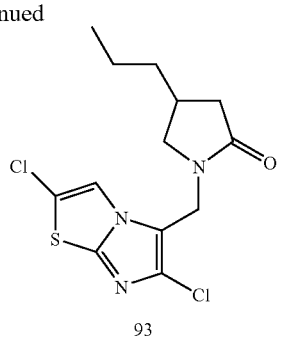

93

66.1. Synthesis of (5-chloro-2-imino-1,3-thiazol-3 (2H)-yl)acetic acid hydrobromide x171

At room temperature, 5-chloro-1,3-thiazol-2-amine x170 (1.49 g, 11.03 mmol, 1 eq) is added to a well stirred solution of bromoacetic acid (1.68 g, 11.03 mmol, 1 eq) in EtOH (50 ml). The mixture is heated at reflux during 8 hours. After cooling, the resulting precipitate is filtrated dried under vacuum to yield 288 mg of (5-chloro-2-imino-1,3-thiazol-3 (2H)-yl)acetic acid hydrobromide x171 as a white solid.

Yield: 10%.

LC-MS (MH$^+$): 193/195

66.2. Synthesis of 2,6-dichloroimidazo[2,1-b][1,3]thiazole x172

POCl$_3$ (0.5 ml, 5.27 mol, 5 eq) is added to a suspension of acid x171 (0.288 g, 1.05 mol, 1 eq) and N,N-diethylaniline (0.17 ml, 1.05 mmol, 1 eq) in toluene (10 ml). The mixture is heated at reflux during 3 hours. After cooling, the resulting black mixture is poured on crushed ice. The aqueous layer is extracted with AcOEt (3×10 ml) and the combined organic layers are dried on anhydrous MgSO$_4$, filtered and evaporated under reduced pressure to yield 171 mg of 2,6-dichloroimidazo[2,1-b][1,3]thiazole x172 as a yellow powder.

Yield: 85%.

LC-MS (MH$^+$): 193/195/197.

66.3. Synthesis of 1-[(2,6-dichloroimidazo[2,1-b][1,3]thiazol-5-yl)methyl]-4-propylpyrrolidin-2-one 93

At room temperature, AlCl$_3$ (0.237 g, 1.78 mmol, 2 eq) is added to a solution of 2,6-dichloroimidazo[2,1-b][1,3]thiazole x172 (0.171 g, 0.89 mmol, 1 eq) and 1-(chloromethyl)-4-propylpyrrolidin-2-one x63 (0.185 g, 1.06 mmol, 1.2 eq) in 1,4-dioxane (25 ml). The mixture is heated at reflux during 2 hours. After cooling, water (20 ml) is added and the aqueous layer is extracted with CH$_2$Cl$_2$ (3×20 ml). The combined organic layers are dried on anhydrous MgSO$_4$, filtered and evaporated under reduced pressure. The crude is purified on silicagel (CH$_2$Cl$_2$/AcOEt: 9/1) yielding 200 mg of 1-[(2,6-dichloroimidazo[2,1-b][1,3]thiazol-5-yl)methyl]-4-propylpyrrolidin-2-one 93 as a white solid.

Yield: 74%.

LC-MS (MH$^+$): 332/334/336.

128

Example 67

Synthesis of 1-[(2-chloroimidazo[1,2-a]pyridin-3-yl) methyl]-4-propylpyrrolidin-2-one 17

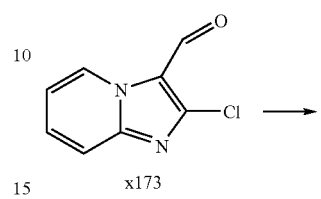

x173

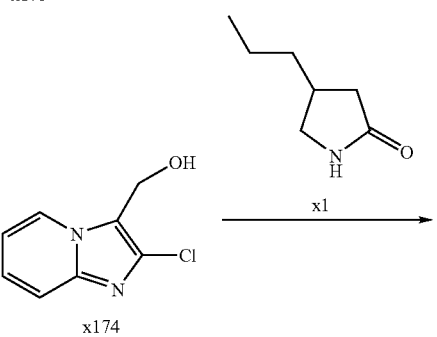

x174

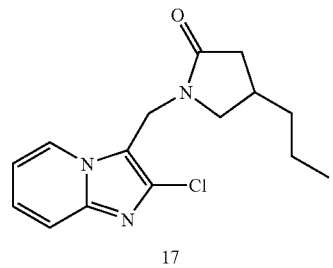

17

67.1. Synthesis of (2-chloroimidazo[1,2-a]pyridin-3-yl)methanol x174

NaBH$_4$ (1.52 g, 41.33 mmol, 1.5 eq) is added to a solution of 2-chloroimidazo[1,2-a]pyridine-3-carbaldehyde x173 (4.96 g, 27.56 mmol, 1 eq) in EtOH (100 ml). After 1 hour at room temperature, water (100 ml) is added and the aqueous layer is extracted with CH$_2$Cl$_2$ (3×50 ml). The combined organic layers are dried on anhydrous MgSO$_4$, filtered and evaporated under reduced pressure. The resulting white solid is recrystallized in CH$_2$Cl$_2$/hexane to yield 3.9 g of (2-chloroimidazo[1,2-a]pyridin-3-yl)methanol x174.

Yield: 78%.

LC-MS (MH$^+$): 183/185.

67.2. Synthesis of 1-[(2-chloroimidazo[1,2-a]pyridin-3-yl)methyl]-4-propylpyrrolidin-2-one 17

1-[(2-chloroimidazo[1,2-a]pyridin-3-yl)methyl]-4-propylpyrrolidin-2-one 17 is synthesized according to the procedure described in example 36.4.

Yield: 8.5%.

LC-MS (MH$^+$): 292/294.

Example 68

Synthesis of 1-(3H-imidazo[4,5-b]pyridin-7-ylmethyl)-4-propylpyrrolidin-2-one 95

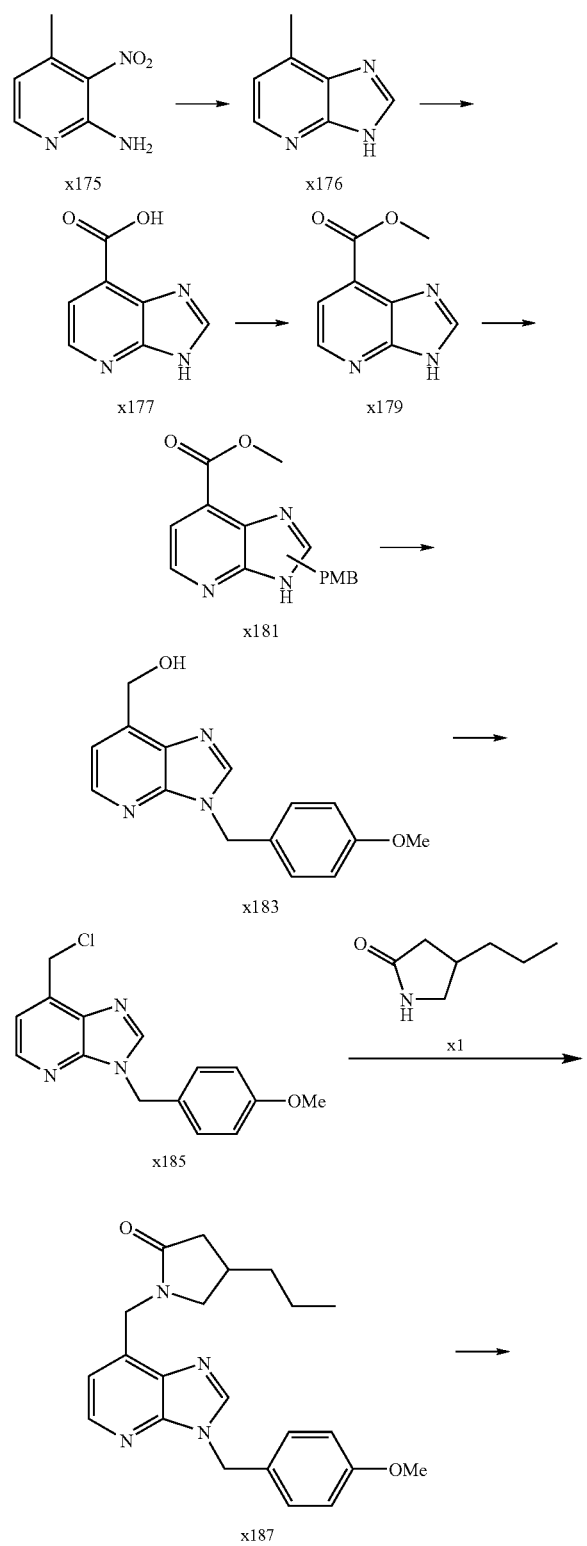

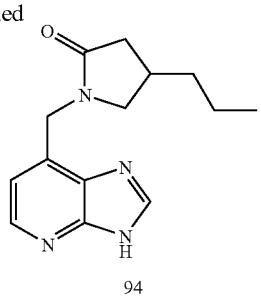

68.1. Synthesis of 7-methyl-3H-imidazo[4,5-b]pyridine x176

Raney Nickel (2.5 g) is added to a mixture of commercially available 4-methyl-3-nitro-pyridin-2-ylamine x175 (7.0 g, 45.7 mmol) in methanol (300 ml), and the obtained reaction mixture is hydrogenated in the Parr apparatus at the hydrogen pressure 3 atm until the total conversion of compound x175 is attained for approximately 1.5-2 h. The catalyst is separated by filtration, the filtrate is washed with methanol, and the alcohol solution is evaporated to dryness. $CH(OMe)_3$ (100 ml) and PTSA (0.5 g) are added to the residue, and an air reflux condenser is mounted. The apparatus is argon-blown, and the obtained reaction mixture is heated to 125° C. under vigorous stirring for 10 h. The formed solution is evaporated, and the residue is dissolved in 5% HCl (100 ml). The solution is refluxed for 1 h and evaporated to one-third volume. The solution is neutralized to pH 7 and extracted with 10% tert-butanol in chloroform (4×100 ml). The organic layer is dried over anhydrous $Na_2SO_4$, and the solvent is evaporated. The residue is purified by chromatography on silicagel (chloroform/methanol) to afford 7-methyl-3H-imidazo[4,5-b]pyridine x176.

Yield: 70%.

LC-MS (MH$^+$): 134.

68.2. Synthesis of 3H-imidazo[4,5-b]pyridine-7-carboxylic acid x177

$Na_2CO_3$ (3.3 g, 1 eq, 31.5 mmol) and water (200 ml) are added to product 7-methyl-3H-imidazo[4,5-b]pyridine x176 (4.2 g, 31.5 mmol). The reaction mixture is heated until boiled, which caused its transformation into a solution. $KMnO_4$ (12.5 g, 2.5 eq, 78.9 mmol) is added in small portions to the obtained boiling solution. After $KMnO_4$ is added completely, the reaction mixture is additionally kept at 100° C. for 1 h and cooled to 50-60° C. $MnO_2$ is filtered off, and the residue is additionally washed with hot water (2×50 ml) on a filter. The obtained aqueous solution is evaporated in vacuum to a volume of 50 ml, cooled to 5° C., and acidified with 10% HCl to pH 2-3. The obtained suspension is kept at 5° C. for 1 h. The formed precipitate is separated by filtration, washed with ice-cold water (2×10 ml), and vacuum-dried (1 mm Hg) over $P_2O_5$ overnight to give 2.06 g of 3H-imidazo[4,5-b]pyridine-7-carboxylic acid x177.

Yield: 40%.

LC-MS (MH$^+$): 164.

The following compound may be synthesized according to the same method:

| x178 | 2-methyl-1H-imidazo[4,5-b]pyridine-7-carboxylic acid | LC-MS (MH+): 178 |
|------|------|------|

68.3. Synthesis of methyl 3H-imidazo[4,5-b]pyridine-7-carboxylate x179

Absolute methanol (30 ml) is added to acid x177 (2.0 g). Concentrated $H_2SO_4$ (4 ml) is added to the obtained suspension at 0° C. The reaction mixture is refluxed under protection from the air moisture and vigorous stirring for 10 h. After 3 h the solid is completely dissolved. The next morning the reaction mixture is evaporated to half-volume in the vacuum of a rotary evaporator and neutralized under cooling with ice with aqueous ammonia to pH 8-9. The formed precipitate is quickly separated by filtration, washed with ice-cold water (2×30 ml), and dried over $P_2O_5$ overnight to afford 1.74 g of methyl 3H-imidazo[4,5-b]pyridine-7-carboxylate x179.

Yield: 80%.

LC-MS (MH+): 257.

The following compound may be synthesized according to the same method:

| x180 | methyl 2-methyl-1H-imidazo[4,5-b]pyridine-7-carboxylate | LC-MS (MH+): 192 |
|------|------|------|

68.4. Synthesis of the mixture of methyl 3-(4-methoxybenzyl)-3H-imidazo[4,5-b]pyridine-7-carboxylate and methyl 1-(4-methoxybenzyl)-3H-imidazo[4,5-b]pyridine-7-carboxylate (75/25) x181

60% NaH in mineral oil (0.42 g, 1.1 eq, 10.6 mmol) is added in argon under vigorous stirring at 0° C. to a mixture methyl 3H-imidazo[4,5-b]pyridine-7-carboxylate x179 (1.7 g, 9.6 mmol) in absolute DMF (30 ml). The mixture is stirred at the same temperature for 20 min, and a solution, which contained a mixture of p-methoxybenzyl chloride (1.8 g, 1.2 eq, 11.5 mmol) and tetrabutylammonium bromide (0.62 g, 0.2 eq, 1.9 mmol) in absolute DMF (10 ml). The reaction mixture is stirred at 5° C. for 3 h and then at room temperature for 16 h. Then DMF is evaporated at 45° C. at the residual pressure 1 mmHg. The residue is distributed in the system 10% aqueous $NaH_2PO_4$-ethyl acetate. The aqueous layer is additionally subjected to extraction with ethyl acetate. The combined organic extracts are dried over anhydrous $Na_2SO_4$ and evaporated. The residue is purified by chromatography on silicagel (dichloromethane/ethanol) to afford 2.0 g of the 75/25 regioisomeric mixture of methyl 3-(4-methoxybenzyl)-3H-imidazo[4,5-b]pyridine-7-carboxylate and methyl 1-(4-methoxybenzyl)-3H-imidazo[4,5-b]pyridine-7-carboxylate x181. We found that it is more advantageous to separate the isomers at the next step in this case, i.e., after reduction of the ester function into the alcohol one.

Yield: 70%.

LC-MS (MH+): 298.

The following compound may be synthesized according to the same method:

| x182 | mixture of methyl 3-(4-methoxybenzyl)-2-methyl-3H-imidazo[4,5-b]pyridine-7-carboxylate and methyl 1-(4-methoxybenzyl)-2-methyl-1H-imidazo[4,5-b]pyridine-7-carboxylate | LC-MS (MH+): 312 |
|------|------|------|

68.5. Synthesis of [3-(4-methoxybenzyl)-3H-imidazo[4,5-b]pyridin-7-yl]methanol x183

Compound x181 (1.95 g, 6.56 mmol, 75/25 mixture of the two regioisomers) is dissolved in absolute ethanol. $NaBH_4$ (0.48 g, 4 eq, 12.76 mmol) is added at 5° C. under stirring. The cooling bath is removed after 4 h, and the reaction mixture is allowed to heat up to room temperature. The stirring is continued at this temperature for 20 h. The reaction mixture is evaporated in the vacuum of a rotary evaporator at 35° C., and the residue is partitioned in an ethyl acetate/saturated aqueous $NaHCO_3$ mixture. The organic layer is dried with anhydrous sodium sulfate and evaporated. The crude reaction mixture is purified by chromatography on silicagel (dichloromethane/methanol). Evaporation of the corresponding fractions followed by vacuum drying affords [3-(4-methoxybenzyl)-3H-imidazo[4,5-b]pyridin-7-yl]methanol x183 (1.06 g).

Yield: 59%.

LC-MS (MH+): 270.

The following compound may be synthesized according to the same method:

| x184 | [3-(4-methoxybenzyl)-2-methyl-3H-imidazo[4,5-b]pyridin-7-yl]methanol | LC-MS (MH+): 284 |
|------|------|------|

68.6. Synthesis of 1-{[3-(4-methoxybenzyl)-3H-imidazo[4,5-b]pyridin-7-yl]methyl}-4-propylpyrrolidin-2-one x187

[3-(4-methoxybenzyl)-3H-imidazo[4,5-b]pyridin-7-yl]methanol x183 (0.5 g, 1.86 mmol) is dissolved in dichloromethane (20 ml). $SOCl_2$ (2 ml) is added dropwise. The reaction mixture is refluxed for 1 h. The volatiles are distilled off in the vacuum of a rotary evaporator. Then 50 ml of chloroform is distilled off additionally from the residue. The residual chloroform solution is added dropwise at 0° C. to a vigorously stirred saturated aqueous solution of $NaHCO_3$. The organic phase is separated, dried with anhydrous sodium sulfate, and evaporated. The residue is kept under 1 mmHg for 1.5 h at 40° C. to afford 7-(chloromethyl)-3-(4-methoxybenzyl)-3H-imidazo[4,5-b]pyridine x185 sufficiently pure for the next step.

7-(chloromethyl)-3-(4-methoxybenzyl)-2-methyl-3H-imidazo[4,5-b]pyridine x186 may be obtained according to the same method.

4-propylpyrrolidin-2-one x1 (0.26 g, 1.1 eq with respect to x183, 2.0 mmol) is dissolved in absolute DMF (10 ml). Then 60% NaH (0.080 g, 1.1 eq, 2.0 mmol) is added at 0° C. in a flow of argon. The reaction mixture is stirred for 10 min at 0° C., and then for 10 min at room temperature to complete the reaction. Then the mixture is cooled again to 0° C. A solution of the chloride x185 prepared above in absolute DMF (5 ml) additionally containing 0.1 g (0.2 eq, 0.32 mmol) of tetrabutylammonium bromide is added dropwise to the obtained suspension. The reaction mixture is stirred at 5° C. for 4 h. The cooling bath is removed, and the stirring is continued at room temperature overnight. The next morning the DMF is evaporated at 45° C. under 1 mmHg. The residue is partitioned in 10% aqueous NaH₂PO₄/ethyl acetate mixture. The aqueous layer is subjected to additional extraction with ethyl acetate. The combined extracts are dried with anhydrous sodium sulfate and evaporated. The residue is purified by chromatography to afford 0.6 g of 1-{[3-(4-methoxybenzyl)-3H-imidazo[4,5-b]pyridin-7-yl]methyl}-4-propylpyrrolidin-2-one x187.

Yield: 85% (calculated from alcohol x183)

LC-MS (MH⁺): 458.

The following compounds may be synthesized according to the same method:

| x188 | 1-{[3-(4-methoxybenzyl)-3H-imidazo[4,5-b]pyridin-7-yl]methyl}-4-phenylpyrrolidin-2-one | LC-MS (MH⁺): 412 |
| x189 | 1-{[3-(4-methoxybenzyl)-2-methyl-3H-imidazo[4,5-b]pyridin-7-yl]methyl}-4-propylpyrrolidin-2-one | LC-MS (MH⁺): 393 |

68.7. Synthesis of 1-(3H-imidazo[4,5-b]pyridin-7-ylmethyl)-4-propylpyrrolidin-2-one 95

A solution containing 1-{[3-(4-methoxybenzyl)-3H-imidazo[4,5-b]pyridin-7-yl]methyl}-4-propylpyrrolidin-2-one x187 (0.6 g), anisole (0.4 ml) and concentrated H₂SO₄ (0.2 ml) in trifluoroacetic acid (4 ml) is stirred in a flow of argon at 20° C. for 2 h. The homogeneous reaction mixture is added dropwise at 0° C. to a mixture of a saturated aqueous solution of NaHCO₃ (50 ml) and ethyl acetate (50 ml). The organic layer is separated. The aqueous one (pH~8) is subjected to additional extraction with chloroform containing 10% of tert-butanol. The combined organic layers are dried with anhydrous sodium sulfate and evaporated. The residue is purified by chromatography on silicagel (chloroform/methanol) to afford 1-(3H-imidazo[4,5-b]pyridin-7-ylmethyl)-4-propylpyrrolidin-2-one 95 (0.34 g).

Yield: 85%.

LC-MS (MH⁺): 259.

Compounds 1, 2, 96 and 102 may be synthesized according to the same method.

Example 69

Synthesis of 4-propyl-1-{[5-(trifluoromethyl)-3H-imidazo[4,5-b]pyridin-7-yl]methyl}pyrrolidin-2-one 103

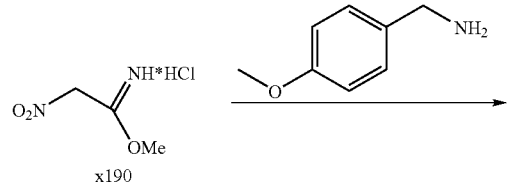

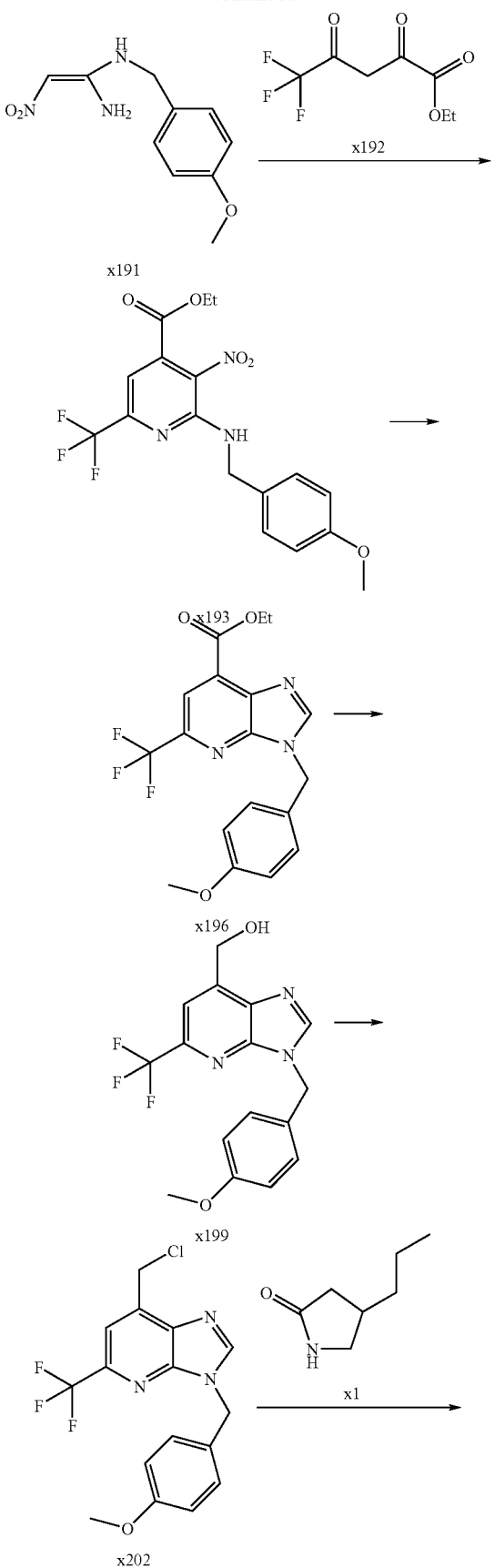

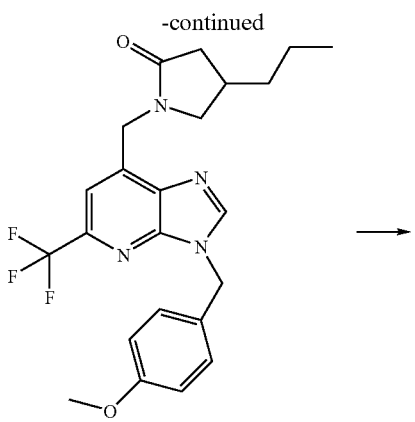

x205

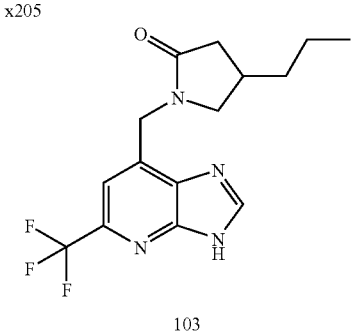

103

69.1. Synthesis of N-(4-methoxybenzyl)-2-nitroethylene-1,1-diamine x191

Hydrochloride x190 (from *Chem. Ber.* 1963, 96, 3306; *Arch. Pharm.* 1986, 319 (1), 14; *J. Heterocycl. Chem.* 1995, 32 (3) 963; *Synthesis* (GE) 1991, 10, 835; 6.14 g, 39.7 mmol) is dissolved in absolute methanol (90 ml). A solution of sodium methoxide [freshly prepared from 0.96 g (1.05 eq) of sodium] in absolute methanol (20 ml) is added dropwise at 0° C. The obtained suspension is stirred additionally for 20 min at 0° C. NaCl is filtered off, and the filtrate is evaporated to a volume of 30 ml. 4-Methoxyaniline (10.9 g, 2 eq, 79.4 mmol) is added, and the reaction mixture is refluxed for 1.5 h. The reaction mixture is evaporated to a minimum volume and diluted with 150 ml ether. The formed precipitate is separated by filtration, washed with ether, and vacuum-dried to afford 8.4 g of N-(4-methoxybenzyl)-2-nitroethylene-1,1-diamine x191.
Yield: 95%.
LC-MS (MH$^+$): 224.

69.2. Synthesis of ethyl 2-[(4-methoxybenzyl) amino]-3-nitro-6-(trifluoromethyl)isonicotinate x193

A mixture of ethyl 5,5,5-trifluoro-2,4-dioxopentanoate x192 (described in the following work: *Izvestiya Akademii Nauk SSSR, Seriya Khimicheskaya* (*Russian Chemical Bulletin*), 1990, 6. 1410-1414 (see Kondrat'ev, P. N.; Skryabina, Z. E.; Saloutin, V. I.; Rudaya, M. N.; Sinitsyna, T. A.; Pashkevich, K. I.; BACCAT; *Bull. Acad. Sci. USSR Div. Chem. Sci.* (*Engl. Transl.*); 39; 6; 1990; 1273-1277; IASKA6); 1.8 g, 8.5 mmol) and (E)-N-(4-methoxybenzyl)-2-nitroethylene-1,1-diamine x191 (2.1 g, 1.1 eq, 9.3 mmol) in absolute ethanol (70 ml) is refluxed in a flow of argon for 48 h. The reaction mixture is evaporated to dryness. The residue is dissolved in chloroform. The solution is filtered, and the filtrate is evaporated. The residue is purified by chromatography on silicagel (CCl$_4$/MeCN) to give 2.7 g of ethyl 2-[(4-methoxybenzyl) amino]-3-nitro-6-(trifluoromethyl)isonicotinate x193.
Yield: 80%.
LC-MS (MH$^+$): 400.

The following compounds may be synthesized according to the same method:

| | | |
|---|---|---|
| x194 | ethyl 2-[(4-methoxybenzyl)amino]-3-nitro-6-phenylisonicotinate | LC-MS (MH$^+$): 408 |
| x195 | ethyl 2-[(4-methoxybenzyl)amino]-6-methyl-3-nitroisonicotinate | LC-MS (MH$^+$): 346 |

69.3. Synthesis of ethyl 3-(4-methoxybenzyl)-5-(trifluoromethyl)-3H-imidazo[4,5-b]pyridine-7-carboxylate x196

Ethyl 2-[(4-methoxybenzyl)amino]-3-nitro-6-(trifluoromethyl)isonicotinate x193 (2.6 g, 6.5 mmol) is dissolved in methanol (100 ml), and Raney nickel (0.8 g) is added. The starting compound is hydrogenated in a Parr apparatus under a hydrogen pressure of 3 atm until the conversion of x193 is complete (1.5-2 h). The catalyst is filtered off and washed with methanol. The filtrate is evaporated to dryness. Triethyl orthoformate (100 ml) and p-toluene sulfonic acid (0.15 g) are added. The flask is equipped with a reflux condenser. The apparatus is flushed with argon, and the obtained reaction mixture is heated under vigorous stirring to 150° C. for 6 h. The reaction solution is evaporated in vacuum. The residue is partitioned between dichloromethane and a saturated aqueous solution of NaHCO$_3$. The organic layer is dried with anhydrous sodium sulfate and evaporated. The target product is purified by chromatography on silicagel (dichloromethane/acetone) to afford 1.5 g of ethyl 3-(4-methoxybenzyl)-5-(trifluoromethyl)-3H-imidazo[4,5-b]pyridine-7-carboxylate x196.
Yield: 60%.
LC-MS (MH$^+$): 380.

The following compound may be synthesized according to the same method:

| | | |
|---|---|---|
| x197 | ethyl 3-(4-methoxybenzyl)-5-phenyl-3H-imidazo[4,5-b]pyridine-7-carboxylate | LC-MS (MH$^+$): 388 |
| x198 | ethyl 3-(4-methoxybenzyl)-5-methyl-3H-imidazo[4,5-b]pyridine-7-carboxylate | LC-MS (MH$^+$): 326 |

69.4. Synthesis of [3-(4-methoxybenzyl)-5-(trifluoromethyl)-3H-imidazo[4,5-b]pyridin-7-yl]methanol x199

This step is realized as described in example 68.5. for the synthesis of [3-(4-methoxybenzyl)-3H-imidazo[4,5-b]pyridin-7-yl]methanol x183 with the use of 3 eq of NaBH$_4$ for 1.45 g (3.8 mmol) of ethyl 3-(4-methoxybenzyl)-5-(trifluoromethyl)-3H-imidazo[4,5-b]pyridine-7-carboxylate x196. Purification by chromatography on silicagel affords 0.58 g of [3-(4-methoxybenzyl)-5-(trifluoromethyl)-3H-imidazo[4,5-b]pyridin-7-yl]methanol x199.
Yield: 45%.
LC-MS (MH$^+$): 338.

The following compound may be synthesized according to the same method:

| | | |
|---|---|---|
| x200 | [3-(4-methoxybenzyl)-5-phenyl-3H-imidazo[4,5-b]pyridin-7-yl]methanol | LC-MS (MH+): 346 |
| x201 | [3-(4-methoxybenzyl)-5-methyl-3H-imidazo[4,5-b]pyridin-7-yl]-methanol | LC-MS (MH+): 284 |

69.5. Synthesis of 1-{[3-(4-methoxybenzyl)-5-(trifluoromethyl)-3H-imidazo[4,5-b]pyridin-7-yl]methyl}-4-propylpyrrolidin-2-one x205

[3-(4-methoxybenzyl)-5-(trifluoromethyl)-3H-imidazo[4,5-b]pyridin-7-yl]methanol x199 (0.55 g, 1.63 mmol) is dissolved in dichloromethane (20 ml). SOCl$_2$ (2 ml) is added dropwise. The reaction mixture is refluxed for 1 h. The volatiles are rotary-evaporated. Then 50 ml of chloroform is additionally distilled off from the residue. The resulting chloroform solution is added dropwise at 0° C. under vigorous stirring to saturated aqueous NaHCO$_3$. The organic phase is separated, dried with anhydrous sodium sulfate, evaporated, and dried under 1 mmHg for 1.5 h at 40° C. 7-(chloromethyl)-3-(4-methoxybenzyl)-5-(trifluoromethyl)-3H-imidazo[4,5-b]pyridine x202 (0.55 g, 95%) sufficiently pure for the next step is obtained.

7-(chloromethyl)-3-(4-methoxybenzyl)-5-phenyl-3H-imidazo[4,5-b]pyridine x203 and 7-(chloromethyl)-3-(4-methoxybenzyl)-5-methyl-3H-imidazo[4,5-b]pyridine x204 may be obtained according to the same method.

4-propylpyrrolidin-2-one x1 (0.22 g, 1.1 eq with respect to x199, 1.7 mmol) is dissolved in absolute THF (10 ml). A 1.06 M solution of Li-HMDS in THF (1.76 ml, 1.1 eq, 1.87 mmol) is added at −78° C. in a flow of argon. The reaction mixture is stirred for 15 min at −30° C. and cooled again to −78° C. A solution of 7-(chloromethyl)-3-(4-methoxybenzyl)-5-(trifluoromethyl)-3H-imidazo[4,5-b]pyridine x202 in absolute THF (10 ml) is added dropwise at this temperature. The reaction mixture is allowed to heat up slowly to room temperature. In order to complete the reaction, the reaction mixture is refluxed the next morning for 1 h, and then partitioned between saturated aqueous NH$_4$Cl and ethyl acetate. The organic layer is dried with anhydrous sodium sulfate and evaporated. The product is purified by HPLC (water/acetonitrile) to afford 0.14 g of 1-{[3-(4-methoxybenzyl)-5-(trifluoromethyl)-3H-imidazo[4,5-b]pyridin-7-yl]methyl}-4-propylpyrrolidin-2-one x205 (0.14 g).

Yield: 20%.

LC-MS (MH+): 447.

The following compound may be synthesized according to the same method:

| | | |
|---|---|---|
| x206 | 1-{[3-(4-methoxybenzyl)-5-phenyl-3H-imidazo[4,5-b]pyridin-7-yl]methyl}-4-propylpyrrolidin-2-one | LC-MS (MH+): 489 |
| x207 | 1-{[3-(4-methoxybenzyl)-5-methyl-3H-imidazo[4,5-b]pyridin-7-yl]methyl}-4-propylpyrrolidin-2-one | LC-MS (MH+): 393 |

69.6. Synthesis of 4-propyl-1-{[5-(trifluoromethyl)-3H-imidazo[4,5-b]pyridin-7-yl]methyl}pyrrolidin-2-one 103

This step is realized as described in example 68.7. for the synthesis of 1-(3H-imidazo[4,5-b]pyridin-7-ylmethyl)-4-propylpyrrolidin-2-one 95. In this case, the deprotection occurs very slowly. In order to complete the reaction, the reaction mixture is kept in a flow of argon at 37° C. for 5 days. From 0.13 g of compound x205, 60 mg of 4-propyl-1-{[5-(trifluoromethyl)-3H-imidazo[4,5-b]pyridin-7-yl]methyl}pyrrolidin-2-one 103 are obtained.

Yield: 70%.

LC-MS (MH+): 327.

Compounds 97, 98 and 101 may be synthesized according to the same method.

Example 70

Synthesis of 1-[(6-bromo-3H-imidazo[4,5-b]pyridin-7-yl)methyl]-4-propylpyrrolidin-2-one 99

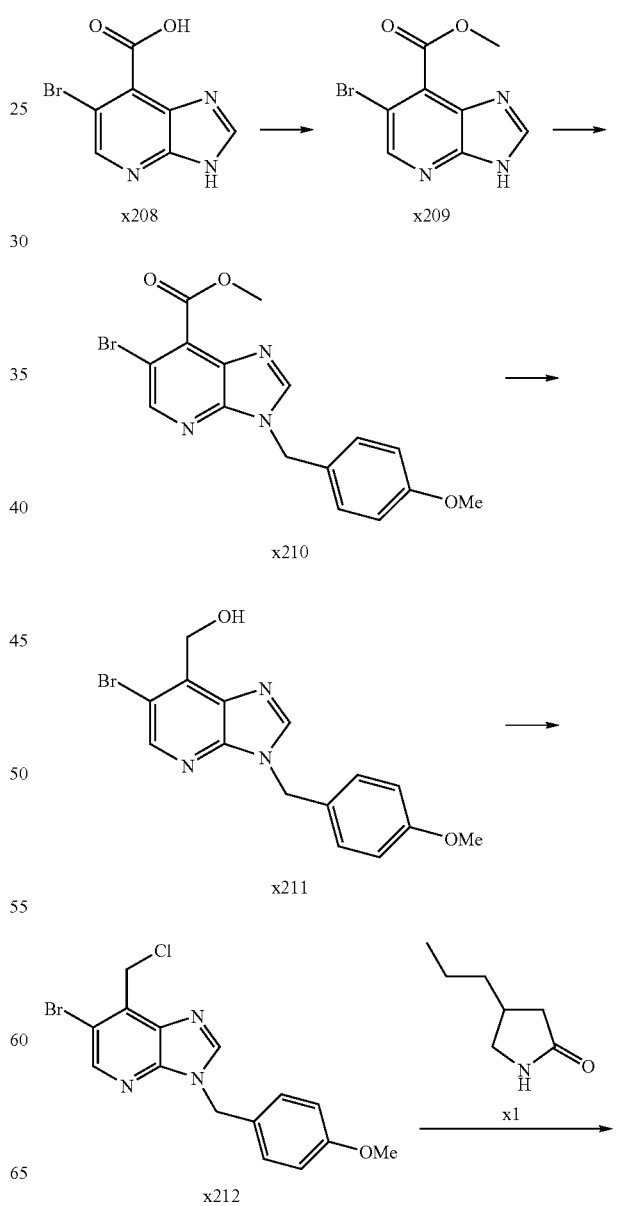

-continued

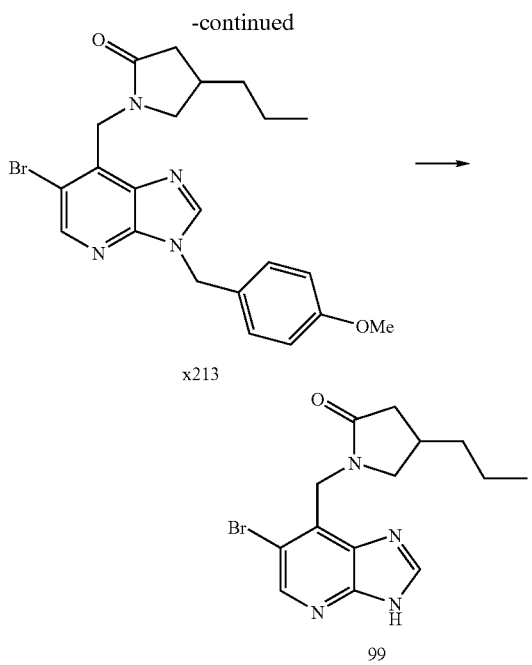

70.1. Synthesis of methyl 6-bromo-1H-imidazo[4,5-b]pyridine-7-carboxylate x209

Absolute methanol (30 ml) is added to 6-bromo-1H-imidazo[4,5-b]pyridine-7-carboxylic acid x208 (Zerenex; 2.2 g, 9.1 mmol). Concentrated $H_2SO_4$ (4 ml) is added to the obtained suspension at 0° C. The reaction mixture is refluxed under protection from the air moisture and vigorous stirring for 10 h. The reaction mixture is then evaporated to half-volume in the vacuum of a rotary evaporator and neutralized under cooling with ice with aqueous ammonia to pH 8-9. The formed precipitate is quickly separated by filtration, washed with ice-cold water (2×30 ml), and dried over $P_2O_5$ at 1 mmHg overnight to afford methyl 6-bromo-1H-imidazo[4,5-b]pyridine-7-carboxylate x209 (1.63 g).
Yield: 70%.
LC-MS (MH$^+$): 257.

70.2. Synthesis of methyl 6-bromo-3-(4-methoxy-benzyl)-3H-imidazo[4,5-b]pyridine-7-carboxylate x210

Methyl 6-bromo-1H-imidazo[4,5-b]pyridine-7-carboxylate x209 (1.425 g, 5.56 mmol) is suspended in absolute THF (40 ml) and 60% NaH (0.235 g, 1.05 eq, 5.84 mmol) is added at 0° C. under vigorous stirring. The reaction mixture is stirred for 15 min until compound x209 is completely dissolved. Tetrabutylammonium bromide (0.54 g, 0.3 eq, 1.67 mmol) is added to the obtained solution. Then p-methoxybenzyl chloride (0.96 g, 1.1 eq, 6.12 mmol) is added dropwise. The reaction mixture is refluxed in a flow of argon for 5 h. The next morning the reaction mixture is evaporated. The residue is dissolved in ethyl acetate. A solid is filtered off. The organic phase is washed with 10% $NaH_2PO_4$, dried with anhydrous sodium sulfate and evaporated. The residue is purified by chromatography on silicagel to afford 1.26 g of protected compound x210.
Yield: 60%.
LC-MS (MH$^+$): 377.

70.3. Synthesis of [6-bromo-3-(4-methoxybenzyl)-3H-imidazo[4,5-b]pyridin-7-yl]methanol x211

Methyl 6-bromo-3-(4-methoxybenzyl)-3H-imidazo[4,5-b]pyridine-7-carboxylate x210 (1.2 g, 3.19 mmol) is dissolved in absolute ethanol. $NaBH_4$ (0.36 g, 3 eq, 9.57 mmol) is added at 5° C. under stirring. The cooling bath is removed after 4 h, and the reaction mixture is allowed to heat up to room temperature. The stirring is continued at this temperature for 20 h. The reaction mixture is evaporated in the vacuum of a rotary evaporator at 35° C., and the residue is partitioned in ethyl acetate/saturated aqueous $NaHCO_3$ mixture. The organic layer is dried with anhydrous sodium sulfate and evaporated. The crude product is purified by chromatography on silicagel (dichloromethane/methanol) to afford 0.72 g of [6-bromo-3-(4-methoxybenzyl)-3H-imidazo[4,5-b]pyridin-7-yl]methanol x211.
Yield: 65%.
LC-MS (MH$^+$): 349.

70.4. Synthesis of 1-{[6-bromo-3-(4-methoxybenzyl)-3H-imidazo[4,5-b]pyridin-7-yl]methyl}-4-propylpyrrolidin-2-one x213

Primary alcohol x211 (0.61 g, 1.75 mmol) is dissolved in dichloromethane (20 ml) and $SOCl_2$ (2 ml) is added dropwise. The reaction mixture is refluxed for 1 h. The volatiles are distilled off in the vacuum of a rotary evaporator. Then 50 ml of chloroform are distilled off additionally from the residue. The residual chloroform solution is added dropwise at 0° C. to a vigorously stirred saturated aqueous solution of $NaHCO_3$. The organic phase is separated, dried with anhydrous sodium sulfate, and evaporated. The residue is kept under 1 mmHg for 1.5 h at 40° C. The obtained 6-bromo-7-(chloromethyl)-3-(4-methoxybenzyl)-3H-imidazo[4,5-b]pyridine x212 (0.59 g, 94%) is sufficiently pure for the next step.

4-propylpyrrolidin-2-one x1 (0.23 g, 1.1 eq, 1.8 mmol) is dissolved in absolute DMF (10 ml). Then 60% NaH (0.072 g, 1.1 eq, 1.8 mmol) is added at 0° C. in a flow of argon. The reaction mixture is stirred for 10 min at 0° C., and then for 10 min at room temperature to complete the reaction. The mixture is cooled again to 0° C. and a solution of 6-bromo-7-(chloromethyl)-3-(4-methoxybenzyl)-3H-imidazo[4,5-b]pyridine x212 (0.59 g, 1 eq) in absolute DMF (5 ml) additionally containing 0.1 g (0.2 eq, 0.32 mmol) of tetrabutylammonium bromide is added dropwise to the obtained suspension. The reaction mixture is stirred for 4 h at 5° C., then overnight at room temperature. The DMF is evaporated at 45° C. under 1 mmHg. The residue is partitioned in 10% aqueous $NaH_2PO_4$/ethyl acetate mixture. The aqueous layer is subjected to additional extraction with ethyl acetate. The combined extracts are dried with anhydrous sodium sulfate and evaporated. The residue is purified by chromatography on silicagel to afford 0.52 g of 1-{[6-bromo-3-(4-methoxybenzyl)-3H-imidazo[4,5-b]pyridin-7-yl]methyl}-4-propylpyrrolidin-2-one x213.
Yield: 65% (calculated from alcohol x211).
LC-MS (MH$^+$): 458.

70.5. Synthesis of 1-[(6-bromo-3H-imidazo[4,5-b]pyridin-7-yl)methyl]-4-propylpyrrolidin-2-one 99

A solution containing 1-{[6-bromo-3-(4-methoxybenzyl)-3H-imidazo[4,5-b]pyridin-7-yl]methyl}-4-propylpyrrolidin-2-one x213 (0.5 g, 0.1 mmol), anisole (0.4 ml) and concentrated $H_2SO_4$ (0.2 ml) in trifluoroacetic acid (4 ml) is stirred in a flow of argon at 20° C. for 2 h. The homogeneous reaction mixture is added dropwise at 0° C. to a mixture of a saturated aqueous solution of NaHCO$_3$ (50 ml) and ethyl acetate (50 ml). The organic layer is separated. The aqueous one (pH ~8) is subjected to additional extraction with chloroform containing 10% of tert-butanol. The combined organic layers are dried with anhydrous sodium sulfate and evaporated. The residue is purified by chromatography on silicagel (chloroform/methanol) to afford 0.31 g of 1-[(6-bromo-3H-imidazo[4,5-b]pyridin-7-yl)methyl]-4-propylpyrrolidin-2-one 99.

Yield: 85%.
LC-MS (MH$^+$): 337/339.

Example 71

Synthesis of 1-[(6-phenyl-3H-imidazo[4,5-b]pyridin-7-yl)methyl]-4-propylpyrrolidin-2-one 105

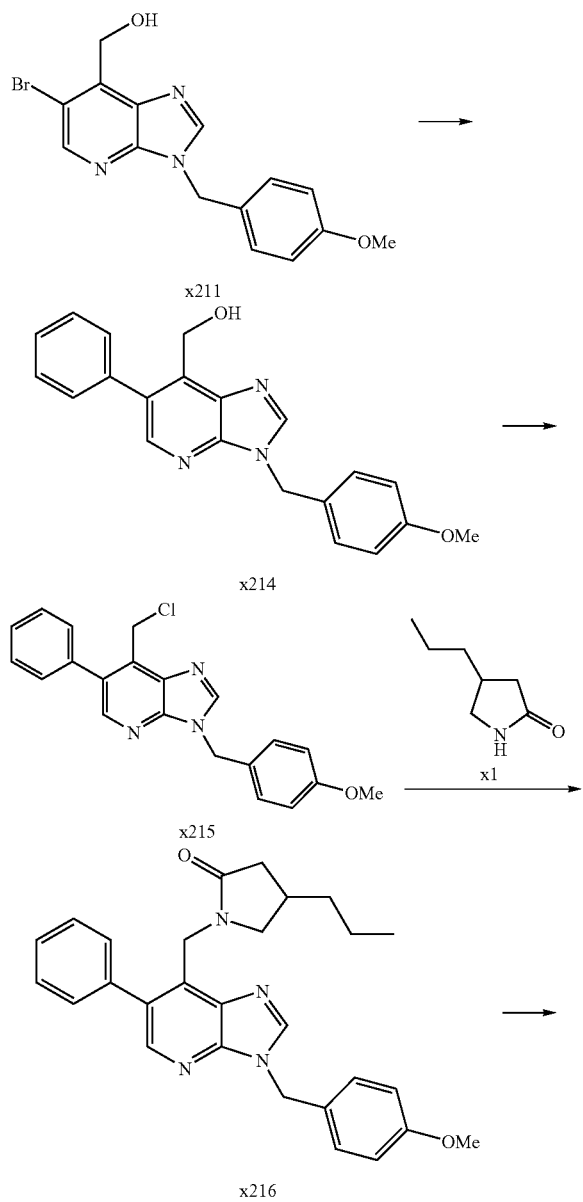

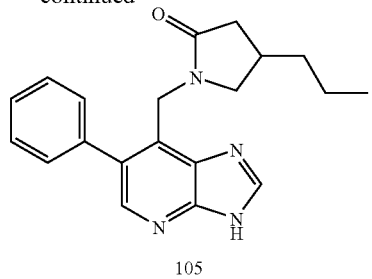

71.1. Synthesis of [3-(4-methoxybenzyl)-6-phenyl-3H-imidazo[4,5-b]pyridin-7-yl]methanol x214

A reactor containing [6-bromo-3-(4-methoxybenzyl)-3H-imidazo[4,5-b]pyridin-7-yl]methanol x211 (0.55 g, 1.58 mmol) in propionitrile (4 ml) and methanol (1 ml) is charged sequentially with phenylboronic acid (0.24 g, 1.25 eq, 1.98 mmol), sodium carbonate (0.34 g) in water (1.6 ml, 2 eq as a 2 M aqueous solution, 3.16 mmol), and tetrabutylammonium bromide (0.1 g, 0.2 eq, 0.32 mmol). The content of the reactor is evacuated several times and subsequently flushed with argon. Then tetrakis(triphenylphosphine)palladium(0) (0.09 g, 5 mol %, 0.08 mmol) is added. The reactor is equipped with a reflux condenser. The whole apparatus is evacuated twice and subsequently flushed with argon. The reaction mixture is kept for 26 h in a flow of argon under vigorous stirring at a bath temperature of 110° C. In the process, the strongly heterogeneous reaction mixture transforms into a solution. When the reaction is complete, the obtained solution is partitioned in 10% aqueous NaH$_2$PO$_4$/ethyl acetate mixture. The organic layer is additionally washed with saturated aqueous NaHCO$_3$, dried with anhydrous sodium sulfate and evaporated in vacuum. The obtained compound is purified by chromatography on silicagel (chloroform/isopropanol) to afford 0.46 g of [3-(4-methoxybenzyl)-6-phenyl-3H-imidazo[4,5-b]pyridin-7-yl]methanol x214.

Yield: 85%.
LC-MS (MH$^+$): 346.

71.2. Synthesis of 1-{[3-(4-methoxybenzyl)-6-phenyl-3H-imidazo[4,5-b]pyridin-7-yl]methyl}-4-propylpyrrolidin-2-one x216

This compound is synthesized according to the method described in example 70.4 with 7-(chloromethyl)-3-(4-methoxybenzyl)-6-phenyl-3H-imidazo[4,5-b]pyridine x215 as intermediate.

Yield: 87%.
LC-MS (MH$^+$): 455.

71.3. Synthesis of 1-[(6-phenyl-3H-imidazo[4,5-b] pyridin-7-yl)methyl]-4-propylpyrrolidin-2-one 105

This compound is synthesized according to the method described in example 70.5, using 1-{[3-(4-methoxybenzyl)-6-phenyl-3H-imidazo[4,5-b]pyridin-7-yl]methyl}-4-propylpyrrolidin-2-one x216 as starting material.

Yield: 85%.
LC-MS (MH$^+$): 335.

Example 72

Synthesis of 1-[(6-methyl-3H-imidazo[4,5-b]pyridin-7-yl)methyl]-4-propylpyrrolidin-2-one 104

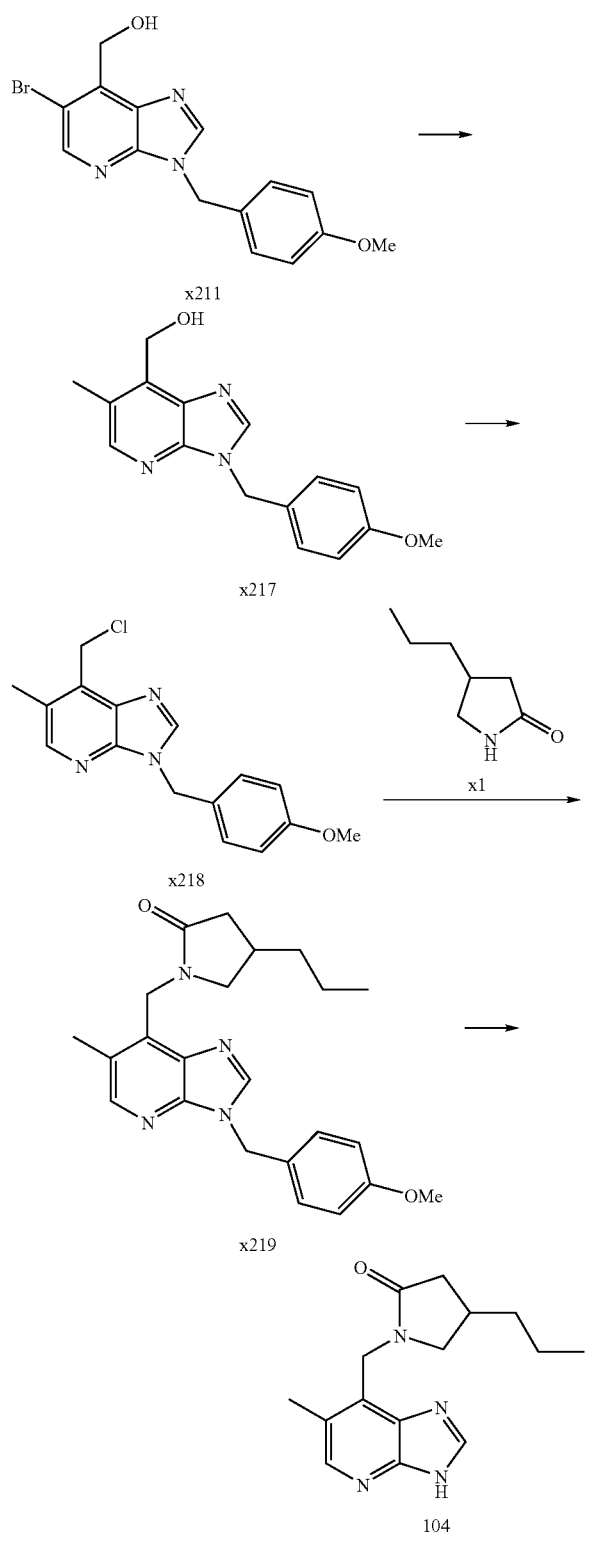

72.1. Synthesis of [3-(4-methoxybenzyl)-6-methyl-3H-imidazo[4,5-b]pyridin-7-yl]methanol x217

The bromine-containing alcohol x211 (1.7 g, 4.9 mmol) is dissolved in absolute freshly distilled dioxane (15 ml). [1,1'-Bis(diphenylphosphino)ferrocene]dichloropalladium(II) (0.072 g, 2 mol %, 0.098 mmol) is added in a flow of argon. A 1.2 M solution of $ZnMe_2$ in toluene (8.2 ml, 2 eq, 9.8 mmol) is added dropwise to the obtained suspension. The reaction mixture is refluxed in a flow of argon for 1.5 h and neutralized with a saturated aqueous solution of $K_2CO_3$. Ethyl acetate (100 ml) is added. The inorganic solid is filtered off. The organic layer is separated, dried with anhydrous sodium sulfate, and evaporated in vacuum. The obtained product is purified by chromatography on silicagel (chloroform/methanol) to afford 1.18 g of [3-(4-methoxybenzyl)-6-methyl-3H-imidazo[4,5-b]pyridin-7-yl]methanol x217.

Yield: 85%.

LC-MS (MH+): 284.

72.2. Synthesis of 1-{[3-(4-methoxybenzyl)-6-methyl-3H-imidazo[4,5-b]pyridin-7-yl]methyl}-4-propylpyrrolidin-2-one x219

This compound is synthesized according to the method described in example 70.4, with 7-(chloromethyl)-3-(4-methoxybenzyl)-6-methyl-3H-imidazo[4,5-b]pyridine x218 as intermediate.

Yield: 87%.

LC-MS (MH+): 393.

72.3. Synthesis of 1-[(6-methyl-3H-imidazo[4,5-b]pyridin-7-yl)methyl]-4-propylpyrrolidin-2-one 104

This compound is synthesized according to the method described in example 70.5, using 1-{[3-(4-methoxybenzyl)-6-methyl-3H-imidazo[4,5-b]pyridin-7-yl]methyl}-4-propylpyrrolidin-2-one x219 as starting material.

Yield: 85%.

LC-MS (MH+): 273.

Example 73

Synthesis of 1-[(2-phenyl-3H-imidazo[4,5-b]pyridin-7-yl)methyl]-4-propylpyrrolidin-2-one 100

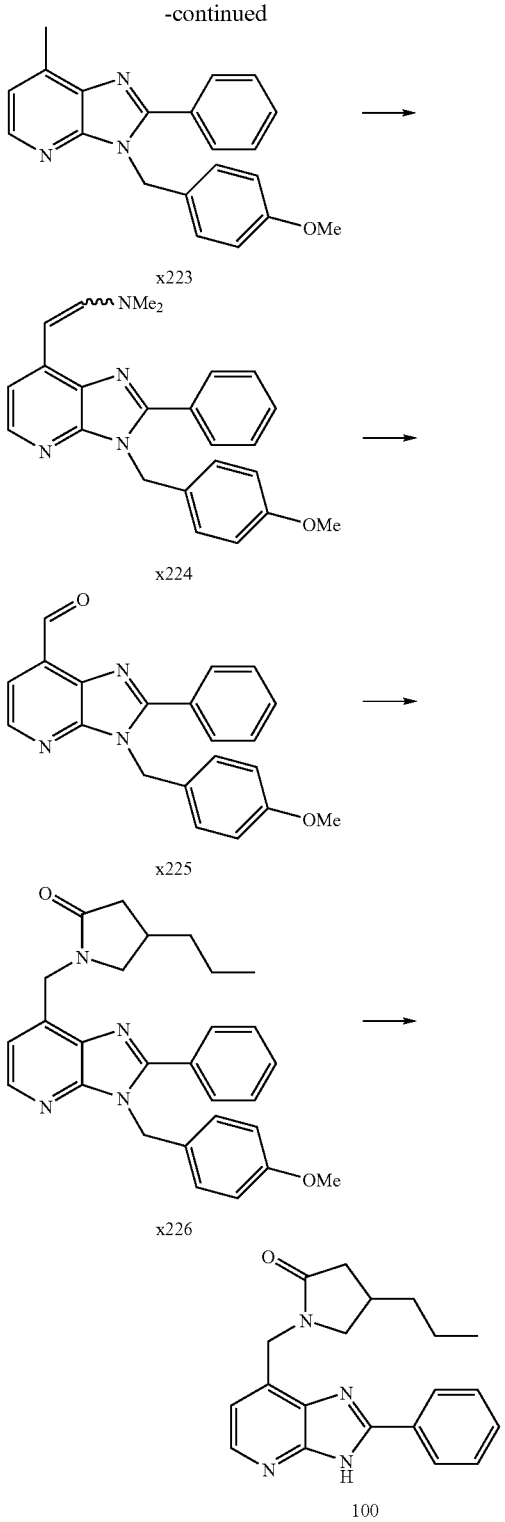

ratus at the hydrogen pressure 3 atm until the total conversion of compound x220 is attained for approximately 1.5-2 h. The catalyst is separated by filtration, the filtrate is washed with methanol, and the alcohol solution is evaporated to dryness. The residue is dissolved in sulfolane (10 ml), then PhC(OMe)$_3$ (5.7 g, 1.2 eq, 31.3 mmol) and PTSA (0.3 g) are added, and an air reflux condenser is mounted. The apparatus is argon-blown, and the obtained reaction mixture is heated to 165° C. under vigorous stirring for 10 h. Water (100 ml), saturated aqueous NaHCO$_3$ (5 ml), and hexane (50 ml) are added to the reaction mixture. The obtained suspension is stirred for 5 min, and the residue is separated by filtration. The residue is washed with water (50 ml) and hexane (100 ml), and vacuum-dried over P$_2$O$_5$ to a constant weight at 45° C. to give 7-methyl-2-phenyl-3H-imidazo[4,5-b]pyridine x221 (2.2 g).

Yield: 40%.

LC-MS (MH$^+$): 210.

The following compound may be synthesized according to the same method:

| | |
|---|---|
| x222 | 2,7-dimethyl-3H-imidazo[4,5-b]pyridine LC-MS (MH$^+$): 148 |

73.2. Synthesis of 3-(4-methoxybenzyl)-7-methyl-2-phenyl-3H-imidazo[4,5-b]pyridine x223

Isomerically pure 3-(4-methoxybenzyl)-7-methyl-2-phenyl-3H-imidazo[4,5-b]pyridine x223 (2.3 g) is obtained following the experimental procedure of example 70.2, using 2.1 g (10 mmol) of 7-methyl-2-phenyl-3H-imidazo[4,5-b]pyridine x221.

Yield: 70%.

LC-MS (MH$^+$): 330.

73.3. Synthesis of 2-[3-(4-methoxybenzyl)-2-phenyl-3H-imidazo[4,5-b]pyridin-7-yl]-N,N-dimethylethylenamine x224

(Me$_2$N)$_2$CHOtBu (1.8 g, 1.5 eq, 10.2 mmol) is added in argon to a solution of 3-(4-methoxybenzyl)-7-methyl-2-phenyl-3H-imidazo[4,5-b]pyridine x223 (2.25 g, 6.8 mmol) in absolute 1,2-dimethoxyethane (7 ml), and the obtained solution is kept at 60° C. for 16 h. Then the solution is additionally refluxed for 4 h. The reaction mixture is cooled to room temperature, diluted with hexane, and kept at 3° C. for 1 h. The formed precipitate of enamine is separated by filtration, washed with hexane, and vacuum-dried to afford 2 g of 2-[3-(4-methoxybenzyl)-2-phenyl-3H-imidazo[4,5-b]pyridin-7-yl]-N,N-dimethylethylenamine x224 (purity 90% according to the LC/MS data).

Yield: 70%.

LC-MS (MH$^+$): 385.

73.4. Synthesis of 3-(4-methoxybenzyl)-2-phenyl-3H-imidazo[4,5-b]pyridine-7-carbaldehyde x225

Sodium periodate (3.3 g, 3 eq, 15 mmol) is added under vigorous stirring to a suspension of 2-[3-(4-methoxybenzyl)-2-phenyl-3H-imidazo[4,5-b]pyridin-7-yl]-N,N-dimethylethylenamine x224 (2 g, about 5 mmol) in a 1/1 water/THF mixture (60 ml). The mixture is stirred at room temperature until the complete conversion of starting enamine is attained for approximately 5 h. Ethyl acetate (100 ml) and saturated aqueous NaHCO$_3$ (50 ml) are added to the mixture. The mixture is stirred, and the precipitate of inorganic salts is filtered off. The organic layer is separated from the obtained two-phase mixture and dried over anhydrous $Na_2SO_4$. The solution is evaporated, and the residue is purified by chromatography on silicagel (dichloromethane/isopropanol) to 1 g of 3-(4-methoxybenzyl)-2-phenyl-3H-imidazo[4,5-b]pyridine-7-carbaldehyde x225.
Yield 60%.
LC-MS ($MH^+$): 344.

73.5. Synthesis of 1-{[3-(4-methoxybenzyl)-2-phenyl-3H-imidazo[4,5-b]pyridin-7-yl]methyl}-4-propylpyrrolidin-2-one x226

Ethyl 3-(nitromethyl)hexanoate (0.52 g, 1.1 eq, 2.55 mmol) is dissolved in absolute methanol (8 ml). Then 10% Pd/C (0.2 g) and ammonium formate (1 g) are added under vigorous stirring. After 15 min, the mixture is diluted with ether (100 ml) and filtered. The solid on the filter is washed with ether (2×50 ml). A solution of 3-(4-methoxybenzyl)-2-phenyl-3H-imidazo[4,5-b]pyridine-7-carbaldehyde x225 (1 g, 1 eq, 2.9 mmol) in methanol (5 ml) is added immediately. The combined solution is evaporated in the vacuum of a rotary evaporator. The residue is dissolved in methanol (10 ml), $CH(OMe)_3$ (0.5 ml) is added and the obtained solution is stirred at room temperature for 16 h. An excess of $NaBH_4$ (1 g in several small portions) is then added under vigorous stirring for 20 min. The reaction mixture is evaporated in the vacuum of a rotary evaporator. The residue is partitioned between ethyl acetate and water. The organic phase is separated, dried with anhydrous sodium sulfate, and evaporated. The residue is dissolved in acetonitrile (10 ml), and the solution is refluxed for 24 h to complete the cyclization. The solvent is distilled off. The residue is purified by chromatography on silicagel ($CCl_4$/MeCN) to yield 0.79 g of 1-{[3-(4-methoxybenzyl)-2-phenyl-3H-imidazo[4,5-b]pyridin-7-yl]methyl}-4-propylpyrrolidin-2-one x226.
Yield: 60%.
LC-MS ($MH^+$): 414.

73.6. Synthesis of 1-[(2-phenyl-3H-imidazo[4,5-b]pyridin-7-yl)methyl]-4-propylpyrrolidin-2-one 100

Deprotection step of 1-{[3-(4-methoxybenzyl)-2-phenyl-3H-imidazo[4,5-b]pyridin-7-yl]methyl}-4-propylpyrrolidin-2-one x226 is performed as described in example 68.7 to afford 1-[(2-phenyl-3H-imidazo[4,5-b]pyridin-7-yl)methyl]-4-propylpyrrolidin-2-one 100.
LC-MS ($MH^+$): 335.

Example 74

Synthesis of 4-phenyl-1-{[3-(trifluoromethyl)[1,2,4]triazolo[4,3-b]pyridazin-7-yl]methyl}pyrrolidin-2-one 255

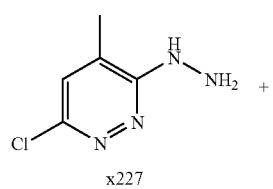

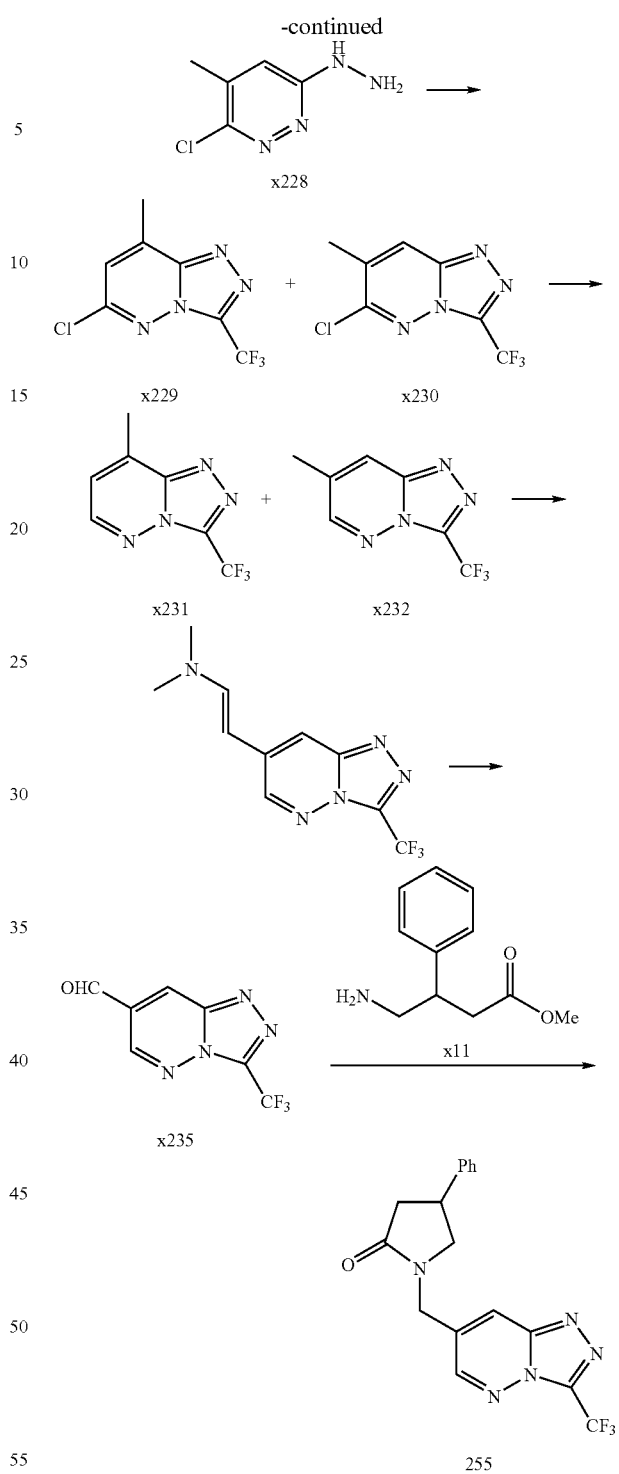

74.1 Synthesis of 6-chloro-8-methyl-3-(trifluoromethyl)[1,2,4]triazolo[4,3-b]pyridazine x229 and 6-chloro-7-methyl-3-(trifluoromethyl)[1,2,4]triazolo[4,3-b]pyridazine x230

In the absence of air moisture, the 3:1 regioisomeric mixture of 6-chloro-4-methylpyridazin-3(2H)-one hydrazone x227 and 6-chloro-5-methylpyridazin-3(2H)-one hydrazone x228 (7.88 g, 4.97 mmol, obtained according to R. J. Cregge, J. E. Coutant, U.S. Pat. No. 4,578,464, 1986) is dissolved in TFA (77 ml) and kept under stirring at the bath temperature 90° C. for 16 h. The reaction mixture is cooled, TFA is removed under reduced pressure, and the residue is dissolved in dichloromethane (200 ml). The solution is washed with a saturated NaHCO₃ solution and dried over anhydrous Na₂SO₄. The solution is evaporated and vacuum-dried to give the mixture of intermediates x229 and x230 in the molar ratio 2.6:1 according to the ¹H NMR data as a white solid mass.

Yield: 87% (10.24 g).

¹H NMR (DMSO-d₆): 2.44 (d, J=1.23 Hz), 2.69 (d, J=1.23 Hz), 7.66 (d, J=1.22 Hz), 8.59 (d, J=1.22 Hz).

74.2. Synthesis of 8-methyl-3-(trifluoromethyl)[1,2,4]triazolo[4,3-b]pyridazine x231 and 7-methyl-3-(trifluoromethyl)[1,2,4]triazolo[4,3-b]pyridazine x232

The mixture of intermediates x229 and x230 (10 g, 42.3 mmol) is dissolved in ethanol (640 ml). Pd/C (10%, 2.8 g) and aqueous ammonia (25%, 172 ml) are added, and the mixture is hydrogenated in the Parr apparatus under the hydrogen pressure 2 atm at room temperature for 50 min. The reaction mixture is filtered through the Celite layer, and Celite is washed with ethanol. The combined extracts are evaporated, and the residue is dissolved in chloroform. The solution is washed with brine and dried over anhydrous Na₂SO₄. The solvent is removed under reduced pressure and the residue (8.6 g) is purified by chromatography on silicagel (hexane/ethyl acetate 1/1) to give the 1:3 mixture of isomers x231 and x232 (0.48 g), the 2:1 mixture of isomers x231 and x232 (1.16 g), and isomer x232 (1.70 g; yield: 27.5% calculated for starting isomer x230).

Total yield: 39%.

x232: ¹H NMR (DMSO-d₆): 2.46 (d, J=1.22 Hz, 3H), 8.35 (t, J=1.71 Hz, 1H), 8.78 (d, 1.96 Hz, 1H).

74.3 Synthesis of N,N-dimethyl-2-[3-(trifluoromethyl)[1,2,4]triazolo[4,3-b]pyridazin-7-yl]ethylenamine x233

Brederick's reagent (1-tert-butoxy-N,N,N,N-tetramethylmethanediamine, 2.8 ml, 13.5 mmol, 1.6 eq) is added under stirring to a solution of 7-methyl-3-(trifluoromethyl)[1,2,4]triazolo[4,3-b]pyridazine x232 (1.70 g, 8.4 mmol) in dry DME (32 ml). The reaction mixture is refluxed for 4 h, cooled to room temperature and stirred overnight for 16 h. The formed precipitate is separated by filtration and dried to give crude N,N-dimethyl-2-[3-(trifluoromethyl)[1,2,4]triazolo[4,3-b]pyridazin-7-yl]ethylenamine x233 (0.44 g) as a yellow powder. The Brederick's reagent (0.5 ml, 2.4 mmol) is additionally added to the mother liquor, which contained unreacted regioisomer x232 according to the TLC data, and the obtained mixture is refluxed for 8 h. Then the reaction mixture is cooled to room temperature, diluted with hexane (10 ml), and kept overnight. The formed precipitate is separated by filtration and dried to give additionally intermediate x233 (0.32 g,).

Total yield: 35% (0.76 g).

¹H NMR (DMSO-d₆): 2.94 (s, 6H), 5.13 (d, J=13.4 Hz, 1H), 7.67-7.70 (m, 2H), 8.8 (s, 1H).

N,N-dimethyl-2-(3-phenyl[1,2,4]triazolo[4,3-b]pyridazin-7-yl)ethylenamine x234 may be prepared according to the same method.

74.4. Synthesis of 3-(trifluoromethyl)[1,2,4]triazolo[4,3-b]pyridazine-7-carbaldehyde x235

A finely-ground powder of NaIO₄ is added to a solution of 7-methyl-3-(trifluoromethyl)-[1,2,4]triazolo[4,3-b]pyridazine x233 (0.52 g, 2.0 mmol) in absolute methanol (42 ml). The reaction mixture is stirred at room temperature for 1.5 h and diluted with an equal volume of dichloromethane. The mixture is filtered through the Celite layer, and the solvents are removed under reduced pressure. The residue (0.5 g) is purified by chromatography on silicagel (hexane/ethyl acetate 3/2) to yield 0.34 g of 3-(trifluoromethyl)[1,2,4]triazolo[4,3-b]pyridazine-7-carbaldehyde x235 as a white solid.

Yield: 78%.

¹H NMR (CDCl₃): 8.70 (d, J=1.95 Hz, 1H); 9.03 (d, J=1.71 Hz, 1H), 10.17 (s, 1H).

3-phenyl[1,2,4]triazolo[4,3-b]pyridazine-7-carbaldehyde x236 may be prepared according to the same method.

74.5. Synthesis of 4-phenyl-1-{[3-(trifluoromethyl)[1,2,4]triazolo[4,3-b]pyridazin-7-yl]methyl}pyrrolidin-2-one 255

Methyl 4-amino-3-phenylbutanoate hydrochloride x11 (0.19 g, 0.83 mmol, 1.05 eq) is added to a solution of aldehyde x235 (0.17 g, 0.79 mmol) in dry dichloroethane (DCE) (7.8 ml). The mixture is kept at room temperature for 30 min, cooled to 10-12° C., and a solution of triethylamine (0.15 ml, 0.83 mmol, 1.05 eq) in dry DME (2.5 ml) is added dropwise. The mixture is additionally stirred at the same temperature for 1 h and cooled to 0-5° C. Then STAB (0.23 g, 1.10 mmol, 1.4 eq) is added in portions under vigorous stirring. The mixture is additionally stirred at 0-5° C. for 30 min and kept at room temperature overnight. Then the mixture is heated to 60° C. for 2 h and cooled to room temperature. An equal volume of dichloromethane is added, and the mixture is washed with 10% K₂CO₃ (2×10 ml). The mixture is dried over anhydrous Na₂SO₄ and evaporated. The oily residue is triturated with ether, and the formed crystals are separated by filtration, washed twice with ether, and vacuum-dried to give white fine-crystalline 4-phenyl-1-{[3-(trifluoromethyl)[1,2,4]triazolo[4,3-b]pyridazin-7-yl]methyl}pyrrolidin-2-one 255.

Yield: 36% (0.101 g).

LC-MS (MH⁺): 362.

Example 75

Synthesis of 4-propyl-1-{[3-(trifluoromethyl)[1,2,4]triazolo[4,3-b]pyridazin-8-yl]methyl}pyrrolidin-2-one 258

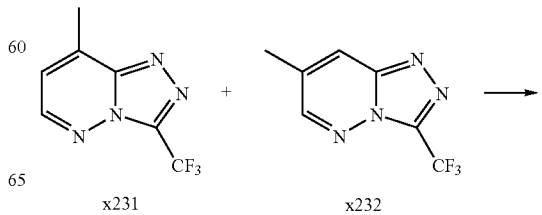

x231 + x232 →

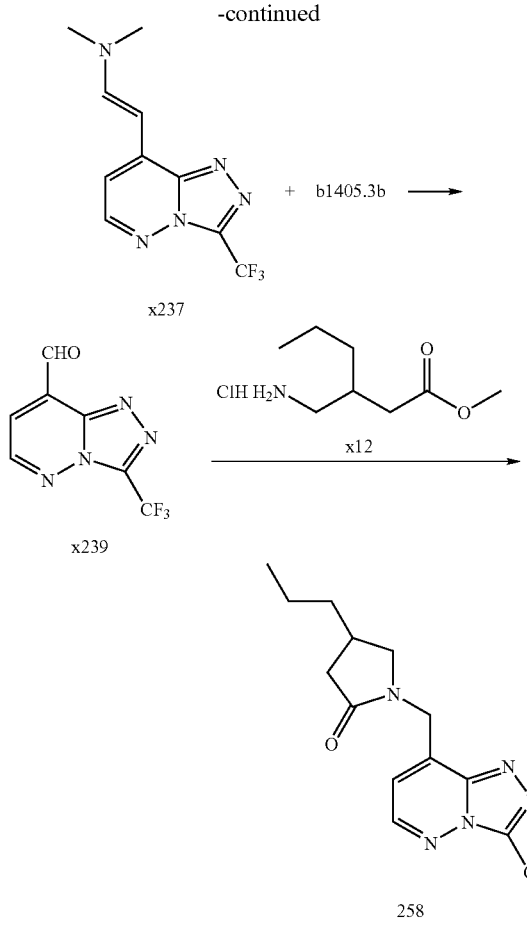

75.1. Synthesis of N,N-dimethyl-2-[3-(trifluoromethyl)[1,2,4]triazolo[4,3-b]pyridazin-8-yl]ethylenamine b1502.5a The isomeric mixture (3 g, 6.3 mmol.) of 8-methyl-3-(trifluoromethyl)[1,2,4]triazolo[4,3-b]pyridazine x231 and 7-methyl-3-(trifluoromethyl)[1,2,4]triazolo[4,3-b]pyridazine x232 is dissolved in DME (30 ml), and Brederick's reagent (1.7 g, 10.0 mmol, 1.6 eq) is added to the obtained solution. The reaction mixture is stirred at 60-65° C. for 4 h, cooled to room temperature, and excess solvents are removed under reduced pressure. The residue is vacuum-dried to give the mixture of enamine x237 and starting isomer x232 (2.24 g) in the molar ratio 2.5:1 according to the $^1$H NMR data. This mixture is used for the next step without further purification.

2-[6-chloro-3-(trifluoromethyl)[1,2,4]triazolo[4,3-b]pyridazin-8-yl]-N,N-dimethylethylenamine x238 may be synthesized according to the same method.

75.2 Synthesis of 3-(trifluoromethyl)[1,2,4]triazolo[4,3-b]pyridazine-8-carbaldehyde x239

The previous mixture (x237 and starting isomer x232) is dissolved in absolute methanol (137 ml), and finely-ground NaIO$_4$ (4.24 g, 19.8 mmol) is added to the obtained solution. The reaction mixture is stirred at room temperature for 4.5 h, diluted with an equal volume of dichloromethane, and filtered through the Celite layer. The solvents are removed under reduced pressure. The residue is purified by chromatography on silicagel (hexane/ethyl acetate 1/1) to yield 3-(trifluoromethyl)[1,2,4]triazolo[4,3-b]pyridazine-8-carbaldehyde x239 as a white solid substance (0.42 g).

Yield: 31%.

$^1$H NMR (DMSO-d$_6$): 8.04 (d, J=4.40 Hz, 1H), 9.14 (d, J=4.40 Hz, d, 1H), 10.49 (s, 1H).

75.3. Synthesis of 4-propyl-1-{[3-(trifluoromethyl)[1,2,4]triazolo[4,3-b]pyridazin-8-yl]methyl}pyrrolidin-2-one 258

4-propyl-1-{[3-(trifluoromethyl)[1,2,4]triazolo[4,3-b]pyridazin-8-yl]methyl}pyrrolidin-2-one 258 is synthesized as described in example 74.5 from the aldehyde x239 (0.182 g, 0.84 mol), methyl 3-(aminomethyl)hexanoate hydrochloride x12 (0.165 g, 0.84 mmol), TEA (0.123 ml, 0.885 mmol), and NaBH(OAc)$_3$ (0.25 g, 1.18 mmol) in DCE (11.3 ml).

Yield: 30% (0.084 g).

LC-MS (MH$^+$): 258.

Compound 257 may be synthesized according to the same method.

Example 76

Synthesis of 4-phenyl-1-[(3-phenyl[1,2,4]triazolo[4,3-b]pyridazin-8-yl)methyl]pyrrolidin-2-one 259

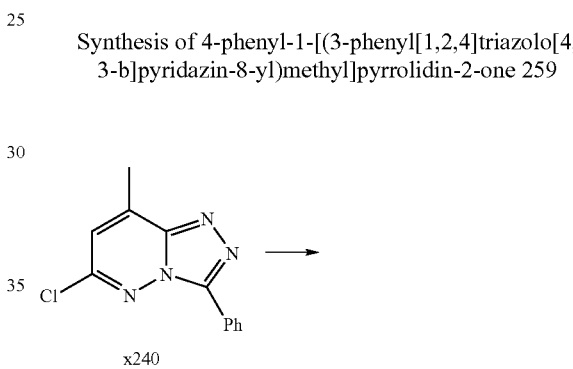

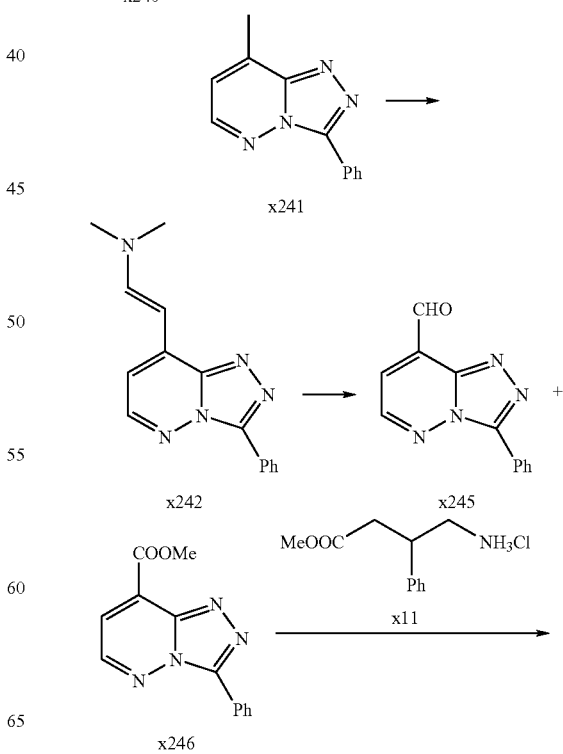

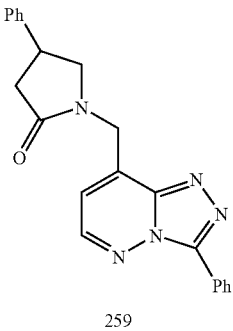

259

76.1. Synthesis of 8-methyl-3-phenyl[1,2,4]triazolo[4,3-b]pyridazine x241

6-chloro-8-methyl-3-phenyl[1,2,4]triazolo[4,3-b]pyridazine x240 is dissolved in ethanol (300 ml), and 10% Pd/C (0.9 g) and 25% aqueous ammonia (60 ml) are added. The mixture is hydrogenated in the Parr apparatus under hydrogen pressure 2.5 atm at room temperature for 1 h 10. The reaction mixture is filtered through a Celite layer, which is washed with ethanol. The combined filtrates are evaporated, and the residue is dissolved in dichloromethane. The solution is washed with brine and dried over anhydrous $Na_2SO_4$. The solvent is removed under reduced pressure to afford 2.9 g of 8-methyl-3-phenyl[1,2,4]triazolo[4,3-b]pyridazine x241.

Yield: 85%.

$^1$H NMR (DMSO-$d_6$): 2.67 (d, J=1.23 Hz, 3H), 7.54-7.64 (m, 4H), 8.37-8.39 (m, 2H), 8.61 (d, J=4.4 Hz, 1H).

76.2. Synthesis of N,N-dimethyl-2-(3-phenyl[1,2,4]triazolo[4,3-b]pyridazin-8-yl)ethylenamine x242

Brederick's reagent (3.2 g, 18 mmol) is added to a solution of 8-methyl-3-phenyl[1,2,4]triazolo[4,3-b]pyridazine x241 (2.9 g, 18 mmol) in DME (26 ml), and the reaction mixture is stirred at 60° C. for 2 h. Then the mixture is cooled to room temperature, the solvents are removed under reduced pressure, and the residue (4.9 g) of N,N-dimethyl-2-(3-phenyl[1,2,4]triazolo[4,3-b]pyridazin-8-yl)ethylenamine x242 is used for the next step without additional purification.

2-(6-chloro-3-phenyl[1,2,4]triazolo[4,3-b]pyridazin-8-yl)-N,N-dimethylethylenamine x243 and 2-(6-chloro[1,2,4]triazolo[4,3-b]pyridazin-8-yl)-N,N-dimethylethylenamine x244 may be synthesized according to the same method.

76.3. Synthesis of 3-phenyl[1,2,4]triazolo[4,3-b]pyridazine-8-carbaldehyde x245 and methyl 3-phenyl[1,2,4]triazolo[4,3-b]pyridazine-8-carboxylate x246

Crude enamine x242 is dissolved in absolute ethanol (86 ml). A finely-ground $NaIO_4$ powder (8.86 g, 41.4 mmol) is added, and the reaction mixture is vigorously stirred at room temperature for 4 h. Then the mixture is diluted with an equal volume of dichloromethane, filtered through a Celite layer, and the solvents are removed under reduced pressure. The residue (5.9 g) is purified by chromatography on silicagel (ethyl acetate) to afford, according to the $^1$H NMR data, a 2:1 mixture of 3-phenyl[1,2,4]triazolo[4,3-b]pyridazine-8-carbaldehyde x245 and methyl 3-phenyl[1,2,4]triazolo[4,3-b]pyridazine-8-carboxylate x246 (1.2 g).

$^1$H NMR (DMSO-$d_6$): 4.03 (s), 7.57-7.67 (m), 7.85 (t, J=4.16 Hz), 8.33-8.39 (m), 8.89 (d, J=4.41 Hz), 9.01 (d, J=4.15 Hz), 10.55 (s).

The mixture of 6-chloro[1,2,4]triazolo[4,3-b]pyridazine-8-carbaldehyde x247 and methyl 6-chloro[1,2,4]triazolo[4,3-b]pyridazine-8-carboxylate x248 (1/2 ratio) may be obtained according to the same method.

LC-MS (MH$^+$): 187 and 213.

76.4. Synthesis of 4-phenyl-1-[(3-phenyl[1,2,4]triazolo[4,3-b]pyridazin-8-yl)methyl]pyrrolidin-2-one 259

This step is realized as described in example 74.5 from the previously synthesized mixture of x245 and x246 (0.60 g), methyl 4-amino-3-phenylhexanoate hydrochloride x11 (0.39 g, 1.7 mmol), TEA (0.23 ml, 1.66 mmol), and NaBH(OAc)$_3$ (0.56 g, 2.6 mmol) in DCE (30 ml). The crude compound is purified by chromatography on silicagel (ethyl acetate) to afford 0.57 g of product 4-phenyl-1-[(3-phenyl[1,2,4]triazolo[4,3-b]pyridazin-8-yl)methyl]pyrrolidin-2-one 259.

Yield: 90%.

LC-MS (MH$^+$): 370.

Compounds 257 and 261 may be synthesized according to the same method.

Example 77

Synthesis of 1-[(6-chloro-3-phenyl[1,2,4]triazolo[4,3-b]pyridazin-8-yl)methyl]-4-propylpyrrolidin-2-one 260

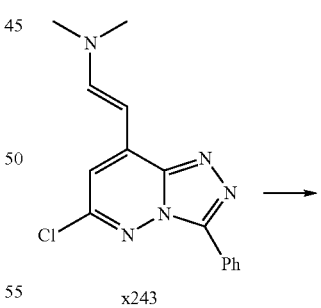

x243

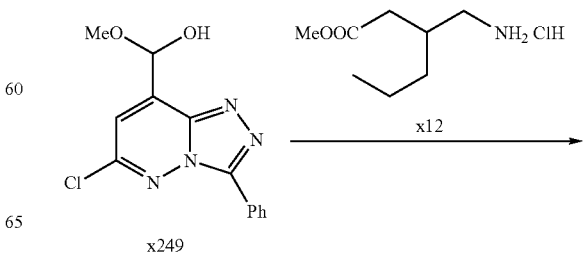

x249

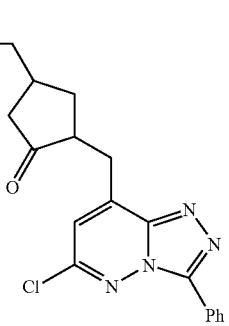

260

77.1. Synthesis of (6-chloro-3-phenyl[1,2,4]triazolo[4,3-b]pyridazin-8-yl)(methoxy)methanol x249

Analogously to the procedure described in example 76.3, from a solution of 2-(6-chloro-3-phenyl[1,2,4]triazolo[4,3-b]pyridazin-8-yl)-N,N-dimethylethylenamine x243 (1.84 g, 6.14 mmol) in absolute methanol (30 ml) and NaIO$_4$ (3.92 g, 18.4 mmol) under stirring for 24 h. Semiacetal x249 (0.73 g) is obtained after purification by chromatography on silicagel (hexane/ethyl acetate 1/1).
Yield: 41%.
$^1$H NMR (DMSO-d$_6$): 3.47 (s, 3H), 6.05 (d, J=7 Hz, 1H), 7.41 (s, 1H), 7.51 (d, J=7.34 Hz, 1H), 7.57-7.66 (m, 4H).
The same method is used for the synthesis of [6-chloro-3-(trifluoromethyl)[1,2,4]triazolo[4,3-b]pyridazin-8-yl](methoxy)methanol x250 but in this case, the compound is also observed as its hydrate and its methyl hemiacetal.

77.2. Synthesis of 1-[(6-chloro-3-phenyl[1,2,4]triazolo[4,3-b]pyridazin-8-yl)methyl]-4-propylpyrrolidin-2-one 260

This step is realized as described in example 74.5 from semiacetal x249 (0.37 g, 1.3 mmol), methyl 3-(aminomethyl)hexanoate hydrochloride x12 (0.26 g, 1.33 mmol), triethylamine (0.19 ml, 1.33 mmol), and NaHB(OAc)$_3$ (0.38 g, 1.8 mmol) in DCE (20 ml). After purification by chromatography on silicagel (hexane/ethyl acetate 1/1), 1-[(6-chloro-3-phenyl[1,2,4]triazolo[4,3-b]pyridazin-8-yl)methyl]-4-propylpyrrolidin-2-one 260 (0.23 g) is obtained.
Yield: 49%.
LC-MS (MH$^+$): 370/372.
Compounds 262 and 263 may be synthesized according to the same method.

Example 78

Synthesis of 1-(isoxazol-4-ylmethyl)-4-propylpyrrolidin-2-one 157

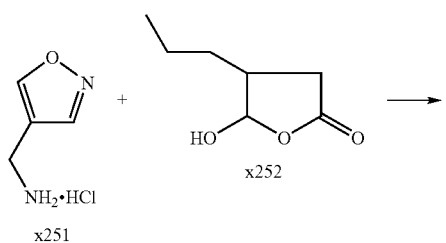

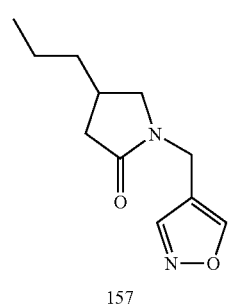

157

A solution of 5-hydroxy-4-propyldihydrofuran-2(3H)-one x252 (0.44 g, 3.0 mmol) in dry DCE (8 ml), DIEA (0.364 g, 2.8 mmol), and several drops AcOH is added to a suspension of 1-isoxazol-4-ylmethanamine hydrochloride x251 (0.46 g, 3.0 mmol) in dry DCE, and NaHB(OAc)$_3$ (0.976 g, 2.3 mmol) is added in 50 min. The reaction mixture is stirred at room temperature for 72 h and washed with 20% K$_2$CO$_3$ (2×25 ml). The aqueous layer is subjected to extraction with dichloromethane (3×30 ml). The combined organic layers are washed with brine (40 ml), dried over Na$_2$SO$_4$, and evaporated. The residue (0.55 g) is purified by chromatography on silicagel (chloroform/ethyl acetate 1/1) to afford 0.202 g of 1-(isoxazol-4-ylmethyl)-4-propylpyrrolidin-2-one 157 (yield 0.202 g, 32%).
Yield: 32%.
LC-MS (MH$^+$): 209.

Example 79

Synthesis of 4-propyl-1-(1H-pyrrolo[2,3-b]pyridin-5-ylmethyl)pyrrolidin-2-one 241

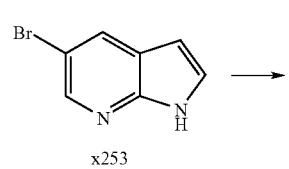

x253

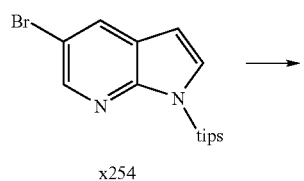

x254

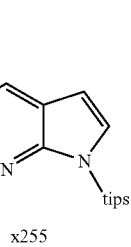

x255

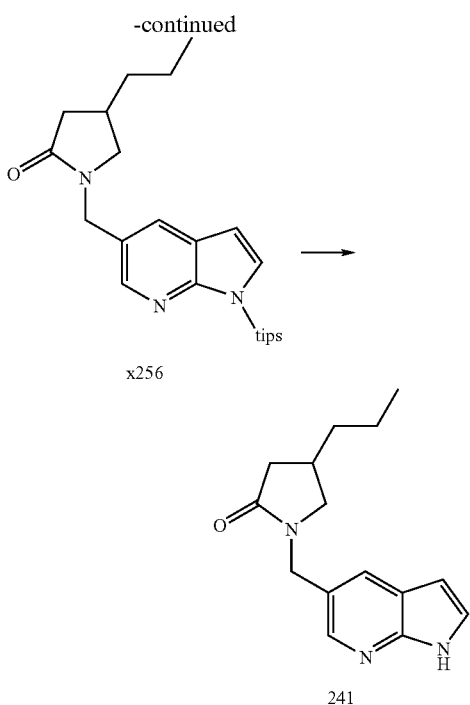

79.1. Synthesis of 5-bromo-1-(triisopropylsilyl)-1H-pyrrolo[2,3-b]pyridine x254

The commercially available 5-bromo-1H-pyrrolo[2,3-b]pyridine x253 (0.94 g, 4.77 mmol) is dissolved in freshly distilled absolute 1,2-dimethoxyethane (15 ml). Then 100% NaH (0.126 g, 1.1 eq, 5.25 mmol, obtained by washing a 60% NaH emulsion with hexane in a flow of argon) is added at 0° C. under vigorous stirring. The reaction mixture is taken away from the cooling bath and stirred for 15 min at room temperature. After this, triisopropylsilyl chloride (1.1 g, 1.2 eq, 5.73 mmol) is added dropwise, and tetrabutylammonium bromide (0.307 g, 0.2 eq, 0.95 mmol) is added. The reaction mixture is stirred for 5 h in a flow of argon, cooled, and poured into 5% aqueous NaHCO$_3$ (10 ml). The product is extracted with hexane (2×100 ml). The combined extracts are dried with anhydrous sodium sulfate and evaporated. The residue is purified by chromatography on silicagel (hexane/CCl$_4$) to afford 1.15 g of 5-bromo-1-(triisopropylsilyl)-1H-pyrrolo[2,3-b]pyridine x254.
Yield: 70%.
LC-MS (MH$^+$): 354.

79.2. Synthesis of 1-(triisopropylsilyl)-1H-pyrrolo[2,3-b]pyridine-5-carbaldehyde x255

Bromide x254 (1.1 g, 3.11 mmol) is dissolved in freshly distilled absolute THF (40 ml). A 1.7 M solution of t-BuLi in pentane (1.92 ml, 1.05 eq) is added dropwise at –100° C. under vigorous stirring in a flow of argon. The reaction mixture is stirred for 45 min and meanwhile allowed to heat up slowly to –78° C. After this, a solution of N-formylpiperidine (0.42 g, 1.2 eq, 3.73 mmol) in freshly distilled absolute THF (5 ml) is added dropwise for 5 min. The mixture is allowed to heat up to 0° C. under stirring in the cooling bath, and then poured into a mixture of saturated aqueous NH$_4$Cl (20 ml) and 1:1 hexane/ether mixture (100 ml). The organic phase is separated, dried with anhydrous sodium sulfate, and evaporated. The residue is purified by chromatography on silicagel, CCl$_4$/MeCN) to afford 0.7 g of 1-(triisopropylsilyl)-1H-pyrrolo[2,3-b]pyridine-5-carbaldehyde x255.
Yield: 75%.
LC-MS (MH$^+$): 303.

79.3. Synthesis of 4-propyl-1-{[1-(triisopropylsilyl)-1H-pyrrolo[2,3-b]pyridin-5-yl]methyl}pyrrolidin-2-one x256

Ethyl 3-(nitromethyl)hexanoate (0.52 g, 1.1 eq, 2.55 mmol) is dissolved in absolute methanol (8 ml). Then 10% Pd/C (0.2 g) and ammonium formate (1 g) are added under vigorous stirring. After 15 min, the mixture is diluted with ether (100 ml) and filtered. The solid on the filter is washed with ether (2×50 ml). A solution of aldehyde x255 (0.7 g, 1 eq, 2.3 mmol) in methanol (5 ml) is added immediately. The combined solution is evaporated in the vacuum of a rotary evaporator. The residue is dissolved in methanol (10 ml), CH(OMe)$_3$ (0.5 ml) is added, and the obtained solution is stirred at room temperature for 16 h. An excess of NaBH$_4$ (1 g in several small portions) is then added to the reaction solution under vigorous stirring for 20 min. The reaction mixture is evaporated in the vacuum of a rotary evaporator. The residue is partitioned between ethyl acetate and water. The organic phase is separated, dried with anhydrous sodium sulfate, and evaporated. The residue is dissolved in acetonitrile (10 ml), and the solution is refluxed for 24 h to complete the cyclization. The solvent is distilled off. The residue is purified by chromatography on silicagel (CCl$_4$/MeCN) to afford 4-propyl-1-{[1-(triisopropylsilyl)-1H-pyrrolo[2,3-b]pyridin-5-yl]methyl}pyrrolidin-2-one x256.
Yield: 75% (0.72 g).
LC-MS (MH$^+$): 414.

79.4. Synthesis of 4-propyl-1-(1H-pyrrolo[2,3-b]pyridin-5-ylmethyl)pyrrolidin-2-one 241

4-propyl-1-{[1-(triisopropylsilyl)-1H-pyrrolo[2,3-b]pyridin-5-yl]methyl}pyrrolidin-2-one x256 (0.7 g, 1.7 mmol) is dissolved in absolute THF (7 ml). A 1 M solution of tetrabutylammonium fluoride in THF (1.7 M, 1 eq) is added. The obtained solution is stirred for 10 min at room temperature and poured into a mixture of ether (100 ml) and water (20 ml). The organic phase is separated, dried with anhydrous sodium sulfate, and evaporated. The residue is purified by chromatography on silicagel (dichloromethane/isopropanol) to yield 0.43 g of 4-propyl-1-(1H-pyrrolo[2,3-b]pyridin-5-ylmethyl)pyrrolidin-2-one 241.
Yield: 99%.
LC-MS (MH$^+$): 258.

Example 80

Synthesis of 4-propyl-1-(1H-pyrrolo[2,3-b]pyridin-4-ylmethyl)pyrrolidin-2-one 240

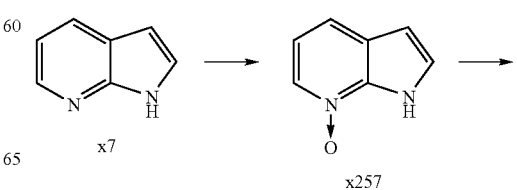

-continued

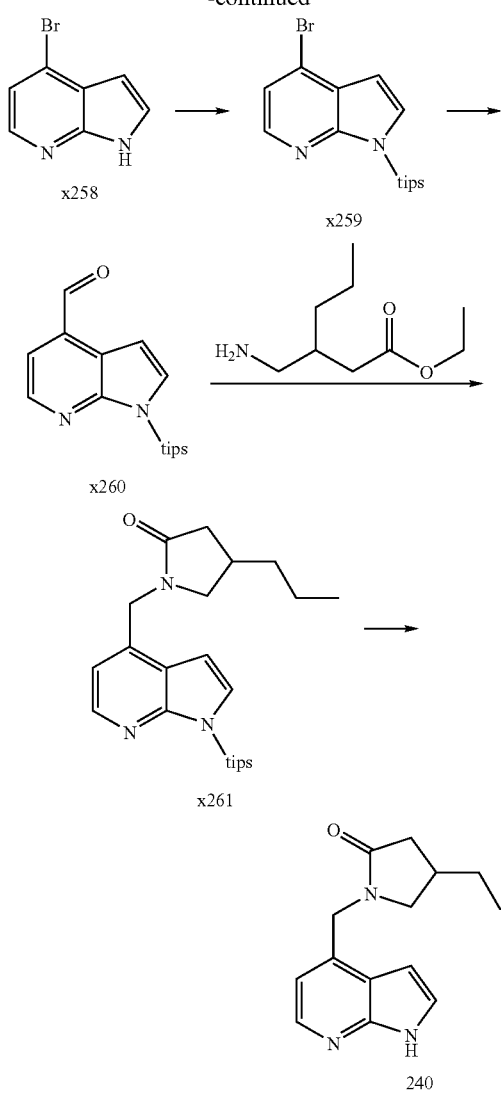

80.1. Synthesis of 1H-pyrrolo[2,3-b]pyridine 7-oxide x257

The commercially available 1H-pyrrolo[2,3-b]pyridine x7 (6.0 g, 50.8 mmol) is dissolved in 1,2-dimethoxyethane (50 ml). A solution of 70-75% m-chloroperbenzoic acid (17 g, 1.4 eq, 71.1 mmol) in 1,2-dimethoxyethane (40 ml) is added under cooling with cold water at a temperature below 25° C. The obtained suspension of the salt is stirred additionally for 1 h, kept overnight at −20° C. and filtered. The solid on the filter is washed with ether (2×30 ml) and air-dried. The obtained product is dissolved in a minimum of water. The pH of the solution is adjusted to 9 by the addition of aqueous $K_2CO_3$ under stirring and cooling with cold water. The formed suspension of the free N-oxide x257 is kept at +3° C. overnight and filtered. The product is washed with ice-cold water (2×10 ml) and dried over $P_2O_5$ under 1 mmHg to yield 1H-pyrrolo[2,3-b]pyridine 7-oxide x257 (3.4 g).

Yield: 41%.
LC-MS (MH$^+$): 135.

80.2 Synthesis of 4-bromo-1H-pyrrolo[2,3-b]pyridine x258

1H-pyrrolo[2,3-b]pyridine 7-oxide x257 (3.4 g, 25.4 mmol) and tetramethylammonium bromide (4.7 g, 1.2 eq, 30.4 mmol) are dissolved in DMF (33 ml). Then $Ms_2O$ (8.8 g, 2 eq, 50.8 mmol) is added at 0° C. in small portions. The obtained mixture is stirred for 1 h at 0° C., then for 4 h at room temperature, and diluted with water (66 ml). The pH is adjusted to 7 with solid NaOH, and 130 ml more of water is added. The resulting suspension is kept at 5° C. for 1 h. The precipitate is separated by filtration, washed with ice-cold water (2×10 ml), and dried over $P_2O_5$ under 1 mmHg. The crude sample of x258 (~80% pure) is purified to the analytically pure state by HPLC to yield 2.2 g of 4-bromo-1H-pyrrolo[2,3-b]pyridine x258.

Yield: 45%.
LC-MS (MH$^+$): 198.

80.3. Synthesis of 4-propyl-1-(1H-pyrrolo[2,3-b]pyridin-4-ylmethyl)pyrrolidin-2-one 240.

The further transformation of bromide x258 into the target product 240 is carried out in complete accordance with the transformation of bromide b191-1 into product ucb-108891-1 as described in examples 79.2 to 79.4. The yields are similar for intermediates 4-bromo-1-(triisopropylsilyl)-1H-pyrrolo[2,3-b]pyridine x259, 1-(triisopropylsilyl)-1H-pyrrolo[2,3-b]pyridine-4-carbaldehyde x260 and 4-propyl-1-{[1-(triisopropylsilyl)-1H-pyrrolo[2,3-b]pyridin-4-yl]methyl}pyrrolidin-2-one x261. As a result, 1.0 g (5.1 mmol) of 4-bromo-1H-pyrrolo[2,3-b]pyridine x258 affords 0.45 g of 4-propyl-1-(1H-pyrrolo[2,3-b]pyridin-4-ylmethyl)pyrrolidin-2-one 240.

Overall yield: 35%.
LC-MS (MH$^+$): 258.

Example 81

Synthesis of 1-[(2-fluoroindolizin-3-yl)methyl]-4-propylpyrrolidin-2-one 264

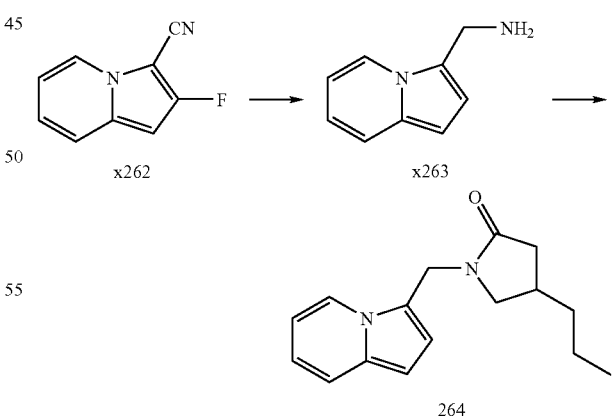

81.1. Synthesis of 1-(2-fluoroindolizin-3-yl)methanamine x263

LiAlH$_4$ (0.175 g, 4.6 mmol) is added in portions under stirring in argon to a solution of 2-fluoroindolizine-3-carbonitrile x262 [X. Fang, Y.-M. Wu, J. Deng, S.-W. Wang, *Tetrahedron* 2004, 60, 5487-5493] (0.46 g, 2.9 mmol) in absolute ether (15 ml) for 3 min. The reaction mixture is stirred at room temperature for 30 min, cooled to 0-5° C., and quenched by the addition of a 10% NaOH solution (4 ml). The organic layer is separated, and the aqueous layer is subjected to extraction with ether (3×10 ml). The combined organic extracts are dried over anhydrous $Na_2SO_4$. The solvents are removed reduced pressure to give 1-(2-fluoroindolizin-3-yl)methanamine x263 (0.38 g).

Yield: 85%.

$^1$H NMR (DMSO-$d_6$): 1.81 (s broad, 2H), 4.00 (s, 2H), 6.23 (s, 1H), 6.65 (t, J=6.85 Hz, 1H), 6.80 (t, J=8.8 Hz, 1H), 7.37 (d, J=8.81 Hz, 1H), 8.24 (d, J=8.09 Hz, 1H).

81.2. Synthesis of 1-[(2-fluoroindolizin-3-yl)methyl]-4-propylpyrrolidin-2-one 264

A solution of 1-(2-fluoroindolizin-3-yl)methanamine x263 (0.38 g, 2.3 mmol) and 5-hydroxy-4-propyldihydrofuran-2 (3H)-one x252 (0.33 g, 2.3 mmol) in DCE (12 ml) is kept at room temperature for 2 h, then STAB (0.74 g, 3.5 mmol) is added, and the mixture is stirred overnight. The reaction mixture is kept under stirring at 50° C. for 2 h, cooled to room temperature, and diluted with dichloromethane (10 ml). The mixture is washed with a 20% $K_2CO_3$ solution (2×15 ml), and the aqueous layer is washed with brine (25 ml), dried over anhydrous $Na_2SO_4$ and evaporated. The residue (0.60 g) is purified by chromatography on silica gel (gradient: chloroform to chloroform/methanol 50/1) to isolate a product of approximately 80% purity (0.162 g). This product is purified by chromatography on silicagel (hexane/ethyl acetate 5/2) to afford pure 1-[(2-fluoroindolizin-3-yl)methyl]-4-propylpyrrolidin-2-one 264 (0.126 g).

Yield: 20%.

LC-MS (MH$^+$): 275.

Example 82

Synthesis of 1-[(2-chloro-1H-pyrrol-1-yl)methyl]-4-propylpyrrolidin-2-one 299

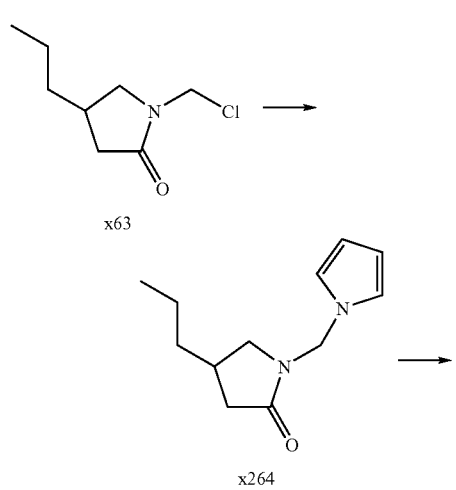

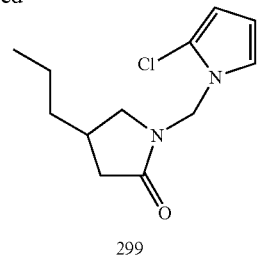

82.1 Synthesis of 4-propyl-1-(1H-pyrrol-1-ylmethyl)pyrrolidin-2-one x264

18-Crown-6 (0.158 g, 0.2 eq, 0.6 mmol) is dissolved in absolute ether (20 ml). A 1.7 M solution of potassium tert-amylate in toluene (1.93 ml, 1.1 eq, 3.28 mmol) is added dropwise in a flow of argon. The reaction mixture is stirred for 15 min at room temperature. Pyrrole (0.2 g, 1 eq, 2.98 mmol) is added. The reaction mixture is cooled to −15° C., and a solution of 1-(chloromethyl)-4-propylpyrrolidin-2-one x63 (0.603 g, 1.15 eq, 3.43 mmol) in absolute ether (5 ml) is added dropwise. The resulting solution is stirred for 16 h at 20° C. The contents of the flask are partitioned between 10 ml of water and 30 ml of ethyl acetate. The organic layer is separated. The aqueous one is subjected to additional extraction with ethyl acetate (2×20 ml). The combined extracts are dried with anhydrous $Na_2SO_4$ and evaporated. Purification by chromatography on silicagel (dichloromethane/acetone) afford 0.091 g of 4-propyl-1-(1H-pyrrol-1-ylmethyl)pyrrolidin-2-one x264.

Yield: 15%.

$^1$H NMR (CDCl$_3$): 0.87 (t, J=7.10 Hz, 3H), 1.23-1.40 (m, 4H), 2.06 (dd, J 7.0; 16.6 Hz, 1H), 2.30 (hept, J=7.33 Hz, 1H), 2.06 (dd, J 8.5; 16.6 Hz, 1H), 2.90 (dd, J 6.8; 9.2 Hz, 1H), 3.40 (dd, J 8.05; 9.2 Hz, 1H), 5.24 (d, J=13.7 Hz, 1H), 5.32 (d, J=13.7 Hz, 1H), 6.17 (t, J=2.20 Hz, 2H), 6.74 (t, J=2.20 Hz, 2H).

82.2. Synthesis of 1-[(2-chloro-1H-pyrrol-1-yl)methyl]-4-propylpyrrolidin-2-one 299

4-propyl-1-(1H-pyrrol-1-ylmethyl)pyrrolidin-2-one x264 (0.182 g, 0.88 mmol) is dissolved in absolute THF (3 ml). A solution of N-chlorosuccinimide (0.118 g, 1 eq) in absolute THF (1 ml) is added dropwise in a flow of argon at 0° C. The obtained solution is allowed to heat up slowly to room temperature in the cooling bath under stirring for 16 h. CCl$_4$ (30 ml) is then added to the obtained solution. A small amount of a precipitate is filtered off, and the filtrate is evaporated. 1-[(2-chloro-1H-pyrrol-1-yl)methyl]-4-propylpyrrolidin-2-one 299 is isolated from the residue by reverse-phase HPLC (eluent: acetonitrile/water).

Yield: 50% (0.106 g).

LC-MS (MH$^+$): 241/243.

1-[(2,5-dichloro-1H-pyrrol-1-yl)methyl]-4-propylpyrrolidin-2-one 298 may be synthesized analogously using 2 eq. of N-chlorosuccinimide.

Yield: 70%.

LC-MS (MH$^+$): 275/277/279.

Example 83

Synthesis of 1-[(2-cyclopropyl-6-phenylimidazo[2,1-b][1,3,4]thiadiazol-5-yl)methyl]-4-propylpyrrolidin-2-one 90

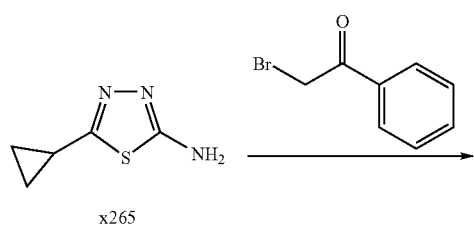

x265

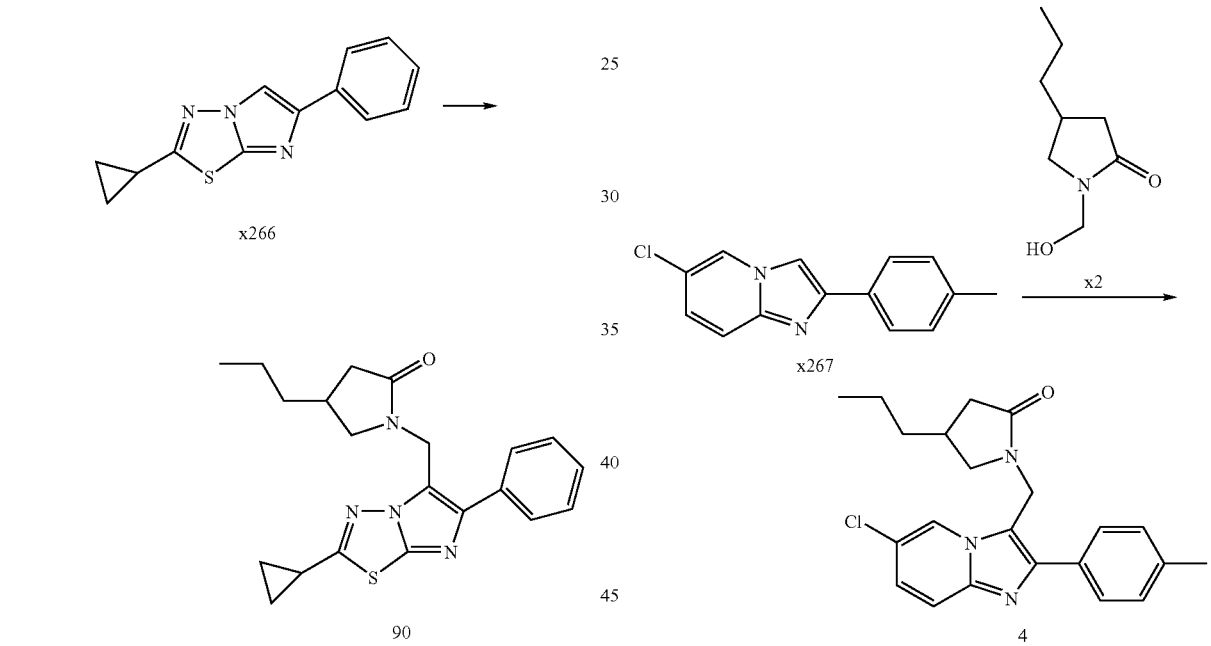

83.1. Synthesis of 2-cyclopropyl-6-phenylimidazo[2,1-b][1,3,4]thiadiazole x266

A mixture of bromoacetophenone (0.775 g, 3.895 mmol, 1.1 eq) and 5-cyclopropyl-2-amino-thiadiazole x265 (0.5 g, 3.54 mmol, 1 eq) in EtOH (20 ml) are heated in microwave at 120° C. during 5 hours. Water (20 ml) is added then the aqueous layer is extracted with $CH_2Cl_2$ (3×30 ml). The combined organic layers are dried on anhydrous $MgSO_4$, filtered off and evaporated under reduced pressure to yield pure 2-cyclopropyl-6-phenylimidazo[2,1-b][1,3,4]thiadiazole x266 as a yellow powder (850 mg, Yield: 25%.

LC-MS ($MH^+$): 242.

83.2. Synthesis of 1-[(2-cyclopropyl-6-phenylimidazo[2,1-b][1,3,4]thiadiazol-5-yl)methyl]-4-propylpyrrolidin-2-one 90

1-[(2-cyclopropyl-6-phenylimidazo[2,1-b][1,3,4]thiadiazol-5-yl)methyl]-4-propylpyrrolidin-2-one 90 is synthesized according to the method described in example 66.3, using 2-cyclopropyl-6-phenylimidazo[2,1-b][1,3,4]thiadiazole x266 as starting material.

Yield: 38%.

LC-MS ($MH^+$): 381.

Example 84

Synthesis of 1-{[6-chloro-2-(4-methylphenyl)imidazo[1,2-a]pyridin-3-yl]methyl}-4-propylpyrrolidin-2-one 4

To a refluxing solution of acetic acid (8 ml) and sulfuric acid (2 drops) is added, dropwised, a solution of 1-(hydroxymethyl)-4-propylpyrrolidin-2-one x2 (400 mg, 2.54 mmol) in 3 ml of acetic acid. 6-chloro-2-(4-methylphenyl)imidazo[1,2-a]pyridine x267 (309 mg, 1.27 mmol, 0.5 eq) is then added in once. The reaction mixture is refluxed for 3 days. After cooling, the reaction mixture is slowly poored in 150 ml of concentrated sodium hydroxyde solution (40% wt) and the crude product is extracted by dichloromethane (4×150 ml). The cumulated organic layers are dried over $MgSO_4$, filtered and condensed under reduced pressure leading to the crude product which is purified by flash chromatography over silicagel (hexane/ethyl acetate 80/20). 1-{[6-chloro-2-(4-methylphenyl)imidazo[1,2-a]pyridin-3-yl]methyl}-4-propylpyrrolidin-2-one 4 is recrystallized in ethyl acetate.

Yield: 9%.

LC-MS ($MH^+$): 382/384.

Example 85

Synthesis of 1-{[6-hydroxy-2-(trifluoromethyl)imidazo[1,2-b]pyridazin-3-yl]methyl}-4-propylpyrrolidin-2-one 45

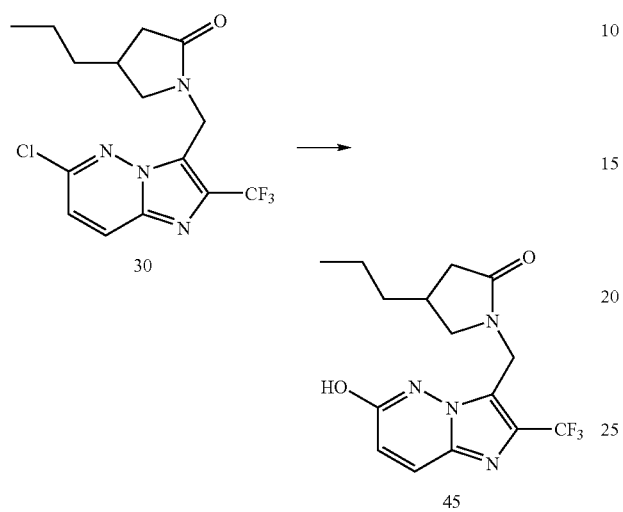

A solution of 1-{[6-chloro-2-(trifluoromethyl)imidazo[1,2-b]pyridazin-3-yl]methyl}-4-propylpyrrolidin-2-one 30 (500 mg, 1.38 mmol), sodium hydroxide (110 mg, 2.77 mmol, 2 eq) in 5 ml of a 1/1 mixture of acetonitrile and water is heated in a microwave oven for 20 min ($T_{max}$ 150° C.). Acetonitrile is removed from reaction mixture under reduced pressure, the aqueous layer is acidified using aqueous hydrochloric acid solution and the crude product is then extracted by ethyl acetate (3×20 ml). The cumulated organic layers are dried over $MgSO_4$, filtered and condensed under reduced pressure leading to an oily residue which is purified by preparative chromatography on silicagel (dichloromethane/isopropanol 99/1). The resulting solid is dried in a vacuum oven and recrystallized in ethyl acetate to afford 1-{[6-hydroxy-2-(trifluoromethyl)imidazo[1,2-b]pyridazin-3-yl]methyl}-4-propylpyrrolidin-2-one 45.

Yield: 10%.

LC-MS (MH+): 343.

Example 86

Synthesis of 1-{[6-amino-2-(trifluoromethyl)imidazo[1,2-b]pyridazin-3-yl]methyl}-4-propylpyrrolidin-2-one 53

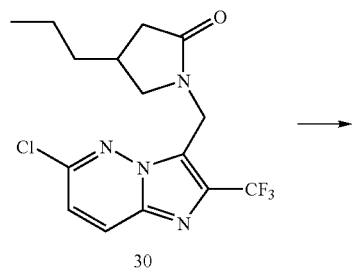

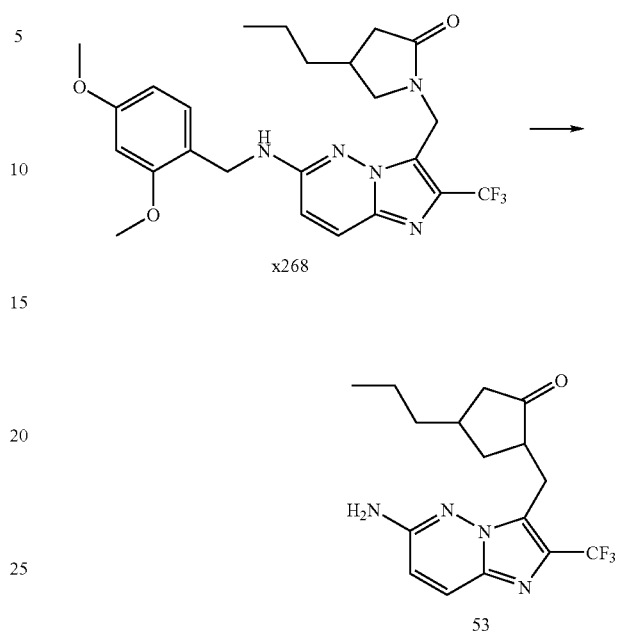

86.1. Synthesis of 1-{[6-[(2,4-dimethoxybenzyl)amino]-2-(trifluoromethyl)imidazo[1,2-b]pyridazin-3-yl]methyl}-4-propylpyrrolidin-2-one x268

1-{[6-[(2,4-dimethoxybenzyl)amino]-2-(trifluoromethyl)imidazo[1,2-b]pyridazin-3-yl]methyl}-4-propylpyrrolidin-2-one x268 is prepared according to the method described in example 39.

LC-MS (MH+): 492.

86.2. Synthesis of 1-{[6-amino-2-(trifluoromethyl)imidazo[1,2-b]pyridazin-3-yl]methyl}-4-propylpyrrolidin-2-one 53

1-{[6-[(2,4-dimethoxybenzyl)amino]-2-(trifluoromethyl)imidazo[1,2-b]pyridazin-3-yl]methyl}-4-propylpyrrolidin-2-one x268 (396 mg, 0.83 mmol) is stirred at room temperature in trifluoroacetic acid until its complete consumption (17 hours). After TFA removal under reduced pressure, the residue is taken in saturated $K_2CO_3$ aqueous solution and extracted with ethyl acetate (3×15 ml). The cumulated organic layers are dried over $MgSO_4$, filtered and condensed under reduced pressure to yield the crude material which is purified by reverse phase preparative chromatography (gradient acetonitrile/water/TFA) to afford 1-{[6-amino-2-(trifluoromethyl)imidazo[1,2-b]pyridazin-3-yl]methyl}-4-propylpyrrolidin-2-one 53.

Yield: 11%.

LC-MS (MH+): 342.

Example 87

Synthesis of 4-(2-bromo-2,2-difluoroethyl)-1-{[6-(propylamino)-2-(trifluoromethyl)-imidazo[1,2-b]pyridazin-3-yl]methyl}pyrrolidin-2-one 56

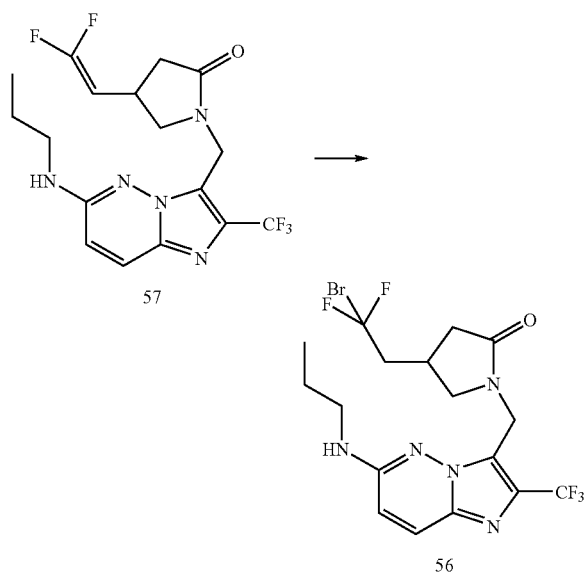

4-(2,2-difluorovinyl)-1-{[6-(propylamino)-2-(trifluoromethyl)imidazo[1,2-b]pyridazin-3-yl]methyl}-pyrrolidin-2-one 57 (178 mg, 0.44 mmol) is dissolved in an aqueous solution of bromhydric acid (62% wt, 5 ml). The resulting solution is kept under agitation for 17 hours at room temperature. After neutralization until alkaline pH with saturated $K_2CO_3$ aqueous solution, the title compound is isolated after extraction with dichloromethane (3×15 ml), drying of the cumulated organic layers over $MgSO_4$, filtration and evaporation of the solvent under reduced pressure. The resulting product is re-crystallized in ethyl acetate to afford 4-(2-bromo-2,2-difluoroethyl)-1-{[6-(propylamino)-2-(trifluoromethyl)imidazo[1,2-b]pyridazin-3-yl]methyl}pyrrolidin-2-one 56.

Yield: 69%.
LC-MS (MH+): 484/486.

Example 88

Synthesis of 4-(2,2-difluorovinyl)-1-{[2-(trifluoromethyl)imidazo[1,2-b]pyridazin-3-yl]methyl}pyrrolidin-2-one 64 and 4-(2,2-difluoroethyl)-1-{[2-(trifluoromethyl)imidazo[1,2-b]pyridazin-3-yl]methyl}pyrrolidin-2-one 67

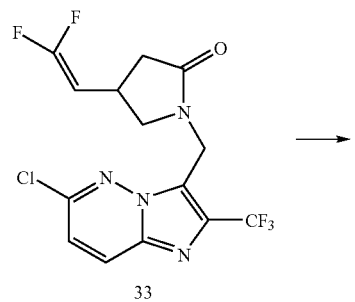

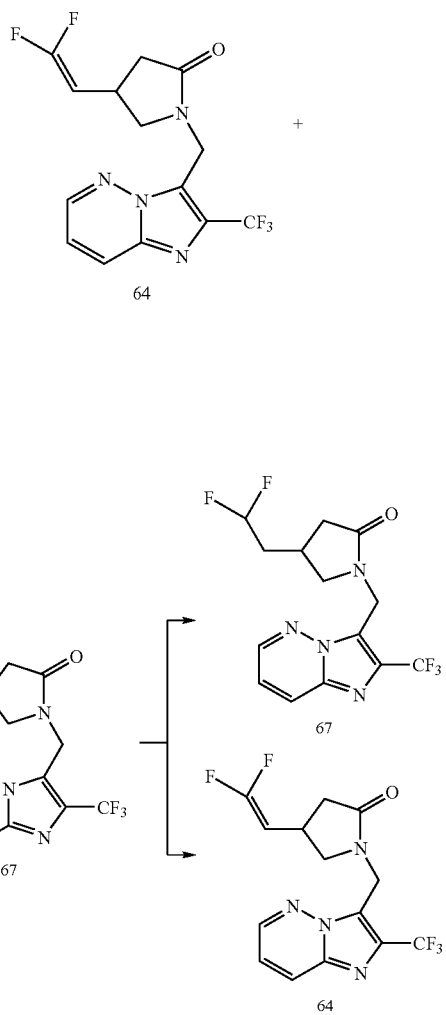

A mixture of 1-{[6-chloro-2-(trifluoromethyl)imidazo[1,2-b]pyridazin-3-yl]methyl}-4-(2,2-difluorovinyl)pyrrolidin-2-one 33 (500 mg, 1.31 mmol), palladium on charcoal (10% wt, 50 mg) in 20 ml of ethanol, is hydrogenated (5 bars of $H_2$) during 17 hours. After filtration over celite of the catalyst and solvent evaporation, the two title compounds are purified and separated by preparative chromatography on silicagel ($CH_2Cl_2$/MeOH/$NH_4OH$: 99/1/0.1). Both compounds are recrystallized in ethyl acetate.

4-(2,2-difluorovinyl)-1-{[2-(trifluoromethyl)imidazo[1,2-b]pyridazin-3-yl]methyl}pyrrolidin-2-one 64:

Yield: 24%.
LC-MS (MH+): 347.

4-(2,2-difluoroethyl)-1-{[2-(trifluoromethyl)imidazo[1,2-b]pyridazin-3-yl]methyl}pyrrolidin-2-one 67:

Yield: 16%.
LC-MS (MH+): 349.

Example 89

Synthesis of 1-{[6-(4-methylphenyl)imidazo[2,1-b][1,3,4]thiadiazol-5-yl]methyl}-4-propylpyrrolidin-2-one 87

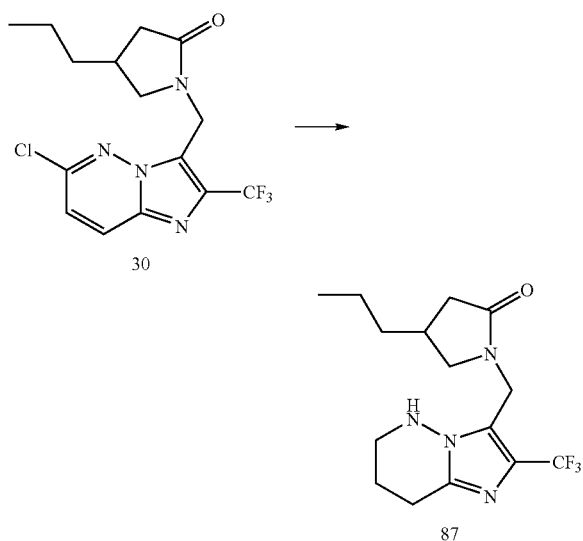

To a solution of 1-{[6-chloro-2-(trifluoromethyl)imidazo[1,2-b]pyridazin-3-yl]methyl}-4-propylpyrrolidin-2-one 30 (72 mg, 0.2 mmol) in methanol (1 ml) is added dropwised sodium borohydride (15 mg, 2 eq, 0.4 mmol). The resulting mixture is stirred at room temperature for 3 days, afterwards a small amount of sodium borohydride is added to complete the reaction. After 17 hours of agitation at room temperature, water (2 ml) is added and methanol is removed under reduced pressure. Addition of 2 ml of saturated aqueous solution of $NH_4Cl$ is followed by extraction with ethyl acetate (3×5 ml). Drying of the cumulated organic layers over $MgSO_4$, filtration and evaporation afford the crude product which is purified by reverse phase preparative chromatography over silicagel (gradient acetonitrile/water/TFA) to yield 1-{[6-(4-methylphenyl)imidazo[2,1-b][1,3,4]thiadiazol-5-yl]methyl}-4-propylpyrrolidin-2-one 87.

Yield: 72%.
LC-MS ($MH^+$): 331.

Example 90

Synthesis of 4-propyl-1-(1H-pyrrolo[2,3-c]pyridin-2-ylmethyl)pyrrolidin-2-one 242

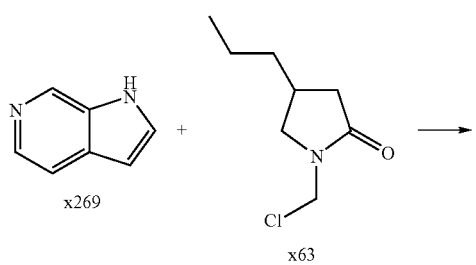

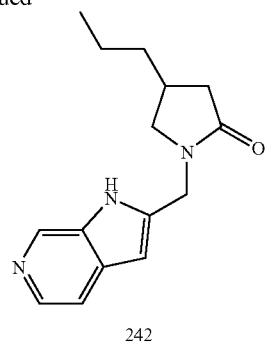

Potassium terbutoxide (522 mg, 4.65 mmol, 1.1 eq) is added to a solution of 6-azaindole x269 (500 mg, 4.23 mmol) in 4 ml of THF at 0° C. After 1 hour of reaction at 0° C., a freshly prepared solution of 4-(chloromethyl)-4-propylpyrrolidin-2-one x63 (0.814 mg, 4.65 mmol, 1.1 eq, in 3 ml of THF) at 0° C. The reaction mixture is warmed to room temperature. After 3 days of agitation, water (10 ml) is added and the aqueous layer is washed with ethyl acetate (3×15 ml). The aqueous layer is then neutralized until pH 9 and extracted with dichloromethane (3×15 ml). The cumulated dichloromethane layers are dried over $MgSO_4$, filtrated and condensed under reduced pressure. The resulting residue is purified by preparative chromatography on silicagel ($CH_2Cl_2$/$MeOH$/$NH_4OH$ 96/4/0.4 (v/v/v)), recrystallized in ethyl acetate, leading to 4-propyl-1-(1H-pyrrolo[2,3-c]pyridin-2-ylmethyl)pyrrolidin-2-one 242 as a solid.

Yield: 7.5%.
LC-MS ($MH^+$): 258.

Example 91

Synthesis of 1-[(5-chloro-2-cyclopropylpyrazolo[1,5-a]pyrimidin-3-yl)methyl]-4-(2,2-difluorovinyl)pyrrolidin-2-one 219

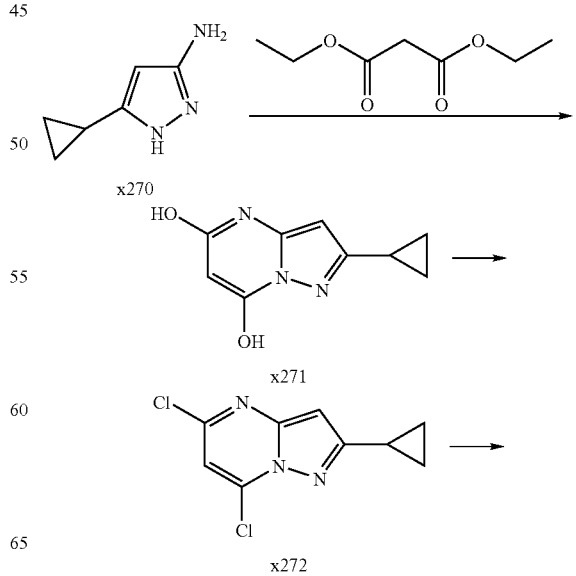

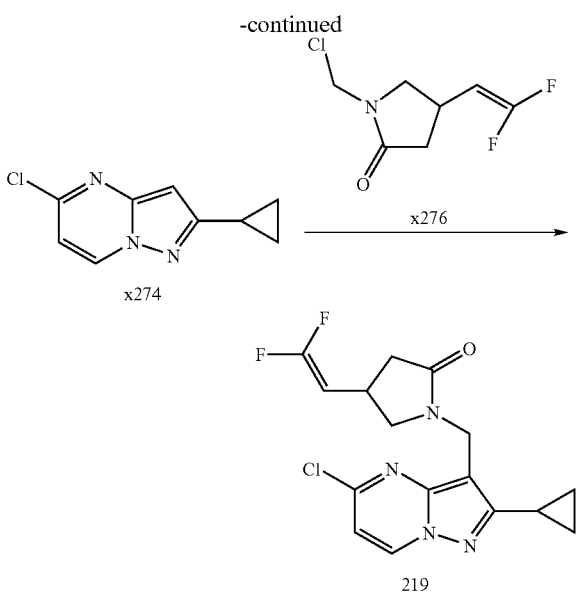

91.1. Synthesis of 5,7-dichloro-2-cyclopropylpyrazolo[1,5-a]pyrimidine x272

A sodium ethoxide solution (EtOH/EtONa, 0.5 N, 400 ml) containing diethyl malonate (50 mmol, 1 eq., 5.8 ml, 6.6 g) and 5-cyclopropyl-1H-pyrazol-3-amine (50 mmol, 1 eq., 6.16 g) is refluxed for 7 hours. After cooling to room temperature, an aqueous hydrochloric acid solution (5 N, 240 ml) is added until pH 5 is obtained. Volatiles are then removed under reduce pressure and the residue dried under vacuum to afford 2-cyclopropyl-7-hydroxypyrazolo[1,5-a]pyrimidin-5 (4H)-one x271. To this residue is successively added $POCl_3$ (125 ml, 1.34 mol) and N,N-dimethylaniline (12.5 ml, 0.1 mol, 2 eq.) and the resulting mixture is refluxed during 3 hours. After cooling to room temperature, the reaction mixture is poured on ice and stirred during one hour at this temperature. The reaction mixture is extracted with dichloromethane, and the resulting organic phase is washed twice with water. The organic phase is dried over $Na_2SO_4$, filtered and evaporated under reduce pressure. The crude product is purified chromatography on silicagel ($CH_2Cl_2$/hexane: 40/60) to afford 5.85 g of 5,7-dichloro-2-cyclopropylpyrazolo[1,5-a]pyrimidine x272 as a solid.

Yield: 52%.

LC-MS (MH$^+$): 228/230/232.

5,7-dichloro-2-cyclopropyl-6-methylpyrazolo[1,5-a]pyrimidine x273 (LC-MS (MH$^+$): 242/244/246) may be synthesized according to the same method.

91.2. Synthesis of 5-chloro-2-cyclopropylpyrazolo[1,5-a]pyrimidine x274

To a solution of 5,7-dichloro-2-cyclopropylpyrazolo[1,5-a]pyrimidine x272 (26.7 mmol, 1 eq., 6.08 g) in 125 ml of AcOH is added Zn powder (0.107 mol, 4 eq, 6.97 g). The mixture is then stirred for 48 hours at room temperature. After this time, the solvent is evaporated under reduce pressure and the reaction mixture poured on water, quenched with $NaHCO_3$, and extracted with dichloromethane. The organic layer is dried over $Na_2SO_4$, filtered and evaporated under reduced pressure. The crude product is purified by chromatography on silicagel ($CH_2Cl_2$/hexane: 50/50) to afford 5-chloro-2-cyclopropylpyrazolo[1,5-a]pyrimidine x274 as a solid (3.60 g).

Yield: 70%.

LC-MS (MH$^+$): 194/196.

5-chloro-2-cyclopropyl-6-methylpyrazolo[1,5-a]pyrimidine x275 (LC-MS (MH$^+$): 208/210) may be synthesized according to the same method.

91.3. Synthesis of 1-[(5-chloro-2-cyclopropylpyrazolo[1,5-a]pyrimidin-3-yl)methyl]-4-(2,2-difluorovinyl)pyrrolidin-2-one 219

To a solution of 1-(chloromethyl)-4-(2,2-difluorovinyl) pyrrolidin-2-one x276 (2.55 mmol, 2 eq, 500 mg) in 15 ml of dioxane at 0° C. are added successively $AlCl_3$ (5.1 mmol, 2 eq, 680 mg) and 5-chloro-2-cyclopropylpyrazolo[1,5-a]pyrimidine x274 (2.55 mmol, 1 eq, 495 mg). The mixture is stirred at reflux for 1 hour, then quenched with an aqueous saturated $NH_4Cl$ solution and the resulting mixture extracted with AcOEt. The cumulated organic layers are washed with water, dried over $MgSO_4$, filtered and evaporated under reduced pressure. The crude product is purified by chromatography on silicagel ($CH_2Cl_2$/MeOH/$NH_4OH$: 98/2/0.2), followed by a crystallization step in hexane. 1-[(5-chloro-2-cyclopropylpyrazolo[1,5-a]pyrimidin-3-yl)methyl]-4-(2,2-difluorovinyl)pyrrolidin-2-one 219 is obtained as a solid (623 mg).

Yield: 69%.

LC-MS (MH$^+$): 353/355.

Compound 220 may be prepared according to the same method.

Example 92

Synthesis of benzyl 1-methyl-5-[(2-oxo-4-propylpyrrolidin-1-yl)methyl]-1H-imidazol-2-ylcarbamate 130

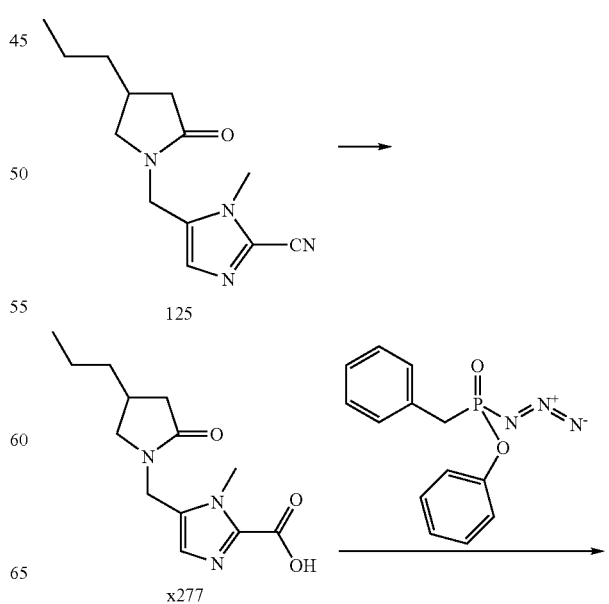

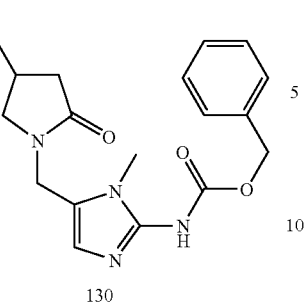

130

92.1. Synthesis of 1-methyl-5-[(2-oxo-4-propylpyrrolidin-1-yl)methyl]-1H-imidazole-2-carboxylic acid x277

In a Parr pressure bottle, compound 125 (1.8 g, 7.34 mmol) is dissolved in 80 ml of HCl (18% w/w) and the reaction is heated overnight at 100° C. Another portion of HCl (37% w/w, 10 ml) is added and heating is restarted for 6 h at 100° C. The mixture is cooled down to 20° C. overnight, evaporated to dryness and dried by azeotropic distillation with toluene to afford 1-methyl-5-[(2-oxo-4-propylpyrrolidin-1-yl)methyl]-1H-imidazole-2-carboxylic acid x277 (2.3 g, quantitative) which is used in the next step without any further purification.

92.2. Synthesis of benzyl 1-methyl-5-[(2-oxo-4-propylpyrrolidin-1-yl)methyl]-1H-imidazol-2-ylcarbamate 130

In a two neck flas, fitted with a reflux condenser, under argon, diphenylphosphoryl azide (0.37 g) is added to 1-methyl-5-[(2-oxo-4-propylpyrrolidin-1-yl)methyl]-1H-imidazole-2-carboxylic acid x277 (1 g, 3.33 mmol, carefully dried by azeotropic distillation with toluene) dissolved in toluene (dried on Na) at room temperature, followed by Et$_3$N (0.7 ml). The reaction mixture is stirred overnight at room temperature. Benzyl alcohol (0.69 ml) is added and the reaction mixture is heated rapidly at 90° C. for one hour, cooled down to room temperature and evaporated to dryness. The solid residue is diluted in DCM, washed with aqueous NaHCO$_3$, and the organic layer is dried with MgSO$_4$, filtered and concentrated in vacuo. The reaction mixture is purified several times by column chromatography on silicagel (CH$_2$Cl$_2$/MTBE/MeOH/NH$_4$OH 50/48/1.98/0.2) to afford benzyl 1-methyl-5-[(2-oxo-4-propylpyrrolidin-1-yl)methyl]-1H-imidazol-2-ylcarbamate 130 (0.04 g).

Yield: 3.2%.
LC-MS (MH$^+$): 371.

Example 93

Synthesis of 1-[(1-benzyl-5-chloro-1H-pyrazol-4-yl)methyl]-4-propylpyrrolidin-2-one 178

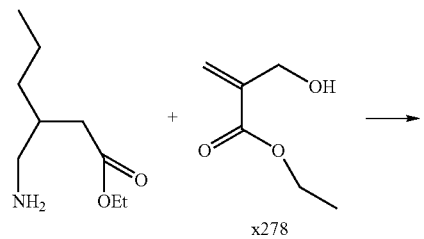

x278

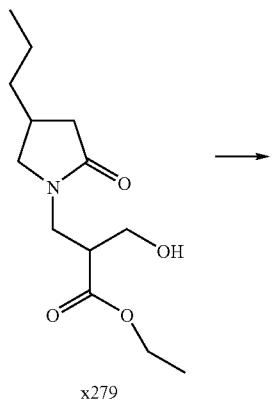

x279

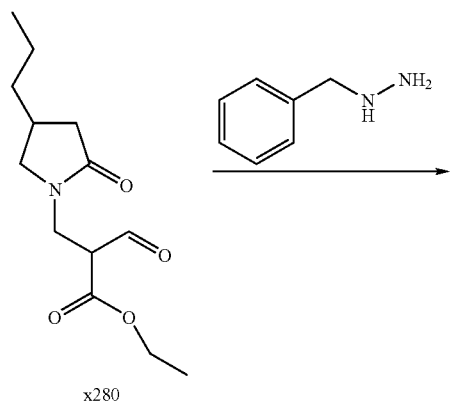

x280

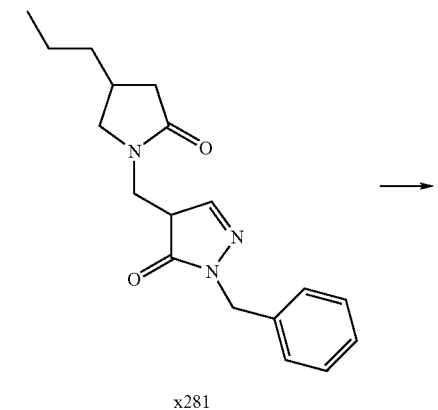

x281

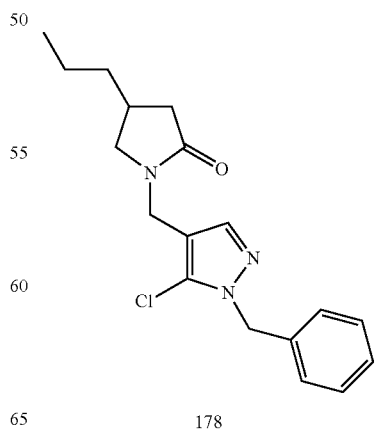

178

93.1 Synthesis of ethyl 3-hydroxy-2-[(2-oxo-4-propylpyrrolidin-1-yl)methyl]propanoate x279

In a three neck flask, fitted with a reflux condenser, under argon, a solution of ethyl 3-(aminomethyl)hexanoate (11.8 g, 0.042 mol) in EtOH (50 ml) is added via a pump-syringe (5 ml/h) onto a solution of ethyl 2-(hydroxymethyl)acrylate x278 (5 g, 0.038 mol) and Et$_3$N (8.03 ml) in THF (100 ml) at room temperature. After 6 h, the reaction mixture is filtered on celite, washed with saturated NaHCO$_3$ and the aqueous layer is extracted with CH$_2$Cl$_2$ (2×150 ml), dried with MgSO$_4$, filtered and concentrated in vacuo. The crude reaction mixture is purified by chromatography on silicagel (CH$_2$Cl$_2$/MTBE/MeOH 50/49/1), to afford 3.7 g of ethyl 3-hydroxy-2-[(2-oxo-4-propylpyrrolidin-1-yl)methyl]propanoate c279.
Yield: 37%.
LC-MS (MH$^+$): 258.

93.2. Synthesis of ethyl 2-formyl-3-(2-oxo-4-propylpyrrolidin-1-yl)propanoate x280

In a three neck flask, fitted with a magnetic stirrer, under inert atmosphere, DMSO (dried on CaH$_2$, 0.83 g, 0.01 mol) in CH$_2$Cl$_2$ (5 ml) is added onto a solution of (COCl)$_2$ (0.72 g, 0.0052 mol) in CH$_2$Cl$_2$ (5 ml) cooled at −78° C. After 0.5 h at −78° C., ethyl 3-hydroxy-2-[(2-oxo-4-propylpyrrolidin-1-yl)methyl]propanoate x279 (0.92 g, 0.0035 mol) in CH$_2$Cl$_2$ (10 ml) is added, stirred for 2.5 h at −60° C., quenched with Et$_3$N (2.75 ml), stirred overnight at 4° C., washed with saturated NH$_4$Cl and extracted 3 times with CH$_2$Cl$_2$. The combined organic phases are dried over MgSO$_4$, filtered, concentrated in vacuo to give the crude x280 (1.2 g) which is used in the next step without any further purification.
LC-MS (MH$^+$): 256.

93.3. Synthesis of 2-benzyl-4-[(2-oxo-4-propylpyrrolidin-1-yl)methyl]-2,4-dihydro-3H-pyrazol-3-one x281

In a three neck flask, fitted with a magnetic stirrer, under inert atmosphere, ethyl 2-formyl-3-(2-oxo-4-propylpyrrolidin-1-yl)propanoate x280 (0.9 g) in PhMe (10 ml) is added onto a solution of Et$_3$N (1.6 ml) and PhCH$_2$NHNH$_2$.2HCl (0.75 g, 0.0039 mol.) in PhMe (30 ml) at room temperature. The mixture is heated up to 40° C. for 12 h, cooled down to room temperature, washed with NH$_4$Cl (saturated) and the aqueous layer is acidified to pH 3 by addition of HCl (5 N). After 3 extractions with EtOAc, the organic layers are dried over MgSO$_4$, concentrated in vacuo to afford the crude reaction mixture which is purified by chromatography on silicagel (first purification with CH$_2$Cl$_2$/MeOH/NH$_4$OH 98/018/0.02; second purification with EtOAC/iPrOH 95/5; third purification by preparative reverse phase LC/MS) to afford 2-benzyl-4-[(2-oxo-4-propylpyrrolidin-1-yl)methyl]-2,4-dihydro-3H-pyrazol-3-one x281 as a red oil (0.18 g).
Yield: 14%.
LC-MS (MH$^+$): 314.

93.4. Synthesis of 1-[(1-benzyl-5-chloro-1H-pyrazol-4-yl)methyl]-4-propylpyrrolidin-2-one 178

In a three neck flask, fitted with a magnetic stirrer, under inert atmosphere, a mixture of POCl$_3$ (0.13 g, 0.9 mmol), 2-benzyl-4-[(2-oxo-4-propylpyrrolidin-1-yl)methyl]-2,4-dihydro-3H-pyrazol-3-one x281 (0.18 g, 0.43 mmol) and PhMe (4 ml) is heated at 95° C. for 2 h, cooled down to room temperature overnight and quenched with saturated NaHCO$_3$. The aqueous layer is extracted 3 times with CH$_2$Cl$_2$, combined organic phases are dried over MgSO$_4$, filtered and concentrated in vacuo to afford the crude chloride which is purified by column chromatography on silicagel (CH$_2$Cl$_2$/MeOH/NH$_4$OH: 8/4/0.04 (v/v/v)) followed by a second purification by preparative HPLC to afford 0.036 g of 1-[(1-benzyl-5-chloro-1H-pyrazol-4-yl)methyl]-4-propylpyrrolidin-2-one 178 as a solid.
LC-MS (MH$^+$): 332/334.

Example 94

Synthesis of 1-[(2-aminopyridin-3-yl)methyl]-4-propylpyrrolidin-2-one 230

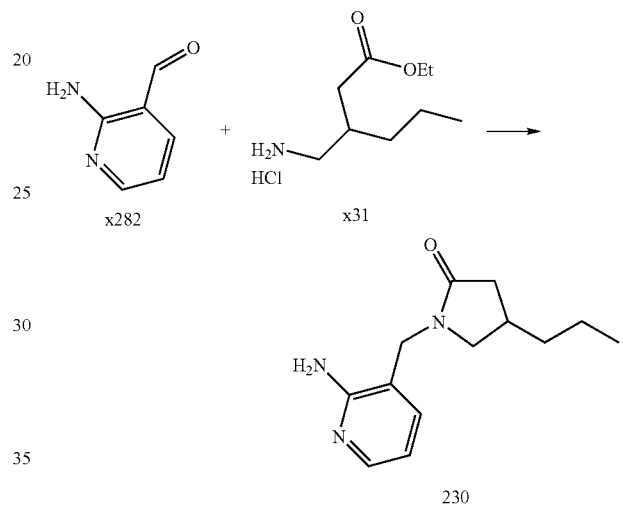

To a solution of 2-aminonicotinaldehyde x282 (8.19 mmol, 1 eq, 1 g) in 10 ml of EtOH, is added ethyl 3-(aminomethyl)hexanoate hydrochloride x31 (9.83 mmol, 1.2 eq, 2.06 g) and the resulting solution is stirred at room temperature for 1 h30. Then, triethylamine (9.0 mmol, 1.1 eq, 909 mg) is added and the mixture is stirred during 0.5 hour. Sodium borohydride is then added (9.83 mmol, 1.2 eq, 372 mg). The resulting mixture is stirred at room temperature for 20 hours, heated at 55° C. for 21 hours and then overnight at room temperature. Volatiles are removed under vacuum and CH$_2$Cl$_2$ (50 ml) and water (25 ml) are added. The organic layer is washed with water (25 ml) and dried over MgSO$_4$. After filtration, volatiles are removed under reduced pressure. The crude product is purified by chromatography on silicagel (CH$_2$Cl$_2$/MeOH/NH$_4$OH 98/2/0.2 (v/v/v)) and recrystallized in AcOEt to afford 1-[(2-aminopyridin-3-yl)methyl]-4-propylpyrrolidin-2-one 230 as a white solid (152 mg).
Yield: 8%.
LC-MS (MH$^+$): 234.

Table I indicates the stereochemical information in the columns headed "configuration": the first one indicates whether a compound has no stereogenic center (achiral), is a pure enantiomer (pure), a racemate or is a mixture of two stereoisomers, possibly in unequal proportions (mixture); the second one contains the stereochemical assignment for the recognised center, following the IUPAC numbering used in the "IUPAC name" column. A number alone indicates the existence of both configurations at that center. A number followed by 'R' or 'S' indicates the known absolute configuration at that center. A number followed by '§' indicates the existence of only one but unknown absolute configuration at that center. The letter (A, B) in front is a way of distinguishing the various enantiomers of the same structure. Table 1 indicates also the type of salt, which is synthesized (if not the free base), the IUPAC name of the compound, the ion peak observed in mass spectroscopy and the optical rotation in the case of chiral compounds.

TABLE 1

| n° | Config | Salt | IUPAC Name | MH+ (M+.) | $^1$H NMR delta (CDCl$_3$ unless otherwise specified) |
|---|---|---|---|---|---|
| 1 | 4 | | 1-[(1-methyl-1H-benzimidazol-6-yl)methyl]-4-propylpyrrolidin-2-one | 272 | (DMSO): 0.83 (t, 7.16 Hz, 3H), 1.15-1.39 (m, 4H), 2.00 (dd, 16.31, 7.53 Hz, 1H), 2.25 (m, 1H), 2.44 (dd, 16.31, 8.53 Hz, 1H), 2.86 (m, 1H), 3.35 (m, 1H), 3.82 (s, 3H), 4.47 (s, 2H), 7.07 (d, 8.04 Hz, 1H), 7.40 (s, 1H), 7.60 (d, 8.04 Hz, 1H), 8.16 (s, 1H) |
| 2 | 4 | | 1-(1H-benzimidazol-7-ylmethyl)-4-propylpyrrolidin-2-one | 258 | 0.89 (t, J 7.18 Hz, 3H), 1.23-1.32 (m, 2H), 1.34-1.40 (m, 2H), 2.14 (dd, J 16.87, 7.81 Hz, 1H), 2.34 (m, 1H), 2.59 (dd, J 16.87, 8.81 Hz, 1H), 3.04 (dd, J 9.82, 6.92 Hz, 1H), 3.51 (dd, J 9.57, 8.31 Hz, 1H), 4.59 (d, J 17.60 Hz, 1H), 4.64 (d, J 17.60 Hz, 1H), 7.12 (d, J 7.05 Hz, 1H), 7.22 (t, J 7.31 Hz, 1H), 7.81 (d, J 8.06 Hz, 1H), 8.04 (s, 1H), 11.14 (s (broad), 1H) |
| 3 | 4 | 1 CF$_3$COOH | 1-(imidazo[1,2-a]pyridin-3-ylmethyl)-4-propylpyrrolidin-2-one | 258 | 0.82 (m, 3H), 1.24 (m, 4H), 2.01 (dd, 25.62, 12.32 Hz, 1H), 2.26 (m, 1H), 2.42 (d, 25.86 Hz, 1H), 2.92 (dd, 14.64, 10.86 Hz, 1H), 3.40 (m, 1H), 4.84 (m, 3H), 7.58 (td, 10.25, 3.23 Hz, 1H), 7.99 (m, 2H), 8.23 (s, 1H), 8.75 (d, 10.74 Hz, 1H) |
| 4 | 4 | | 1-{[6-chloro-2-(4-methylphenyl)imidazo[1,2-a]pyridin-3-yl]methyl}-4-propylpyrrolidin-2-one | 382/384 | 0.82 (t, 7.04 Hz, 3H), 1.23 (m, 4H), 2.09 (m, 1H), 2.21 (m, 1H), 2.42 (s Hz, 3H), 2.56 (dd, 16.60, 8.30 Hz, 1H), 2.71 (dd, 9.05, 6.92 Hz, 1H), 3.18 (m, 1H), 4.94 (m, 2H), 7.20 (d, 9.56 Hz, 1H), 7.28 (m, 2H), 7.60 (m, 3H), 8.43 (s, 1H) |
| 5 | 4 | | 1-{[2-(4-chlorophenyl)-6-methylimidazo[1,2-a]pyridin-3-yl]methyl}-4-propylpyrrolidin-2-one | 382/384 | 0.81 (m, 3H), 1.21 (m, 4H), 2.09 (m, 1H), 2.19 (m, 1H), 2.35 (s, 3H), 2.55 (dd, 16.60, 8.30 Hz, 1H), 2.68 (m, 1H), 3.15 (t, 8.68 Hz, 1H), 4.93 (m, 2H), 7.12 (d, 9.05 Hz, 1H), 7.27 (d, 0.75 Hz, 1H), 7.45 (d, 7.55 Hz, 2H), 7.55 (d, 9.31 Hz, 1H), 7.69 (d, 7.29 Hz, 2H), 8.08 (s, 1H) |
| 6 | 4 | 1 CF$_3$COOH | 1-[(5-methylimidazo[1,2-a]pyridin-3-yl)methyl]-4-phenylpyrrolidin-2-one | 306 | 2.69 (m, 1H), 2.90 (m, 1H), 2.96 (s, 3H), 3.30 (m, 1H), 3.65 (m, 2H), 4.87 (dd, 16.10, 3.65 Hz, 1H), 5.28 (dd, 16.10, 3.77 Hz, 1H), 6.99 (m, 1H), 7.16 (m, 2H), 7.29 (m, 4H), 7.58 (m, 1H), 7.78 (d, 4.02 Hz, 1H), 8.11 (dd, 8.55, 3.40 Hz, 1H) |
| 7 | 4 | 1 CF$_3$COOH | 1-(imidazo[1,2-a]pyridin-3-ylmethyl)-4-phenylpyrrolidin-2-one | 292 | 2.64 (m, 1H), 2.82 (m, 2H), 3.33 (dd, 14.64, 10.98 Hz, 1H), 3.56 (m, 1H), 3.71 (m, 1H), 4.90 (m, 2H), 7.09 (m, 2H), 7.29 (m, 4H), 7.75 (m, 1H), 7.89 (s, 1H), 8.28 (m, 1H), 8.84 (d, 10.98 Hz, 1H) |
| 8 | 4 | 1 HCl | 1-[(6-methylimidazo[1,2-a]pyridin-3-yl)methyl]-4-propylpyrrolidin-2-one | 272 | 0.87 (m, 3H), 1.30 (m, 4H), 2.11 (m, 1H), 2.32 (m, 1H), 2.57 (m, 4H), 2.96 (t, 6.67 Hz, 1H), 3.46 (m, 1H), 4.85 (m, 2H), 7.16 (m, 1H), 8.02 (d, 44.52 Hz, 2H), 8.73 (m, 1H) |
| 9 | 4 | 1 HCl | 1-[(6-bromoimidazo[1,2-a]pyridin-3-yl)methyl]-4-propylpyrrolidin-2-one | 336 | 0.89 (t, 7.17 Hz, 3H), 1.34 (m, 4H), 2.14 (dd, 16.85, 8.05 Hz, 1H), 2.37 (m, 1H), 2.60 (dd, 17.10, 8.68 Hz, 1H), 3.00 (dd, 8.80, 7.42 Hz, 1H), 3.49 (t, 8.80 Hz, 1H), 4.85 (m, 2H), 7.89 (d, 9.56 Hz, 1H), 8.10 (s, 1H), 8.24 (d, 9.56 Hz, 1H), 9.19 (s, 1H) |
| 10 | 4 | 1 HCl | 1-[(8-methylimidazo[1,2-a]pyridin-3-yl)methyl]-4-propylpyrrolidin-2-one | 272 | 0.87 (t, 11.10 Hz, 3H), 1.31 (m, 4H), 2.11 (m, 1H), 2.32 (m, 1H), 2.57 (m, 1H), 2.97 (m, 4H), 3.49 (m, 1H), 4.92 (m, 2H), 7.27 (m, 1H), 7.58 (d, 11.47 Hz, 1H), 8.26 (s, 1H), 8.73 (d, 10.74 Hz, 1H) |
| 11 | 4 | 1 HCl | 1-[(6-iodoimidazo[1,2-a]pyridin-3-yl)methyl]-4-propylpyrrolidin-2-one | 384 | 0.89 (m, 3H), 1.32 (m, 4H), 2.14 (dd, 26.60, 12.57 Hz, 1H), 2.36 (m, 1H), 2.60 (m, 1H), 2.99 (dd, 15.37, 11.10 Hz, 1H), 3.48 (m, 1H), 4.83 (m, 2H), 8.01 (m, 2H), 8.11 (dd, 15.13, 1.22 Hz, 1H), 9.26 (s, 1H) |
| 12 | 4 | 1 CF$_3$COOH | 1-{[8-chloro-6-(trifluoromethyl)imidazo[1,2-a]pyridin-3-yl]methyl}-4-propylpyrrolidin-2-one | 360/362 | 0.87 (t, 11.22 Hz, 3H), 1.30 (m, 4H), 2.13 (m, 1H), 2.33 (m, 1H), 2.59 (m, 1H), 2.94 (dd, 15.13, 10.98 Hz, 1H), 3.42 (m, 1H), 4.79 (m, 2H), 7.56 (d, 2.20 Hz, 1H), 7.88 (s, 1H), 9.08 (m, 1H) |

TABLE 1-continued

| n° | Config | Salt | IUPAC Name | MH+ (M+.) | 1H NMR delta (CDCl3 unless otherwise specified) |
|---|---|---|---|---|---|
| 13 | 4 | 1 HCl | 1-[(7-methylimidazo[1,2-a]pyridin-3-yl)methyl]-4-propylpyrrolidin-2-one | 272 | 0.88 (t, 11.22 Hz, 3H), 1.31 (m, 4H), 2.16 (m, 1H), 2.34 (m, 1H), 2.57 (m, 4H), 2.97 (dd, 14.88, 11.10 Hz, 1H), 3.46 (m, 1H), 4.85 (m, 2H), 7.67 (dd, 14.64, 1.83 Hz, 1H), 8.01 (s, 1H), 8.18 (d, 14.88 Hz, 1H), 8.85 (s, 1H) |
| 14 | 4 | 1 HCl | 1-[(6,8-dibromoimidazo[1,2-a]pyridin-3-yl)methyl]-4-propylpyrrolidin-2-one | 414/416/418 | 0.88 (t, 7.04 Hz, 3H), 1.33 (m, 4H), 2.11 (dd, 16.85, 8.30 Hz, 1H), 2.35 (m, 1H), 2.57 (dd, 16.85, 8.80 Hz, 1H), 3.09 (m, 1H), 3.62 (m, 1H), 5.00 (m, 2H), 8.06 (s, 1H), 8.78 (s, 1H), 9.30 (s, 1H) |
| 15 | 4 | 1 HCl | 1-[(6,8-dichloroimidazo[1,2-a]pyridin-3-yl)methyl]-4-propylpyrrolidin-2-one | 326/328/330 | 0.88 (t, 7.04 Hz, 3H), 1.33 (m, 4H), 2.12 (dd, 17.10, 8.17 Hz, 1H), 2.35 (m, 1H), 2.57 (dd, 16.85, 8.55 Hz, 1H), 3.09 (m, 1H), 3.62 (m, 1H), 4.99 (d, 27.92 Hz, 2H), 7.79 (s, 1H), 8.75 (s, 1H), 9.15 (s, 1H) |
| 16 | 4 | | 1-[(6-chloroimidazo[1,2-a]pyridin-3-yl)methyl]-4-propylpyrrolidin-2-one | 292/294 | 0.86 (t, 7.17 Hz, 3H), 1.29 (m, 4H), 2.12 (dd, 16.60, 8.05 Hz, 1H), 2.29 (m, 1H), 2.58 (dd, 16.85, 8.68 Hz, 1H), 2.86 (dd, 9.56, 6.79 Hz, 1H), 3.34 (dd, 9.56, 8.17 Hz, 1H), 4.73 (m, 2H), 7.19 (dd, 9.56, 2.01 Hz, 1H), 7.57 (m, 2H), 8.50 (m, 1H) |
| 17 | 4 | | 1-[(2-chloroimidazo[1,2-a]pyridin-3-yl)methyl]-4-propylpyrrolidin-2-one | 292/294 | 0.86 (t, 7.14 Hz, 3H), 1.29 (m, 4H), 2.08 (m, 1H), 2.27 (m, 1H), 2.53 (dd, 16.85, 8.70 Hz, 1H), 2.93 (m, 1H), 3.44 (m, 1H), 4.77 (m, 2H), 6.89 (t, 6.78 Hz, 1H), 7.29 (m, 1H), 7.54 (d, 8.98 Hz, 1H), 8.42 (d, 6.96 Hz, 1H) |
| 18 | 4 | | 1-[(2-cyclopropyl-6-fluoroimidazo[1,2-a]pyridin-3-yl)methyl]-4-(2,2-difluorovinyl)pyrrolidin-2-one | 336 | 1.24 (m, 2H), 1.36 (m, 2H), 2.04 (m, 1H), 2.29 (m, 1H), 2.71 (dd, 17.07, 8.66 Hz, 1H), 3.18 (m, 2H), 3.53 (m, 1H), 4.19 (m, 1H), 4.84 (m, 2H), 7.51 (m, 1H), 8.24 (m, 1H), 8.73 (s Hz, 1H) |
| 19 | 4 | | 1-[(6-chloro-2-cyclopropylimidazo[1,2-a]pyridin-3-yl)methyl]-4-(2,2-difluorovinyl)pyrrolidin-2-one | 352/354 | (DMSO): 0.94 (m, 4H), 2.21 (m, 2H), 2.5 (m, 1H), 2.98-3.13 (m, 2H), 3.46 (t, 8.16 Hz, 1H), 4.63 (m, 1H), 4.82 (s Hz, 2H), 7.24 (dd, 9.54, 1.76 Hz, 1H), 7.48 (d, 9.54 Hz, 1H), 8.56 (d, 1.25 Hz, 1H) |
| 20 | 4 | 1 CF3COOH | 1-(imidazo[1,2-a]pyrimidin-3-ylmethyl)-4-propylpyrrolidin-2-one | 259 | 0.82 (m, 3H), 1.24 (m, 4H), 1.99 (dd, 25.62, 12.32 Hz, 1H), 2.25 (m, 1H), 2.42 (m, 1H), 2.92 (dd, 14.64, 11.10 Hz, 1H), 3.39 (m, 1H), 4.83 (m, 2H), 7.61 (dd, 10.98, 6.95 Hz, 1H), 8.19 (s, 1H), 8.96 (dd, 6.83, 2.56 Hz, 1H), 9.08 (dd, 10.98, 2.56 Hz, 1H) |
| 21 | 4 | | 1-{[2-(4-chlorophenyl)imidazo[1,2-a]pyrimidin-3-yl]methyl}-4-propylpyrrolidin-2-one | 369/371 | 0.82 (m, 3H), 1.22 (m, 4H), 2.08 (dd, 16.85, 7.80 Hz, 1H), 2.21 (m, 1H), 2.54 (dd, 16.85, 8.43 Hz, 1H), 2.75 (m, 1H), 3.22 (t, 8.68 Hz, 1H), 4.96 (m, 2H), 6.92 (dd, 5.53, 4.28 Hz, 1H), 7.48 (d, 7.55 Hz, 2H), 7.78 (d, 7.55 Hz, 2H), 8.61 (m, 1H), 8.79 (d, 6.79 Hz, 1H) |
| 22 | 4 | | 1-(imidazo[1,2-a]pyrimidin-3-ylmethyl)-4-phenylpyrrolidin-2-one | 293 | 2.46 (dd, 26.35, 13.66 Hz, 1H), 2.92 (dd, 14.64, 10.74 Hz, 1H), 3.24 (m, 1H), 3.46 (m, 1H), 4.53 (s, 2H), 6.90 (m, 6H), 7.47 (s, 1H), 8.29 (dd, 6.59, 3.17 Hz, 1H), 8.57 (dd, 10.98, 3.17 Hz, 1H) |
| 23 | 4 | | 1-[(6-chloroimidazo[1,2-a]pyrimidin-3-yl)methyl]-4-propylpyrrolidin-2-one | 293/295 | 0.87 (t, 7.17 Hz, 3H), 1.31 (m, 4H), 2.11 (dd, 16.85, 8.05 Hz, 1H), 2.31 (m, 1H), 2.57 (dd, 16.85, 8.55 Hz, 1H), 2.93 (dd, 9.56, 7.04 Hz, 1H), 3.40 (m, 1H), 4.71 (m, 2H), 7.77 (s, 1H), 8.50 (d, 2.52 Hz, 1H), 8.99 (d, 2.52 Hz, 1H) |
| 24 | 4 | | 1-{[6-chloro-2-(trifluoromethyl)imidazo[1,2-a]pyrimidin-3-yl]methyl}-4-propylpyrrolidin-2-one | 361/363 | 0.89 (t, 7.20 Hz, 3H), 1.33 (m, 4H), 2.11 (dd, 16.92, 8.08 Hz, 1H), 2.33 (m, 1H), 2.57 (dd, 16.92, 8.59 Hz, 1H), 2.98 (dd, 9.60, 7.07 Hz, 1H), 3.46 (m, 1H), 4.85 (m, 2H), 8.63 (d, 2.53 Hz, 1H), 9.25 (d, 2.53 Hz, 1H) |
| 25 | 4 | | 1-[(6-phenylimidazo[1,2-b][1,2,4]triazin-7-yl)methyl]-4-propylpyrrolidin-2-one | 336 | 0.81 (m, 3H), 1.19 (m, 4H), 2.03 (m, 1H), 2.15 (d, 7.55 Hz, 1H), 2.51 (dd, 16.62, 8.44 Hz, 1H), 2.74 (dd, 9.32, 6.67 Hz, 1H), 3.21 (m, 1H), 5.16 (m, 2H), 7.45 (m, 1H), 7.49 (m, 2H), 7.97 (d, 7.05 Hz, 2H), 8.41 (d, 2.01 Hz, 1H), 8.49 (d, 2.01 Hz, 1H) |
| 26 | 4 | | 1-{[6-chloro-2-(4-methylphenyl)imidazo[1,2-b]pyridazin-3-yl]methyl}-4-propylpyrrolidin-2-one | 383/385 | 0.84 (m, 3H), 1.24 (m, 4H), 1.56 (s, 3H), 2.04 (m, 1H), 2.19 (dd, J = 3.27, 3.27, 2.01, 0.88 Hz, 1H), 2.50 (m, 1H), 2.85 (dd, 9.31, 6.92 Hz, 1H), 3.32 (m, 1H), 5.07 (d, 1.76 Hz, |

TABLE 1-continued

| n° | Config | Salt | IUPAC Name | MH⁺ (M⁺.) | ¹H NMR delta (CDCl₃ unless otherwise specified) |
|---|---|---|---|---|---|
| | | | | | 2H), 7.12 (d, 9.31 Hz, 1H), 7.46 (d, 8.30 Hz, 2H), 7.87 (d, 8.55 Hz, 2H), 7.93 (d, 9.56 Hz, 1H) |
| 27 | 4 | | 1-{[6-chloro-2-(4-chlorophenyl)imidazo[1,2-b]pyridazin-3-yl]methyl}-4-propylpyrrolidin-2-one | 403/405/407 | 0.84 (m, 3H), 1.23 (m, 4H), 2.04 (m, 1H), 2.20 (m, 1H), 2.50 (m, 1H), 2.85 (m, 1H), 3.33 (m, 1H), 5.08 (s, 2H), 7.12 (dd, 9.31, 2.01 Hz, 1H), 7.46 (dd, 8.30, 1.63 Hz, 2H), 7.87 (dd, 8.30, 1.51 Hz, 2H), 7.93 (dd, 9.31, 1.89 Hz, 1H) |
| 28 | 4 | | 1-[(6-chloroimidazo[1,2-b]pyridazin-3-yl)methyl]-4-propylpyrrolidin-2-one | 293/295 | 0.89 (m, 3H), 1.33 (m, 4H), 2.09 (dd, 16.35, 7.67 Hz, 1H), 2.33 (m, 1H), 2.55 (dd, 16.35, 8.68 Hz, 1H), 3.01 (m, 1H), 3.50 (m, 1H), 4.85 (s, 2H), 7.07 (dd, 9.56, 1.26 Hz, 1H), 7.75 (s, 1H), 7.91 (dd, 9.56, 1.26 Hz, 1H) |
| 29 | 4 | | 1-[(6-chloroimidazo[1,2-b]pyridazin-3-yl)methyl]-4-phenylpyrrolidin-2-one | 327/329 | 2.60 (dd, 17.10, 8.17 Hz, 1H), 2.86 (dd, 17.10, 8.93 Hz, 1H), 3.38 (m, 1H), 3.57 (m, 1H), 3.79 (m, 1H), 4.93 (m, 2H), 7.07 (d, 9.31 Hz, 1H), 7.17 (d, 7.55 Hz, 2H), 7.31 (m, 4H), 7.79 (s, 1H), 7.91 (m, 1H) |
| 30 | 4 | | 1-{[6-chloro-2-(trifluoromethyl)imidazo[1,2-b]pyridazin-3-yl]methyl}-4-propylpyrrolidin-2-one | 361/363 | 0.87 (t, 7.17 Hz, 3H), 1.30 (m, 4H), 2.09 (dd, 16.60, 7.80 Hz, 1H), 2.29 (m, 1H), 2.54 (dd, 16.85, 8.68 Hz, 1H), 2.84 (dd, 9.05, 6.79 Hz, 1H), 3.32 (m, 1H), 5.01 (m, 2H), 7.25 (m, 1H), 8.00 (d, 9.56 Hz, 1H) |
| 31 | 4 | | 1-{[6-chloro-2-(trifluoromethyl)imidazo[1,2-b]pyridazin-3-yl]methyl}-4-(2,3,5-trifluorophenyl)pyrrolidin-2-one | 449/451 | 2.57 (dd, 17.10, 7.55 Hz, 1H), 2.87 (dd, 17.10, 9.05 Hz, 1H), 3.21 (dd, 9.56, 6.29 Hz, 1H), 3.69 (t, 8.93 Hz, 1H), 3.82 (m, 1H), 5.09 (m, 2H), 6.62 (m, 1H), 6.81 (m, 1H), 7.28 (m, 1H), 8.00 (d, 9.56 Hz, 1H) |
| 32 | | | 1-{[6-chloro-2-(trifluoromethyl)imidazo[1,2-b]pyridazin-3-yl]methyl}pyrrolidin-2-one | 319/321 | 1.97 (m, 2H), 2.39 (t, 8.05 Hz, 2H), 3.24 (t, 7.04 Hz, 2H), 5.02 (s, 2H), 7.20 (d, 9.56 Hz, 1H), 7.96 (d, 9.56 Hz, 1H) |
| 33 | 4 | | 1-{[6-chloro-2-(trifluoromethyl)imidazo[1,2-b]pyridazin-3-yl]methyl}-4-(2,2-difluorovinyl)pyrrolidin-2-one | 381/383 | 2.23 (dd, 16.83, 8.04 Hz, 1H), 2.66 (dd, 16.83, 8.79 Hz, 1H), 2.98 (dd, 9.04, 7.28 Hz, 1H), 3.12 (m, 1H), 3.44 (t, 8.67 Hz, 1H), 4.18 (dd, 24.36, 9.42 Hz, 1H), 5.03 (m, 2H), 7.32 (m, 1H), 8.08 (d, 9.54 Hz, 1H) |
| 34 | 4 | | 1-{[6-chloro-2-(trifluoromethyl)imidazo[1,2-b]pyridazin-3-yl]methyl}-4-phenylpyrrolidin-2-one | 395/397 | 2.60 (dd, 16.92, 8.08 Hz, 1H), 2.86 (dd, 17.18, 8.97 Hz, 1H), 3.19 (m, 1H), 3.52 (m, 1H), 3.63 (t, 8.71 Hz, 1H), 5.09 (m, 2H), 7.14 (d, 7.58 Hz, 2H), 7.28 (m, 4H), 7.98 (d, 9.35 Hz, 1H) |
| 35 | | | 5-chloro-1-{[6-chloro-2-(trifluoromethyl)imidazo[1,2-b]pyridazin-3-yl]methyl}-1,3-dihydro-2H-indol-2-one | 401/403/405 | 3.60 (s, 2H), 5.43 (s, 2H), 6.66 (d, 8.34 Hz, 1H), 7.12 (dd, 8.59, 1.89 Hz, 1H), 7.18 (d, 9.60 Hz, 1H), 7.22 (d, 0.51 Hz, 1H), 7.97 (d, 9.60 Hz, 1H) |
| 36 | 4 | | 1-{[6-methoxy-2-(trifluoromethyl)imidazo[1,2-b]pyridazin-3-yl]methyl}-4-propylpyrrolidin-2-one | 357 | 0.85 (m, 3H), 1.28 (m, 4H), 2.06 (dd, 16.67, 7.96 Hz, 1H), 2.26 (m, 1H), 2.53 (dd, 16.67, 8.59 Hz, 1H), 2.76 (m, 1H), 3.27 (m, 1H), 4.03 (s, 3H), 4.97 (m, 2H), 6.85 (d, 9.85 Hz, 1H), 7.84 (d, 9.85 Hz, 1H) |
| 37 | 4 | | 1-[(6-chloro-2-cyclopropylimidazo[1,2-b]pyridazin-3-yl)methyl]-4-propylpyrrolidin-2-one | 333/335 | 0.89 (m, 3H), 1.05 (m, 4H), 1.32 (m, 4H), 2.07 (dd, 16.42, 7.32 Hz, 1H), 2.29 (m, 2H), 2.53 (dd, 16.42, 8.46 Hz, 1H), 2.93 (m, 1H), 3.44 (m, 1H), 4.93 (s, 2H), 6.99 (d, 9.35 Hz, 1H), 7.75 (d, 9.35 Hz, 1H) |
| 38 | 4 | | 1-{[6-isopropoxy-2-(trifluoromethyl)imidazo[1,2-b]pyridazin-3-yl]methyl}-4-propylpyrrolidin-2-one | 385 | 0.83 (t, 7.18 Hz, 3H), 1.27 (m, 4H), 1.40 (dd, 6.04, 3.78 Hz, 6H), 2.06 (dd, 16.37, 7.93 Hz, 1H), 2.25 (m, 1H), 2.52 (dd, 16.62, 8.81 Hz, 1H), 2.76 (dd, 9.32, 6.92 Hz, 1H), 3.26 (m, 1H), 4.94 (m, 2H), 5.31 (m, 1H), 6.78 (d, 9.82 Hz, 1H), 7.82 (d, 9.57 Hz, 1H) |
| 39 | 4 | | 1-{[6-(benzyloxy)-2-(trifluoromethyl)imidazo[1,2-b]pyridazin-3-yl]methyl}-4-propylpyrrolidin-2-one | 433 | 0.86 (m, 3H), 1.26 (m, 4H), 2.04 (dd, 16.42, 7.96 Hz, 1H), 2.23 (m, 1H), 2.50 (dd, 16.67, 8.59 Hz, 1H), 2.73 (dd, 9.35, 6.95 Hz, 1H), 3.23 (m, 1H), 4.97 (m, 2H), 5.45 (s, 2H), 6.88 (d, 9.60 Hz, 1H), 7.37 (m, 3H), 7.58 (d, 6.82 Hz, 2H), 7.87 (d, 9.85 Hz, 1H) |
| 40 | 4 | | 1-{[6-cyclopropyl-2-(trifluoromethyl)imidazo[1,2-b]pyridazin-3-yl]methyl}-4-propylpyrrolidin-2-one | 367 | 0.85 (t, 8 Hz, 3H), 1.14-1.35 (m, 8H), 2.08 (m, 2H), 2.25 (m, 1H), 2.55 (dd, 8 & 16 Hz, 1H), 2.72 (dd, 8 & 12 Hz, 1H), 3.24 (t, 8 Hz, 1H), 4.98 (dd, 16 & 24 Hz, 2H), 7.06 (d, 8 Hz, 1H), 7.85 (d, 8 Hz, 1H) |

TABLE 1-continued

| n° | Config | Salt | IUPAC Name | MH+ (M+.) | ¹H NMR delta (CDCl₃ unless otherwise specified) |
|---|---|---|---|---|---|
| 41 | 4 | | 1-{[6-(dimethylamino)-2-(trifluoromethyl)imidazo[1,2-b]pyridazin-3-yl]methyl}-4-propylpyrrolidin-2-one | 370 | 0.85 (t, 7.20 Hz, 3H), 1.27 (m, 4H), 2.06 (dd, 16.67, 7.96 Hz, 1H), 2.24 (m, 1H), 2.52 (dd, 16.67, 8.59 Hz, 1H), 2.73 (dd, 9.35, 6.69 Hz, 1H), 3.14 (s, 6H), 3.28 (m, 1H), 4.97 (d, 10.61 Hz, 2H), 6.89 (d, 10.1 Hz, 1H), 7.71 (d, 10.10 Hz, 1H) |
| 42 | 4 | | 4-(2,2-difluorovinyl)-1-{[6-methoxy-2-(trifluoromethyl)imidazo[1,2-b]pyridazin-3-yl]methyl}pyrrolidin-2-one | 377 | 2.21 (dd, 16.83, 8.29 Hz, 1H), 2.64 (dd, 16.83, 8.79 Hz, 1H), 2.90 (dd, 9.54, 7.28 Hz, 1H), 3.09 (m, 1H), 3.38 (m, 1H), 4.03 (s, 3H), 4.11 (dd, 9.54, 2.01 Hz, 1H), 4.18 (dd, 9.54, 2.01 Hz, 1H), 4.99 (m, 2H), 6.84 (d, 9.54 Hz, 1H), 7.92 (d, 9.54 Hz, 1H) |
| 43 | 4 | | 4-(2-chloro-2,2-difluoroethyl)-1-{[6-chloro-2-(trifluoromethyl)imidazo[1,2-b]pyridazin-3-yl]methyl}pyrrolidin-2-one | 417/419/421 | 2.22 (m, 1H), 2.45 (m, 2H), 2.72 (m, 2H), 3.03 (m, 1H), 3.54 (m, 1H), 5.02 (m, 2H), 7.24 (d, 9.54 Hz, 1H), 8.00 (d, 9.54 Hz, 1H) |
| 44 | 4 | | 1-{[6-(methylamino)-2-(trifluoromethyl)imidazo[1,2-b]pyridazin-3-yl]methyl}-4-propylpyrrolidin-2-one | 356 | 0.85 (t, 7.15 Hz, 3H), 1.28 (m, 4H), 2.07 (dd, 16.56, 7.91 Hz, 1H), 2.26 (m, 1H), 2.53 (dd, 16.56, 8.53 Hz, 1H), 2.76 (dd, 9.29, 6.78 Hz, 1H), 3.00 (d, 5.02 Hz, 3H), 3.27 (m, 1H), 4.68 (d, 4.77 Hz, 1H), 4.93 (m, 2H), 6.57 (d, 9.79 Hz, 1H), 7.63 (d, 9.79 Hz, 1H) |
| 45 | 4 | | 1-{[6-hydroxy-2-(trifluoromethyl)imidazo[1,2-b]pyridazin-3-yl]methyl}-4-propylpyrrolidin-2-one | 343 | 0.87 (t, 7.16 Hz, 3H), 1.30 (m, 4H), 2.27 (m, 2H), 2.66 (dd, 16.58, 8.16 Hz, 1H), 2.79 (dd, 9.54, 6.66 Hz, 1H), 3.31 (m, 2H), 4.96 (m, 2H), 6.88 (d, 9.54 Hz, 1H), 7.86 (d, 9.80 Hz, 1H) |
| 46 | 4 | | 1-{[6-(methylthio)-2-(trifluoromethyl)imidazo[1,2-b]pyridazin-3-yl]methyl}-4-propylpyrrolidin-2-one | 373 | 0.87 (m, 3H), 1.30 (m, 4H), 2.08 (m, 1H), 2.28 (m, 1H), 2.54 (dd, 16.58, 8.79 Hz, 1H), 2.67 (s, 3H), 2.81 (dd, 9.54, 6.91 Hz, 1H), 3.28 (m, 1H), 5.04 (m, 2H), 7.03 (d, 9.54 Hz, 1H), 7.83 (d, 9.54 Hz, 1H) |
| 47 | 4 | | 4-(2-bromo-2,2-difluoroethyl)-1-{[6-chloro-2-(trifluoromethyl)imidazo[1,2-b]pyridazin-3-yl]methyl}pyrrolidin-2-one | 461/463/465 | 0.86 (t, 7.18 Hz, 3H), 1.29 (m, 4H), 2.07 (m, 1H), 2.29 (m, 1H), 2.53 (dd, 16.62, 8.56 Hz, 1H), 2.80 (dd, 9.32, 7.05 Hz, 1H), 3.31 (m, 1H), 3.54 (s Hz, 3H), 5.08 (m, 2H), 7.83 (d, 9.57 Hz, 1H), 8.28 (d, 9.57 Hz, 1H) |
| 48 | 4 | | 1-{[6-(methylsulfonyl)-2-(trifluoromethyl)imidazo[1,2-b]pyridazin-3-yl]methyl}-4-propylpyrrolidin-2-one | 405 | 0.86 (t, 7.16 Hz, 3H), 1.29 (m, 4H), 2.08 (dd, 16.58, 8.16 Hz, 1H), 2.29 (m, 1H), 2.53 (dd, 16.58, 8.67 Hz, 1H), 2.82 (dd, 9.04, 7.16 Hz, 1H), 3.29 (m, 1H), 3.54 (s, 3H), 4.98 (m, 2H), 7.83 (d, 9.54 Hz, 1H), 8.26 (d, 9.54 Hz, 1H) |
| 49 | 4 | 1 CF₃COOH | 1-{[6-(methylsulfinyl)-2-(trifluoromethyl)imidazo[1,2-b]pyridazin-3-yl]methyl}-4-propylpyrrolidin-2-one | 389 | 0.84 (m, 3H), 1.24 (m, 4H), 2.04 (m, 1H), 2.27 (m, 1H), 2.50 (m, 1H), 2.81 (m, 1H), 3.08 (s Hz, 3H), 3.31 (m, 1H), 5.04 (m, 2H), 7.89 (d, 9.57 Hz, 1H), 8.27 (d, 9.57 Hz, 1H) |
| 50 | 4 | | 1-{[6-chloro-2-(trifluoromethyl)imidazo[1,2-b]pyridazin-3-yl]methyl}-4-(2,2,2-trifluoroethyl)pyrrolidin-2-one | 401/403 | 2.23 (m, 3H), 2.66 (m, 2H), 3.02 (dd, 9.29, 7.03 Hz, 1H), 3.47 (m, 1H), 5.02 (m, 2H), 7.28 (m, 1H), 8.02 (d, 9.54 Hz, 1H) |
| 51 | 4 | 2 CF₃COOH | 1-[(6-chloro-2-cyclobutylimidazo[1,2-b]pyridazin-3-yl)methyl]-4-propylpyrrolidin-2-one | 347/349 | 0.89 (t, 7.05 Hz, 3H), 1.32 (m, 4H), 2.11 (m, 3H), 2.45 (m, 6H), 3.03 (dd, 9.57, 6.92 Hz, 1H), 3.52 (m, 1H), 4.02 (quint, 8.88 Hz, 1H), 4.82 (m, 2H), 7.40 (d, 9.57 Hz, 1H), 8.65 (d, 9.54 Hz, 1H) |
| 52 | 4 | | 1-{[6-chloro-2-(4-methylphenyl)imidazo[1,2-b]pyridazin-3-yl]methyl}-4-(2,2-difluorovinyl)pyrrolidin-2-one | 403/405 | 2.16 (dd, 16.83, 7.79 Hz, 1H), 2.41 (s, 3H), 2.61 (dd, 16.83, 8.54 Hz, 1H), 2.96 (m, 2H), 3.38 (m, 1H), 4.00 (m, 1H), 5.11 (s, 2H), 7.11 (d, 9.29 Hz, 1H), 7.32 (d, 8.04 Hz, 2H), 7.75 (d, 8.04 Hz, 2H), 7.93 (d, 9.29 Hz, 1H) |
| 53 | 4 | | 1-{[6-amino-2-(trifluoromethyl)imidazo[1,2-b]pyridazin-3-yl]methyl}-4-propylpyrrolidin-2-one | 342 | 0.85 (t, 8 Hz, 3H), 1.21-1.35 (m, 4H), 2.08 (dd, 8 & 16 Hz, 1H), 2.25 (m, 1H), 2.55 (dd, 8 & 16 Hz, 1H), 2.75 (t, 8 Hz, 1H), 3.25 (t, 8 Hz, 1H), 4.78 (s, 2H), 4.89 (dd, 16 & 36 Hz, 2H), 6.66 (d, 8 Hz, 1H), 7.74 (d, 8 Hz, 1H) |
| 54 | 4 | | 1-{[6-(ethylamino)-2-(trifluoromethyl)imidazo[1,2-b]pyridazin-3-yl]methyl}-4-propylpyrrolidin-2-one | 370 | 0.85 (t, 7.03 Hz, 3H), 1.28 (m, 7H), 2.06 (dd, 16.58, 7.91 Hz, 1H), 2.25 (m, 1H), 2.52 (dd, 16.58, 8.54 Hz, 1H), 2.75 (dd, 9.29, 6.91 Hz, 1H), 3.26 (t, 8.67 Hz, 1H), 3.50 (m, 2H), 4.54 (m, 1H), 4.92 (m, 2H), 6.54 (d, 9.54 Hz, 1H), 7.63 (d, 9.80 Hz, 1H) |
| 55 | 4 | | 4-propyl-1-{[6-(propylamino)-2-(trifluoromethyl)imidazo[1,2-b]pyridazin-3-yl]methyl}pyrrolidin-2-one | 384 | 0.85 (t, 7.15 Hz, 3H), 1.02 (t, 7.40 Hz, 3H), 1.27 (m, 4H), 1.67 (m, 2H), 2.06 (dd, 16.56, 7.78 Hz, 1H), 2.25 (m, 1H), 2.52 (dd, 16.56, 8.66 Hz, 1H), 2.75 (dd, 9.54, 6.78 Hz, 1H), |

TABLE 1-continued

| n° | Config | Salt | IUPAC Name | MH+ (M+.) | 1H NMR delta (CDCl3 unless otherwise specified) |
|---|---|---|---|---|---|
| | | | | | 3.25 (m, 1H), 3.37 (m, 2H), 4.58 (t, 5.27 Hz, 1H), 4.91 (m, 2H), 6.55 (d, 9.54 Hz, 1H), 7.63 (d, 9.79 Hz, 1H) |
| 56 | 4 | | 4-(2-bromo-2,2-difluoroethyl)-1-{[6-(propylamino)-2-(trifluoromethyl)imidazo[1,2-b]pyridazin-3-yl]methyl}pyrrolidin-2-one | 484/486 | 1.02 (m, 3H), 1.68 (m, 2H), 2.20 (m, 1H), 2.49 (m, 2H), 2.68 (m, 2H), 2.93 (m, 1H), 3.39 (m, 3H), 4.55 (s, 1H), 4.93 (q, 15.07 Hz, 2H), 6.55 (m, 1H), 7.64 (m, 1H) |
| 57 | 4 | | 4-(2,2-difluorovinyl)-1-{[6-(propylamino)-2-(trifluoromethyl)imidazo[1,2-b]pyridazin-3-yl]methyl}pyrrolidin-2-one | 404 | 1.02 (t, 7.43 Hz, 3H), 1.68 (m, 2H), 2.20 (dd, 16.69, 8.07 Hz, 1H), 2.63 (dd, 16.69, 8.62 Hz, 1H), 2.88 (m, 1H), 3.07 (m, 1H), 3.37 (m, 3H), 4.14 (m, 1H), 4.56 (t, 5.14 Hz, 1H), 4.93 (m, 2H), 6.56 (d, 9.72 Hz, 1H), 7.64 (d, 9.72 Hz, 1H) |
| 58 | 4 | | 4-(2,2-difluorovinyl)-1-{[6-methoxy-2-(4-methylphenyl)imidazo[1,2-b]pyridazin-3-yl]methyl}pyrrolidin-2-one | 399 | 2.17 (dd, 16.58, 8.04 Hz, 1H), 2.40 (s, 3H), 2.62 (dd, 16.58, 8.67 Hz, 1H), 2.86 (dd, 9.54, 6.78 Hz, 1H), 2.98 (m, 1H), 3.33 (m, 1H), 4.02 (s, 3H), 5.07 (d, 3.01 Hz, 2H), 6.74 (d, 9.80 Hz, 1H), 7.28 (d, 8.04 Hz, 2H), 7.68 (d, 8.29 Hz, 2H), 7.82 (d, 9.80 Hz, 1H) |
| 59 | 4 | 1 CF3COOH | 4-propyl-1-{[6-pyrrolidin-1-yl-2-(trifluoromethyl)imidazo[1,2-b]pyridazin-3-yl]methyl}pyrrolidin-2-one | 396 | 0.86 (t, 7.24 Hz, 3H), 1.24 (m, 2H), 1.39 (m, 2H), 2.05 (m, 4H), 2.20 (m, 1H), 2.30 (m, 1H), 2.67 (dd, 16.85, 8.43 Hz, 1H), 2.82 (dd, 9.71, 6.78 Hz, 1H), 3.32 (m, 1H), 3.49 (t, 6.60 Hz, 4H), 4.96 (m, 2H), 6.83 (d, 9.89 Hz, 1H), 7.94 (d, 9.89 Hz, 1H) |
| 60 | 4 | | 4-(2-bromo-2,2-difluoroethyl)-1-{[6-methoxy-2-(trifluoromethyl)imidazo[1,2-b]pyridazin-3-yl]methyl}pyrrolidin-2-one | 457/459 | 2.21 (m, 1H), 2.50 (m, 2H), 2.72 (m, 2H), 2.95 (m, 1H), 3.43 (m, 1H), 4.03 (s, 3H), 4.99 (m, 2H), 6.87 (d, 9.71 Hz, 1H), 7.86 (d, 9.71 Hz, 1H) |
| 61 | 4 | | 1-{[6-(cyclopropylamino)-2-(trifluoromethyl)imidazo[1,2-b]pyridazin-3-yl]methyl}-4-(2,2-difluorovinyl)pyrrolidin-2-one | 402 | 0.58 (dd, 3.48, 1.65 Hz, 2H), 0.89 (dd, 6.60, 1.65 Hz, 2H), 2.21 (dd, 16.67, 8.06 Hz, 1H), 2.65 (m, 2H), 2.90 (dd, 9.71, 6.96 Hz, 1H), 3.08 (m, 1H), 3.38 (m, 1H), 4.15 (m, 1H), 4.96 (m, 3H), 6.80 (d, 9.71 Hz, 1H), 7.72 (d, 9.71 Hz, 1H) |
| 62 | 4 | | 1-[(6-chloro-2-cyclopropylimidazo[1,2-b]pyridazin-3-yl)methyl]-4-(2,2-difluorovinyl)pyrrolidin-2-one | 353/355 | 1.06 (m, 4H), 2.23 (m, 2H), 2.64 (dd, 16.83, 8.54 Hz, 1H), 3.09 (m, 2H), 3.56 (t, 8.29 Hz, 1H), 4.19 (dd, 24.36, 9.29 Hz, 1H), 4.94 (s, 2H), 7.01 (d, 9.29 Hz, 1H), 7.76 (d, 9.29 Hz, 1H) |
| 63 | 4 | | 4-(2,2-difluorovinyl)-1-{[6-(isopropylamino)-2-(trifluoromethyl)imidazo[1,2-b]pyridazin-3-yl]methyl}pyrrolidin-2-one | 404 | 1.27 (m, 6H), 2.19 (m, 1H), 2.63 (dd, 16.69, 8.80 Hz, 1H), 2.89 (dd, 9.54, 7.24 Hz, 1H), 3.07 (m, 1H), 3.36 (m, 1H), 4.13 (m, 2H), 4.33 (m, 1H), 4.93 (m, 2H), 6.50 (d, 9.72 Hz, 1H), 7.64 (d, 9.72 Hz, 1H) |
| 64 | 4 | | 4-(2,2-difluorovinyl)-1-{[2-(trifluoromethyl)imidazo[1,2-b]pyridazin-3-yl]methyl}pyrrolidin-2-one | 347 | 2.23 (dd 8 & 20 Hz, 1H), 2.65 (dd 8 & 20 Hz, 1H), 2.93 (dd 8 & 12 Hz, 1H), 3.39 (t 12 Hz, 1H), 4.13 (dd 12 & 18 Hz, 1H), 5.07 (dd 16 & 40 Hz, 2H), 7.23 (dd, 1H), 8.07 (d, 1H), 8.52 (d, 1H) |
| 65 | 4 | | 1-{[2-cyclopropyl-6-(propylamino)imidazo[1,2-b]pyridazin-3-yl]methyl}-4-(2,2-difluorovinyl)pyrrolidin-2-one | 376 | 0.99 (m, 7H), 1.67 (m, 2H), 2.17 (m, 2H), 2.63 (dd, 16.58, 8.54 Hz, 1H), 3.05 (m, 2H), 3.32 (q, 6.53 Hz, 2H), 3.52 (t, 8.54 Hz, 1H), 4.22 (m, 2H), 4.86 (s, 2H), 6.35 (d, 9.54 Hz, 1H), 7.50 (d, 9.54 Hz, 1H) |
| 66 | 4 | | 1-({2-cyclopropyl-6-[(2-fluoroethyl)amino]imidazo[1,2-b]pyridazin-3-yl}methyl)-4-(2,2-difluorovinyl)pyrrolidin-2-one | 380 | 0.99 (m, 4H), 2.08 (s, 1H), 2.20 (dd, 16.81, 8.16 Hz, 1H), 2.63 (dd, 16.81, 8.78 Hz, 1H), 2.96 (dd, 9.54, 7.15 Hz, 1H), 3.09 (d, 8.28 Hz, 1H), 3.45 (m, 1H), 3.72 (m, 2H), 4.16 (m, 1H), 4.66 (m, 3H), 4.85 (s, 2H), 6.41 (d, 9.54 Hz, 1H), 7.54 (d, 9.54 Hz, 1H) |
| 67 | 4 | | 1-({2-cyclopropyl-6-[(2,2-difluoroethyl)amino]imidazo[1,2-b]pyridazin-3-yl}methyl)-4-(2,2-difluorovinyl)pyrrolidin-2-one | 398 | 1.00 (m, 4H), 2.09 (m, 1H), 2.20 (dd, 16.56, 8.16 Hz, 1H), 2.63 (dd, 16.56, 8.78 Hz, 1H), 2.98 (dd, 9.54, 7.28 Hz, 1H), 3.09 (m, 1H), 3.46 (m, 1H), 3.82 (m, 2H), 4.16 (m, 1H), 4.62 (s, 1H), 4.86 (d, 1.76 Hz, 2H), 6.05 (m, 1H), 6.43 (d, 9.54 Hz, 1H), 7.57 (d, 9.54 Hz, 1H) |
| 68 | 4 | | 1-({2-cyclopropyl-6-[(2,2,2-trifluoroethyl)amino]imidazo[1,2-b]pyridazin-3-yl}methyl)-4-(2,2-difluorovinyl)pyrrolidin-2-one | 416 | 1.00 (m, 4H), 2.11 (m, 1H), 2.20 (dd, 16.83, 8.29 Hz, 1H), 2.63 (dd, 16.83, 8.79 Hz, 1H), 2.97 (dd, 9.54, 7.16 Hz, 1H), 3.08 (m, 1H), 3.45 (m, 1H), 4.15 (m, 3H), 4.61 (t, 6.66 Hz, 1H), 4.87 (s, 2H), 6.44 (d, 9.54 Hz, 1H), 7.60 (d, 9.54 Hz, 1H) |

TABLE 1-continued

| n° | Config | Salt | IUPAC Name | MH+ (M+.) | 1H NMR delta (CDCl3 unless otherwise specified) |
|---|---|---|---|---|---|
| 69 | 4 | | 4-(2,2-difluoroethyl)-1-{[2-(trifluoromethyl)imidazo[1,2-b]pyridazin-3-yl]methyl}pyrrolidin-2-one | 349 | 1.95 (m, 3H), 2.17 (m, 1H), 2.60 (m, 3H), 2.94 (m, 1H), 3.40 (m, 1H), 5.07 (m, 2H), 5.80 (m, 1H), 7.23 (dd, 9.29, 4.52 Hz, 1H), 8.06 (d, 9.29 Hz, 1H), 8.51 (d, 4.27 Hz, 1H) |
| 70 | 4 | | 1-{[2-cyclopropyl-6-(cyclopropylamino)imidazo[1,2-b]pyridazin-3-yl]methyl}-4-(2,2-difluorovinyl)pyrrolidin-2-one | 374 | 0.58 (d, 2.51 Hz, 1H), 0.83 (d, 5.02 Hz, 2H), 0.99 (d, 4H), 2.18 (m, 2H), 2.63 (m, 2H), 3.07 (m, 2H), 3.54 (m, 1H), 4.18 (m, 1H), 4.76 (s, 1H), 4.86 (s, 2H), 6.61 (d, 9.54 Hz, 1H), 7.57 (d, 9.54 Hz, 1H) |
| 71 | 4 | | 1-[(6-chloro-2-cyclobutylimidazo[1,2-b]pyridazin-3-yl)methyl]-4-(2,2-difluorovinyl)pyrrolidin-2-one | 367/369 | 1.99 (s, 1H), 2.15 (m, 2H), 2.34 (dt, 8.29, 2.61 Hz, 2H), 2.48 (m, 2H), 2.62 (dd, 16.58, 8.67 Hz, 1H), 3.05 (m, 2H), 3.49 (m, 1H), 3.91 (t, 8.67 Hz, 1H), 4.16 (m, 1H), 4.82 (s, 2H), 7.04 (d, 9.29 Hz, 1H), 7.88 (d, 9.29 Hz, 1H) |
| 72 | 4 | | 1-[(6-chloro-2-cyclopropylimidazo[1,2-b]pyridazin-3-yl)methyl]-4-(3-chloro-4-fluorophenyl)pyrrolidin-2-one | 419/421/423 | 1.09 (m, 4H), 2.29 (m, 1H), 2.50 (dd, 16.81, 7.65 Hz, 1H), 2.85 (dd, 16.81, 9.03 Hz, 1H), 3.29 (dd, 9.79, 6.53 Hz, 1H), 3.47 (m, 1H), 3.75 (m, 1H), 5.00 (q, 15.31 Hz, 2H), 7.03 (m, 3H), 7.17 (dd, 6.78, 1.76 Hz, 1H), 7.75 (d, 9.29 Hz, 1H) |
| 73 | 4 | | 1-{[6-(butylamino)-2-(trifluoromethyl)imidazo[1,2-b]pyridazin-3-yl]methyl}-4-(2,2-difluorovinyl)pyrrolidin-2-one | 418 | 0.97 (t, 7.33 Hz, 3H), 1.45 (m, 2H), 1.62 (m, 2H), 2.20 (dd, 16.67, 8.24 Hz, 1H), 2.63 (dd, 16.67, 8.79 Hz, 1H), 2.89 (dd, 9.34, 7.24 Hz, 1H), 3.07 (m, 1H), 3.38 (m, 3H), 4.14 (m, 1H), 4.50 (m, 1H), 4.93 (m, 2H), 6.55 (d, 9.71 Hz, 1H), 7.64 (d, 9.71 Hz, 1H) |
| 74 | 4 | | 1-{[6-(cyclobutylamino)-2-(trifluoromethyl)imidazo[1,2-b]pyridazin-3-yl]methyl}-4-(2,2-difluorovinyl)pyrrolidin-2-one | 414 | 1.88 (m, 4H), 2.22 (dd, 16.83, 8.16 Hz, 1H), 2.50 (m, 2H), 2.65 (dd, 16.83, 8.79 Hz, 1H), 2.87 (dd, 9.54, 7.03 Hz, 1H), 3.07 (m, 1H), 3.35 (m, 1H), 4.14 (m, 1H), 4.32 (m, 1H), 4.74 (d, 6.53 Hz, 1H), 4.93 (m, 2H), 6.53 (d, 9.80 Hz, 1H), 7.65 (d, 9.54 Hz, 1H) |
| 75 | 4 | | 1-[(2-cyclopropyl-6-methoxyimidazo[1,2-b]pyridazin-3-yl)methyl]-4-(2,2-difluorovinyl)pyrrolidin-2-one | 349 | 1.01 (m, 4H), 2.18 (m, 2H), 2.64 (dd, 16.83, 8.67 Hz, 1H), 3.06 (m, 2H), 3.50 (m, 1H), 3.99 (s, 3H), 4.17 (dd, 24.61, 9.42 Hz, 1H), 4.91 (s, 2H), 6.64 (d, 9.54 Hz, 1H), 7.67 (d, 9.29 Hz, 1H) |
| 76 | 4 | | 4-(2,2-difluorovinyl)-1-{[6-ethoxy-2-(trifluoromethyl)imidazo[1,2-b]pyridazin-3-yl]methyl}pyrrolidin-2-one | 391 | 1.45 (t, 7.03 Hz, 3H), 2.20 (dd, 16.83, 8.29 Hz, 1H), 2.63 (dd, 16.58, 8.67 Hz, 1H), 2.90 (dd, 9.54, 7.28 Hz, 1H), 3.08 (m, 1H), 3.37 (m, 1H), 4.14 (m, 1H), 4.43 (q, 7.03 Hz, 2H), 4.97 (m, 2H), 6.84 (d, 9.80 Hz, 1H), 7.84 (d, 9.54 Hz, 1H) |
| 77 | 4 | | 4-(2,2-difluorovinyl)-1-{[6-isopropoxy-2-(trifluoromethyl)imidazo[1,2-b]pyridazin-3-yl]methyl}pyrrolidin-2-one | 405 | 1.40 (dd, 6.05, 3.66 Hz, 6H), 2.20 (dd, 16.67, 8.43 Hz, 1H), 2.63 (dd, 16.85, 8.79 Hz, 1H), 2.91 (dd, 9.34, 7.33 Hz, 1H), 3.08 (m, 1H), 3.36 (m, 1H), 4.14 (m, 1H), 4.89 (m, 1H), 5.03 (m, 1H), 5.31 (m, 1H), 6.79 (d, 9.71 Hz, 1H), 7.82 (d, 9.89 Hz, 1H) |
| 78 | 4 | | 1-{[6-(cyclopropylmethoxy)-2-(trifluoromethyl)imidazo[1,2-b]pyridazin-3-yl]methyl}-4-(2,2-difluorovinyl)pyrrolidin-2-one | 417 | 0.43 (m, 2H), 0.67 (m, 2H), 1.31 (m, 1H), 2.20 (dd, 16.67, 8.43 Hz, 1H), 2.63 (dd, 16.67, 8.79 Hz, 1H), 2.89 (dd, 9.53, 7.24 Hz, 1H), 3.07 (m, 1H), 3.36 (m, 1H), 4.16 (m, 3H), 4.96 (m, 2H), 6.88 (d, 9.71 Hz, 1H), 7.84 (d, 9.71 Hz, 1H) |
| 79 | 4 | | 1-{[6-(cyclobutylmethoxy)-2-(trifluoromethyl)imidazo[1,2-b]pyridazin-3-yl]methyl}-4-(2,2-difluorovinyl)pyrrolidin-2-one | 431 | 1.94 (m, 4H), 2.18 (m, 3H), 2.64 (dd, 16.58, 8.79 Hz, 1H), 2.80 (m, 1H), 2.90 (dd, 9.54, 7.03 Hz, 1H), 3.09 (m, 1H), 3.37 (m, 1H), 4.14 (m, 1H), 4.33 (d, 6.53 Hz, 2H), 4.98 (m, 2H), 6.86 (d, 9.80 Hz, 1H), 7.83 (d, 9.80 Hz, 1H) |
| 80 | 4 | | 1-{[6-(cyclopropyloxy)-2-(trifluoromethyl)imidazo[1,2-b]pyridazin-3-yl]methyl}-4-(2,2-difluorovinyl)pyrrolidin-2-one | 403 | 0.86 (m, 4H), 2.21 (m, 1H), 2.63 (m, 1H), 2.91 (m, 1H), 3.09 (m, 1H), 3.39 (m, 1H), 4.15 (m, 1H), 4.37 (m, 1H), 5.01 (m, 2H), 6.80 (m, 1H), 7.85 (m, 1H) |
| 81 | 4 | | 4-(2,2-difluorovinyl)-1-{[6-propoxy-2-(trifluoromethyl)imidazo[1,2-b]pyridazin-3-yl]methyl}pyrrolidin-2-one | 405 | 1.06 (t, 7.40 Hz, 3H), 1.84 (m, 2H), 2.21 (dd, 16.81, 8.28 Hz, 1H), 2.62 (m, 1H), 2.90 (m, 1H), 3.08 (m, 1H), 3.36 (m, 1H), 4.15 (m, 1H), 4.34 (m, 2H), 4.97 (m, 2H), 6.85 (d, 9.54 Hz, 1H), 7.84 (d, 9.54 Hz, 1H) |
| 82 | 4 | | 3-{[4-(2,2-difluorovinyl)-2-oxopyrrolidin-1-yl]methyl}-2-(trifluoromethyl)imidazo[1,2-b]pyridazine-6-carbonitrile | 372 | 2.23 (dd, 16.87, 8.25 Hz, 1H), 2.66 (dd, 16.87, 8.25 Hz, 1H), 3.04 (m, 1H), 3.15 (m, 1H), 3.46 (t, 8.53 Hz, 1H), 4.19 (m, 1H), 5.07 (m, 2H), 7.49 (d, 9.35 Hz, 1H), 8.23 d, 9.35 Hz, 1H) |

TABLE 1-continued

| n° | Config | Salt | IUPAC Name | MH⁺ (M⁺.) | ¹H NMR delta (CDCl₃ unless otherwise specified) |
|---|---|---|---|---|---|
| 83 | 4 | | 4-(2,2-difluorovinyl)-1-{[6-thien-3-yl-2-(trifluoromethyl)imidazo[1,2-b]pyridazin-3-yl]methyl}pyrrolidin-2-one | 429 | 2.21 (m, 1H), 2.65 (m, 1H), 2.90 (dd, 9.35, 7.15 Hz, 1H), 3.08 (m, 1H), 3.39 (m, 1H), 4.10 (m, 1H), 5.11 (m, 2H), 7.49 (dd, 5.14, 2.93 Hz, 1H), 7.62 (d, 9.54 Hz, 1H), 7.84 (dd, 5.14, 1.19 Hz, 1H), 8.04 (m, 2H) |
| 84 | 4 | | 4-(2,2-difluorovinyl)-1-{[6-phenyl-2-(trifluoromethyl)imidazo[1,2-b]pyridazin-3-yl]methyl}pyrrolidin-2-one | 423 | 2.14 (dd, 16.81, 8.28 Hz, 1H), 2.58 (dd, 16.81, 8.78 Hz, 1H), 2.87 (dd, 9.54, 7.15 Hz, 1H), 3.01 (m, 1H), 3.35 (m, 1H), 4.04 (m, 1H), 5.08 (m, 2H), 7.48 (m, 3H), 7.66 (d, 9.54 Hz, 1H), 8.01 (m, 3H) |
| 85 | 4 | | 4-(2,2-difluorovinyl)-1-{[6-methyl-2-(trifluoromethyl)imidazo[1,2-b]pyridazin-3-yl]methyl}pyrrolidin-2-one | 361 | 2.22 (dd, 16.69, 8.07 Hz, 1H), 2.65 (m, 4H), 2.91 (dd, 9.54, 6.97 Hz, 1H), 3.08 (m, 1H), 3.38 (m, 1H), 4.15 (m, 1H), 5.04 (m, 2H), 7.09 (d, 9.35 Hz, 1H), 7.91 (d, 9.35 Hz, 1H) |
| 86 | 4 | | 4-(2,2-difluorovinyl)-1-{[6-pyridin-3-yl-2-(trifluoromethyl)imidazo[1,2-b]pyridazin-3-yl]methyl}pyrrolidin-2-one | 424 | 2.20 (dd, 16.81, 8.28 Hz, 1H), 2.64 (dd, 16.81, 8.78 Hz, 1H), 2.95 (m, 1H), 3.11 (m, 1H), 3.43 (m, 1H), 4.12 (m, 1H), 5.15 (m, 2H), 7.54 (dd, 8.03, 4.77 Hz, 1H), 7.76 (d, 9.79 Hz, 1H), 8.16 (d, 9.79 Hz, 1H), 8.54 (dt, 8.03, 2.26 Hz, 1H), 8.78 (dd, 4.77, 1.85 Hz, 1H), 9.22 (d, 2.26 Hz, 1H) |
| 87 | 4 | | 4-propyl-1-{[2-(trifluoromethyl)-5,6,7,8-tetrahydroimidazo[1,2-b]pyridazin-3-yl]methyl}pyrrolidin-2-one | 331 | 0.91 (t, 7.15 Hz, 3H), 1.35 (m, 4H), 2.00 (m, 3H), 2.33 (m, 1H), 2.47 (m, 1H), 2.94 (t, 6.65 Hz, 2H), 3.12 (dd, 9.54, 7.03 Hz, 1H), 3.34 (m, 2H), 3.56 (t, 8.78 Hz, 1H), 4.46 (m, 2H), 6.49 (t, 6.15 Hz, 1H) |
| 88 | 4 | | 1-[(6-methylimidazo[2,1-b][1,3,4]thiadiazol-5-yl)methyl]-4-propylpyrrolidin-2-one | 279 | 0.88 (t, 7.05 Hz, 3H), 1.29 (m, 4H), 2.07 (dd, 16.62, 7.81 Hz, 1H), 2.27 (m, 1H), 2.52 (dd, 16.62, 8.56 Hz, 1H), 2.90 (dd, 9.57, 6.80 Hz, 1H), 3.40 (m, 1H), 4.73 (m, 2H), 8.48 (s, 1H) |
| 89 | 4 | | 1-{[6-(4-methylphenyl)imidazo[2,1-b][1,3,4]thiadiazol-5-yl]methyl}-4-propylpyrrolidin-2-one | 355 | 0.84 (m, 3H), 1.25 (m, 4H), 2.06 (dd, 16.49, 7.88 Hz, 1H), 2.21 (m, 1H), 2.39 (s, 3H), 2.53 (dd, 16.30, 8.52 Hz, 1H), 2.82 (m, 1H), 3.30 (m, 1H), 5.00 (m, 2H), 7.27 (m, 2H), 7.63 (d, 7.88 Hz, 2H), 8.55 (s, 1H) |
| 90 | 4 | | 1-[(2-cyclopropyl-6-phenylimidazo[2,1-b][1,3,4]thiadiazol-5-yl)methyl]-4-propylpyrrolidin-2-one | 381 | 0.84 (m, 3H), 1.11-1.33 (m, 8H), 2.04 (dd, 16.51, 7.70 Hz, 1H), 2.14-2.31 (m, 2H), 2.51 (dd, 16.69, 8.53 Hz, 1H), 2.80 (dd, 9.35, 6.69 Hz, 1H), 3.29 (m, 1H), 4.94 (s Hz, 2H), 7.32 (t, 7.43 Hz, 1H), 7.43 (m, 2H), 7.72 (m, 2H) |
| 91 | 4 | 1 CF₃COOH | 1-[(6-methylimidazo[2,1-b][1,3]thiazol-5-yl)methyl]-4-propylpyrrolidin-2-one | 278 | 0.90 (t, 7.17 Hz, 3H), 1.34 (m, 4H), 2.11 (dd, 16.85, 7.92 Hz, 1H), 2.37 (m, 1H), 2.57 (m, 4H), 2.98 (dd, 9.05, 7.04 Hz, 1H), 3.43 (t, 8.68 Hz, 1H), 4.62 (m, 2H), 7.17 (d, 4.28 Hz, 1H), 8.04 (d, 4.28 Hz, 1H) |
| 92 | 4 | | 1-[(6-chloroimidazo[2,1-b][1,3]thiazol-5-yl)methyl]-4-propylpyrrolidin-2-one | 298/300 | 0.88 (t, 7.28 Hz, 3H), 1.32 (m, 4H), 2.06 (dd, 16.83, 7.79 Hz, 1H), 2.31 (m, 1H), 2.51 (dd, 16.83, 8.67 Hz, 1H), 2.99 (dd, 9.80, 6.91 Hz, 1H), 3.47 (m, 1H), 4.61 (m, 2H), 6.84 (d, 4.52 Hz, 1H), 7.77 (d, 4.52 Hz, 1H) |
| 93 | 4 | | 1-[(2,6-dichloroimidazo[2,1-b][1,3]thiazol-5-yl)methyl]-4-propylpyrrolidin-2-one | 332/334/336 | 0.90 (t, 7.28 Hz, 3H), 1.22-1.44 (m, 4H), 2.07 (dd, 16.81, 8.03 Hz, 1H), 2.27-2.40 (m, 1H), 2.53 (dd, 16.81, 8.78 Hz, 1H), 2.99 (dd, 9.79, 6.90 Hz, 1H), 3.47 (m, 1H), 4.55 (m, 2H), 7.81 (s Hz, 1H) |
| 95 | 4 | | 1-(3H-imidazo[4,5-b]pyridin-7-ylmethyl)-4-propylpyrrolidin-2-one | 259 | 0.88 (t, J 6.90 Hz, 3H), 1.22-1.45 (m, 4H), 2.09-2.22 (m, 1H), 2.31-2.42 (m, 1H), 2.59 (dd, J 16.06, 8.53 Hz, 1H), 3.03 (t, J 8.79 Hz, 1H), 3.50 (t, J 8.53 Hz, 1H), 4.61 (s, 1H), 4.97 (m, 1H), 7.08-7.15 (m, 1H), 8.28-8.53 (m, 2H), 11.26 and 13.27 (two s broad, 1H) |
| 96 | 4 | | 1-(3H-imidazo[4,5-b]pyridin-7-ylmethyl)-4-phenylpyrrolidin-2-one | 293 | (DMSO): 2.49-2.58 (m, 1H), 2.78 (dd, J 16.31, 8.78 Hz, 1H), 3.31-3.38 (m, 1H overlapped with solvent signal), 3.65 (m, 1H), 3.76 (t, J 8.54 Hz, 1H), 4.84 (s (broad), 2H), 7.08 (d, J 4.77 Hz, 1H), 7.20-7.26 (m, 1H), 7.28-7.33 (m, 4H), 8.30 (s (broad), 1H), 8.43 (s (broad), 1H), 13.12 (s (broad), 1H) |

TABLE 1-continued

| n° | Config | Salt | IUPAC Name | MH+ (M+.) | 1H NMR delta (CDCl3 unless otherwise specified) |
|---|---|---|---|---|---|
| 97 | 4 | | 4-phenyl-1-[(5-phenyl-3H-imidazo[4,5-b]pyridin-7-yl)methyl]pyrrolidin-2-one | 369 | (DMSO): 2.49-2.59 (m, 1H), 2.82 (dd, J 16.56, 8.78 Hz, 1H), 3.38 (dd, J 9.29, 7.03 Hz, 1H, overlapped with solvent signal), 3.66 (m, 1H), 3.82 (t, J 8.78 Hz, 1H), 4.88 (s, 2H), 7.20-7.25 (m, 1H), 7.27-7.32 (m, 5H), 7.42 (t, J 7.28 Hz, 1H), 7.50 (t, J 7.28 Hz, 2H), 7.58 (s, 1H), 8.03 (d, J 7.53 Hz, 2H), 8.46 (s, 1H) |
| 98 | 4 | | 4-phenyl-1-{[5-(trifluoromethyl)-3H-imidazo[4,5-b]pyridin-7-yl]methyl}pyrrolidin-2-one | 361 | (DMSO): 2.55 (m, 1H), 2.81 (dd, 16.58, 8.79 Hz, 1H), 3.38 (m, 2H), 3.64 (m, 1H), 3.79 (m, 1H), 4.89 (s, 2H), 7.27 (m, 5H), 7.52 (s Hz, 1H), 8.73 (s Hz, 1H), 13.23-13.75 (broad singlet, 1H) |
| 99 | 4 | | 1-[(6-bromo-3H-imidazo[4,5-b]pyridin-7-yl)methyl]-4-propylpyrrolidin-2-one | 337/339 | 0.81 (t, J 7.15 Hz, 3H), 1.22 (m, 4H), 1.98 (dd, J 16.31, 7.65 Hz, 1H), 2.24 (m, 1H), 2.41 (dd, J 16.31, 8.53 Hz, 1H), 2.79 (dd, J 9.03, 6.78 Hz, 1H), 3.25 (t, J 8.66 Hz, 1H), 4.79 (m, 2H), 8.48 (d, J 7.53 Hz, 2H), 13.28 (s, 1H) |
| 100 | 4 | | 1-[(2-phenyl-3H-imidazo[4,5-b]pyridin-7-yl)methyl]-4-propylpyrrolidin-2-one | 335 | 0.84 (t, J 7.15 Hz, 3H), 1.20-1.34 (m, 2H), 1.34-1.40 (m, 2H), 2.08 (dd, J 16.31, 7.78 Hz, 1H), 2.36 (m, 1H), 2.47 (m, 1H, overlapped with solvent signal), 3.05 (dd, J 9.29, 7.03 Hz, 1H), 3.51 (t, J 8.66 Hz, 1H), 4.80 (s, 2H), 7.01 (d, J 4.77 Hz, 1H), 7.50-7.60 (m, 3H), 8.23-8.31 (m, 3H), 13.57 (s, 1H) |
| 101 | 4 | | 1-[(5-methyl-3H-imidazo[4,5-b]pyridin-7-yl)methyl]-4-propylpyrrolidin-2-one | 273 | 0.85 (t, J 7.15 Hz, 3H), 1.19-1.32 (m, 2H), 1.34-1.45 (m, 2H), 2.04 (dd, J 16.31, 7.65 Hz, 1H), 2.32 (m, 1H), 2.45 (m, 1H, overlapped with solvent signal), 2.53 (s, 3H), 2.97 (t, J 7.0 Hz, 1H), 3.44 (t, J 8.66 Hz, 1H), 4.69 (s, 2H), 6.86 (s, 1H), 8.30 (s, 1H), 12.88 (s, 1H) |
| 102 | 4 | | 1-[(2-methyl-3H-imidazo[4,5-b]pyridin-7-yl)methyl]-4-propylpyrrolidin-2-one | 273 | (DMSO): 0.85 (t, J 7.15 Hz, 3H), 1.20-1.30 (m, 2H), 1.32-1.39 (m, 2H), 2.05 (dd, J 16.31, 7.65 Hz, 1H), 2.32 (m, 1H), 2.45 (m, 1H overlapped with solvent signal), 2.52 (s, 3H), 2.96 (t, J 9.03 Hz, 1H), 3.42 (t, J 8.66 Hz, 1H), 4.69 (s (broad), 2H), 6.90 (d, J 5.02 Hz, 1H), 8.16 (s, 1H), 12.80 (s, 1H, another broad signal appears at 12.4 ppm) |
| 103 | 4 | | 4-propyl-1-{[5-(trifluoromethyl)-3H-imidazo[4,5-b]pyridin-7-yl]methyl}pyrrolidin-2-one | 327 | 0.84 (t, J 7.15 Hz, 3H), 1.18-1.30 (m, 2H), 1.31-1.40 (m, 2H), 2.05 (dd, J 16.31, 7.28 Hz, 1H), 2.32 (m, 1H), 2.48 (m, 1H overlapped with solvent signal), 3.00 (dd, J 9.29, 6.40 Hz, 1H), 3.48 (t, J 8.66 Hz, 1H), 4.81 (s, 2H), 7.45 (s, 1H), 8.72 (s, 1H) |
| 104 | 4 | | 1-[(6-methyl-3H-imidazo[4,5-b]pyridin-7-yl)methyl]-4-propylpyrrolidin-2-one | 273 | 0.79 (t, J 7.15 Hz, 3H), 1.11-1.28 (m, 4H), 1.98 (dd, J 16.31, 7.78 Hz, 1H), 2.21 (m, 1H), 2.32 (s, 3H), 2.42 (dd, J 16.56, 8.66 Hz, 1H), 2.76 (dd, J 9.54, 6.78 Hz, 1H), 3.21 (t, J 9.3 Hz, 1H), 4.71 (d, J 14.3 Hz, 1H), 4.78 (d, J 14.3 Hz, 1H), 8.19 (s, 1H), 8.37 (s, 1H), 12.82 (s (broad), 1H) |
| 105 | 4 | | 1-[(6-phenyl-3H-imidazo[4,5-b]pyridin-7-yl)methyl]-4-propylpyrrolidin-2-one | 335 | 0.78 (t, J 6.90 Hz, 3H), 1.06-1.18 (m, 4H), 1.67 (dd, J 15.81, 7.78 Hz, 1H), 1.98 (m, 1H), 2.12 (dd, J 15.81, 8.5 Hz, 1H), 2.56 (s, 1H), 3.01 (s, 1H), 4.76 (s, 2H), 7.38-7.48 (m, 5H), 8.20 (s, 1H), 8.48 (s, 1H), 13.11 (s (broad), 1H) |
| 106 | A-1§ | | 1-[1-(1H-imidazol-4-yl)propyl]pyrrolidin-2-one | 194 | 1.00 (t, J 7.0, 3H), 1.90-2.10 (m, 4H), 2.30-2.40 (m, 2H), 3.28 (m, 1H), 3.39 (m, 1H), 4.90 (m, 1H), 6.90 (s, 1H), 7.60 (s, 1H) |
| 107 | B-1§ | | 1-[1-(1H-imidazol-4-yl)propyl]pyrrolidin-2-one | 194 | 1.00 (t, J 7.0, 3H), 1.90-2.10 (m, 4H), 2.30-2.40 (m, 2H), 3.28 (m, 1H), 3.39 (m, 1H), 4.90 (m, 1H), 6.90 (s, 1H), 7.60 (s, 1H) |
| 108 | | | 1-[(5-methyl-1H-imidazol-4-yl)methyl]pyrrolidin-2-one | 180 | (DMSO): 1.85 (m, 2H), 2.10 (s, 3H), 2.15 (t, J 7.1 Hz, 2H), 3.20 (t, J 7.1 Hz, 2H), 4.20 (s, 2H), 7.35 (s, 1H) |
| 109 | | | 1-[(2-methyl-1H-imidazol-4-yl)methyl]pyrrolidin-2-one | | (DMSO): 1.90 (m, 2H), 2.25 (t, J 7 Hz and s, 5H), 3.25 (t, J 7 Hz, 2H), 4.20 (s, 2H), 6.75 (s, 1H) |
| 110 | 4 | 1 CF3COOH | 1-(1H-imidazol-4-ylmethyl)-4-propylpyrrolidin-2-one | | (CD3CN): 0.91 (t, J 7.17 Hz, 3H); 1.29-1.43 (m, 4H); 1.95-2.06 (m, 1H overlapped with solvent); 2.33-2.48 (m, 2H); 3.01 (t, J 7.55 Hz, 1H), 3.47 (t, J 8.19 Hz, 1H); 4.48 (s, 2H), 7.29 (s, 1H), 8.43 (s, 1H) |

TABLE 1-continued

| n° | Config | Salt | IUPAC Name | MH+ (M+.) | 1H NMR delta (CDCl3 unless otherwise specified) |
|---|---|---|---|---|---|
| 111 | 4,4 | 1 CF3COOH | 1-({1-[(2-oxo-4-propylpyrrolidin-1-yl)methyl]-1H-imidazol-4-yl}methyl)-4-propylpyrrolidin-2-one | | 0.80-0.95 (m, 6H), 1.25-1.50 (m, 8H), 2.14 (m, 2H), 2.30-2.65 (m, 4H), 3.06 (dd, J 8.0, 16.0 Hz, 2H), 3.56 (t, J 8.0 Hz, 2H), 4.45 (d, J 8.0 Hz, 1H), 4.55 (d, J 8.0 Hz, 1H), 5.50 (s, 2H), 7.19 (s, 1H), 8.62 (s, 1H) |
| 112 | 4 | | 1-[(5-chloro-1H-imidazol-4-yl)methyl]-4-(2,3,5-trifluorophenyl)pyrrolidin-2-one | 330/332 | 2.54 (dd, J 17.0, 7.2 Hz, 1H), 2.85 (dd, J 17.2, 8.7 Hz, 1H), 3.39-3.51 (m, 1H), 3.77-3.92 (m, 2H), 4.43 (d, J 17.0 Hz, 1H), 4.50 (d, J 17.0 Hz, 1H), 6.58-6.72 (m, 1H), 6.79-6.92 (m, 1H), 7.45-7.56 (m, 1H), 10.67-11.13 (s broad, 1H) |
| 113 | 4 | | 1-[(5-bromo-1H-imidazol-4-yl)methyl]-4-(2,3,5-trifluorophenyl)pyrrolidin-2-one | 374/376 | 2.54 (dd, J 8.0, 17.0 Hz, 1H), 2.85 (dd, J 6.0, 16.0 Hz, 1H), 3.41-3.51 (m, 1H), 3.79-3.90 (m, 2H), 4.41 (d, J 15.0 Hz, 1H), 4.53 (d, J 15.0 Hz, 1H), 6.58-6.75 (m, 1H), 6.78-6.99 (m, 1H), 7.43-7.73 (m, 1H), 11.03-11.38 (m, 1H) |
| 114 | | | 1-[(5-bromo-1H-imidazol-4-yl)methyl]-5-chloro-1,3-dihydro-2H-indol-2-one | 326/328/330 | 3.63 (s, 2H), 4.80 (s, 2H), 6.74 (d, J 8.28 Hz, 1H), 7.28 (d, 8.28 Hz, 1H), 7.35 (s, 1H), 7.59 (s, 1H), 12.48 (s, 1H) |
| 115 | | | 1-(1H-imidazol-5-ylmethyl)pyrrolidin-2-one | | 2.00 (m, 2H), 2.89 (t, J 8.2, 2H), 3.44 (t, J 7.0, 2H), 4.42 (s, 2H), 6.94 (s, 1H), 7.58 (s, 1H) |
| 116 | | 1 HCl | 1-[(1-methyl-1H-imidazol-5-yl)methyl]pyrrolidin-2-one | 180 | (DMSO) 1.90 (m, 2H), 2.25 (t, J 8 Hz, 2H), 3.25 (t, J 7.0, 2H), 3.85 (s, 3H), 4.42 (s, 2H), 7.6 (s, 1H), 9.1 (s, 1H) |
| 117 | | | 1-methyl-5-[(2-oxopyrrolidin-1-yl)methyl]-1H-imidazole-4-carbonitrile | 205 | 1.99-2.15 (m, 2H), 2.36-3.48 (m, 2H), 3.37-3.46 (m, 2H), 3.72 (s, 3H), 4.58 (s, 2H), 7.46 (s, 1H) |
| 118 | 4 | 1 HCl | 1-(1H-imidazol-5-ylmethyl)-4-phenylpyrrolidin-2-one | 242 | 2.62 (dd, J 9.0, 17.1 Hz, 1H), 2.84 (dd, J 8.8, 17.1 Hz, 1H), 3.43 (t, J 7.6 Hz, 1H), 3.60-3.70 (m, 1H), 3.83 (t, J 8.7 Hz, 1H), 4.59 (d, J 15.0 Hz, 1H), 4.75 (d, J 15.0 Hz, 1H), 7.13-7.21 (m, 5H), 7.37 (s, 1H), 9.23 (s, 1H), 10.76 (s broad, 1H) |
| 119 | 4 | 1 HCl | 1-[(1-methyl-1H-imidazol-5-yl)methyl]-4-phenylpyrrolidin-2-one | 256 | 2.61 (dd, J 8.0, 17.0 Hz, 1H), 2.85 (dd, J 8.0, 17.0 Hz, 1H), 3.32 (dd, J 8.85, 7.06 Hz, 1H), 3.52-3.80 (m, 2H), 4.00 (s, 3H), 4.50 (d, J 15.8 Hz, 1H), 4.74 (d, J 15.8 Hz, 1H), 7.13-7.38 (m, 5H), 7.46 (s, 1H), 9.56 (s, 1H) |
| 120 | | | 1-[(4-methoxy-1-methyl-1H-imidazol-5-yl)methyl]pyrrolidin-2-one | 210 | 1.87-2.05 (m, 2H), 2.37 (t, J 7.0 Hz, 2H), 3.30 (t, J 7.0 Hz, 2H), 3.57 (s, 3H), 3.91 (s, 3H), 4.38 (s, 2H), 7.05 (s, 1H) |
| 121 | 4 | 1 HCl | 1-[(1-methyl-1H-imidazol-5-yl)methyl]-4-propylpyrrolidin-2-one | 222 | 0.90 (t, J 7.06 Hz, 3H), 1.21-1.47 (m, 4H), 2.09 (dd, J 16.56, 7.86 Hz, 1H), 2.26-2.48 (m, 2H), 2.55 (dd, J 16.56, 8.54 Hz, 1H), 2.91 (dd, J 9.38, 6.94 Hz, 1H), 3.40 (dd, J 9.3, 8.0 Hz, 1H), 3.96 (s, 3H), 4.44 (d, J 15.8 Hz, 1H), 4.61 (d, J 15.8 Hz, 1H), 7.41 (s, 1H), 9.54 (s, 1H) |
| 122 | 4 | | 1-methyl-5-[(2-oxo-4-propylpyrrolidin-1-yl)methyl]-1H-imidazole-4-carbonitrile | | 0.91 (t, J 7 Hz, 3H), 1.35 (m, 4H), 2.08 (dd, J 16.5, 7.8 Hz, 1H), 2.35 (m, 1H), 2.54 (m, 1H), 3.00 (m, 1H), 3.48 (m, 1H), 3.70 (s, 3H), 4.56 (q, J 15.6 Hz, 2H), 7.46 (s, 1H) |
| 123 | 4 | | 1-methyl-5-[(2-oxo-4-propylpyrrolidin-1-yl)methyl]-1H-imidazole-4-carboxamide | 265 | 0.88 (t, J 6.9 Hz, 3H), 1.30 (m, 3H), 2.05 (m, 1H), 2.26 (m, 1H), 2.50 (m, 1H), 2.97 (dd, J 10.4, 6.9 Hz, 1H), 3.49 (dd, J 10.2, 7.9 Hz, 1H), 3.69 (s, 3H), 4.93 (s, 2H), 5.35 (s broad, 1H), 7.04 (s broad, 1H), 7.36 (s, 1H) |
| 124 | 4 | 1 HCl | N-benzyl-2-{5-[(2-oxo-4-propylpyrrolidin-1-yl)methyl]-1H-imidazol-1-yl}acetamide | 355 | (DMSO): 0.84 (t, J 6.94 Hz, 3H), 1.08-1.39 (m, 4H), 1.77-1.97 (m, 1H), 2.07-2.36 (m, 2H), 2.79 (m, 1H), 3.20-3.6 (m, 1H, overlapped with solvent signal), 4.32 (m, 2H), 4.47 (m, 2H), 4.97 (d, J 1.53 Hz, 2H), 7.23-7.38 (m, 5H), 7.62 (d, J 0.61 Hz, 1H), 8.90 (m, 1H), 8.98 (m, 1H) |
| 125 | 4 | 1 CF3COOH | 1-methyl-5-[(2-oxo-4-propylpyrrolidin-1-yl)methyl]-1H-imidazole-2-carbonitrile | 247 | 0.91 (t, J 7.0 Hz, 3H), 1.34 (m, 4H), 2.13 (m, 1H), 2.32 (d, J 7.9 Hz, 1H), 2.57 (m, 1H), 2.89 (dd, J 9.5, 6.9 Hz, 1H), 3.36 (m, 1H), 3.80 (s, 3H), 4.47 (m, 2H), 7.13 (s, 1H) |
| 126 | 4 | | 1-[(4-chloro-1H-imidazol-5-yl)methyl]-4-propylpyrrolidin-2-one | 242/244 | 0.91 (t, J 7.30 Hz, 3H), 1.24-1.35 (m, 2H), 1.36-1.44 (m, 2H), 2.06 (dd, J 16.62, 7.81 Hz, 1H), 2.37 (m, 1H), 2.51 (dd, J 16.62, 8.81 Hz, 1H), 3.08 (dd, J 9.82, 6.92 Hz, 1H), 3.54 (dd, J 9.57, 8.18 Hz, 1H), 4.35 (m, 2H), 7.44 (s, 1H), 10.78 (s, 1H) |

TABLE 1-continued

| n° | Config | Salt | IUPAC Name | MH⁺ (M⁺.) | ¹H NMR delta (CDCl₃ unless otherwise specified) |
|---|---|---|---|---|---|
| 127 | 4 | | 1-methyl-5-{[2-oxo-4-(2,3,5-trifluorophenyl)pyrrolidin-1-yl]methyl}-1H-imidazole-4-carbonitrile | 335 | (DMSO): 2.59 (dd, J 16.93, 5.43 Hz, 1H), 2.89 (dd, J 17.18, 7.07 Hz, 1H), 3.42 (m, 1H), 3.76 (d, J 2.27 Hz, 3H), 3.83 (s, 2H), 4.66 (s, 2H), 6.65 (dd, J 5.31, 2.78 Hz, 1H), 6.80-6.90 (m, 1H), 7.50 (s, 1H) |
| 128 | 4 | | 1-[(4-bromo-1-methyl-1H-imidazol-5-yl)methyl]-4-propylpyrrolidin-2-one | 300/302 | (DMSO): 0.90 (t, J 7.20 Hz, 3H), 1.24-1.44 (m, 4H), 2.06 (dd, J 16.67, 7.83 Hz, 1H), 2.31 (m, 1H), 2.52 (dd, J 16.93, 8.72 Hz, 1H), 2.93 (dd, J 9.85, 6.82 Hz, 1H), 3.42 (dd, J 9.60, 8.08 Hz, 1H), 3.65 (s, 3H), 4.44 (m, 2H), 7.37 (s, 1H) |
| 129 | 4 | | 1-[(2,4-dichloro-1-methyl-1H-imidazol-5-yl)methyl]-4-propylpyrrolidin-2-one | 290/292/294 | 0.91 (t, J 7.07 Hz, 3H), 1.26-1.36 (m, 2H), 1.36-1.45 (m, 2H), 2.07 (dd, J 16.67, 7.96 Hz, 1H), 2.32 (m, 1H), 2.52 (dd, J 16.67, 8.59 Hz, 1H), 2.93 (dd, J 9.60, 6.95 Hz, 1H), 3.45 (t, J 9.35 Hz, 1H), 3.58 (s, 3H), 4.46 (m, 2H), 4.36 (d, J 15.6 Hz, 1H), 4.47 (d, J 15.6 Hz, 1H) |
| 130 | 4 | 1 CF₃COOH | benzyl 1-methyl-5-[(2-oxo-4-propylpyrrolidin-1-yl)methyl]-1H-imidazol-2-ylcarbamate | 371 | 0.92 (t, J 7.18 Hz, 3H), 1.24-1.37 (m, 2H), 1.37-1.49 (m, 2H), 2.14 (dd, J 16.87, 7.81 Hz, 1H), 2.37 (m, 1H), 2.60 (dd, J 16.87, 8.56 Hz, 1H), 2.91 (t, J 7.68 Hz, 1H), 3.38 (t, J 8.31 Hz, 1H), 3.60 (s, 3H), 4.38 (d, J 15.7 Hz, 1H), 4.55 (d, J 15.7 Hz, 1H), 5.24 (s, 2H), 7.02 (s, 1H), 7.36 (m, 5H), 8.62 (s (broad), 2H) |
| 131 | 4 | | 1-[(4-chloro-1-methyl-1H-imidazol-5-yl)methyl]-4-propylpyrrolidin-2-one | 256/258 | 0.90 (t, J 7.20 Hz, 3H), 1.24-1.41 (m, 4H), 2.06 (dd, J 16.67, 7.96 Hz, 1H), 2.31 (m, 1H), 2.52 (dd, J 16.93, 8.72 Hz, 1H), 2.93 (dd, J 9.85, 6.82 Hz, 1H), 3.42 (dd, J 9.85, 8.08 Hz, 1H), 3.63 (s, 3H), 4.40 (d, J 15.4 Hz, 1H), 4.49 (d, J 15.4 Hz, 1H), 7.31 (s, 1H) |
| 132 | 4 | 1 CF₃COOH | 1-[(2-bromo-1-methyl-1H-imidazol-5-yl)methyl]-4-propylpyrrolidin-2-one | 300/302 | 0.91 (t, J 7.30 Hz, 3H), 1.30-1.45 (m, 4H), 2.13 (dd, J 17.12, 8.18 Hz, 1H), 2.35 (m, 1H), 2.59 (dd, J 16.87, 8.81 Hz, 1H), 2.91 (dd, J 9.57, 7.05 Hz, 1H), 3.39 (dd, J 9.57, 8.06 Hz, 1H), 3.65 (s, 3H), 4.37 (d, J 15.7 Hz, 1H), 4.54 (d, J 15.4 Hz, 1H), 7.21 (s, 1H) |
| 133 | 4 | 1 CF₃COOH | 1-[(2-chloro-1-methyl-1H-imidazol-5-yl)methyl]-4-propylpyrrolidin-2-one | 256/258 | 0.92 (t, J 7.18 Hz, 3H), 1.30 (m, 2H), 1.42 (m, 2H), 2.18 (dd, J 17.12, 8.18 Hz, 1H), 2.38 (m, 1H), 2.64 (dd, J 16.87, 8.69 Hz, 1H), 2.96 (dd, J 9.57, 7.05 Hz, 1H), 3.43 (m, 1H), 3.66 (s, 3H), 4.48 (m, 2H), 7.15 (s, 1H) |
| 134 | | | 5-chloro-1-(1H-imidazol-5-ylmethyl)-1,3-dihydro-2H-indol-2-one | 248/250 | 3.60 (s, 2H), 4.73 (s, 2H), 7.04 (s, 1H), 7.05 (d, J 8.3 Hz, 1H), 7.25 (d, J 8.3 Hz, 1H), 7.53 (s, 1H), 11.94 (s, 1H) |
| 135 | 4 | | 1-[(2,4-dichloro-1H-imidazol-5-yl)methyl]-4-(2,3,5-trifluorophenyl)pyrrolidin-2-one | 364/366/368 | 2.60 (dd, J 7.5, 17.1 Hz, 1H), 2.91 (dd, J 17.07, 8.78 Hz, 1H), 3.47 (dd, J 10.0, 13.0 Hz, 1H), 3.83-3.92 (m, 2H), 4.41 (d, J 15.3 Hz, 1H) 4.48 (d, J 15.3 Hz, 1H), 6.67-6.71 (m, 1H), 6.83-6.90 (m, 1H), 11.63 (s (broad), 1H) |
| 136 | 4 | | 1-[(2,4-dichloro-1-methyl-1H-imidazol-5-yl)methyl]-4-(2,3,5-trifluorophenyl)pyrrolidin-2-one | 378/380/382 | 2.57 (m, 1H), 2.86 (m, 1H), 3.35 (m, 1H), 3.63 (s, 3H), 3.74-3.83 (m, 2H), 4.48 (d, J 15.8 Hz, 1H) 4.54 (d, J 15.8 Hz, 1H), 6.67-6.71 (m, 1H), 6.83-6.90 (m, 1H) |
| 137 | 4 | | 1-[(2-chloro-1-methyl-1H-imidazol-5-yl)methyl]-4-(2,3,5-trifluorophenyl)pyrrolidin-2-one | 344/346 | 2.58 (dd, J 17.12, 7.81 Hz, 1H), 2.88 (dd, J 17.0, 9.19 Hz, 1H), 3.28 (dd, J 9.82, 6.55 Hz, 1H), 3.58 (s, 3H), 3.68 (t, J 9.54 Hz, 1H), 3.74-3.82 (m, 1H), 4.47 (d, J 15.8 Hz, 1H), 4.51 (d, J 15.8 Hz, 1H), 6.60-6.64 (m, 1H), 6.82-6.90 (m, 1H), 6.91 (s, 1H) |
| 138 | 4 | 1 CF₃COOH | 1-[(4-bromo-1-methyl-1H-imidazol-5-yl)methyl]-4-(2,3,5-trifluorophenyl)pyrrolidin-2-one | 388/390 | 2.59 (dd, J 17.07, 7.53 Hz, 1H), 2.88 (dd, J 17.07, 8.78 Hz, 1H), 3.37 (dd, J 10.8, 3.01 Hz, 1H), 3.74-3.84 (m, 5H with a s, 3H at 3.76), 4.55 (s, 2H), 6.63 (s (broad), 1H), 6.60-6.68 (m, 1H), 6.82-6.90 (m, 1H), 7.74 (s, 1H) |
| 139 | | | 5-chloro-1-[(1-methyl-1H-imidazol-5-yl)methyl]-1,3-dihydro-2H-indol-2-one | 262/264 | 3.56 (s, 2H), 3.64 (s, 3H), 4.89 (s, 2H), 6.88 (d, J 8.53 Hz, 1H), 7.13 (s, 1H), 7.20 (d, J 8.28 Hz, 1H), 7.23 (s, 1H), 7.40 (s, 1H) |
| 140 | 4 | 1 CF₃COOH | 1-[(4-chloro-1-methyl-1H-imidazol-5-yl)methyl]-4-(2,3,5-trifluorophenyl)pyrrolidin-2-one | 344 | 2.57 (dd, J 17.3, 6.7 Hz, 1H), 2.87 (dd, J 17.3, 6.7 Hz, 1H), 3.36 (m, 1H), 3.72 (s, 3H), 3.74-3.82 (m, 2H), 4.54 (s, 2H), 6.59-6.66 (m, 1H), 6.82-6.89 (m, 1H), 7.53 (s, 1H) |
| 141 | 4 | | 1-(1H-indol-2-ylmethyl)-4-propylpyrrolidin-2-one | 257 | 0.83 (t, 7.05 Hz, 3H), 1.27 (m, 4H), 2.08 (m, 1H), 2.23 (m, 1H), 2.54 (dd, 16.37, 8.56 Hz, |

TABLE 1-continued

| n° | Config | Salt | IUPAC Name | MH+ (M+.) | 1H NMR delta (CDCl3 unless otherwise specified) |
|---|---|---|---|---|---|
| | | | | | 1H), 2.86 (dd, 9.57, 6.80 Hz, 1H), 3.34 (m, 1H), 4.63 (m, 2H), 7.13 (m, 2H), 7.21 (m, 1H), 7.38 (d, 8.06 Hz, 1H), 7.68 (d, 8.06 Hz, 1H), 8.32 (s, 1H) |
| 142 | 4 | | 1-(1H-indol-3-ylmethyl)-4-propylpyrrolidin-2-one | 257 | 0.83 (t, 7.04 Hz, 3H), 1.25 (m, 4H), 2.09 (dd, 16.35, 7.80 Hz, 1H), 2.22 (m, 1H), 2.54 (dd, 16.35, 8.55 Hz, 1H), 2.86 (dd, 9.31, 7.04 Hz, 1H), 3.34 (t, 8.80 Hz, 1H), 4.62 (m, 2H), 7.16 (m, 3H), 7.37 (d, 8.05 Hz, 1H), 7.68 (d, 7.80 Hz, 1H), 8.54 (s, 1H) |
| 143 | 4 | | 3-[(2-oxo-4-propylpyrrolidin-1-yl)methyl]-1H-indole-5-carbonitrile | 282 | 0.85 (t, 7.18 Hz, 3H), 1.29 (m, 4H), 2.11 (dd, 16.62, 7.81 Hz, 1H), 2.28 (m, 1H), 2.57 (dd, 16.62, 8.69 Hz, 1H), 2.89 (dd, 9.57, 6.80 Hz, 1H), 3.37 (m, 1H), 4.62 (m, 2H), 7.32 (d, 2.27 Hz, 1H), 7.44 (m, 2H), 8.04 (s, 1H), 9.35 (s, 1H) |
| 144 | 4 | | 1-[(2-methyl-1H-indol-3-yl)methyl]-4-propylpyrrolidin-2-one | 271 | 0.83 (t, 7.04 Hz, 3H), 1.26 (m, 4H), 2.07 (dd, 16.60, 7.92 Hz, 1H), 2.20 (m, 1H), 2.45 (s, 3H), 2.52 (dd, 16.35, 8.55 Hz, 1H), 2.83 (dd, 9.81, 6.92 Hz, 1H), 3.30 (m, 1H), 4.58 (m, 2H), 7.11 (m, 2H), 7.30 (m, 1H), 7.57 (d, 7.55 Hz, 1H), 8.07 (s, 1H) |
| 145 | 4 | | 1-[(7-methoxy-1H-indol-3-yl)methyl]-4-propylpyrrolidin-2-one | 287 | 0.83 (t, 7.17 Hz, 3H), 1.27 (m, 4H), 2.08 (dd, 16.35, 8.05 Hz, 1H), 2.21 (m, 1H), 2.54 (dd, 16.60, 8.43 Hz, 1H), 2.85 (dd, 9.56, 6.92 Hz, 1H), 3.33 (m, 1H), 3.95 (s, 3H), 4.60 (m, 2H), 6.66 (d, 7.80 Hz, 1H), 7.04 (t, 7.80 Hz, 1H), 7.12 (d, 2.26 Hz, 1H), 7.27 (m, 1H), 8.38 (s, 1H) |
| 146 | 4 | 1 CF3COOH | 1-[(6-nitro-1H-indol-3-yl)methyl]-4-propylpyrrolidin-2-one | 302 | 0.84 (t, 7.17 Hz, 3H), 1.28 (m, 4H), 2.12 (dd, 16.60, 7.80 Hz, 1H), 2.28 (m, 1H), 2.58 (dd, 16.60, 8.80 Hz, 1H), 2.90 (dd, 9.56, 6.79 Hz, 1H), 3.38 (m, 1H), 4.65 (m, 2H), 7.48 (d, 2.52 Hz, 1H), 7.74 (d, 8.80 Hz, 1H), 8.00 (dd, 8.80, 2.01 Hz, 1H), 8.36 (d, 2.01 Hz, 1H), 9.37 (s, 1H) |
| 147 | 4 | 1 CF3COOH | 4-propyl-1-{[6-(trifluoromethyl)-1H-indol-3-yl]methyl}pyrrolidin-2-one | 325 | 0.84 (t, 7.04 Hz, 3H), 1.27 (m, 4H), 2.10 (dd, 16.60, 7.92 Hz, 1H), 2.24 (m, 1H), 2.57 (dd, 16.60, 8.55 Hz, 1H), 2.86 (dd, 9.56, 6.79 Hz, 1H), 3.34 (dd, 9.31, 7.92 Hz, 1H), 4.63 (m, 2H), 7.31 (d, 2.26 Hz, 1H), 7.37 (dd, 8.55, 0.88 Hz, 1H), 7.67 (m, 1H), 7.77 (d, 8.55 Hz, 1H), 8.33 (m, 1H) |
| 148 | 4 | 1 CF3COOH | 1-[(5-nitro-1H-indol-3-yl)methyl]-4-propylpyrrolidin-2-one | 302 | 0.85 (t, 7.17 Hz, 3H), 1.29 (m, 4H), 2.19 (dd, 16.60, 7.92 Hz, 1H), 2.33 (m, 1H), 2.66 (dd, 16.60, 8.55 Hz, 1H), 2.99 (dd, 9.56, 6.79 Hz, 1H), 3.46 (m, 1H), 4.66 (m, 2H), 7.37 (d, 2.01 Hz, 1H), 7.44 (d, 8.80 Hz, 1H), 8.10 (dd, 8.80, 2.01 Hz, 1H), 8.61 (d, 2.01 Hz, 1H), 9.22 (s, 1H) |
| 149 | 4 | 1 CF3COOH | 1-[(7-fluoro-1H-indol-3-yl)methyl]-4-propylpyrrolidin-2-one | 275 | 0.84 (t, 7.18 Hz, 3H), 1.26 (m, 4H), 2.10 (dd, 16.37, 7.93 Hz, 1H), 2.24 (m, 1H), 2.55 (dd, 16.37, 8.44 Hz, 1H), 2.86 (dd, 9.57, 6.67 Hz, 1H), 3.34 (m, 1H), 4.61 (m, 2H), 6.91 (dd, 11.08, 7.81 Hz, 1H), 7.02 (td, 7.81, 4.78 Hz, 1H), 7.19 (d, 2.27 Hz, 1H), 7.44 (d, 7.81 Hz, 1H), 8.61 (s, 1H) |
| 150 | 4 | 1 CF3COOH | 1-[(5-chloro-2-methyl-1H-indol-3-yl)methyl]-4-propylpyrrolidin-2-one | 305/307 | 0.85 (m, 3H), 1.28 (m, 4H), 2.17 (m, 1H), 2.27 (m, 1H), 2.44 (s, 3H), 2.63 (m, 1H), 2.87 (dd, 9.82, 6.80 Hz, 1H), 3.34 (m, 1H), 4.54 (m, 2H), 7.09 (dd, 8.56, 2.01 Hz, 1H), 7.19 (m, 1H), 7.50 (m, 1H), 8.05 (s, 1H) |
| 151 | 4, 1 | | 1-[1H-indol-3-yl(phenyl)methyl]-4-propylpyrrolidin-2-one | 333 | 0.83 (m, 3H), 1.29 (m, 4H), 2.17 (m, 2H), 2.60 (m, 1H), 2.85 (m, 1H), 3.37 (m, 1H), 6.85 (m, 1H), 6.92 (d, 2.52 Hz, 1H), 7.05 (m, 1H), 7.19 (m, 1H), 7.35 (m, 6H), 8.14 (s, 1H) |
| 152 | 4, 1 | | 1-[1-(1H-indol-3-yl)propyl]-4-propylpyrrolidin-2-one | 285 | 0.86 (t, 7.07 Hz, 3H), 1.02 (t, 7.20 Hz, 3H), 1.25 (m, 6H), 2.01 (m, 1H), 2.22 (m, 1H), 2.51 (m, 1H), 2.72 (m, 1H), 3.16 (m, 1H), 5.53 (m, 1H), 7.10 (m, 2H), 7.20 (m, 1H), 7.36 (d, 8.08 Hz, 1H), 7.67 (m, 1H), 8.23 (s Hz, 1H) |
| 153 | 4, 1 | | 1-[2-furyl(1H-indol-3-yl)methyl]-4-propylpyrrolidin-2-one | 323 | 0.84 (m, 3H), 1.27 (m, 4H), 2.13 (m, 2H), 2.57 (m, 1H), 3.03 (dd, 9.60, 6.57 Hz, 1H), 3.30 (dd, 9.60, 7.58 Hz, 1H), 6.32 (d, 2.53 Hz, 1H), 6.38 (s, 1H), 7.11 (m, 2H), 7.22 (t, |

TABLE 1-continued

| n° | Config | Salt | IUPAC Name | MH+ (M+.) | 1H NMR delta (CDCl3 unless otherwise specified) |
|---|---|---|---|---|---|
| 154 | 1, 4 | | 3-[(2-oxo-4-propylpyrrolidin-1-yl)(phenyl)methyl]-1H-indole-5-carbonitrile | 358 | 7.45 Hz, 1H), 7.38 (d, 8.08 Hz, 1H), 7.43 (s, 1H), 7.55 (d, 8.08 Hz, 1H), 8.25 (s, 1H) 0.87 (m, 3H), 1.31 (m, 4H), 2.16 (m, 1H), 2.34 (m, 1H), 2.64 (m, 1H), 2.83 (m, 1H), 3.35 (m, 1H), 6.82 (m, 1H), 7.12 (dd, 10.04, 1.88 Hz, 1H), 7.35 (m, 6H), 7.63 (m, 1H), 8.53 (m, 1H) |
| 155 | 4 | | 1-(1H-indol-4-ylmethyl)-4-propylpyrrolidin-2-one | 257 | 0.83 (t, 7.20 Hz, 3H), 1.26 (m, 4H), 2.12 (m, 1H), 2.24 (m, 1H), 2.57 (dd, 16.17, 8.46 Hz, 1H), 2.81 (dd, 9.85, 6.82 Hz, 1H), 3.28 (dd, 9.60, 8.08 Hz, 1H), 4.73 (m, 2H), 6.66 (m, 1H), 6.97 (d, 7.07 Hz, 1H), 7.14 (m, 1H), 7.20 (t, 2.78 Hz, 1H), 7.36 (d, 8.34 Hz, 1H), 8.55 (s, 1H) |
| 156 | 4 | | 1-(1H-indol-7-ylmethyl)-4-propylpyrrolidin-2-one | 257 | 0.85 (t, 7.20 Hz, 3H), 1.28 (m, 4H), 2.09 (dd, 16.67, 8.08 Hz, 1H), 2.28 (m, 1H), 2.53 (dd, 16.67, 8.84 Hz, 1H), 2.97 (dd, 9.85, 6.95 Hz, 1H), 3.45 (dd, 9.850, 8.84 Hz, 1H), 4.60 (m, 2H), 6.53 (dd, 3.03, 2.15 Hz, 1H), 7.01 (m, 2H), 7.24 (m, 1H), 7.61 (d, 7.33 Hz, 1H), 10.02 (s, 1H) |
| 157 | 4 | | 1-(isoxazol-4-ylmethyl)-4-propylpyrrolidin-2-one | 209 | (DMSO): 0.86 (t, J 7.15 Hz, 3H), 1.21-1.36 (m, 4H), 1.95 (dd, J 16.06, 7.53 Hz, 1H), 2.27 (m, 1H), 2.38 (dd, J 8.78, 16.06 Hz, 1H), 2.91 (dd, J 9.29, 6.78 Hz, 1H), 3.39 (t, J 8.28 Hz, 1H), 4.25 (s, 2H), 8.53 (s, 1H), 8.88 (s, 1H) |
| 158 | 4 | | 1-[(1-phenyl-1H-pyrazol-4-yl)methyl]-4-(2,3,5-trifluorophenyl)pyrrolidin-2-one | 372 | 2.56 (dd, J 16.87, 7.55 Hz, 1H), 2.86 (dd, J 16.87, 8.94 Hz, 1H), 3.36 (dd, J 10.8, 14.7 Hz, 1H), 3.74-3.86 (m, 2H), 4.45 (d, J 14.8 Hz, 1H), 4.51 (d, J 14.8 Hz, 1H), 6.68 (m, 1H), 6.82 (m, 1H), 7.29 (t, J 7.5 Hz, 1H), 7.45 (t, J 7.4 Hz, 2H), 7.64-7.69 (m, 3H), 7.92 (s, 1H) |
| 159 | 4 | | 1-[(1-methyl-1H-pyrazol-4-yl)methyl]-4-(2,3,5-trifluorophenyl)pyrrolidin-2-one | 310 | 2.52 (dd, J 16.87, 7.55 Hz, 1H), 2.84 (dd, J 16.87, 9.06 Hz, 1H), 3.30 (dd, J 9.57, 6.17 Hz, 1H), 3.70-3.82 (m, 2H), 3.88 (s, 3H), 4.33 (d, J 14.8 Hz, 1H), 4.43 (d, J 14.8 Hz, 1H), 6.64 (m, 1H), 6.83 (m, 1H), 7.35 (s, 1H), 7.41 (s, 1H) |
| 160 | 4 | | 1-[(1-benzyl-1H-pyrazol-4-yl)methyl]-4-(2,3,5-trifluorophenyl)pyrrolidin-2-one | 386 | 2.51 (dd, J 16.87, 7.30 Hz, 1H), 2.83 (dd, J 16.87, 9.06 Hz, 1H), 3.28 (dd, J 9.57, 6.29 Hz, 1H), 3.69 (dd~t, J 9.0 Hz, 1H), 3.82 (m, 1H), 4.33 (d, J 15.1 Hz, 1H), 4.43 (d, J 15.1 Hz, 1H), 5.27 (s, 2H), 6.64 (m, 1H), 6.83 (m, 1H), 7.20-7.22 (m, 2H), 7.30-7.37 (m, 4H), 7.47 (s, 1H) |
| 161 | 4 | | 4-(2,3,5-trifluorophenyl)-1-[(1,3,5-trimethyl-1H-pyrazol-4-yl)methyl]pyrrolidin-2-one | 338 | 2.20 (s, 3H), 2.22 (s, 3H), 2.52 (dd, J 16.87, 7.30 Hz, 1H), 2.84 (dd, J 16.87, 9.32 Hz, 1H), 3.19 (dd, J 9.82, 6.17 Hz, 1H), 3.60 (t, J 9.1 Hz, 1H), 3.69-3.71 (m, 4H with s at 3.71, 3H), 4.25 (d, J 14.8 Hz, 1H), 4.37 (d, J 14.8 Hz, 1H), 6.60 (m, 1H), 6.82 (m, 1H) |
| 162 | 4 | | 4-phenyl-1-(1H-pyrazol-4-ylmethyl)pyrrolidin-2-one | 242 | 2.58 (dd, J 16.67, 8.46 Hz, 1H), 2.84 (dd, J 16.93, 9.09 Hz, 1H), 3.33 (dd, J 9.35, 6.95 Hz, 1H), 3.53 (m, 1H), 3.69 (m, 1H), 4.45 (s, 2H), 7.17 (d, J 8.3 Hz, 2H), 7.24-7.28 (m, 2H including solvent signal), 7.31 (t, J 7.1 Hz, 2H), 7.56 (s, 2 H) |
| 163 | 4 | | 1-({1-[(4-methylphenyl)sulfonyl]-1H-pyrazol-4-yl}methyl)-4-(2,3,5-trifluorophenyl)pyrrolidin-2-one | 450 | 2.43 (s, 3H), 2.56 (dd, J 16.87, 7.93 Hz, 1H), 2.84 (dd, J 16.87, 9.19 Hz, 1H), 3.28 (dd, J 9.57, 6.80 Hz, 1H), 3.68 (t, J 9.1 Hz, 1H), 3.80 (m, 1H), 4.38 (m, 2H), 6.65-6.69 (m, 1H), 6.83-6.89 (m, 1H), 7.34 (d, J 8.31 Hz, 2H), 7.66 (s, 1H), 7.89 (d, J 8.31 Hz, 2H), 8.04 (s, 1H) |
| 164 | 4 | | 1-(1H-pyrazol-4-ylmethyl)-4-(2,3,5-trifluorophenyl)pyrrolidin-2-one | 296 | 2.55 (dd, J 16.87, 7.55 Hz, 1H), 2.86 (dd, J 16.87, 8.94 Hz, 1H), 3.31 (dd, J 9.32, 6.29 Hz, 1H), 3.68-3.84 (m, 2H), 4.43 (d, J 15.1 Hz, 1H), 4.50 (d, J 15.1 Hz, 1H), 6.63-6.65 (m, 1H), 6.79-6.86 (m, 1H), 7.67 (s (broad), 2H), 10.74 (s (broad), 1H) |

TABLE 1-continued

| n° | Config | Salt | IUPAC Name | MH⁺ (M⁺·) | ¹H NMR delta (CDCl₃ unless otherwise specified) |
|---|---|---|---|---|---|
| 165 | 4 | | 1-[(5-chloro-1,3-dimethyl-1H-pyrazol-4-yl)methyl]-4-(2,3,5-trifluorophenyl)pyrrolidin-2-one | 358/360 | 2.23 (s, 3H), 2.54 (dd, J 16.93, 7.83 Hz, 1H), 2.84 (dd, J 16.93, 9.22 Hz, 1H), 3.21 (dd, J 9.85, 6.69 Hz, 1H), 3.63 (t, J 9.3 Hz, 1H), 3.73-3.81 (m, 4H with s at 3.77 ppm), 4.38 (d, J 15.4 Hz, 1H), 4.34 (d, J 15.4 Hz, 1H), 6.66 (m, 1H), 6.83 (m, 1H) |
| 166 | 4 | | 1-[(1-chloro-1H-pyrazol-4-yl)methyl]-4-(2,3,5-trifluorophenyl)pyrrolidin-2-one | 330/332 | 2.53 (dd, J 17.43, 7.71 Hz, 1H), 2.86 (dd, J 17.18, 9.09 Hz, 1H), 3.50 (dd, J 9.60, 6.32 Hz, 1H), 3.86 (m, 1H), 3.91 (t, J 8.59 Hz, 3H), 5.45 (d, J 13.9 Hz, 1H), 4.50 (d, J 13.9 Hz, 1H), 6.55-6.60 (m, 1H), 6.80-6.90 (m, 1H), 7.44 (s, 1H), 7.61 (s, 1H) |
| 167 | 4 | | 1-[(3,5-dimethyl-1H-pyrazol-4-yl)methyl]-4-(2,3,5-trifluorophenyl)pyrrolidin-2-one | 324 | 2.26 (s, 6H), 2.54 (dd, J 16.95, 7.67 Hz, 1H), 2.85 (dd, J 16.55, 9.08 Hz, 1H), 3.19 (dd, J 9.69, 6.46 Hz, 1H), 3.61 (t, J 9.3 Hz, 1H), 3.72-3.79 (m, 1H), 4.31 (d, J 14.1 Hz, 1H), 4.38 (d, J 14.1 Hz, 1H), 6.60-6.65 (d, J 6.86 Hz, 1H), 6.80-6.85 (m, 1H) |
| 168 | 4 | | 1-[(3-methyl-1H-pyrazol-4-yl)methyl]-4-(2,3,5-trifluorophenyl)pyrrolidin-2-one | 310 | 2.31 (s, 3H), 2.54 (dd, J 16.87, 7.55 Hz, 1H), 2.85 (dd, J 16.87, 9.06 Hz, 1H), 3.25 (dd, J 9.57, 6.42 Hz, 1H), 3.67 (t, J 8.8 Hz, 1H), 3.72-3.83 (m, 1H), 4.35 (d, J 14.9 Hz, 1H), 4.43 (d, J 14.9 Hz, 1H), 6.60-6.65 (m, 1H), 6.80-6.85 (m, 1H), 7.46 (s, 1H) |
| 169 | 4 | | 1-[(5-amino-1,3-dimethyl-1H-pyrazol-4-yl)methyl]-4-(2,3,5-trifluorophenyl)pyrrolidin-2-one | 339 | 2.15 (s, 3H), 2.50 (dd, J 16.93, 7.07 Hz, 1H), 2.83 (dd, J 16.93, 8.84 Hz, 1H), 3.35 (dd, J 9.35, 5.68 Hz, 1H), 3.58 (s, 3H), 3.74-3.86 (m, 2H), 4.12 (d, J 15.4 Hz, 1H), 4.22-4.25 (m, 3H), 6.60-6.65 (m, 1H), 6.80-6.85 (m, 1H) |
| 170 | 4 | 1 CF₃COOH | 1-[(5-amino-1-methyl-1H-pyrazol-4-yl)methyl]-4-propylpyrrolidin-2-one | 237 | (D₂O): 0.81 (t, J 7.20 Hz, 3H), 1.13-1.27 (m, 2H), 1.26-1.35 (m, 2H), 2.11 (dd, J 17.18, 6.95 Hz, 1H), 2.35 (m, 1H), 2.56 (dd, J 16.93, 8.84 Hz, 1H), 3.01 (dd, J 10.11, 6.06 Hz, 1H), 3.47 (dd, J 10.11, 8.08 Hz, 1H), 3.65 (s, 3H), 4.15 (d, J 15.6 Hz, 1H), 4.24 (d, J 15.6 Hz, 1H), 7.59 (s, 1H) |
| 171 | A-4§ | | (−)-1-(1H-pyrazol-4-ylmethyl)-4-(2,3,5-trifluorophenyl)pyrrolidin-2-one | 296 | 2.55 (dd, J 16.81, 7.65 Hz, 1H), 2.86 (dd, J 16.81, 8.91 Hz, 1H), 3.31 (dd, J 9.54, 6.27 Hz, 1H), 3.70-3.85 (m, 2H), 4.42 (d, J 14.8 Hz, 1H), 4.50 (d, J 14.8 Hz, 1H), 6.60-6.70 (m, 1H), 6.80-6.85 (m, 1H), 7.57 (s, 2H), 11.02 (s (broad), 1H) |
| 172 | B-4§ | | (+)-1-(1H-pyrazol-4-ylmethyl)-4-(2,3,5-trifluorophenyl)pyrrolidin-2-one | 296 | 2.55 (dd, J 16.81, 7.65 Hz, 1H), 2.86 (dd, J 16.81, 8.91 Hz, 1H), 3.31 (dd, J 9.54, 6.27 Hz, 1H), 3.70-3.85 (m, 2H), 4.42 (d, J 14.8 Hz, 1H), 4.50 (d, J 14.8 Hz, 1H), 6.60-6.70 (m, 1H), 6.80-6.85 (m, 1H), 7.57 (s, 2H), 11.12 (s (broad), 1H) |
| 173 | | 1 H₂O | 1-(1H-pyrazol-4-ylmethyl)-1,3-dihydro-2H-indol-2-one | 214 | (DMSO): 3.58 (s, 2H), 4.74 (s, 2H), 6.99 (t, J 7.1 Hz, 1H), 7.05 (d, J 7.58 Hz, 1H), 7.20-7.27 (m, 2H), 7.47 (s (broad), 1H), 7.70 (s (broad), 1H), 7.90 (s (broad), 1H), 12.71 (m, 1H) |
| 174 | | | 5-chloro-1-(1H-pyrazol-4-ylmethyl)-1,3-dihydro-2H-indol-2-one | 248/250 | (DMSO): 3.64 (s, 2H), 4.86 (s, 2H), 6.96 (d, J 8.28 Hz, 1H), 7.29 (d, J 8.53 Hz, 1H), 7.32 (s, 1H), 7.61 (s (broad), 2H), 12.66 (m, 1H) |
| 175 | | | 5-chloro-1-({1-[(4-methylphenyl)sulfonyl]-1H-pyrazol-4-yl}methyl)-1,3-dihydro-2H-indol-2-one | 402/404 | (DMSO): 2.38 (s, 3H), 3.62 (s, 2H), 4.74 (s, 2H), 6.96 (d, J 8.28 Hz, 1H), 7.26 (d, J 8.56 Hz, 1H), 7.33 (s, 1H), 7.45 (d, J 8.0 Hz, 2H), 7.77-7.83 (m, 2H), 8.46 (s, 1H) |
| 176 | 4 | | 1-{[5-chloro-1-methyl-3-(trifluoromethyl)-1H-pyrazol-4-yl]methyl}-4-propylpyrrolidin-2-one | 324/326 | 0.89 (t, J 7.3 Hz, 3H), 1.33 (m, 4H), 2.11 (dd, J 16.6, 8.1 Hz, 1H), 2.30 (m, 1H), 2.57 (dd, J 16.9, 8.8 Hz, 1H), 2.82 (dd, J 9.6, 7.1 Hz, 1H), 3.29 (m, 1H), 3.90 (s, 3H), 4.45 (q, J 15.1 Hz, 2H) |
| 177 | 4 | 2 CF₃COOH | 1-[(5-amino-1H-pyrazol-4-yl)methyl]-4-(2,3,5-trifluorophenyl)pyrrolidin-2-one | 311 | (DMSO-CDCl₃): 2.61 (dd, J 17.0, 7.7 Hz, 1H), 2.91 (dd, J 17.0, 8.7 Hz, 1H), 3.40 (dd, J 9.2, 6.7 Hz, 1H), 3.75-3.92 (m, 2H), 4.28-4.35 (m, 2H overlapped with solvent signal), 6.63-6.65 (m, 1H), 6.79-6.86 (m, 1H), 7.26 (m, 1H overlapped with solvent signal), 7.46 (s, 2H) |
| 178 | 4 | 1 CF₃COOH | 1-[(1-benzyl-5-chloro-1H-pyrazol-4-yl)methyl]-4-propylpyrrolidin-2-one | 332/334 | 0.89 (t, J 7.3 Hz, 3H), 1.32 (m, 4H), 2.07 (dd, J 16.56, 7.78 Hz, 1H), 2.29 (m, 1H), 2.52 (dd, J 16.56, 8.66 Hz, 1H), 2.87 (dd, J |

TABLE 1-continued

| n° | Config | Salt | IUPAC Name | MH+ (M+.) | ¹H NMR delta (CDCl₃ unless otherwise specified) |
|---|---|---|---|---|---|
| | | | | | 9.54, 6.78 Hz, 1H), 3.34 (m, 1H), 4.30 (s, 2H), 5.32 (s, 2H), 7.21 (d, J 7.03 Hz, 2H), 7.28-7.37 (m, 3H), 7.51 (s, 1H) |
| 179 | 4 | | 1-[(1,3-dimethyl-1H-pyrazol-5-yl)methyl]-4-(2,3,5-trifluorophenyl)pyrrolidin-2-one | 324 | 2.22 (s, 3H), 2.58 (dd, J 16.93, 8.08 Hz, 1H), 2.86 (dd, J 17.18, 9.22 Hz, 1H), 3.27 (dd, J 9.60, 6.82 Hz, 1H), 3.60-3.70 (m, 1H), 3.79 (m, 4H), 4.47 (d, J 15.4 Hz, 1H), 4.52 (d, J 15.4 Hz, 1H), 5.95 (s, 1H), 6.60-6.70 (m, 1H), 6.80-6.90 (m, 1H) |
| 180 | 4 | | 1-({1-[(4-methylphenyl)sulfonyl]-1H-pyrazol-5-yl}methyl)-4-(2,3,5-trifluorophenyl)pyrrolidin-2-one | 450 | |
| 181 | 4 | | 1-(1H-pyrazol-5-ylmethyl)-4-(2,3,5-trifluorophenyl)pyrrolidin-2-one | 296 | 2.55 (dd, J 16.8, 7.3 Hz, 1H), 2.88 (dd, J 16.8, 8.97 Hz, 1H), 3.39 (dd, J 5.7, 9.3 Hz, 1H), 3.76-3.86 (m, 2H), 4.53 (d, J 14.9 Hz, 1H), 4.63 (d, J 14.9 Hz, 1H), 6.28 (d, J 2.0 Hz, 1H), 6.68-6.70 (m, 1H), 6.80-6.84 (m, 1H), 7.55 (d, J 2.0 Hz, 1H) |
| 182 | 4 | | 1-[(4-bromo-1-methyl-1H-pyrazol-5-yl)methyl]-4-(2,3,5-trifluorophenyl)pyrrolidin-2-one | 388/390 | 2.56 (dd, J 16.93, 7.71 Hz, 1H), 2.86 (dd, J 17.18, 8.84 Hz, 1H), 3.31 (dd, J 9.60, 6.44 Hz, 1H), 3.71-3.82 (m, 2H), 3.93 (s, 3H), 4.55 (d, J 15.4 Hz, 1H), 4.63 (d, J 15.4 Hz, 1H), 6.60-6.70 (m, 1H), 6.80-90 (m, 1H), 7.44 (s, 1H) |
| 183 | 4 | | 1-[(1-methyl-1H-pyrazol-5-yl)methyl]-4-(2,3,5-trifluorophenyl)pyrrolidin-2-one | | 2.59 (dd, J 17.12, 7.93 Hz, 1H), 2.87 (dd, J 17.12, 9.19 Hz, 1H), 3.27 (dd, J 9.82, 6.67 Hz, 1H), 3.67 (dd~t, J 9.31 Hz, 1H), 3.78 (m, 1H), 3.87 (s, 3H), 4.54 (d, J 15.4 Hz, 1H), 4.61 (d, J 15.4 Hz, 1H), 6.18 (d, J 1.76 Hz, 1H), 6.64 (m, 1H), 6.85 (m, 1H), 7.42 (d, J 1.76 Hz, 1H) |
| 184 | 4 | | 1-[(6-bromo-2-methylpyrazolo[1,5-a]pyrimidin-3-yl)methyl]-4-propylpyrrolidin-2-one | 351/353 | 0.86 (t, 7.20 Hz, 3H), 1.30 (m, 4H), 2.07 (dd, 16.67, 7.83 Hz, 1H), 2.25 (m, 1H), 2.51 (m, 4H), 2.87 (dd, 9.60, 6.82 Hz, 1H), 3.36 (dd, 9.60, 7.96 Hz, 1H), 4.64 (m, 2H), 8.40 (d, 2.27 Hz, 1H), 8.68 (d, 2.27 Hz, 1H) |
| 185 | 4 | | 1-[(2-methylpyrazolo[1,5-a]pyrimidin-3-yl)methyl]-4-propylpyrrolidin-2-one | 273 | 0.86 (t, 7.20 Hz, 3H), 1.29 (m, 4H), 2.07 (dd, 16.67, 7.96 Hz, 1H), 2.25 (m, 1H), 2.52 (m, 4H), 2.89 (dd, 9.60, 6.82 Hz, 1H), 3.37 (m, 1H), 4.67 (m, 2H), 6.75 (dd, 6.82, 4.04 Hz, 1H), 8.43 (dd, 3.79, 1.64 Hz, 1H), 8.56 (m, 1H) |
| 186 | 4 | | 1-[(6-bromo-2-phenylpyrazolo[1,5-a]pyrimidin-3-yl)methyl]-4-propylpyrrolidin-2-one | 413/415 | 0.81 (m, 3H), 1.18 (m, 4H), 1.98 (dd, 16.37, 7.81 Hz, 1H), 2.11 (m, 1H), 2.45 (dd, 16.56, 8.53 Hz, 1H), 2.74 (dd, 9.54, 6.65 Hz, 1H), 3.22 (m, 1H), 4.91 (s, 2H), 7.46 (m, 3H), 7.79 (m, 2H), 8.47 (d, 2.01 Hz, 1H), 8.82 (d, 2.01 Hz, 1H) |
| 187 | 4 | | 1-[(6-bromo-2-thien-2-ylpyrazolo[1,5-a]pyrimidin-3-yl)methyl]-4-propylpyrrolidin-2-one | 419/421 | 0.83 (t, 7.30 Hz, 3H), 1.24 (m, 4H), 2.08 (m, 1H), 2.21 (m, 1H), 2.54 (dd, 16.62, 8.44 Hz, 1H), 2.80 (dd, 9.57, 6.67 Hz, 1H), 3.27 (m, 1H), 4.93 (m, 2H), 7.18 (m, 1H), 7.42 (d, 5.04 Hz, 1H), 7.76 (d, 3.78 Hz, 1H), 8.46 (d, 2.01 Hz, 1H), 8.78 (d, 2.01 Hz, 1H) |
| 188 | 4 | | 4-propyl-1-[(2-thien-2-ylpyrazolo[1,5-a]pyrimidin-3-yl)methyl]pyrrolidin-2-one | 341 | 0.82 (m, 3H), 1.24 (m, 4H), 1.71 (s, 1H), 2.14 (m, 2H), 2.54 (dd, 16.31, 8.53 Hz, 1H), 2.82 (dd, 9.79, 6.78 Hz, 1H), 3.29 (m, 1H), 4.96 (m, 2H), 7.18 (m, 1H), 7.41 (m, 1H), 7.76 (m, 1H), 8.48 (dd, 4.02, 1.76 Hz, 1H), 8.66 (dd, 7.03, 1.51 Hz, 1H) |
| 189 | 4 | | 1-[(6-bromo-2-cyclopropylpyrazolo[1,5-a]pyrimidin-3-yl)methyl]-4-propylpyrrolidin-2-one | 377/379 | 0.84 (m, 3H), 1.01 (m, 4H), 1.28 (m, 4H), 2.17 (m, 3H), 2.55 (m, 1H), 2.87 (m, 1H), 3.35 (m, 1H), 4.72 (s, 2H), 8.36 (m, 1H), 8.61 (m, 1H) |
| 190 | 4 | | 1-[(6-bromo-2-tert-butylpyrazolo[1,5-a]pyrimidin-3-yl)methyl]-4-propylpyrrolidin-2-one | 393/395 | 0.96 (t, 7.05 Hz, 3H), 1.38 (m, 4H), 1.54 (s, 9H), 2.20 (dd, 16.37, 8.06 Hz, 1H), 2.32 (m, 1H), 2.65 (dd, 16.37, 8.56 Hz, 1H), 2.87 (dd, 9.82, 6.92 Hz, 1H), 3.33 (m, 1H), 4.94 (m, 2H), 8.51 (d, 2.01 Hz, 1H), 8.83 (d, 2.01 Hz, 1H) |
| 191 | 4 | | 1-[(2-phenylpyrazolo[1,5-a]pyrimidin-3-yl)methyl]-4-propylpyrrolidin-2-one | 335 | 0.81 (m, 3H), 1.18 (s, 4H), 1.96 (m, 1H), 2.09 (m, 1H), 2.45 (dd, 16.31, 8.53 Hz, 1H), 2.75 (m, 1H), 3.23 (m, 1H), 4.94 (s, 2H), 6.85 (m, 1H), 7.47 (m, 3H), 7.81 (d, 7.53 Hz, 2H), 8.50 (s, 1H), 8.69 (d, 7.03 Hz, 1H) |

TABLE 1-continued

| n° | Config | Salt | IUPAC Name | MH+ (M+.) | ¹H NMR delta (CDCl₃ unless otherwise specified) |
|---|---|---|---|---|---|
| 192 | 4 | | 1-[(2-tert-butyl-6-cyclopropylpyrazolo[1,5-a]pyrimidin-3-yl)methyl]-4-propylpyrrolidin-2-one | 355 | 0.72 (m, 2H), 0.84 (m, 3H), 1.04 (m, 2H), 1.26 (m, 4H), 1.43 (m, 9H), 1.93 (m, 1H), 2.16 (m, 2H), 2.53 (m, 1H), 2.77 (m, 1H), 3.22 (m, 1H), 4.84 (m, 2H), 8.32 (m, 2H) |
| 193 | 4 | | 1-{[2-(2-furyl)pyrazolo[1,5-a]pyrimidin-3-yl]methyl}-4-propylpyrrolidin-2-one | 325 | 0.82 (t, 7.15 Hz, 3H), 1.25 (m, 4H), 2.09 (m, 1H), 2.20 (m, 1H), 2.54 (dd, 16.56, 8.41 Hz, 1H), 2.82 (dd, 9.79, 6.78 Hz, 1H), 3.29 (dd, 9.54, 7.91 Hz, 1H), 4.95 (m, 2H), 6.57 (dd, 3.26, 1.88 Hz, 1H), 6.85 (dd, 7.03, 4.02 Hz, 1H), 7.21 (d, 3.26 Hz, 1H), 7.59 (d, 1.25 Hz, 1H), 8.50 (dd, 4.02, 1.76 Hz, 1H), 8.68 (dd, 7.03, 1.76 Hz, 1H) |
| 194 | 4 | | 1-[(2-methyl-6-thien-2-ylpyrazolo[1,5-a]pyrimidin-3-yl)methyl]-4-propylpyrrolidin-2-one | 355 | 0.86 (t, 7.18 Hz, 3H), 1.30 (m, 4H), 2.08 (dd, 16.56, 7.78 Hz, 1H), 2.26 (m, 1H), 2.53 (m, 4H), 2.91 (dd, 9.79, 6.78 Hz, 1H), 3.40 (dd, 9.54, 8.03 Hz, 1H), 4.68 (m, 2H), 7.15 (m, 1H), 7.32 (d, 3.51 Hz, 1H), 7.38 (d, 5.02 Hz, 1H), 8.68 (m, 1H), 8.73 (m, 1H) |
| 195 | 4 | | 1-[(2-methyl-6-phenylpyrazolo[1,5-a]pyrimidin-3-yl)methyl]-4-propylpyrrolidin-2-one | 349 | 0.87 (t, 7.15 Hz, 3H), 1.32 (m, 4H), 2.09 (dd, 16.62, 7.93 Hz, 1H), 2.27 (m, 1H), 2.53 (m, 4H), 2.93 (dd, 9.79, 6.78 Hz, 1H), 3.41 (dd, 9.54, 8.03 Hz, 1H), 4.70 (m, 2H), 7.50 (m, 5H), 8.71 (m, 2H) |
| 196 | 4 | | 1-{[2-methyl-6-(1H-pyrrol-2-yl)pyrazolo[1,5-a]pyrimidin-3-yl]methyl}-4-propylpyrrolidin-2-one | 338 | 0.85 (t, 7.05 Hz, 3H), 1.28 (m, 4H), 2.10 (dd, 16.62, 7.81 Hz, 1H), 2.27 (m, 1H), 2.42 (s, 3H), 2.54 (dd, 16.56, 8.53 Hz, 1H), 2.93 (dd, 9.82, 6.80 Hz, 1H), 3.41 (m, 1H), 4.64 (m, 2H), 6.31 (m, 1H), 6.54 (m, 1H), 6.92 (m, 1H), 8.67 (m, 1H), 8.76 (m, 1H), 10.27 (m, 1H) |
| 197 | 4 | | 1-({6-[(1E)-hex-1-enyl]-2-methylpyrazolo[1,5-a]pyrimidin-3-yl}methyl)-4-propylpyrrolidin-2-one | 355 | 0.86 (t, J 7.3 Hz, 3H), 0.94 (t, J 7.3 Hz, 3H), 1.35 (m, 8H), 2.07 (dd, J 16.4, 7.8 Hz, 1H), 2.24 (m, 3H), 2.52 (m, 4H), 2.88 (m, 1H), 3.36 (m, 1H), 4.65 (m, 2H), 6.29 (s, 2H), 8.39 (s, 1H), 8.54 (s, 1H) |
| 198 | 4 | | 1-[(6-chloro-2-phenylpyrazolo[1,5-a]pyrimidin-3-yl)methyl]-4-propylpyrrolidin-2-one | 369/371 | 0.80 (s, 3H), 1.17 (m, 4H), 2.03 (m, 2H), 2.45 (dd, 16.11, 8.31 Hz, 1H), 2.74 (m, 1H), 3.21 (t, 8.31 Hz, 1H), 4.91 (s, 2H), 7.44 (m, 3H), 7.79 (m, 2H), 8.42 (s, 1H), 8.73 (s, 1H) |
| 199 | 4 | | 1-{[2-methyl-6-(phenylethynyl)pyrazolo[1,5-a]pyrimidin-3-yl]methyl}-4-propylpyrrolidin-2-one | 373 | 0.87 (m, 3H), 1.30 (m, 4H), 2.07 (m, 1H), 2.26 (m, 1H), 2.53 (m, 4H), 2.90 (dd, 9.57, 6.80 Hz, 1H), 3.38 (m, 1H), 4.66 (m, 2H), 7.39 (m, 3H), 7.56 (m, 2H), 8.50 (d, 1.51 Hz, 1H), 8.69 (d, 1.76 Hz, 1H) |
| 200 | 4 | | 1-[(6-bromo-2-phenylpyrazolo[1,5-a]pyrimidin-3-yl)methyl]-4-(2,2-difluorovinyl)pyrrolidin-2-one | 433/435 | 2.09 (dd, 16.81, 7.78 Hz, 1H), 2.56 (dd, 16.56, 8.53 Hz, 1H), 2.91 (m, 2H), 3.33 (m, 1H), 3.94 (ddd, 24.6, 9.54, 2.0 Hz, 1H), 4.93 (m, 2H), 7.48 (m, 3H), 7.79 (m, 2H), 8.48 (d, 2.26 Hz, 1H), 8.82 (d, 2.01 Hz, 1H) |
| 201 | 4 | | 1-[(6-hydroxy-2-methylpyrazolo[1,5-a]pyrimidin-3-yl)methyl]-4-propylpyrrolidin-2-one | 289 | 0.84 (t, 7.15 Hz, 3H), 1.28 (m, 4H), 2.13 (m, 1H), 2.29 (m, 1H), 2.48 (s, 3H), 2.59 (dd, 16.56, 8.53 Hz, 1H), 2.92 (dd, 9.54, 7.03 Hz, 1H), 3.39 (t, 8.91 Hz, 1H), 4.70 (m, 2H), 8.23 (d, 1.76 Hz, 1H), 9.01 (d, 2.01 Hz, 1H), 10.56 (m, 1H) |
| 202 | 4 | | 1-[(6-methyl-2-phenylpyrazolo[1,5-a]pyrimidin-3-yl)methyl]-4-propylpyrrolidin-2-one | 349 | 0.80 (t, 6.02 Hz, 3H), 1.17 (m, 4H), 1.97 (m, 1H), 2.09 (m, 1H), 2.44 (m, 4H), 2.74 (dd, 9.54, 6.69 Hz, 1H), 3.22 (m, 1H), 4.91 (s, 2H), 7.41 (m, 1H), 7.48 (m, 2H), 7.79 (m, 2H), 8.37 (m, 1H), 8.47 (m, 1H) |
| 203 | 4 | | 4-(2,2-difluorovinyl)-1-[(2-phenylpyrazolo[1,5-a]pyrimidin-3-yl)methyl]pyrrolidin-2-one | 355 | 0.81 (t, 6.69 Hz, 3H), 1.19 (m, 4H), 1.97 (m, 1H), 2.13 (m, 1H), 2.47 (dd, 16.32, 8.53 Hz, 1H), 2.78 (dd, 9.54, 6.69 Hz, 1H), 3.27 (t, 8.89 Hz, 1H), 4.91 (m, 2H), 6.86 (m, 1H), 7.18 (t, 8.53 Hz, 2H), 7.83 (dd, 8.07, 5.50 Hz, 2H), 8.50 (d, 4.03 Hz, 1H), 8.67 (d, 6.79 Hz, 1H) |
| 204 | 4 | | 1-[(6-methoxy-2-phenylpyrazolo[1,5-a]pyrimidin-3-yl)methyl]-4-propylpyrrolidin-2-one | 365 | 0.80 (m, 3H), 1.16 (m, 4H), 1.94 (m, 1H), 2.14 (m, 1H), 2.45 (dd, J 16.3, 8.4 Hz, 1H), 2.74 (dd, J 9.2, 6.8 Hz, 1H), 3.22 (m, 1H), 3.90 (s, 3H), 4.90 (s, 2H), 7.40 (m, 1H), 7.47 (m, 2H), 7.78 (d, J 8.1 Hz, 2H), 8.24 (d, J 1.5 Hz, 1H), 8.38 (s, 1H) |

TABLE 1-continued

| n° | Config | Salt | IUPAC Name | MH⁺ (M⁺.) | ¹H NMR delta (CDCl₃ unless otherwise specified) |
|---|---|---|---|---|---|
| 205 | 4 | 1 C₂H₂O₄ | 1-[(5-chloropyrazolo[1,5-a]pyrimidin-3-yl)methyl]-4-propylpyrrolidin-2-one | 293/295 | 0.88 (t, 7.06 Hz, 3H), 1.32 (m, 4H), 2.10 (dd, 16.32, 7.70 Hz, 1H), 2.31 (m, 1H), 2.55 (dd, 16.51, 8.80 Hz, 1H), 2.99 (m, 1H), 3.46 (m, 1H), 4.63 (s, 2H), 6.80 (d, 7.15 Hz, 1H), 8.13 (m, 1H), 8.54 (d, 7.15 Hz, 1H) |
| 206 | 4 | | 4-(2,2-difluorovinyl)-1-[(5,6-dimethyl-2-phenylpyrazolo[1,5-a]pyrimidin-3-yl)methyl]pyrrolidin-2-one | 383 | 2.10 (dd, 16.56, 7.53 Hz, 1H), 2.32 (s, 3H), 2.55 (m, 4H), 2.89 (m, 2H), 3.34 (m, 1H), 3.94 (m, 1H), 4.91 (m, 2H), 7.44 (m, 3H), 7.77 (d, 7.28 Hz, 2H), 8.36 (s, 1H) |
| 207 | 4 | | 4-(2,2-difluorovinyl)-1-[(6-fluoro-5-methyl-2-phenylpyrazolo[1,5-a]pyrimidin-3-yl)methyl]pyrrolidin-2-one | 387 | 2.10 (dd, 16.56, 7.53 Hz, 1H), 2.56 (dd, 16.56, 8.53 Hz, 1H), 2.64 (d, 3.01 Hz, 3H), 2.89 (m, 2H), 3.33 (m, 1H), 3.94 (m, 1H), 4.91 (m, 2H), 7.47 (m, 3H), 7.76 (m, 2H), 8.52 (d, 4.27 Hz, 1H) |
| 208 | 4 | | 1-[(5-methoxypyrazolo[1,5-a]pyrimidin-3-yl)methyl]-4-propylpyrrolidin-2-one | 289 | 0.88 (t, 7.15 Hz, 3H), 1.31 (m, 4H), 2.07 (dd, 16.56, 7.78 Hz, 1H), 2.28 (m, 1H), 2.53 (dd, 16.56, 8.78 Hz, 1H), 2.95 (dd, 9.54, 6.90 Hz, 1H), 3.44 (dd, 9.79, 8.16 Hz, 1H), 4.01 (s, 3H), 4.56 (s, 2H), 6.32 (d, 7.28 Hz, 1H), 7.93 (s, 1H), 8.37 (d, 7.28 Hz, 1H) |
| 209 | 4 | | 1-{[2-(4-bromophenyl)pyrazolo[1,5-a]pyrimidin-3-yl]methyl}-4-(2,2-difluorovinyl)pyrrolidin-2-one | 433/435 | 2.24 (dd, 17.07, 7.65 Hz, 1H), 2.69 (dd, 17.07, 8.53 Hz, 1H), 3.01 (m, 2H), 3.45 (m, 1H), 4.02 (m, 1H), 4.94 (s, 2H), 6.92 (dd, 7.03, 4.02 Hz, 1H), 7.66 (m, 4H), 8.54 (d, 3.51 Hz, 1H), 8.73 (d, 7.03 Hz, 1H) |
| 210 | 4 | | 1-{[2-(4-fluorophenyl)pyrazolo[1,5-a]pyrimidin-3-yl]methyl}-4-propylpyrrolidin-2-one | 353 | 0.82 (m, 3H), 1.19 (m, 4H), 1.98 (m, 1H), 2.13 (m, 1H), 2.47 (dd, J 16.3, 8.4 Hz, 1H), 2.78 (dd, J 9.5, 6.6 Hz, 1H), 3.27 (t, J 9.0 Hz, 1H), 4.91 (s, 2H), 6.87 (m, 1H), 7.18 (t, J 8.4 Hz, 2H), 7.83 (dd, J 8.1, 5.5 Hz, 2H), 8.48 (d, J 4.0 Hz, 1H), 8.67 (d, J 6.8 Hz, 1H) |
| 211 | 4 | | 4-(2,2-difluorovinyl)-1-[(6-methyl-2-phenylpyrazolo[1,5-a]pyrimidin-3-yl)methyl]pyrrolidin-2-one | 369 | 2.09 (m, 1H), 2.41 (s, 3H), 2.56 (dd, 16.81, 8.53 Hz, 1H), 2.90 (m, 2H), 3.34 (m, 1H), 3.94 (m, 1H), 4.93 (m, 2H), 7.45 (m, 3H), 7.78 (d, 7.28 Hz, 2H), 8.37 (m, 1H), 8.48 (m, 1H) |
| 212 | 4 | | 4-(2,2-difluorovinyl)-1-[(5-methyl-2-phenylpyrazolo[1,5-a]pyrimidin-3-yl)methyl]pyrrolidin-2-one | 369 | 2.09 (dd, 16.69, 7.52 Hz, 1H), 2.55 (dd, 16.69, 8.44 Hz, 1H), 2.62 (s, 3H), 2.90 (m, 2H), 3.35 (m, 1H), 3.94 (m, 1H), 4.92 (m, 2H), 6.70 (d, 6.97 Hz, 1H), 7.46 (m, 3H), 7.78 (m, 2H), 8.52 (d, 7.15 Hz, 1H) |
| 213 | 4 | | 4-(2,2-difluorovinyl)-1-[(2-thien-2-ylpyrazolo[1,5-a]pyrimidin-3-yl)methyl]pyrrolidin-2-one | 361 | 2.23 (dd, 16.69, 7.79 Hz, 1H), 2.66 (dd, 16.69, 8.71 Hz, 1H), 3.00 (m, 2H), 3.41 (dd, 9.54, 7.78 Hz, 1H), 4.07 (m, 1H), 4.98 (m, 2H), 6.85 (dd, 6.97, 4.03 Hz, 1H), 7.19 (m, 1H), 7.43 (d, 5.14 Hz, 1H), 7.75 (d, 3.67 Hz, 1H), 8.48 (dd, 3.85, 1.47 Hz, 1H), 8.66 (m, 1H) |
| 214 | 4 | | 1-{[2-(4-chlorophenyl)-6-methylpyrazolo[1,5-a]pyrimidin-3-yl]methyl}-4-propylpyrrolidin-2-one | 383/385 | 0.81 (m, 3H), 1.19 (m, 4H), 2.01 (m, 1H), 2.13 (m, 1H), 2.46 (m, 4H), 2.77 (dd, 9.72, 6.69 Hz, 1H), 3.25 (m, 1H), 4.89 (s, 2H), 7.45 (d, 8.62 Hz, 2H), 7.77 (d, 8.62 Hz, 2H), 8.38 (m, 1H), 8.46 (m, 1H) |
| 215 | 4 | | 1-{[2-(4-chlorophenyl)pyrazolo[1,5-a]pyrimidin-3-yl]methyl}-4-(2,2-difluorovinyl)pyrrolidin-2-one | 389/391 | 2.24 (dd, 16.87, 7.70 Hz, 1H), 2.69 (dd, 17.06, 8.62 Hz, 1H), 2.99 (m, 2H), 3.45 (m, 1H), 4.02 (m, 1H), 4.94 (s, 2H), 6.92 (dd, 7.15, 4.13 Hz, 1H), 7.48 (d, 8.44 Hz, 2H), 7.75 (d, 8.40 Hz, 2H), 8.54 (dd, 4.03, 1.65 Hz, 1H), 8.72 (dd, 6.97, 1.65 Hz, 1H) |
| 216 | 4 | | 1-[(6-chloro-2-phenylpyrazolo[1,5-a]pyrimidin-3-yl)methyl]-4-(2,2-difluorovinyl)pyrrolidin-2-one | 389/391 | 2.11 (dd, 16.69, 7.70 Hz, 1H), 2.56 (dd, 16.51, 8.53 Hz, 1H), 2.89 (m, 2H), 3.33 (m, 1H), 3.94 (m, 1H), 4.93 (m, 2H), 7.49 (m, 3H), 7.78 (m, 2H), 8.43 (d, 2.20 Hz, 1H), 8.72 (d, 2.20 Hz, 1H) |
| 217 | 4 | | 1-{[6-chloro-2-(4-chlorophenyl)pyrazolo[1,5-a]pyrimidin-3-yl]methyl}-4-(2,2-difluorovinyl)pyrrolidin-2-one | 423/425/427 | 2.15 (dd, 16.69, 7.70 Hz, 1H), 2.59 (dd, 16.69, 8.62 Hz, 1H), 2.95 (m, 2H), 3.38 (m, 1H), 4.01 (m, 1H), 4.90 (s, 2H), 7.48 (d, 8.44 Hz, 2H), 7.78 (d, 8.44 Hz, 2H), 8.44 (d, 2.20 Hz, 1H), 8.71 (d, 2.38 Hz, 1H) |
| 218 | 4 | | 1-[(2-cyclopropyl-5-methylpyrazolo[1,5-a]pyrimidin-3-yl)methyl]-4-(2,2-difluorovinyl)pyrrolidin-2-one | 333 | 1.03 (m, 4H), 2.20 (m, 2H), 2.56 (s, 3H), 2.65 (dd, 16.51, 8.71 Hz, 1H), 3.01 (m, 1H), 3.10 (m, 1H), 3.48 (m, 1H), 4.18 (m, 1H), 4.75 (s, 2H), 6.56 (d, 7.15 Hz, 1H), 8.34 (d, 7.15 Hz, 1H) |
| 219 | 4 | | 1-[(5-chloro-2-cyclopropylpyrazolo[1,5-a]pyrimidin-3-yl)methyl]-4-(2,2-difluorovinyl)pyrrolidin-2-one | 353/355 | 1.04 (m, 4H), 2.21 (m, 2H), 2.65 (dd, 16.81, 8.66 Hz, 1H), 3.03 (m, 1H), 3.12 (m, 1H), 3.49 (m, 1H), 4.20 (m, 1H), 4.73 (s Hz, 2H), 6.68 (d, 7.28 Hz, 1H), 8.38 (d, 7.28 Hz, 1H) |

TABLE 1-continued

| n° | Config | Salt | IUPAC Name | MH+ (M+.) | 1H NMR delta (CDCl3 unless otherwise specified) |
|---|---|---|---|---|---|
| 220 | 4 | | 1-[(5-chloro-2,6-dimethylpyrazolo[1,5-a]pyrimidin-3-yl)methyl]-4-(2,2-difluorovinyl)pyrrolidin-2-one | 341/343 | 2.22 (dd, 16.56, 8.03 Hz, 1H), 2.36 (d, 0.50 Hz, 3H), 2.47 (s, 3H), 2.64 (m, 1H), 3.08 (m, 2H), 3.49 (m, 1H), 4.19 (m, 1H), 4.61 (s, 2H), 8.35 (d, 0.75 Hz, 1H) |
| 221 | 4 | | 1-[(5-bromo-1H-pyrazolo[3,4-b]pyridin-3-yl)methyl]-4-(2,2-difluorovinyl)pyrrolidin-2-one | 357/359 | (DMSO) 2.19 (dd, 16.28, 8.14 Hz, 1H), 2.53 (m, 1H), 3.08 (m, 2H), 3.48 (m, 1H), 4.66 (m, 2H), 8.41 (d, 2.03 Hz, 1H), 8.60 (d, 2.03 Hz, 1H), 13.76 (s, 1H) |
| 222 | | | 1-(pyridazin-4-ylmethyl)pyrrolidin-2-one | | (DMSO): 1.95 (quint, J 7.79 Hz, 2H), 2.29 (t, J 8.22 Hz, 2H), 3.28 (t, J 7.10 Hz, 2H), 4.42 (s, 2H), 7.44-7.48 (m, 1H), 9.08 (m, 1H), 9.12 (dd, J 1.15, 4.12 Hz, 1H). |
| 223 | | | 1-[(1-oxidopyridin-2-yl)methyl]pyrrolidin-2-one | 193 | 2.20 (m, 2H), 2.40 (t, J 8.0 Hz, 2H), 3.55 (t, J 8.0 Hz, 2H), 4.70 (s, 2H), 7.15-7.35 (m, 3H overlapped with solvent signal), 8.25 (d, J 7.40 Hz, 1H) |
| 224 | 4 | 1 HCl | 4-propyl-1-(pyridin-3-ylmethyl)pyrrolidin-2-one | 219 | (DMSO): 0.79 (t, J 7.0 Hz, 3H), 1.18-1.33 (m, 4H), 2.03 (dd, J 11.2, 8.7 Hz, 1H), 2.39-2.50 (m, 2H), 2.99 (dd ~= t, J 10.8 Hz, 1H), 3.43 (t, J 10.8 Hz, 1H), 4.48 (d, J 15.7 Hz, 1H), 4.61 (d, J 15.7 Hz, 1H), 8.01 (m, 1H), 8.40 (d, J 8.29 Hz, 1H), 8.68-8.73 (m, 2H) |
| 225 | A-1§ | | (+)-1-(1-pyridin-3-ylpropyl)pyrrolidin-2-one | | 0.96 (t, J 7.32 Hz, 3H), 1.96 (m, 4H), 2.41 (m, 2H), 3.02 (m, 1H), 3.33 (m, 1H), 5.23 (dd, J 9.23, 6.75 Hz, 1H), 7.26 (m, 1H), 7.63 (m, 1H), 8.50-8.60 (m, 2H) |
| 226 | B-1§ | | (−)-1-(1-pyridin-3-ylpropyl)pyrrolidin-2-one | (204) | 0.96 (t, J 7.32 Hz, 3H), 1.96 (m, 4H), 2.41 (m, 2H), 3.02 (m, 1H), 3.33 (m, 1H), 5.23 (dd, J 9.23, 6.75 Hz, 1H), 7.26 (m, 1H), 7.63 (m, 1H), 8.50-8.60 (m, 2H) |
| 227 | | | 5-chloro-1-[(2-fluoropyridin-3-yl)methyl]-1,3-dihydro-2H-indol-2-one | | (DMSO): 3.77 (s, 2H), 4.49 (s, 2H), 6.97 (d, J 8.39 Hz, 1H), 7.31-7.39 (m, 2H), 7.44 (d, J 2 Hz, 1H), 7.82 (t, J 8.09 Hz, 1H), 8.21 (d, J 4.72 Hz, 1H) |
| 228 | 4 | | 1-[(6-chloropyridin-3-yl)methyl]-4-propylpyrrolidin-2-one | 253/255 | (DMSO): 0.86 (t, J 7.3 Hz, 3H), 1.30 (m, 4H), 2.01 (dd, J 16.2, 7.6 Hz, 1H), 2.29 (m, 1H), 2.43 (m, 1H), 2.89 (dd, J 9.3, 6.6 Hz, 1H), 3.37 (m, 1H), 4.39 (s, 2H), 7.51 (d, J 8.1 Hz, 1H), 7.71 (dd, J 8.3, 2.5 Hz, 1H), 8.31 (d, J 2.3 Hz, 1H) |
| 229 | 4 | | 1-{[6-(benzylamino)pyridin-3-yl]methyl}-4-propylpyrrolidin-2-one | 324 | (DMSO): 0.85 (t, J 7.1 Hz, 3H), 1.27 (m, 4H), 1.95 (dd, J 16.4, 7.6 Hz, 1H), 2.23 (m, 1H), 2.39 (dd, J 16.2, 8.6 Hz, 1H), 2.82 (dd, J 9.3, 6.6 Hz, 1H), 3.31 (m, 1H), 4.18 (m, 1H), 4.46 (d, J 6.1 Hz, 2H), 6.49 (d, J 8.6 Hz, 1H), 7.05 (t, J 5.8 Hz, 1H), 7.28 (m, 5H), 7.84 (d, J 1.5 Hz, 1H) |
| 230 | 4 | | 1-[(2-aminopyridin-3-yl)methyl]-4-propylpyrrolidin-2-one | 234 | 0.89 (t, J 7.2 Hz, 3H), 1.32 (m, 4H), 2.09 (m, 1H), 2.32 (m, 1H), 2.55 (dd, J 16.7, 8.6 Hz, 1H), 2.89 (dd, J 9.5, 6.8 Hz, 1H), 3.36 (m, 1H), 4.28 (m, 2H), 5.34 (s, 2H), 6.56 (dd, J 7.2, 5.1 Hz, 1H), 7.26 (m, 1H), 8.02 (dd, J 5.0, 1.7 Hz, 1H) |
| 231 | 4 | | 4-propyl-1-(1H-pyrrolo[2,3-b]pyridin-3-ylmethyl)pyrrolidin-2-one | | 0.84 (t, J 7.20 Hz, 3H), 1.27 (m, 4H), 2.09 (dd, 16.42, 7.96 Hz, 1H), 2.24 (m, 1H), 2.55 (dd, 16.42, 8.59 Hz, 1H), 2.86 (dd, 9.60, 6.57 Hz, 1H), 3.34 (m, 1H), 4.60 (m, 2H), 7.10 (dd, 8.08, 4.67 Hz, 1H), 7.31 (s, 1H), 8.06 (d, 7.83 Hz, 1H), 8.34 (d, 4.29 Hz, 1H), 10.51 (s, 1H) |
| 232 | 4 | | 1-[(2-isopropyl-1H-pyrrolo[2,3-b]pyridin-3-yl)methyl]-4-propylpyrrolidin-2-one | 300 | 0.83 (t, 7.18 Hz, 3H), 1.26 (m, 4H), 1.48 (dd, 7.05, 1.51 Hz, 6H), 2.08 (dd, 16.37, 7.81 Hz, 1H), 2.23 (m, 1H), 2.54 (dd, 16.37, 8.56 Hz, 1H), 2.82 (dd, 9.57, 6.80 Hz, 1H), 3.28 (m, 1H), 3.44 (m, 1H), 4.62 (m, 2H), 7.10 (dd, 7.81, 4.91 Hz, 1H), 8.02 (m, 1H), 8.29 (d, 4.28 Hz, 1H), 12.37 (s, 1H) |
| 233 | 4 | | 1-[(2-phenyl-1H-pyrrolo[2,3-b]pyridin-3-yl)methyl]-4-propylpyrrolidin-2-one | 334 | (DMSO) 0.87 (t, 6.95 Hz, 3H), 1.28 (m, 4H), 2.05 (dd, 16.42, 7.58 Hz, 1H), 2.23 (s, 1H), 2.52 (dd, 16.42, 8.59 Hz, 1H), 2.8 (d, 6.32 Hz, 1H), 3.28 (m, 1H), 4.78 (s, 2H), 7.23 (dd, 7.83, 4.67 Hz, 1H), 7.59 (d, 7.33 Hz, 1H), 7.66 (m, 2H), 7.79 (m, 2H), 8.08 (dd, 7.83, 1.26 Hz, 1H), 8.38 (dd, 4.80, 1.52 Hz, 1H) |

TABLE 1-continued

| n° | Config | Salt | IUPAC Name | MH+ (M+.) | 1H NMR delta (CDCl3 unless otherwise specified) |
|---|---|---|---|---|---|
| 234 | 4 | | 4-propyl-1-[(2-propyl-1H-pyrrolo[2,3-b]pyridin-3-yl)methyl]pyrrolidin-2-one | 300 | 0.83 (t, 6.95 Hz, 3H), 1.03 (t, 7.33 Hz, 3H), 1.27 (m, 4H), 1.82 (m, 2H), 2.08 (dd, 16.42, 7.83 Hz, 1H), 2.23 (m, 1H), 2.54 (dd, 16.42, 8.59 Hz, 1H), 2.84 (m, 3H), 3.30 (m, 1H), 4.59 (m, 2H), 7.09 (m, 1H), 8.00 (d, 7.58 Hz, 1H), 8.20 (m, 1H), 11.41 (s, 1H) |
| 235 | 4 | | 1-[(6-bromo-1H-pyrrolo[2,3-b]pyridin-3-yl)methyl]-4-propylpyrrolidin-2-one | 336/338 | 0.84 (t, 7.15 Hz, 3H), 1.13-1.46 (m, 4H), 2.09 (dd, 16.56, 7.78 Hz, 1H), 2.25 (m, 1H), 2.55 (dd, 16.56, 8.53 Hz, 1H), 2.86 (dd, 9.54, 6.78 Hz, 1H), 3.34 (m, 1H), 4.58 (s, 2H), 7.24 (d, 8.28 Hz, 1H), 7.36 (s, 1H), 7.96 (d, 8.28 Hz, 1H), 11.23 (s, 1H) |
| 236 | 4 | | 1-[(1-benzoyl-6-bromo-1H-pyrrolo[2,3-b]pyridin-3-yl)methyl]-4-propylpyrrolidin-2-one | 440/442 | 0.87 (t, 7.15 Hz, 3H), 1.20-1.40 (m, 4H), 2.09 (dd, 16.56, 7.91 Hz, 1H), 2.29 (m, 1H), 2.56 (dd, 16.56, 8.66 Hz, 1H), 2.89 (dd, 9.29, 6.78 Hz, 1H), 3.38 (m, 1H), 4.55 (m, 2H), 7.33 (d, 8.28 Hz, 1H), 7.51 (t, 7.65 Hz, 2H), 7.65 (t, 7.53 Hz, 1H), 7.71 (s, 1H), 7.78 (d, 7.53 Hz, 2H), 7.91 (d, 8.28 Hz, 1H) |
| 237 | 4 | | 1-[(6-phenyl-1H-pyrrolo[2,3-b]pyridin-3-yl)methyl]-4-propylpyrrolidin-2-one | 334 | 0.83 (m, 3H), 1.27 (m, 4H), 2.10 (dd, 16.56, 8.03 Hz, 1H), 2.24 (m, 1H), 2.56 (dd, 16.56, 8.53 Hz, 1H), 2.85 (dd, 9.29, 7.03 Hz, 1H), 3.33 (m, 1H), 4.59 (m, 2H), 7.08 (s, 1H), 7.46 (m, 1H), 7.52 (m, 3H), 8.01 (d, 7.28 Hz, 2H), 8.12 (d, 8.03 Hz, 1H), 11.65 (s, 1H) |
| 238 | 4 | | 1-[(5-bromo-1H-pyrrolo[2,3-b]pyridin-3-yl)methyl]-4-(2,2-difluorovinyl)pyrrolidin-2-one | 356/358 | 2.25 (dd, 16.81, 8.28 Hz, 1H), 2.68 (dd, 16.81, 8.78 Hz, 1H), 2.99 (dd, 9.29, 7.15 Hz, 1H), 3.10 (m, 1H), 3.45 (m, 1H), 4.12 (ddd, 24.35, 9.54, 1.76 Hz, 1H), 4.58 (m, 2H), 7.33 (d, 2.26 Hz, 1H), 8.17 (d, 2.01 Hz, 1H), 8.37 (d, 2.01 Hz, 1H), 10.32 (s, 1H) |
| 239 | 4 | | 1-[(7-oxido-1H-pyrrolo[2,3-b]pyridin-3-yl)methyl]-4-propylpyrrolidin-2-one | 274 | 0.84 (m, 3H), 1.27 (m, 4H), 2.07 (dd, 16.56, 7.78 Hz, 1H), 2.24 (m, 1H), 2.53 (dd, 16.56, 8.53 Hz, 1H), 2.84 (dd, 9.54, 6.78 Hz, 1H), 3.32 (m, 1H), 4.55 (s, 2H), 7.07 (dd, 7.78, 6.40 Hz, 1H), 7.37 (s, 1H), 7.86 (d, 7.78 Hz, 1H), 8.22 (d, 6.27 Hz, 1H), 13.35 (m, 1H) |
| 240 | 4 | | 4-propyl-1-(1H-pyrrolo[2,3-b]pyridin-4-ylmethyl)pyrrolidin-2-one | 258 | 0.86 (t, J 7.15 Hz, 3H), 1.20-1.42 (m, 4H), 2.15 (dd, J 16.56, 7.78 Hz, 1H), 2.31 (m, 1H), 2.61 (dd, J 16.56, 8.53 Hz, 1H), 2.86 (dd, J 9.54, 6.90 Hz, 1H), 3.33 (t, J 8.0 Hz, 1H), 4.72 (d, J 15.0 Hz, 1H), 4.76 (d, J 15.0 Hz, 1H), 6.59 (d, J 3.51 Hz, 1H), 6.97 (d, J 4.77 Hz, 1H), 7.37 (d, J 3.51 Hz, 1H), 8.34 (s, 1H), 10.79 (s (broad), 1H) |
| 241 | 4 | | 4-propyl-1-(1H-pyrrolo[2,3-b]pyridin-5-ylmethyl)pyrrolidin-2-one | 258 | (DMSO): 0.82 (t, J 7.15 Hz, 3H), 1.18-1.35 (m, 4H), 1.98 (dd, J 16.31, 7.78 Hz, 1H), 2.24 (m, 1H), 2.42 (dd, J 16.31, 8.78 Hz, 1H), 2.85 (dd, J 9.29, 6.90 Hz, 1H), 3.35 (m, 1H, overlapped with solvent signal), 4.44 (m, 2H), 6.42 (d, J 1.25 Hz, 1H), 7.47 (t, J 2.76 Hz, 1H), 7.80 (d, J 0.50 Hz, 1H), 8.11 (d, J 1.25 Hz, 1H), 11.63 (s, 1H) |
| 242 | 4 | | 4-propyl-1-(1H-pyrrolo[2,3-c]pyridin-2-ylmethyl)pyrrolidin-2-one | 258 | 0.84 (t, 7.05 Hz, 3H), 1.28 (m, 4H), 2.10 (dd, 16.62, 8.06 Hz, 1H), 2.26 (m, 1H), 2.56 (dd, 16.62, 8.56 Hz, 1H), 2.88 (dd, 9.57, 6.80 Hz, 1H), 3.37 (m, 1H), 4.63 (m, 2H), 7.40 (s, 1H), 7.63 (dd, 5.54, 1.01 Hz, 1H), 8.25 (d, 5.54 Hz, 1H), 8.83 (s, 1H), 1087 (s, 1H) |
| 243 | 4 | | 4-propyl-1-(1H-pyrrolo[2,3-c]pyridin-3-ylmethyl)pyrrolidin-2-one | 258 | 0.78 (t, 7.03 Hz, 3H), 1.20 (m, 4H), 1.94 (dd, 16.31, 7.53 Hz, 1H), 2.17 (m, 1H), 2.39 (dd, 16.56, 8.66 Hz, 1H), 2.77 (dd, 9.54, 6.53 Hz, 1H), 4.48 (m, 2H), 7.49 (d, 5.27 Hz, 1H), 7.55 (s, 1H), 8.07 (d, 5.52 Hz, 1H), 8.72 (s, 1H), 11.63 (m, 1H) |
| 244 | 4 | | 4-propyl-1-(1H-pyrrolo[3,2-b]pyridin-3-ylmethyl)pyrrolidin-2-one | 258 | 0.85 (t, 7.07 Hz, 3H), 1.26 (m, 4H), 2.07 (m, 1H), 2.26 (m, 1H), 2.51 (dd, 16.67, 8.72 Hz, 1H), 3.12 (dd, 10.11, 6.69 Hz, 1H), 3.62 (dd, 9.85, 8.08 Hz, 1H), 4.72 (m, 2H), 7.13 (dd, 8.08, 4.55 Hz, 1H), 7.44 (s, 1H), 7.68 (dd, 8.08, 1.14 Hz, 1H), 8.48 (d, 1.01 Hz, 1H), 8.94 (s, 1H) |
| 245 | 4 | | 4-propyl-1-(1H-pyrrolo[3,2-c]pyridin-2-ylmethyl)pyrrolidin-2-one | 258 | 0.84 (t, 7.18 Hz, 3H), 1.29 (m, 4H), 2.10 (dd, 16.62, 7.93 Hz, 1H), 2.27 (m, 1H), 2.56 (dd, 16.62, 8.56 Hz, 1H), 2.92 (dd, 9.32, 6.92 Hz, 1H), 3.40 (m, 1H), 4.67 (m, 2H), |

TABLE 1-continued

| n° | Config | Salt | IUPAC Name | MH⁺ (M⁺.) | ¹H NMR delta (CDCl₃ unless otherwise specified) |
|---|---|---|---|---|---|
| 246 | 4 | | 4-propyl-1-(1H-pyrrolo[3,2-c]pyridin-3-ylmethyl)pyrrolidin-2-one | 258 | 7.25 (s, 1H), 7.33 (d, 5.79 Hz, 1H), 8.31 (d, 5.79 Hz, 1H), 9.00 (s, 1H), 10.34 (s, 1H) (DMSO) 0.79 (m, 3H), 1.21 (m, 4H), 1.96 (dd, 16.17, 7.58 Hz, 1H), 2.19 (m, 1H), 2.41 (dd, 16.42, 8.59 Hz, 1H), 2.81 (m, 1H), 3.32 (t, 8.72 Hz, 1H), 4.53 (m, 2H), 7.38 (d, 5.56 Hz, 1H), 7.43 (s, 1H), 8.17 (d, 5.56 Hz, 1H), 8.82 (s, 1H), 11.49 (s, 1H) |
| 247 | 4 | | 4-propyl-1-(1,3,4-thiadiazol-2-ylmethyl)pyrrolidin-2-one | 226 | 0.90 (t, J 7.28 Hz, 3H), 1.25-1.35 (m, 2H), 1.37-1.45 (m, 2H), 2.10 (dd, J 16.81, 7.78 Hz, 1H), 2.37 (m, 1H), 2.56 (dd, J 16.81, 8.53 Hz, 1H), 3.08 (dd, J 9.54, 6.78 Hz, 1H), 3.56 (dd, J 9.54, 7.91 Hz, 1H), 4.92 (s, 2H), 9.12 (s, 1H) |
| 248 | | | 1-[(2-amino-1,3-thiazol-5-yl)methyl]pyrrolidin-2-one | 198 | 1.89 (m, 2H), 2.18 (t, J 8.3 Hz, 2H), 3.15-3.27 (m, 2H with solvent peak), 4.30 (s, 2H), 6.74 (s broad, 2H), 6.76 (s, 1H) |
| 249 | | | 1-(1,3-thiazol-5-ylmethyl)pyrrolidin-2-one | (182) | 1.91 (m, 2H), 2.21 (t, J 7.63 Hz, 2H), 3.24 (t, J 6.9 Hz, 2H), 4.61 (s, 2H), 7.82 (d, J 0.7 Hz, 1H), 9.04 (d, J 0.7 Hz, 1H) |
| 250 | 4 | | 1-[(2-chloro-1,3-thiazol-5-yl)methyl]-4-(2,3,5-trifluorophenyl)pyrrolidin-2-one | 347 | 2.57 (dd, J 16.87, 7.93 Hz, 1H), 2.86 (dd, J 16.87, 8.94 Hz, 1H), 3.35 (dd, J 9.06, 6.55 Hz, 1H), 3.81 (m, 2H), 4.63 (m, 2H), 6.68 (m, 1H), 6.86 (m, 1H), 7.43 (s, 1H) |
| 251 | 4 | | 1-{[2-(dimethylamino)-1,3-thiazol-5-yl]methyl}-4-(2,3,5-trifluorophenyl)pyrrolidin-2-one | 356 | 2.53 (dd, J 16.87, 7.30 Hz, 1H), 2.86 (dd, J 16.87, 9.06 Hz, 1H), 3.08 (s, 6H), 3.32 (dd, J 9.57, 6.04 Hz, 1H), 3.72 (t, J 9.2 Hz, 1H), 3.81 (m, 1H), 4.44 (d, J 15.3 Hz, 1H), 4.44 (d, J 15.3 Hz, 1H), 6.65-6.70 (m, 1H), 6.80-6.85 (m, 1H), 7.02 (s, 1H) |
| 252 | 4 | | 1-{[2-(methylamino)-1,3-thiazol-5-yl]methyl}-4-(2,3,5-trifluorophenyl)pyrrolidin-2-one | 342 | 2.54 (dd, J 16.87, 7.43 Hz, 1H), 2.86 (dd, J 17.12, 8.94 Hz, 1H), 2.96 (s, 3H), 3.33 (dd, J 9.57, 6.29 Hz, 1H), 3.73 (t, J 8.81 Hz, 1H), 3.78-3.85 (m, 1H), 4.46 (d, J 15.3 Hz, 1H), 4.58 (d, J 15.3 Hz, 1H), 5.15 (s broad, 1H), 6.65-6.70 (m, 1H), 6.80-6.85 (m, 1H), 6.99 (s, 1H) |
| 253 | 4 | | 1-[(2-pyrrolidin-1-yl-1,3-thiazol-5-yl)methyl]-4-(2,3,5-trifluorophenyl)pyrrolidin-2-one | 382 | 2.0-2.1 (m, 4H), 2.53 (dd, J 16.87, 7.30 Hz, 1H), 2.86 (dd, J 16.87, 8.94 Hz, 1H), 3.32 (dd, J 9.57, 6.17 Hz, 1H), 3.40-3.50 (m, 4H), 3.72 (t, J 9.3 Hz, 1H), 3.80 (m, 1H), 4.47 (d, J 15.3 Hz, 1H), 4.60 (d, J 15.3 Hz, 1H), 6.65-6.70 (m, 1H), 6.80-6.85 (m, 1H), 7.03 (s, 1H) |
| 254 | 4 | | 5-{[2-oxo-4-(2,3,5-trifluorophenyl)pyrrolidin-1-yl]methyl}-1,3-thiazol-2(3H)-one | 329 | 2.56 (dd, J 16.87, 7.68 Hz, 1H), 2.84 (dd, J 16.87, 8.94 Hz, 1H), 3.37 (t, J 6.3 Hz, 1H), 3.73-3.89 (m, 2H), 4.35 (s~2d, 2H), 6.54 (s, 1H), 6.70-6.75 (m, 1H), 6.82-6.87 (m, 1H), 8.13 (s broad, 1H) |
| 255 | 4 | | 4-phenyl-1-{[3-(trifluoromethyl)[1,2,4]triazolo[4,3-b]pyridazin-7-yl]methyl}pyrrolidin-2-one | 362 | 2.70 (dd, J 17.32, 8.66 Hz, 1H), 2.93 (dd, J 17.07, 8.78 Hz, 1H), 3.41 (dd, J 9.03, 7.28 Hz, 1H), 3.67 (m, 1H), 3.78 (t, J 9.00 Hz, 1H), 4.57 (d, J 15.80 Hz, 1H), 4.72 (d, J 15.80 Hz, 1H), 7.20 (d, J 7.30 Hz, 2H), 7.25-7.29 (m, 1H), 7.34 (t, J 7.03 Hz, 2H) 8.04 (s, 1H), 8.56 (d, J 1.76 Hz, 1H) |
| 256 | 4 | | 4-phenyl-1-[(3-phenyl[1,2,4]triazolo[4,3-b]pyridazin-7-yl)methyl]pyrrolidin-2-one | 370 | (DMSO): 2.60 (dd, J 16.31, 9.29 Hz, 1H), 2.77 (dd, J 16.56, 8.66 Hz, 1H), 3.39 (t, J 8.28 Hz, 1H), 3.74 (q, J 8.53 Hz, 1H), 3.79 (t, J 8.53 Hz, 1H), 4.56 (d, J 16.06 Hz, 1H), 4.67 (d, J 16.06 Hz, 1H), 7.21-7.27 (m, 1H), 7.30-7.35 (m, 4H), 7.55-7.65 (m, 3H), 8.28 (s, 1H), 8.37 (d, J 7.03 Hz, 2H), 8.65 (d, J 2.01 Hz, 1H) |
| 257 | 4 | | 4-phenyl-1-{[3-(trifluoromethyl)[1,2,4]triazolo[4,3-b]pyridazin-8-yl]methyl}pyrrolidin-2-one | 362 | 2.67 (dd, J 17.07, 8.53 Hz, 1H), 2.88 (dd, J 17.07, 8.53 Hz, 1H), 3.61-3.73 (m, 2H), 4.05 (t, J 8.03 Hz, 1H), 4.96 (d, J 16.3 Hz, 1H), 5.02 (d, J 16.3 Hz, 1H), 7.25-7.30 (m, 4H), 7.34 (t, J 7.8 Hz, 2H), 8.50 (d, J 4.52 Hz, 1H) |
| 258 | 4 | | 4-propyl-1-{[3-(trifluoromethyl)[1,2,4]triazolo[4,3-b]pyridazin-8-yl]methyl}pyrrolidin-2-one | 328 | 0.92 (t, J 7.28 Hz, 3H), 1.26-1.34 (m, 2H), 1.39-1.50 (m, 2H), 2.14 (dd, J 16.56, 8.03 Hz, 1H), 2.45 (m, 1H), 2.58 (m, 1H), 3.25 (dd, J 9.29, 7.28 Hz, 1H), 3.73 (t, J 8.78 Hz, 1H), 4.87 (d, J 16.5 Hz, 1H), 4.97 (d, J 16.5 Hz, 1H), 7.21 (d, J 4.27 Hz, 1H), 8.52 (d, J 4.27 Hz, 1H) |

TABLE 1-continued

| n° | Config | Salt | IUPAC Name | MH+ (M+.) | 1H NMR delta (CDCl3 unless otherwise specified) |
|---|---|---|---|---|---|
| 259 | 4 | | 4-phenyl-1-[(3-phenyl[1,2,4]triazolo[4,3-b]pyridazin-8-yl)methyl]pyrrolidin-2-one | 370 | (DMSO): 2.61 (dd, J 16.31, 9.54 Hz, 1H), 2.79 (dd, J 16.56, 8.78 Hz, 1H), 3.52 (t, J 8.53 Hz, 1H), 3.74 (quint, J 8.63 Hz, 1H), 3.90 (t, J 8.78 Hz, 1H), 4.87 (d, J 17.07 Hz, 1H), 4.97 (d, J 17.07 Hz, 1H), 7.24-7.27 (m, 2H), 7.32-7.37 (m, 4H), 7.56-7.65 (m, 3H), 8.38 (d, J 7.03 Hz, 2H), 8.70 (d, J 4.52 Hz, 1H) |
| 260 | 4 | | 1-[(6-chloro-3-phenyl[1,2,4]triazolo[4,3-b]pyridazin-8-yl)methyl]-4-propylpyrrolidin-2-one | 370/372 | 0.89 (t, J 7.28 Hz, 3H), 1.26-1.34 (m, 2H), 1.39-1.45 (m, 2H), 2.10 (dd, J 7.02, 15.06 Hz, 1H), 2.38-2.50 (m, 2H overlapped with solvent signal), 3.15 (dd, J 9.03, 7.15 Hz, 1H), 3.60 (t, J 8.78 Hz, 1H), 4.78 (d, J 17.3 Hz, 1H), 4.89 (d, J 17.3 Hz, 1H), 7.29 (s, 1H), 7.57-7.67 (m, 3H), 8.30 (d, J 8.28 Hz, 2H) |
| 261 | 4 | | 1-[(6-chloro[1,2,4]triazolo[4,3-b]pyridazin-8-yl)methyl]-4-phenylpyrrolidin-2-one | 328/330 | 2.59 (dd, J 16.31, 9.29 Hz, 1H), 2.78 (dd, J 16.31, 8.78 Hz, 1H), 3.49 (t, J 8.28 Hz, 1H), 3.74 (quint, J 8.53 Hz, 1H), 3.87 (t, J 8.66 Hz, 1H), 4.82 (d, J 17.57 Hz, 1H), 4.92 (d, J 17.57 Hz, 1H), 7.23-7.36 (m, 6H), 9.70 (s, 1H) |
| 262 | 4 | | 1-{[6-chloro-3-(trifluoromethyl)[1,2,4]triazolo[4,3-b]pyridazin-8-yl]methyl}-4-phenylpyrrolidin-2-one | 396/398 | 2.59 (dd, J 16.31, 9.41 Hz, 1H), 2.78 (dd, J 16.31, 8.78 Hz, 1H), 3.48 (m, 1H), 3.73 (quint, J 8.53 Hz, 1H), 3.85 (t, J 8.66 Hz, 1H), 4.87 (d, J 17.5 Hz, 1H), 4.93 (d, J 17.5 Hz, 1H), 7.25 (m, 1H), 7.34-7.36 (m, 4H), 7.58 (s, 1H) |
| 263 | 4 | | 1-[(6-chloro-3-phenyl[1,2,4]triazolo[4,3-b]pyridazin-8-yl)methyl]-4-phenylpyrrolidin-2-one | 404/406 | (DMSO): 2.61 (dd, J 16.56, 9.29 Hz, 1H), 2.79 (dd, J 16.31, 8.66 Hz, 1H), 3.51 (t, J 8.54 Hz, 1H), 3.76 (quint, J 8.50 Hz, 1H), 3.90 (t, J 8.66 Hz, 1H), 4.87 (d, J 17.57 Hz, 1H), 4.97 (d, J 17.57 Hz, 1H), 7.23-7.28 (m, 1H), 7.31-7.37 (m, 5H), 7.58-7.66 (m, 3H), 8.30 (d, J 7.03 Hz, 2H) |
| 264 | 4 | | 1-[(2-fluoroindolizin-3-yl)methyl]-4-propylpyrrolidin-2-one | 275 | 0.78 (t, J 7.15 Hz, 3H), 1.10-1.27 (m, 4H), 1.97 (dd, J 16.31, 7.53 Hz, 1H), 2.21 (m, 1H), 2.42 (dd, J 16.31, 8.66 Hz, 1H), 2.78 (dd, J 9.29, 6.53 Hz, 1H), 3.28 (dd, J 9.29, 8.28 Hz, 1H), 4.67 (s, 2H), 6.32 (s, 1H), 6.71 (t, J 7.03 Hz, 1H overlapped with solvent signal), 6.85 (t, J 8.78 Hz, 1H), 7.42 (d, J 9.03 Hz, 1H), 8.13 (d, J 7.03 Hz, 1H) |
| 265 | 4 | | 1-(1H-1,2,3-benzotriazol-1-ylmethyl)-4-propylpyrrolidin-2-one | 259 | 0.84 (t, 7.07 Hz, 3H), 1.27 (m, 4H), 2.07 (dd, 16.92, 8.08 Hz, 1H), 2.29 (m, 1H), 2.54 (dd, 16.92, 8.59 Hz, 1H), 3.01 (dd, 9.85, 6.95 Hz, 1H), 3.55 (dd, 9.60, 7.83 Hz, 1H), 6.09 (s, 2H), 7.40 (m, 1H), 7.52 (m, 1H), 7.85 (d, 8.34 Hz, 1H), 8.06 (d, 8.34 Hz, 1H) |
| 266 | 4 | | 1-[(6-bromo-2-chloro-1H-imidazo[4,5-b]pyridin-1-yl)methyl]-4-propylpyrrolidin-2-one | 371/373 | 0.89 (t, 7.15 Hz, 3H), 1.33 (m, 4H), 2.10 (dd, 17.06, 8.16 Hz, 1H), 2.32 (m, 1H), 2.54 (m, 1H), 3.04 (m, 1H), 3.54 (m, 1H), 5.65 (s, 2H), 8.24 (d, 1.65 Hz, 1H), 8.59 (d, 1.47 Hz, 1H) |
| 267 | 4 | | 1-[(6-bromo-2-phenyl-1H-imidazo[4,5-b]pyridin-1-yl)methyl]-4-propylpyrrolidin-2-one | 413/415 | (DMSO) 0.81 (t, 6.90 Hz, 3H), 1.18 (m, 4H), 1.92 (s, 1H), 2.00 (dd, 17.07, 8.03 Hz, 1H), 2.16 (m, 1H), 2.48 (m, 1H), 2.96 (m, 1H), 5.73 (m, 2H), 7.58 (m, 3H), 7.72 (m, 2H), 8.18 (d, 1.76 Hz, 1H), 8.63 (d, 1.51 Hz, 1H) |
| 268 | 4 | | 1-(3H-imidazo[4,5-b]pyridin-3-ylmethyl)-4-propylpyrrolidin-2-one | 259 | 0.87 (t, 7.04 Hz, 3H), 1.30 (m, 4H), 2.06 (dd, 16.85, 8.05 Hz, 1H), 2.32 (m, 1H), 2.52 (dd, 16.85, 8.55 Hz, 1H), 3.15 (dd, 9.56, 7.04 Hz, 1H), 3.68 (dd, 9.31, 8.05 Hz, 1H), 5.73 (s, 2H), 7.29 (m, 1H), 8.09 (dd, 8.05, 1.26 Hz, 1H), 8.30 (s, 1H), 8.41 (dd, 4.78, 1.26 Hz, 1H) |
| 269 | 4 | | 1-[(6-bromo-3H-imidazo[4,5-b]pyridin-3-yl)methyl]-4-propylpyrrolidin-2-one | 337/339 | 0.88 (m, 3H), 1.31 (m, 4H), 2.05 (dd, 17.06, 8.07 Hz, 1H), 2.33 (m, 1H), 2.52 (dd, 17.06, 8.53 Hz, 1H), 3.13 (m, 1H), 3.66 (m, 1H), 5.68 (s, 2H), 8.22 (s, 1H), 8.28 (s, 1H), 8.46 (s, 1H) |
| 270 | 4 | | 1-[(6-bromo-2-chloro-3H-imidazo[4,5-b]pyridin-3-yl)methyl]-4-propylpyrrolidin-2-one | 371/373 | 0.87 (m, 3H), 1.31 (m, 4H), 2.10 (m, 1H), 2.32 (m, 1H), 2.53 (m, 1H), 2.97 (dd, 9.54, 6.97 Hz, 1H), 3.49 (m, 1H), 5.77 (m, 2H), 8.11 (d, 2.02 Hz, 1H), 8.44 (d, 1.83 Hz, 1H) |
| 271 | 4 | | 1-[(6-bromo-2-phenyl-3H-imidazo[4,5-b]pyridin-3-yl)methyl]-4-propylpyrrolidin-2-one | 413/415 | (DMSO) 0.84 (m, 3H), 1.23 (m, 4H), 1.82 (m, 1H), 2.08 (m, 1H), 2.25 (dd, 16.56, 8.53 Hz, 1H), 2.98 (m, 1H), 3.36 (m, 1H), 5.8 (m, 2H), 7.57 (m, 3H), 7.83 (m, 2H), 8.44 (d, 2.01 Hz, 1H), 8.52 (d, 2.01 Hz, 1H) |

TABLE 1-continued

| n° | Config | Salt | IUPAC Name | MH⁺ (M⁺.) | ¹H NMR delta (CDCl₃ unless otherwise specified) |
|---|---|---|---|---|---|
| 272 | 4 | | 1-[(6-bromo-2-cyclopropyl-3H-imidazo[4,5-b]pyridin-3-yl)methyl]-4-(2,2-difluorovinyl)pyrrolidin-2-one | 397/399 | 1.22 (m, 4H), 2.24 (dd, 17.06, 8.34 Hz, 1H), 2.49 (m, 1H), 2.66 (dd, 17.06, 8.25 Hz, 1H), 3.14 (m, 2H), 3.65 (m, 1H), 4.16 (m, 1H), 5.83 (m, 2H), 8.00 (d, 1.65 Hz, 1H), 8.30 (d, 1.65 Hz, 1H) |
| 273 | 4 | | 1-[(3-chloro-7H-imidazo[4,5-c]pyridazin-7-yl)methyl]-4-propylpyrrolidin-2-one | 294/296 | 0.89 (t, 7.20 Hz, 3H), 1.32 (m, 4H), 2.06 (dd, 17.10, 8.30 Hz, 1H), 2.36 (m, 1H), 2.52 (m, 1H), 3.27 (dd, 9.56, 7.29 Hz, 1H), 3.82 (dd, 9.56, 8.05 Hz, 1H), 5.82 (m, 2H), 7.88 (s, 1H), 8.54 (s, 1H) |
| 274 | 4 | | 1-[(2-chloro-1H-indol-1-yl)methyl]-4-propylpyrrolidin-2-one | 291/293 | 0.84 (t, 7.06 Hz, 3H), 1.26 (m, $$H), 2.06 (dd, 16.87, 7.98 Hz, 1H), 2.24 (m, 1H), 2.51 (dd, 16.87, 8.53 Hz, 1H), 2.85 (dd, 9.54, 6.97 Hz, 1H), 3.38 (m, 1H), 5.68 (dd, 16, 20 Hz, 2H), 6.48 (s, 1H), 7.15 (m, 1H), 7.23 (m, 1H), 7.51 (d, 7.70 Hz, 1H), 7.60 (d, 8.25 Hz, 1H) |
| 275 | 4 | | 1-[(5-methyl-1H-indol-1-yl)methyl]-4-propylpyrrolidin-2-one | 271 | 0.83 (t, 7.06 Hz, 3H), 1.25 (m, 4H), 2.05 (dd, 16.69, 8.16 Hz, 1H), 2.23 (m, 1H), 2.49 (s, 3H), 2.50 (dd, 8, 16 Hz, 1H), 2.81 (dd, 9.17, 6.88 Hz, 1H), 3.31 (m, 1H), 5.54 (s, 2H), 6.43 (d, 2.93 Hz, 1H), 7.05 (d, 8 Hz, 1H), 7.11 (d, 3.12 Hz, 1H), 7.40 (m, 2H) |
| 276 | 4 | | 1-[(6-methyl-1H-indol-1-yl)methyl]-4-propylpyrrolidin-2-one | 271 | 0.84 (t, 7.06 Hz, 3H), 1.26 (m, 4H), 2.06 (dd, 16.69, 8.07 Hz, 1H), 2.25 (m, 1H), 2.51 (m, 4H), 2.83 (dd, 9.35, 6.97 Hz, 1H), 3.33 (m, 1H), 5.53 (d, 2.38 Hz, 2H), 6.46 (d, 3.12 Hz, 1H), 6.97 (d, 7.89 Hz, 1H), 7.08 (d, 3.30 Hz, 1H), 7.31 (s, 1H), 7.49 (d, 8.07 Hz, 1H) |
| 277 | 4 | | 1-[(2-phenyl-1H-indol-1-yl)methyl]-4-propylpyrrolidin-2-one | 333 | 0.76 (m, 3H), 1.10 (m, 4H), 1.90 (m, 1H), 2.07 (m, 1H), 2.36 (m, 2H), 2.82 (m, 1H), 5.68 (m, 2H), 6.55 (s, 1H), 7.17 (m, 1H), 7.26 (m, 1H), 7.46 (m, 5H), 7.61 (m, 2H) |
| 278 | 4 | | 1-[(5-fluoro-1H-indol-1-yl)methyl]-4-propylpyrrolidin-2-one | 275 | 0.84 (m, 3H), 1.25 (m, 4H), 2.06 (dd, 16.87, 7.89 Hz, 1H), 2.24 (m, 1H), 2.52 (dd, 16.87, 8.53 Hz, 1H), 2.81 (dd, 9.17, 6.88 Hz, 1H), 3.32 (m, 1H), 5.54 (s, 2H), 6.46 (d, 3.12 Hz, 1H), 6.97 (td, 8.99, 2.43 Hz, 1H), 7.19 (d, 3.12 Hz, 1H), 7.25 (m, 1H), 7.45 (d, 4.22 Hz, 1H) |
| 279 | 4 | | 1-[(5-bromo-1H-indol-1-yl)methyl]-4-propylpyrrolidin-2-one | 335/337 | 0.84 (t, 7.06 Hz, 3H), 1.26 (m, 4H), 2.05 (dd, 16.87, 7.89 Hz, 1H), 2.25 (m, 1H), 2.52 (dd, 16.87, 8.62 Hz, 1H), 2.81 (dd, 9.17, 6.88 Hz, 1H), 3.32 (m, 1H), 5.54 (d, 1.47 Hz, 2H), 6.45 (m, 1H), 7.16 (d, 3.30 Hz, 1H), 7.30 (dd, 8.80, 1.83 Hz, 1H), 7.42 (m, 1H), 7.74 (d, 1.65 Hz, 1H) |
| 280 | 4 | | 1-[(5-chloro-1H-indol-1-yl)methyl]-4-propylpyrrolidin-2-one | 291/293 | 0.84 (t, 7.06 Hz, 3H), 1.25 (m, 4H), 2.05 (dd, 16.87, 7.98 Hz, 1H), 2.25 (m, 1H), 2.52 (dd, 16.87, 8.62 Hz, 1H), 2.81 (dd, 9.17, 6.88 Hz, 1H), 3.32 (m, 1H), 5.54 (d, 1.65 Hz, 2H), 6.45 (m, 1H), 7.17 (m, 2H), 7.46 (d, 8.80 Hz, 1H), 7.57 (d, 1.83 Hz, 1H) |
| 281 | 4 | | 1-(2,3-dihydro-1H-indol-1-ylmethyl)-4-propylpyrrolidin-2-one | 259 | 0.89 (t, 7.15 Hz, 3H), 1.32 (m, 4H), 2.08 (dd, 16.69, 7.89 Hz, 1H), 2.30 (m, 1H), 2.52 (dd, 16.69, 8.62 Hz, 1H), 3.00 (m, 3H), 3.47 (m, 3H), 4.70 (s, 2H), 6.65 (m, 2H), 7.06 (m, 2H) |
| 282 | 4 | | 1-[(5-fluoro-2-phenyl-1H-indol-1-yl)methyl]-4-propylpyrrolidin-2-one | 351 | 0.77 (m, 3H), 1.10 (m, 4H), 1.93 (m, 1H), 2.06 (d, 7.52 Hz, 1H), 2.30 (dd, 9.35, 6.69 Hz, 1H), 2.40 (dd, 16.51, 8.34 Hz, 1H), 2.80 (dd, 9.35, 7.98 Hz, 1H), 5.65 (m, 2H), 6.49 (s, 1H), 6.97 (td, 9.17, 2.43 Hz, 1H), 7.25 (m, 2H), 7.50 (m, 6H) |
| 322 | 4 | | 1-[(2-oxo-4-propylpyrrolidin-1-yl)methyl]-1H-indole-2-carbonitrile | 282 | (DMSO): 0.78 (t, J 7.15 Hz, 3H), 1.11-1.27 (m, 4H), 1.98 (dd, J 16.56, 7.53 Hz, 1H), 2.23 (m, 1H), 2.43 (dd, J 16.56, 8.53 Hz, 1H), 2.87 (dd, J 6.77, 9.28 Hz, 1H), 3.41 (t, J 8.78 Hz, 1H), 5.69 (d, J 14.8 Hz, 1H), 5.69 (d, J 14.8 Hz, 1H), 7.23 (t, J 7.53 Hz, 1H), 7.43 (t, J 7.03 Hz, 1H), 7.52 (s, 1H), 7.72 (dd, J 6.5, 8.2 Hz, 2H) |
| 323 | 4 | | 1-[(2-bromo-1H-indol-1-yl)methyl]-4-propylpyrrolidin-2-one | 335/337 | (DMSO): 0.76 (t, J 7.15 Hz, 3H), 1.05-1.25 (m, 4H), 1.96 (dd, J 6.56, 7.53 Hz, 1H), 2.18 (m, 1H), 2.41 (dd, J 16.56, 8.66 Hz, 1H), 2.78 (dd, J 9.29, 6.53 Hz, 1H), 3.33 (m, 1H overlapped with solvent signal), 5.64 (s, 2H), 6.72 (s, 1H), 7.09 (t, J 7.28 Hz, 1H), |

TABLE 1-continued

| n° | Config | Salt | IUPAC Name | MH+ (M+.) | ¹H NMR delta (CDCl₃ unless otherwise specified) |
|---|---|---|---|---|---|
| 324 | 4 | | 1-[(2,5-dichloro-1H-indol-1-yl)methyl]-4-propylpyrrolidin-2-one | 325/327 | 7.17 (t, J 7.03 Hz, 1H), 7.51 (d, J 7.78 Hz, 1H), 7.62 (d, J 8.03 Hz, 1H). (DMSO): 0.78 (t, J 7.03 Hz, 3H), 1.11-1.25 (m, 4H), 1.96 (dd, J 16.56, 7.53 Hz, 1H), 2.20 (m, 1H), 2.41 (dd, J 16.81, 8.53 Hz, 1H), 2.81 (dd, J 9.29, 6.53 Hz, 1H), 3.36 (t, J 9.04 Hz, 1H partially overlapped with solvent signal), 5.63 (s, 2H), 6.64 (s, 1H), 7.23 (dd, J 8.78, 2.26 Hz, 1H), 7.58 (d, J 2.01 Hz, 1H), 7.64 (d, J 8.78 Hz, 1H) |
| 283 | 4 | | 1-[(6-amino-9H-purin-9-yl)methyl]-4-propylpyrrolidin-2-one | 275 | 0.88 (t, 7.18 Hz, 3H), 1.30 (m, 4H), 2.06 (dd, 16.87, 8.06 Hz, 1H), 2.34 (m, 1H), 2.52 (dd, 16.87, 8.69 Hz, 1H), 3.15 (dd, 9.57, 7.05 Hz, 1H), 3.67 (dd, 9.57, 8.06 Hz, 1H), 5.61 (s Hz, 2H), 5.81 (s, 2H), 8.05 (s, 1H), 8.38 (s, 1H) |
| 284 | 4 | | 4-propyl-1-(9H-purin-9-ylmethyl)pyrrolidin-2-one | 260 | 0.88 (t, 7.07 Hz, 3H), 1.32 (m, 4H), 2.06 (dd, 16.92, 8.08 Hz, 1H), 2.35 (m, 1H), 2.53 (dd, 17.18, 8.59 Hz, 1H), 3.17 (dd, 9.60, 7.07 Hz, 1H), 3.70 (m, 1H), 5.70 (s, 2H), 8.34 (s, 1H), 9.01 (s, 1H), 9.17 (s, 1H) |
| 285 | 4 | | 1-{[6-(cyclopropylamino)-9H-purin-9-yl]methyl}-4-propylpyrrolidin-2-one | 315 | (DMSO) 0.61 (m, 2H), 0.72 (m, 2H), 0.84 (t, 7.16 Hz, 3H), 1.24 (m, 4H), 1.96 (dd, 16.58, 7.66 Hz, 1H), 2.24 (m, 1H), 2.39 (m, 1H), 3.07 (dd, 9.29, 6.78 Hz, 1H), 3.59 (m, 1H), 5.54 (t, 4.52 Hz, 2H), 7.93 (s, NH, 1H), 8.06 (s, 1H), 8.28 (s, 1H) |
| 286 | 4 | | 1-{[6-(benzylamino)-9H-purin-9-yl]methyl}-4-propylpyrrolidin-2-one | 365 | (DMSO) 0.81 (t, 7.16 Hz, 3H), 1.23 (m, 4H), 1.95 (dd, 16.58, 7.66 Hz, 1H), 2.24 (m, 1H), 2.39 (m, 1H), 3.08 (dd, 9.29, 7.03 Hz, 1H), 3.59 (m, 1H), 4.71 (s, 2H), 5.54 (m, 2H), 7.28 (m, 5H), 8.09 (s, 1H), 8.24 (s, 1H), 8.32 (s, NH, 1H) |
| 287 | 4 | | 4-propyl-1-{[6-(propylamino)-9H-purin-9-yl]methyl}pyrrolidin-2-one | 317 | (DMSO) 0.81 (t, 7.03 Hz, 5H), 0.89 (t, 7.41 Hz, 5H), 1.24 (m, 7H), 1.60 (m, 3H), 1.96 (dd, 16.58, 7.79 Hz, 2H), 2.24 (m, 2H), 2.39 (m, 2H), 3.07 (dd, 9.04, 6.91 Hz, 2H), 3.43 (m, 2H), 3.59 (m, 1H), 5.53 (m, 2H), 7.82 (s, NH, 1H), 8.05 (s, 1H), 8.24 (s, 1H) |
| 288 | 4 | | 1-({6-[(cyclopropylmethyl)amino]-9H-purin-9-yl}methyl)-4-propylpyrrolidin-2-one | 329 | (DMSO) 0.27 (d, 4.52 Hz, 2H), 0.41 (m, 2H), 0.81 (m, 3H), 1.21 (m, 4H), 1.96 (dd, 16.58, 7.79 Hz, 1H), 2.24 (m, 1H), 2.39 (m, 1H), 3.07 (m, 1H), 3.4 (m, 2H), 3.59 (m, 1H), 5.53 (m, 2H), 7.87 (s, NH, 1H), 8.06 (s, 1H), 8.23 (s, 1H) |
| 289 | 4 | | 4-propyl-1-[(6-pyrrolidin-1-yl-9H-purin-9-yl)methyl]pyrrolidin-2-one | 329 | (DMSO) 0.82 (t, 7.16 Hz, 3H), 1.24 (m, 4H), 1.95 (m, 5H), 2.23 (m, 1H), 2.39 (dd, 16.58, 8.54 Hz, 1H), 3.57 (m, 3H), 4.04 (m, 2H), 5.54 (m, 2H), 8.04 (s, 1H), 8.24 (s, 1H) |
| 290 | 4 | | 1-[(5-bromo-3-phenyl-1H-pyrazolo[3,4-b]pyridin-1-yl)methyl]-4-propylpyrrolidin-2-one | 413/415 | 1.47 (t, 7.15 Hz, 3H), 1.91 (m, 4H), 2.57 (dd, 16.56, 8.28 Hz, 1H), 2.90 (m, 1H), 3.02 (m, 1H), 3.86 (dd, 9.79, 7.40 Hz, 1H), 4.38 (dd, 9.54, 7.91 Hz, 1H), 6.44 (s, 2H), 8.16 (m, 5H), 8.67 (d, 2.26 Hz, 1H), 9.30 (d, 2.26 Hz, 1H) |
| 291 | 4 | | 1-[(5-bromo-2H-pyrazolo[3,4-b]pyridin-2-yl)methyl]-4-propylpyrrolidin-2-one | 337/339 | 0.88 (t, 7.05 Hz, 3H), 1.32 (m, 4H), 2.07 (m, 1H), 2.35 (m, 1H), 2.52 (dd, 16.87, 8.56 Hz, 1H), 3.24 (dd, 9.57, 7.30 Hz, 1H), 3.77 (m, 1H), 5.80 (m, 2H), 8.08 (m, 1H), 8.18 (m, 1H), 8.70 (m, 1H) |
| 292 | 4 | | 1-[(5-bromo-3-phenyl-2H-pyrazolo[3,4-b]pyridin-2-yl)methyl]-4-propylpyrrolidin-2-one | 413/415 | 0.86 (t, 7.15 Hz, 3H), 1.30 (m, 4H), 2.08 (m, 1H), 2.30 (m, 1H), 2.55 (dd, 16.81, 8.53 Hz, 1H), 3.05 (dd, 9.54, 6.78 Hz, 1H), 3.57 (m, 1H), 6.00 (m, 2H), 7.48 (m, 3H), 7.92 (d, 7.53 Hz, 2H), 8.46 (d, 2.01 Hz, 1H), 8.62 (d, 2.01 Hz, 1H) |
| 293 | 4 | | 1-[(2-chloro-1H-pyrrolo[2,3-b]pyridin-1-yl)methyl]-4-propylpyrrolidin-2-one | 292/294 | 0.84 (m, 3H), 1.26 (m, 4H), 2.08 (dd, 16.81, 7.91 Hz, 1H), 2.24 (m, 1H), 2.53 (dd, 16.56, 8.53 Hz, 1H), 2.82 (dd, 9.79, 6.78 Hz, 1H), 3.33 (m, 1H), 5.88 (m, 2H), 6.46 (s, 1H), 7.11 (dd, 7.78, 4.77 Hz, 1H), 7.82 (d, 7.78 Hz, 1H), 8.30 (d, 4.77 Hz, 1H) |
| 294 | 4 | | 4-propyl-1-(1H-pyrrolo[3,2-b]pyridin-1-ylmethyl)pyrrolidin-2-one | 258 | (DMSO) 0.78 (t, 7.03 Hz, 3H), 1.18 (m, 4H), 1.96 (dd, 16.56, 7.53 Hz, 1H), 2.20 (m, 1H), 2.41 (dd, 16.81, 8.53 Hz, 1H), 2.83 (dd, 9.29, 6.53 Hz, 1H), 3.39 (m, 1H), 5.61 (m, 2H), 6.59 (d, 3.01 Hz, 1H), 7.16 (dd, 8.28, |

TABLE 1-continued

| n° | Config | Salt | IUPAC Name | MH+ (M+.) | 1H NMR delta (CDCl3 unless otherwise specified) |
|---|---|---|---|---|---|
| 295 | 4 | | 1-(3,4-dihydroquinolin-1(2H)-ylmethyl)-4-propylpyrrolidin-2-one | 273 | 4.52 Hz, 1H), 7.73 (d, 3.26 Hz, 1H), 7.95 (d, 8.28 Hz, 1H), 8.36 (dd, 4.52, 1.13 Hz, 1H) 0.88 (t, 7.15 Hz, 3H), 1.22-1.44 (m, 4H), 1.94 (m, 2H), 2.07 (dd, 16.56, 7.78 Hz, 1H), 2.29 (m, 1H), 2.52 (dd, 16.56, 8.53 Hz, 1H), 2.77 (t, 6.27 Hz, 2H), 2.97 (dd, 9.54, 6.78 Hz, 1H), 3.35 (m, 2H), 3.46 (dd, 9.29, 8.03 Hz, 1H), 4.83 (m, 2H), 6.64 (t, 7.16 Hz, 1H), 6.79 (d, 8.29 Hz, 1H), 6.97 (d, 7.28 Hz, 1H), 7.06 (m, 1H) |
| 296 | 4 | | 1-(8H-isothiazolo[5,4-b]indol-8-ylmethyl)-4-propylpyrrolidin-2-one | 314 | (DMSO): 0.79 (t, 7.15 Hz, 3H), 1.12-1.37 (m, 4H), 2.01 (m, 1H), 2.23 (m, 1H), 2.44 (dd, 16.58, 8.67 Hz, 1H), 2.93 (m, 1H), 3.45 (t, 8.54 Hz, 1H), 5.74 (s Hz, 2H), 7.34 (m, 4H), 7.77 (d, 8.04 Hz, 1H), 8.11 (d, 7.53 Hz, 1H) |
| 297 | | | 1-(1H-1,2,4-triazol-1-ylmethyl)pyrrolidin-2-one | | (DMSO): 1.94 (m, 2H), 2.28 (t, J 8 Hz, 2H), 2.32-2.44 (m, 2H overlapped with solvent), 1.45 (s, 2H), 8.00 (s, 1H), 8.56 (s, 1H) |
| 298 | 4 | | 1-[(2,5-dichloro-1H-pyrrol-1-yl)methyl]-4-propylpyrrolidin-2-one | 275/277/279 | (DMSO): 0.83 (t, J 7.3 Hz, 3H), 1.24 (m, 4H), 1.96 (dd, J 16.6; 7.3 Hz, 1H; 2.83 (m, 1H), 2.41 (dd, J 16.6; 8.5 Hz, 1H), 2.75 (dd, J 9.3; 6.5 Hz, 1H), 3.29 (m, overlapped with solvent, 1H), 5.38 (s, 2H), 6.22 (s, 2H) |
| 299 | 4 | | 1-[(2-chloro-1H-pyrrol-1-yl)methyl]-4-propylpyrrolidin-2-one | 241/243 | (DMSO): 0.84 (t, J 7.3 Hz, 3H), 1.25 (m, 4H), 1.96 (dd, J 16.6; 7.3 Hz, 1H; 2.83 (m, 1H), 2.24 (dd, J 16.6; 8.5 Hz, 1H), 2.85 (dd, J 9.3; 6.5 Hz, 1H), 3.39 (dd, J 9.3; 7.9 Hz, 1H), 5.27 (d, J 14.5 Hz, 1H), 5.34 (d, J 14.05 Hz, 1H), 6.08 (m, 2H), 6.86 (t, J 2.8 hz, 1H) |
| 300 | 4 | | 1-[(2-chloro-1H-benzimidazol-1-yl)methyl]-4-propylpyrrolidin-2-one | 312/314 | 0.85 (t, 7.02 Hz, 3H), 1.28 (m, 4H), 2.07 (dd, 16.48, 7.93 Hz, 1H), 2.29 (m, 1H), 2.54 (m, 1H), 2.94 (dd, 9.31, 6.87 Hz, 1H), 3.47 (m, 1H), 5.67 (s, 2H), 7.30 (m, 2H), 7.66 (m, 2H) |
| 301 | 4 | | 1-[(2-chloro-1H-benzimidazol-1-yl)methyl]-4-phenylpyrrolidin-2-one | 326 | 2.59 (dd, 17.18, 8.34 Hz, 1H), 2.85 (dd, 17.18, 9.09 Hz, 1H), 3.35 (dd, 9.60, 7.20 Hz, 1H), 3.53 (m, 1H), 3.77 (m, 1H), 5.76 (m, 2H), 7.08 (m, 2H), 7.24 (m, 3H), 7.33 (m, 2H), 7.69 (m, 2H) |
| 302 | 4 | | 2-chloro-1-[(2-oxo-4-propylpyrrolidin-1-yl)methyl]-1H-benzimidazole-5-carbonitrile | 317/319 | (DMSO): 0.80 (t, 7 Hz, 3H), 1.28 (m, 4H), 2 (m, 1H), 2.25 (m, 1H), 2.44 (m, 1H), 2.99 (m, 1H), 3.51 (m, 1H), 5.74 (s, 2H), 7.78 (m, 1H), 7.89 (m, 1H), 8.21 (s, 1H) |
| 303 | 4 | | 2-chloro-1-[(2-oxo-4-propylpyrrolidin-1-yl)methyl]-1H-benzimidazole-6-carbonitrile | 317/319 | (DMSO): 0.85 (t, 7.03 Hz, 3H), 1.28 (m, 4H), 2.02 (m, 1H), 2.28 (m, 1H), 2.44 (m, 1H), 3.02 (m, 1H), 3.51 (m, 1H), 5.72 (s, 2H), 7.70 (m, 1H), 7.81 (m, 1H), 8.23 (s, 1H) |
| 304 | 4 | | 4-propyl-1-[(2,5,6-trichloro-1H-benzimidazol-1-yl)methyl]pyrrolidin-2-one | 360/362/364 | 0.88 (t, 7.05 Hz, 3H), 1.31 (m, 5H), 2.10 (dd, 17.12, 8.18 Hz, 1H), 2.34 (m, 1H), 2.56 (dd, 17.12, 8.56 Hz, 1H), 2.98 (dd, 9.32, 7.05 Hz, 1H), 3.50 (m, 1H), 5.62 (m, 2H), 7.76 (s, 1H), 7.84 (s, 1H) |
| 305 | 4 | | 1-[(2-chloro-6-methoxy-1H-benzimidazol-1-yl)methyl]-4-propylpyrrolidin-2-one | 322/324 | 0.87 (t, 7.15 Hz, 3H), 1.30 (m, 4H), 2.08 (dd, 16.81, 8.16 Hz, 1H), 2.32 (m, 1H), 2.54 (dd, 17.07, 8.66 Hz, 1H), 2.96 (dd, 9.29, 7.03 Hz, 1H), 3.48 (m, 1H), 3.85 (s, 3H), 5.63 (s, 2H), 6.90 (dd, 8.78, 2.38 Hz, 1H), 7.23 (d, 2.38 Hz, 1H), 7.54 (d, 8.78 Hz, 1H) |
| 306 | 4 | | 1-[(2-chloro-5-methoxy-1H-benzimidazol-1-yl)methyl]-4-propylpyrrolidin-2-one | 322/324 | 0.86 (t, 7.15 Hz, 3H), 1.28 (m, 4H), 2.07 (dd, 17.07, 7.91 Hz, 1H), 2.30 (m, 1H), 2.53 (dd, 17.07, 8.66 Hz, 1H), 2.93 (dd, 9.29, 6.90 Hz, 1H), 3.45 (m, 1H), 3.84 (s, 3H), 5.64 (s, 2H), 6.94 (dd, 9.03, 2.38 Hz, 1H), 7.15 (d, 2.26 Hz, 1H), 7.52 (d, 8.78 Hz, 1H) |
| 307 | 4 | | 1-[(2-chloro-6-nitro-1H-benzimidazol-1-yl)methyl]-4-propylpyrrolidin-2-one | 337/339 | 0.88 (t, 7.28 Hz, 3H), 1.33 (m, 4H), 2.11 (dd, 17.08, 8.04 Hz, 1H), 2.36 (m, 1H), 2.58 (dd, 17.08, 8.79 Hz, 1H), 3.03 (dd, 9.29, 7.03 Hz, 1H), 3.55 (m, 1H), 5.76 (m, 2H), 7.76 (d, 8.79 Hz, 1H), 8.24 (dd, 9.04, 2.26 Hz, 1H), 8.72 (d, 2.01 Hz, 1H) |
| 308 | 4 | | 1-[(2-chloro-5-nitro-1H-benzimidazol-1-yl)methyl]-4-propylpyrrolidin-2-one | 337/339 | 0.88 (t, 7.15 Hz, 3H), 1.32 (m, 4H), 2.10 (dd, 17.07, 8.03 Hz, 2H), 2.35 (m, 1H), 2.57 (dd, 17.07, 8.53 Hz, 1H), 3.01 (dd, 9.03, 7.03 Hz, 1H), 3.54 (t, 8.66 Hz, 1H), 5.73 (s, 3H), 7.76 (d, 9.03 Hz, 1H), 8.25 (dd, 9.03, 1.76 Hz, 1H), 8.59 (d, 1.76 Hz, 1H) |

TABLE 1-continued

| n° | Config | Salt | IUPAC Name | MH⁺ (M⁺.) | $^1$H NMR delta (CDCl$_3$ unless otherwise specified) |
|---|---|---|---|---|---|
| 309 | 4 | | 1-[(2-chloro-6-methyl-1H-benzimidazol-1-yl)methyl]-4-propylpyrrolidin-2-one | 306/308 | 0.86 (t, 7.15 Hz, 3H), 1.29 (m, 4H), 2.09 (dd, 16.81, 8.16 Hz, 2H), 2.31 (m, 1H), 2.48 (s, 3H), 2.56 (m, 1H), 2.94 (dd, 9.29, 7.28 Hz, 1H), 3.46 (m, 1H), 5.65 (m, 2H), 7.12 (d, 8.28 Hz, 1H), 7.42 (s, 1H), 7.55 (d, 8.03 Hz, 1H) |
| 310 | 4 | | 1-[(2-chloro-1H-benzimidazol-1-yl)methyl]-4-(2,2-difluorovinyl)pyrrolidin-2-one | 312/314 | 2.23 (dd, 17.07, 8.41 Hz, 1H), 2.66 (dd, 17.07, 8.66 Hz, 1H), 3.12 (m, 2H), 3.58 (m, 1H), 4.13 (m, 1H), 5.71 (m, 2H), 7.26 (s, 1H), 7.32 (m, 2H), 7.64 (m, 1H), 7.69 (m, 1H) |
| 311 | 4 | | 1-[(6-bromo-2-chloro-1H-benzimidazol-1-yl)methyl]-4-propylpyrrolidin-2-one | 370/372/374 | (DMSO): 0.81 (t, 7.15 Hz, 3H), 1.24 (m, 4H), 2.01 (dd, 16.56, 7.78 Hz, 1H), 2.26 (m, 1H), 2.44 (dd, 16.56, 8.53 Hz, 1H), 2.98 (dd, 9.03, 6.78 Hz, 1H), 3.51 (m, 1H), 5.65 (s, 2H), 7.43 (dd, 8.53, 1.51 Hz, 1H), 7.58 (m, 1H), 7.96 (d, 1.76 Hz, 1H) |
| 312 | 4 | | 1-[(5-bromo-2-chloro-1H-benzimidazol-1-yl)methyl]-4-propylpyrrolidin-2-one | 370/372/374 | (DMSO): 0.80 (t, 7.15 Hz, 3H), 1.22 (m, 4H), 1.99 (dd, 16.81, 7.78 Hz, 1H), 2.24 (m, 1H), 2.43 (dd, 16.81, 8.66 Hz, 1H), 2.94 (dd, 9.03, 6.78 Hz, 1H), 3.47 (t, 8.53 Hz, 1H), 5.66 (s, 2H), 7.51 (dd, 8.53, 1.63 Hz, 1H), 7.66 (m, 1H), 7.85 (d, 1.76 Hz, 1H) |
| 313 | 4 | | 1-[(2-chloro-6-fluoro-1H-benzimidazol-1-yl)methyl]-4-propylpyrrolidin-2-one | 310/312 | 0.87 (m, 3H), 1.31 (m, 4H), 2.09 (dd, 16.87, 7.98 Hz, 1H), 2.32 (m, 1H), 2.46 (m, 2H), 2.97 (dd, 9.35, 6.97 Hz, 1H), 3.49 (m, 1H), 5.63 (s, 2H), 7.04 (td, 9.17, 2.38 Hz, 1H), 7.42 (dd, 8.62, 2.38 Hz, 1H), 7.60 (dd, 8.99, 4.68 Hz, 1H) |
| 314 | 4 | | 1-[(2-chloro-5-fluoro-1H-benzimidazol-1-yl)methyl]-4-propylpyrrolidin-2-one | 310/312 | 0.87 (t, 7.15 Hz, 3H), 1.29 (m, 4H), 2.08 (m, 1H), 2.32 (m, 1H), 2.55 (dd, 17.07, 8.53 Hz, 1H), 2.96 (dd, 9.29, 6.78 Hz, 1H), 3.48 (m, 1H), 5.66 (s, 2H), 7.06 (td, 9.29, 2.32 Hz, 1H), 7.36 (dd, 9.03, 2.51 Hz, 1H), 7.62 (dd, 9.03, 4.52 Hz, 1H) |
| 315 | 4 | | 1-[(2,6-dichloro-1H-benzimidazol-1-yl)methyl]-4-propylpyrrolidin-2-one | 326/328/330 | 0.87 (m, 3H), 1.29 (m, 4H), 2.08 (m, 1H), 2.32 (m, 1H), 2.54 (dd, 17.06, 8.62 Hz, 1H), 2.95 (dd, 9.35, 6.97 Hz, 1H), 3.48 (m, 1H), 5.66 (s, 2H), 7.28 (m, 2H), 7.61 (d, 8.62 Hz, 1H), 7.66 (d, 1.83 Hz, 1H) |
| 316 | 4 | | 1-[(2,5-dichloro-1H-benzimidazol-1-yl)methyl]-4-propylpyrrolidin-2-one | 326/328/330 | 0.87 (t, 7.15 Hz, 3H), 1.32 (m, 4H), 2.09 (m, 1H), 2.33 (m, 1H), 2.56 (dd, 17.06, 8.62 Hz, 1H), 2.97 (dd, 9.17, 7.15 Hz, 1H), 3.49 (m, 1H), 5.64 (s, 2H), 7.27 (m, 1H), 7.58 (d, 8.62 Hz, 1H), 7.69 (d, 1.47 Hz, 1H) |
| 317 | 4 | | 1-{[2-chloro-6-(trifluoromethyl)-1H-benzimidazol-1-yl]methyl}-4-propylpyrrolidin-2-one | 360/362 | 0.87 (t, 7.15 Hz, 3H), 1.31 (m, 4H), 2.09 (dd, 16.81, 8.16 Hz, 1H), 2.34 (m, 1H), 2.56 (dd, 17.07, 8.53 Hz, 1H), 2.99 (dd, 9.29, 7.03 Hz, 1H), 3.51 (m, 1H), 5.72 (s, 2H), 7.56 (d, 8.53 Hz, 1H), 7.77 (d, 8.53 Hz, 1H), 8.04 (s Hz, 1H) |
| 318 | 4 | | 1-{[2-chloro-5-(trifluoromethyl)-1H-benzimidazol-1-yl]methyl}-4-propylpyrrolidin-2-one | 360/362 | 0.87 (t, 7.15 Hz, 3H), 1.29 (m, 4H), 2.08 (m, 1H), 2.33 (m, 1H), 2.55 (dd, 16.87, 8.53 Hz, 1H), 2.98 (m, 1H), 3.50 (m, 1H), 5.71 (s, 2H), 7.56 (d, 8.62 Hz, 1H), 7.80 (d, 8.62 Hz, 1H), 7.96 (s, 1H) |
| 319 | | | 1-[(2-chloro-1H-benzimidazol-1-yl)methyl]pyrrolidin-2-one | 250/252 | 2.01 (m, 2H), 2.42 (m, 2H), 3.38 (m, 2H), 5.71 (s, 2H), 7.29 (m, 2H), 7.67 (m, 2H) |
| 320 | 4 | | 1-[(2-chloro-6-hydroxy-1H-benzimidazol-1-yl)methyl]-4-propylpyrrolidin-2-one | 308/310 | (DMSO): 0.80 (t, 7.15 Hz, 3H), 1.23 (m, 4H), 2.00 (dd, 16.81, 7.65 Hz, 1H), 2.24 (m, 1H), 2.44 (dd, 16.56, 8.53 Hz, 1H), 2.91 (dd, 9.03, 6.78 Hz, 1H), 3.43 (m, 1H), 5.54 (m, 2H), 6.73 (dd, 8.78, 2.26 Hz, 1H), 7.02 (m, 1H), 7.38 (m, 1H), 9.53 (s, OH, 1H) |
| 321 | 4 | | 1-[(2-chloro-5-hydroxy-1H-benzimidazol-1-yl)methyl]-4-propylpyrrolidin-2-one | 308/310 | (DMSO): 0.87 (t, 7.28 Hz, 3H), 1.31 (m, 4H), 2.07 (m, 1H), 2.3 (m, 1H), 2.55 (m, 1H), 3.00 (m, 1H), 3.52 (m, 1H), 5.70 (s, 2H), 6.95 (dd, 8.78, 2.01 Hz, 1H), 7 (s, 1H), 7.58 (d, 9.03 Hz, 1H), 9.3 (s, OH, 1H) |

Example 95

LBS Binding Assay

[LBS stands for Levetiracetam Binding Site cf. M. Noyer et al., *Eur. J. Pharmacol.* (1995), 286, 137-146.]

The inhibition constant ($K_i$) of a compound is determined in competitive binding experiments by measuring the binding of a single concentration of a radioactive ligand at equilibrium with various concentrations of the unlabeled test substance. The concentration of the test substance inhibiting 50% of the specific binding of the radioligand is called the IC$_{50}$.

The equilibrium dissociation constant $K_i$ is proportional to the $IC_{50}$ and is calculated using the equation of Cheng and Prusoff (Cheng Y. et al., Biochem. Pharmacol. (1972), 22, 3099-3108).

The concentration range usually encompasses 6 log units with variable steps (0.3 to 0.5 log). Assays are performed in mono- or duplicate, each $K_i$ determination is performed on two different samples of test substance.

Cerebral cortex from 200-250 g male Sprague-Dawley rats are homogenised using a Potter S homogeniser (10 strokes at 1,000 rpm; Braun, Germany) in 20 mmol/l Tris-HCl (pH 7.4), 250 mmol/l sucrose (buffer A); all operations are performed at 4° C. The homogenate is centrifuged at 30,000 g for 15 min. The crude membrane pellet obtained is resuspended in 50 mmol/l Tris-HCl (pH 7.4), (buffer B) and incubated 15 min at 37° C., centrifuged at 30,000 g for 15 min and washed twice with the same buffer. The final pellet is resuspended in buffer A at a protein concentration ranging from 15 to 25 mg/ml and stored in liquid nitrogen.

Membranes (150-200 µg of protein/assay) are incubated at 4° C. for 120 min in 0.5 ml of a 50 mmol/l Tris-HCl buffer (pH 7.4) containing 2 mmol/l $MgCl_2$, 1 to 2 $10^{-9}$ mol/l of [$^3$H]-2-[4-(3-azidophenyl)-2-oxo-1-pyrrolidinyl]butanamide and increasing concentrations of the test compound of formula (I). The non specific binding (NSB) is defined as the residual binding observed in the presence of a concentration of reference substance (e.g. $10^{-3}$ mol/l levetiracetam) that binds essentially all the receptors. Membrane-bound and free radioligands are separated by rapid filtration through glass fiber filters (equivalent to Whatman GF/C or GF/B; VEL, Belgium) pre-soaked in 0.1% polyethyleneimine and $10^{-3}$ mol/l levetiracetam to reduce non specific binding. Samples and filters are rinsed by at least 6 ml of 50 mmol/l Tris-HCl (pH 7.4) buffer. The entire filtration procedure does not exceed 10 seconds per sample. The radioactivity trapped onto the filters is counted by liquid scintillation in a β-counter (Tri-Carb 1900 or TopCount 9206, Camberra Packard, Belgium, or any other equivalent counter). Data analysis is performed by a computerized non linear curve fitting method using a set of equations describing several binding models assuming populations of independent non-interacting receptors, which obey the law of mass.

Example 96

Animal Model of Sound-Susceptible Mice

The objective of this test is to evaluate the anticonvulsant potency of a compound in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. & Schmidt D., Epilepsy Res. (1998), 2, 145-181; Buchhalter J. R., Epilepsia (1993), 34, S31-S41).

Male or female genetically sound-sensitive mice (14-28 g; N=10), derived from a DBA strain originally selected by Dr. Lehmann of the Laboratory of Acoustic Physiology (Paris) and bred in the UCB Pharma Sector husbandry unit since 1978, are used. The experimental design consisted of several groups, one group receiving the vehicle control and the other groups different doses of the test-compound. The compounds are administered intraperitoneally 60 minutes before the induction of audiogenic seizures. The range of the doses administered had a logarithmic progression, generally between $1.0 \times 10^{-5}$ mol/kg and $1.0 \times 10^{-3}$ mol/kg, but lower or higher doses are tested if necessary.

For testing, the animals are placed in small cages, one mouse per cage, in a sound-attenuated chamber. After a period of orientation of 30 seconds, the acoustic stimulus (90 dB, 10-20 kHz) is delivered for 30 seconds via loudspeakers positioned above each cage. During this interval, the mice are observed and the presence of the 3 phases of the seizure activity namely wild running, clonic and tonic convulsions, is recorded. The proportion of mice protected against wild running, clonic and tonic convulsions, respectively, is calculated.

For active compounds, an $ED_{50}$ value, i.e. the dose producing 50% protection relative to the control group, together with 95% confidence limits, is calculated using a Probit Analysis (SAS/STAT® Software, version 6.09, PROBIT procedure) of the proportions of protected mice for each of the 3 phases of the seizure activity.

Compounds synthesized according to the procedure described in examples 1 to 94 and described in table 1 (except compounds 106, 180, 222 and 225) are tested in the SV2 binding assay and/or audiogenic seizure in mice, according to the procedure described above, and are found active.

The invention claimed is:
1. A compound having the structural formula I

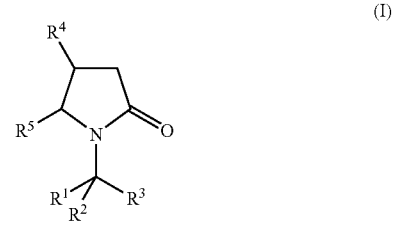

or a geometric isomer, enantiomer, diastereoisomer, or a pharmaceutically acceptable salt thereof, wherein
$R^1$ is hydrogen, $C_{1-12}$ alkyl, aryl or heterocycle;
$R^2$ is hydrogen; or $R^1$ and $R^2$ are linked together to form a $C_{3-6}$ cycloalkyl;
$R^3$ is
a) an unsubstituted or substituted heterocycle linked to the rest of the molecule via one of its C atoms; or
b) an unsubstituted or substituted heterocycle linked to the rest of the molecule via one of its N atoms selected from the group consisting of:
1H-1,2,3-benzotriazol-1-yl;
1H-imidazo[4,5-b]pyridin-1-yl;
3H-imidazo[4,5-b]pyridin-3-yl;
7H-imidazo[4,5-c]pyridazin-7-yl;
1H-indol-1-yl;
2,3-dihydro-1H-indol-1yl;
9H-purin-9-yl;
1H-pyrazolo[3,4-b]pyridin-1-yl;
2H-pyrazolo[3,4-b]pyridin-2-yl;
1H-pyrrolo[2,3-b]pyridin-1-yl;
1H-pyrrolo[3,2-b]pyridin-1-yl;
3,4-dihydroquinolin-1(2H)-yl;
8H-isothiazolo[5,4-b]indol-8-yl;
1H-1,2,4-triazol-1-yl;
1H-1,2,3-triazol-1-yl;
1H-pyrrol-1-yl;
1H-tetrazol-1-yl; and
2-chloro-1H-b enzimidazol-1-yl;
$R^4$ is hydrogen; $C_{1-12}$ alkyl optionally substituted by halogen, $C_{1-4}$ alkoxy, $C_{1-4}$ alkylthio, azido, nitrooxy or aryl; $C_{2-12}$ alkenyl; $C_{2-12}$ alkynyl; substituted or unsubstituted aryl non-substituted by a cycloalkoxy; azido; alkoxycarbonylamino; arylsulfonyloxy; or heterocycle;
R⁵ is hydrogen;
with the provisos that
R⁴ is not hydrogen when R¹, R² and R⁵ are hydrogen, and R³ is substituted or unsubstituted 3-pyridinyl; unsubstituted 4-pyridinyl; 2-(phenylamino)pyrimidin-4-yl; 2-trifluoropyrimidin-4-yl; isoxazol-5-yl 3-substituted by an aryl or an heterocycle; a substituted 1H-pyrazol-5-yl; a substituted 1H-pyrazol-3-yl; a 3-substituted 1,2,4-oxadiazol-5-yl; an unsubstituted or 1-substituted 1H-indol-3-yl; 2-[[4-[2-(1-methylethoxy)phenyl]-1-piperazinyl]methyl]thiazol-5-yl; (2-(4-chlorophenyl)-6-methylimidazo[1,2-a]pyridin-3-yl); 5-(4-methoxyphenyl)-7-trifluoromethyl -pyrazolo[1,5-a]pyrimidin-3-yl; substituted or unsubstituted 1,2,4-triazol-3-yl; substituted or unsubstituted 1,2,4-triazol-5-yl; 4,5,6,7-tetrahydro-2,1-benzisoxazol-3-yl; substituted 4,5-dihydroisoxazol-5-yl; substituted or unsubstituted 1H-1,2,3-benzotriazol-3-yl; 5-substituted 1,2,4-oxadiazol-3-yl; unsubstituted 1H-imidazo[4,5-c]pyridin-2-yl; 1,3-dimethyl-2,6-dioxo-1,2,3,6-tetrahydro-9H-purin-9-yl; substituted or unsubstituted 2-thienyl; substituted or unsubstituted 2-furyl; substituted or unsubstituted 2-pyrrolyl; substituted to unsubstituted 2-benzimidazol-2-yl; or 1-substituted 1H-indol-2-yl;
R⁴ is not phenyl when R¹, R² and R⁵ are hydrogen, and R³ is a substituted 1,2,4-triazol-3-yl; a substituted 1,2,4-triazol-5-yl; or unsubstituted 1H-benzimidazol-2-yl;
R⁴ is not hydrogen or phenyl when R¹ is hydrogen or C₁₋₁₂ alkyl, R² and R⁵ are hydrogen, and R³ is a substituted or unsubstituted non aromatic heterocycle;
R⁴ is not hydrogen when R¹ is C₁₋₁₂ alkyl, R² and R⁵ are hydrogen, and R³ is a 3-substituted 1,2,4-oxadiazol-5-yl or unsubstituted 3-indolyl;
R⁴ is not hydrogen when R¹ is phenyl, C₁₋₁₂ alkyl or heterocycle, R² and R⁵ are hydrogen, and R³ is unsubstituted 1,2,3-benzotriazol-1-yl or unsubstituted 1,2,4-triazol-1-yl;
R¹ is not 1-pyrrolidin-2-one when R², R⁴ and R⁵ are hydrogen, and R³ is 2-furyl;
and R¹ is not 4-(2-pyrimidinyl)-1-piperazinyl when R², R⁴ and R⁵ are hydrogen, and R³ is 1-methyl-1H-pyrrol-2-yl.

2. The compound or a geometric isomer, enantiomer, diastereoisomer, or a pharmaceutically acceptable salt thereof according to claim 1, wherein R³ is a unsubstituted or substituted unsaturated heterocycle comprising at least one sp² hybridized nitrogen in the beta-, gamma- or delta-position of the carbon attached to the methylpyrrolidinone moiety; or a unsubstituted or substituted heterocycle selected from the group consisting of 1H-1,2,3-benzotriazol-1-yl; 1H-imidazo[4,5-b]pyridin-1-yl; 3H-imidazo [4,5-b]pyridin-3-yl; 7H-imidazo[4,5-c]pyridazin-7-yl; 1H-indol-1-yl; 2,3-dihydro-1H-indol-1yl; 9H-purin-9-yl; 1H-pyrazolo[3,4-b]pyridin-1-yl; 2H-pyrazolo[3,4-b]pyridin-2-yl; 1H-pyrrolo[2,3-b]pyridin-1-yl; 1H-pyrrolo[3,2-b]pyridin-1-yl; 3,4-dihydroquinolin-1(2H)-yl; 8H-isothiazolo[5,4-b]indol-8-yl; 1H-1,2,4-triazol-1-yl; 1H-1,2,3-triazol-1-yl; 1H-pyrrol-1-yl; and 1H-tetrazol-1-yl.

3. The compound or a geometric isomer, enantiomer, diastereoisomer, or a pharmaceutically acceptable salt thereof according to claim 1, wherein R³ is a unsubstituted or substituted aromatic heterocycle comprising at least one sp² hybridized nitrogen in the beta-, gamma- or delta-position of the carbon attached to the methylpyrrolidinone moiety; or a unsubstituted or substituted heterocycle selected from the group consisting of 1H-1,2,3-benzotriazol-1-yl; 1H-imidazo[4,5-b]pyridin-1-yl; 3H-imidazo[4,5-b]pyridin-3-yl; 7H-imidazo[4,5-c]pyridazin-7-yl; 1H-indol-1-yl; 2,3-dihydro-1H-indol-1yl; 9H-purin-9-yl; 1H-pyrazolo[3,4-b]pyridin-1-yl; 2H-pyrazolo[3,4-b]pyridin-2-yl; 1H-pyrrolo[2,3-b]pyridin-1-yl; 1H-pyrrolo[3,2-b]pyridin-1-yl; 3,4-dihydroquinolin-1(2H)-yl; 8H-isothiazolo[5,4-b]indol-8-yl; 1H-1,2,4-triazol-1-yl; and 1H-pyrrol-1-yl.

4. The compound or a geometric isomer, enantiomer, diastereoisomer, or a pharmaceutically acceptable salt thereof according to claim 1,

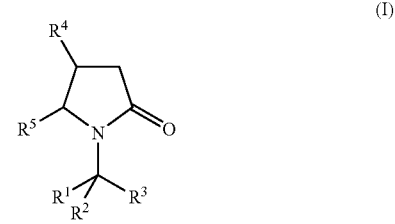

(I)

wherein
R¹ is hydrogen;
R² is hydrogen;
R³ is
(a) a heterocycle selected from the group consisting of:
1H-benzimidazol-6-yl;
1H-benzimidazol-7-yl;
imidazo[1,2-a]pyridin-3-yl;
imidazo[1,2-a]pyrimidin-3-yl;
imidazo[1,2-b][1,2,4]triazin-7-yl;
imidazo[1,2-b]pyridazin-3-yl;
5,6,7,8-tetrahydroimidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
1H-indol-2-yl;
1H-indol-3-yl;
1H-indol-4-yl;
1H-indol-7-yl;
isoxazol-4-yl;
1H-pyrazol-4-yl;
1H-pyrazol-5-yl;
1H-pyrazolo[1,5-a]pyrimidin-3-yl;
1H-pyrazolo[3,4-b]pyridin-3-yl;
pyridazin-4-yl;
pyridin-2-yl;
pyridin-3-yl;
pyridin-4-yl;
1H-pyrrolo[2,3-b]pyridin-3-yl;
1H-pyrrolo[2,3-b]pyridin-4-yl;
1H-pyrrolo[2,3-b]pyridin-5-yl;
1H-pyrrolo[2,3-c]pyridin-2-yl;
1H-pyrrolo[2,3-c]pyridin-3-yl;
1H-pyrrolo[3,2-b]pyridin-3-yl;
1H-pyrrolo[3,2-c]pyridin-2-yl;
1H-pyrrolo[3,2-c]pyridin-3-yl;
1,3,4-thiadiazol-2-yl;
1,3-thiazol-5-yl;
[1,2,4]triazolo[4,3-b]pyridazin-7-yl;
[1,2,4]triazolo[4,3-b]pyridazin-8-yl; and
indolizin-3-yl; or (b) a heterocycle selected from the group consisting of:
  1H-1,2,3-benzotriazol-1-yl;
  1H-imidazo[4,5-b]pyridin-1-yl;
  3H-imidazo[4,5-b]pyridin-3-yl;
  7H-imidazo[4,5-c]pyridazin-7-yl;
  1H-indol-1-yl;
  2,3-dihydro-1H-indol-1yl;
  9H-purin-9-yl;
  1H-pyrazolo[3,4-b]pyridin-1-yl;
  2H-pyrazolo[3,4-b]pyridin-2-yl;
  1H-pyrrolo[2,3-b]pyridin-1-yl;
  1H-pyrrolo[3,2-b]pyridin-1-yl;
  3,4-dihydroquinolin-1(2H)-yl;
  8H-isothiazolo[5,4-b]indol-8-yl;
  1H-1,2,4-triazol-1-yl; and
  1H-pyrrol-1-yl;
$R^4$ is $C_{1-12}$ alkyl optionally substituted by halogen or $C_{1-4}$ alkoxy; $C_{2-12}$ alkenyl; or $C_{2-12}$ alkynyl;
$R^5$ is hydrogen.

5. The compound or a geometric isomer, enantiomer, diastereoisomer, or a pharmaceutically acceptable salt thereof according to claim 4, wherein $R^4$ is n-propyl; 2,2,2-trifluoroethyl; 2-chloro-2,2-difluoroethyl; 2-bromo-2,2-difluoroethyl; or 2,2-difluorovinyl.

6. The compound or a geometric isomer, enantiomer, diastereoisomer, or a pharmaceutically acceptable salt thereof according to claim 4, wherein $R^3$ is a heterocycle selected from the group consisting of:
  imidazo[1,2-a]pyrimidin-3-yl;
  imidazo[1,2-b][1,2,4]triazin-7-yl;
  imidazo[1,2-b]pyridazin-3-yl;
  5,6,7,8-tetrahydroimidazo[1,2-b]pyridazin-3-yl;
  imidazo[2,1-b][1,3,4]thiadiazol-5-yl;
  imidazo[2,1-b][1,3]thiazol-5-yl;
  3H-imidazo[4,5-b]pyridin-7-yl;
  1H-imidazol-4-yl;
  1H-imidazol-5-yl;
  isoxazol-4-yl;
  1H-pyrazol-4-yl;
  1H-pyrazol-5-yl;
  1H-pyrazolo[1,5-a]pyrimidin-3-yl;
  1H-pyrazolo[3,4-b]pyridin-3-yl;
  pyridin-3-yl;
  1H-pyrrolo[2,3-b]pyridin-3-yl;
  1H-pyrrolo[2,3-b]pyridin-4-yl;
  1H-pyrrolo[2,3-b]pyridin-5-yl;
  1H-pyrrolo[2,3-c]pyridin-2-yl;
  1H-pyrrolo[2,3-c]pyridin-3-yl;
  1,3-thiazol-5-yl;
  [1,2,4]triazolo[4,3-b]pyridazin-8-yl; and
  indolizin-3-yl.

7. The compound or a geometric isomer, enantiomer, diastereoisomer, or a pharmaceutically acceptable salt thereof according to claim 4, wherein $R^3$ is imidazo[1,2-a]pyridin-3-yl.

8. The compound or a geometric isomer, enantiomer, diastereoisomer, or a pharmaceutically acceptable salt thereof according to claim 4, wherein $R^3$ is a heterocycle selected from the group consisting of:
  3H-imidazo[4,5-b]pyridin-3-yl;
  1H-indol-1-yl;
  1H-pyrrolo[2,3-b]pyridin-1-yl;
  1H-pyrrolo[3,2-b]pyridin-1-yl; and
  1H-pyrrol-1-yl.

9. The compound or a geometric isomer, enantiomer, diastereoisomer, or a pharmaceutically acceptable salt thereof according to claim 4, wherein
$R^1$, $R^2$ and $R^5$ are hydrogen;
$R^4$ is $C_{1-6}$ alkyl optionally substituted by halogen; $C_{2-6}$ alkenyl optionally substituted by halogen; or $C_{2-12}$ alkynyl optionally substituted by halogen; and
$R^3$ is a heterocycle selected from the group consisting of:
  imidazo[1,2-b]pyridazin-3-yl;
  imidazo[2,1-b][1,3,4]thiadiazol-5-yl;
  imidazo[2,1-b][1,3]thiazol-5-yl;
  3H-imidazo[4,5-b]pyridin-7-yl;
  1H-imidazol-4-yl;
  1H-imidazol-5-yl;
  1H-pyrazol-4-yl;
  1H-pyrazolo[1,5-a]pyrimidin-3-yl;
  pyridin-3-yl;
  1H-pyrrolo[2,3-b]pyridin-3-yl;
  1H-pyrrolo[2,3-b]pyridin-4-yl; and
  1,3-thiazol-5-yl.

10. The compound or a geometric isomer, enantiomer, diastereoisomer, or a pharmaceutically acceptable salt thereof according to claim 4, wherein
$R^1$, $R^2$ and $R^5$ are hydrogen;
$R^4$ is $C_{1-6}$ alkyl optionally substituted by halogen; $C_{2-6}$ alkenyl optionally substituted by halogen; or $C_{2-12}$ alkynyl optionally substituted by halogen; and
$R^3$ is a heterocycle selected from the group consisting of:
  3H-imidazo[4,5-b]pyridin-3-yl;
  3H-imidazo[4,5-b]pyridin-1-yl; and
  1H pyrrolo[2,3-b]pyridin-1-yl.

11. The compound according to claim 1, selected from the group consisting of:
  1-[(1-phenyl-1H-pyrazol-4-yl)methyl]-4-(2,3,5-trifluorophenyl)pyrrolidin-2-one;
  1-[(1-methyl-1H-pyrazol-4-yl)methyl]-4-(2,3,5-trifluorophenyl)pyrrolidin-2-one;
  1-[(1-benzyl-1H-pyrazol-4-yl)methyl]-4-(2,3,5-trifluorophenyl)pyrrolidin-2-one;
  4-(2,3,5-trifluorophenyl)-1-[(1,3,5-trimethyl-1H-pyrazol-4-yl)methyl]pyrrolidin-2-one;
  4-phenyl-1-(1H-pyrazol-4-ylmethyl)pyrrolidin-2-one;
  1-({1-[(4-methylphenyl)sulfonyl]-1H-pyrazol-4-yl}methyl)-4-(2,3,5-trifluorophenyl)pyrrolidin-2-one;
  1-(1H-pyrazol-4-ylmethyl)-4-(2,3,5-trifluorophenyl)pyrrolidin-2-one;
  1-[(5-chloro-1,3-dimethyl-1H-pyrazol-4-yl)methyl]-4-(2,3,5-trifluorophenyl)pyrrolidin-2-one;
  1-[(1-chloro-1H-pyrazol-4-yl)methyl]-4-(2,3,5-trifluorophenyl)pyrrolidin-2-one;
  1-[(3,5-dimethyl-1H-pyrazol-4-yl)methyl]-4-(2,3,5-trifluorophenyl)pyrrolidin-2-one;
  1-[(3-methyl-1H-pyrazol-4-yl)methyl]-4-(2,3,5-trifluorophenyl)pyrrolidin-2-one;
  1-[(5-amino-1,3-dimethyl-1H-pyrazol-4-yl)methyl]-4-(2,3,5-trifluorophenyl)pyrrolidin-2-one;
  1-[(5-amino-1-methyl-1H-pyrazol-4-yl)methyl]-4-propylpyrrolidin-2-one;
  (−)-1-(1H-pyrazol-4-ylmethyl)-4-(2,3,5-trifluorophenyl)pyrrolidin-2-one;
  (+)-1-(1H-pyrazol-4-ylmethyl)-4-(2,3,5-trifluorophenyl)pyrrolidin-2-one;
  1-{[5-chloro-1-methyl-3-(trifluoromethyl)-1H-pyrazol-4-yl]methyl}-4-propylpyrrolidin-2-one;
  1-[(5-amino-1H-pyrazol-4-yl)methyl]-4-(2,3,5-trifluorophenyl)pyrrolidin-2-one;
  1-[(1-benzyl-5-chloro-1H-pyrazol-4-yl)methyl]-4-propylpyrrolidin-2-one;
  1-[(1,3-dimethyl-1H-pyrazol-5-yl)methyl]-4-(2,3,5-trifluorophenyl)pyrrolidin-2-one;

1-(1H-pyrazol-5-ylmethyl)-4-(2,3,5-trifluorophenyl)pyrrolidin-2-one;

1-[(4-bromo-1-methyl-1H-pyrazol-5-yl)methyl]-4-(2,3,5-trifluorophenyl)pyrrolidin-2-one;

1-[(1-methyl-1H-pyrazol-5-yl)methyl]-4-(2,3,5-trifluorophenyl)pyrrolidin-2-one;

1-(1H-1,2,4-triazol-1-ylmethyl)pyrrolidin-2-one;

or a geometric isomer, enantiomer, diastereoisomer,or a pharmaceutically acceptable salt thereof.

12. The compound according to claim 4 wherein $R^3$ is 1H-pyrazol-5-yl or a 1H-pyrazol-4-yl.

13. The compound according to claim 2 wherein $R^3$ is 1H-1,2,4-triazol-1-yl or a 1H-1,2,3-triazol-1-yl.

14. A composition comprising a compound or a geometric isomer, enantiomer, diastereoisomer, or a pharmaceutically acceptable salt thereof according to claim 1 and a pharmaceutically acceptable diluent or carrier.

* * * * *